United States Patent
Parham et al.

(10) Patent No.: US 12,419,192 B2
(45) Date of Patent: Sep. 16, 2025

(54) ORGANIC ELECTROLUMINESCENCE DEVICES

(71) Applicant: Merck Patent GmbH, Darmstadt (DE)

(72) Inventors: Amir Parham, Frankfurt am Main (DE); Jonas Kroeber, Frankfurt am Main (DE); Jens Engelhart, Darmstadt (DE); Anja Jatsch, Frankfurt am Main (DE); Christian Eickhoff, Mannheim (DE); Christian Ehrenreich, Darmstadt (DE); Dominik Joosten, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 994 days.

(21) Appl. No.: 16/972,877

(22) PCT Filed: Jun. 3, 2019

(86) PCT No.: PCT/EP2019/064249
§ 371 (c)(1),
(2) Date: Dec. 7, 2020

(87) PCT Pub. No.: WO2019/233904
PCT Pub. Date: Dec. 12, 2019

(65) Prior Publication Data
US 2022/0336754 A1    Oct. 20, 2022

(30) Foreign Application Priority Data
Jun. 7, 2018 (EP) .................... 18176496

(51) Int. Cl.
| H10K 85/60 | (2023.01) |
| C07D 209/94 | (2006.01) |
| C07D 209/96 | (2006.01) |
| C07D 403/04 | (2006.01) |
| C07D 403/14 | (2006.01) |
| C07D 405/14 | (2006.01) |
| H10K 50/11 | (2023.01) |
| H10K 101/10 | (2023.01) |

(52) U.S. Cl.
CPC ....... *H10K 85/6572* (2023.02); *C07D 209/94* (2013.01); *C07D 209/96* (2013.01); *C07D 403/04* (2013.01); *C07D 403/14* (2013.01); *C07D 405/14* (2013.01); *H10K 85/654* (2023.02); *H10K 85/6574* (2023.02); *H10K 50/11* (2023.02); *H10K 2101/10* (2023.02)

(58) Field of Classification Search
CPC .................. H10K 85/6572; H10K 85/654
See application file for complete search history.

(56) References Cited

U.S. PATENT DOCUMENTS

| 2005/0112400 A1 | 5/2005 | Seo et al. |
| 2006/0115680 A1 | 6/2006 | Hwang et al. |
| 2012/0068170 A1* | 3/2012 | Pflumm ............... H10K 85/633 544/212 |
| 2015/0214492 A1 | 7/2015 | Yen et al. |
| 2016/0225992 A1 | 8/2016 | Ito et al. |
| 2016/0233442 A1 | 8/2016 | Yen et al. |
| 2017/0237017 A1 | 8/2017 | Parham et al. |
| 2018/0006237 A1 | 1/2018 | Anmain et al. |
| 2018/0051206 A1 | 2/2018 | Burkhart et al. |
| 2019/0131543 A1* | 5/2019 | Lee ..................... C07D 401/14 |
| 2019/0185411 A1 | 6/2019 | Lee et al. |
| 2022/0064100 A1 | 3/2022 | Lee et al. |

FOREIGN PATENT DOCUMENTS

| CN | 106661007 A | 5/2017 |
| CN | 107108578 A | 8/2017 |
| CN | 107406352 A | 11/2017 |
| CN | 107629197 A | 1/2018 |
| EP | 3042944 A1 | 7/2016 |
| JP | 2010-098223 A | 4/2010 |
| JP | 2016-147846 A | 8/2016 |
| JP | 2017-503773 A | 2/2017 |
| KR | 10-2006-0059613 A | 6/2006 |
| KR | 10-2017-0063411 A | 6/2017 |
| KR | 10-2017-0130737 A | 11/2017 |
| KR | 10-2018-0013713 A | 2/2018 |
| WO | 2010/136109 A1 | 12/2010 |
| WO | 2015/099486 A1 | 7/2015 |
| WO | 2017/179875 A1 | 10/2017 |
| WO | 2017/200320 A1 | 11/2017 |

OTHER PUBLICATIONS

International Preliminary Report on Patentability received for PCT Patent Application No. PCT/EP2019/064249, mailed on Dec. 17, 2020, 15 pages.
International Search Report and Written Opinion received for PCT Patent Application No. PCT/EP2019/064249, mailed on Sep. 23, 2019, 17 pages. (7 pages of English Translation and 10 pages of Original Document).

* cited by examiner

*Primary Examiner* — Sean M DeGuire
(74) *Attorney, Agent, or Firm* — Faegre Drinker Biddle & Reath LLP

(57) ABSTRACT

The invention relates to organic electroluminescence devices containing indone carbazole derivatives.

13 Claims, No Drawings

ORGANIC ELECTROLUMINESCENCE DEVICES

CROSS-REFERENCE TO RELATED APPLICATIONS

This application is a national stage application (under 35 U.S.C. § 371) of PCT/EP2019/064249, filed Jun. 3, 2019, which claims benefit of European Application No. 18176496.0, filed Jun. 7, 2018, both of which are incorporated herein by reference in their entirety.

The present invention relates to organic electroluminescent devices comprising indenocarbazole derivatives.

Emitting materials used in organic electroluminescent devices (OLEDs) are frequently phosphorescent organometallic complexes. The properties of phosphorescent OLEDs are not just determined by the triplet emitters used. The other materials used, especially the matrix materials, are also of particular significance here. Improvements to these materials can thus also lead to distinct improvements in the OLED properties.

The problem addressed by the present invention is that of providing phosphorescent organic electroluminescent devices having improved properties, especially an improved lifetime with simultaneously good efficiency and low operating voltage. It is a further object of the invention to provide phosphorescent OLEDs having long lifetime, good efficiency and low operating voltage that contain just one matrix material and not a mixture of two matrix materials. The advantage of such an OLED is simplified processing in the production thereof.

It has been found that, surprisingly, this problem is solved by the use of the indenocarbazole derivatives described in detail below as matrix material for phosphorescent emitters. The present invention therefore provides organic electroluminescent devices comprising such compounds as matrix material for phosphorescent emitters. WO 2010/136109 discloses indenocarbazole derivatives as matrix materials for phosphorescent emitters. There is no disclosure of matrix materials according to the present invention.

The present invention provides an organic electroluminescent device comprising anode, cathode and at least one emitting layer containing at least one phosphorescent compound, characterized in that the emitting layer contains at least one compound of formula (1)

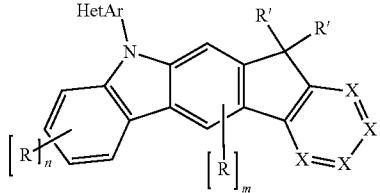

Formula (1)

where the symbols and indices used are as follows:
X two adjacent X are a group of the formula (2) below, and the two other X are CR,

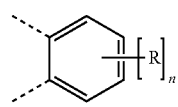

Formula (2)

where the two dotted bonds represent the linkage of this group;

HetAr is an electron-deficient heteroaryl group which has 6 to 18 aromatic ring atoms and may be substituted by one or more R radicals with the proviso that the heteroaryl group contains at least two nitrogen atoms;

R is the same or different at each instance and is H, D, F, Cl, Br, I, $N(R^1)_2$, $N(Ar')_2$, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals and where one or more nonadjacent $CH_2$ groups may be replaced by $Si(R^1)_2$, $C=O$, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals;

R' is the same or different at each instance and is a straight-chain alkyl group having 1 to 20 carbon atoms or a branched or cyclic alkyl group having 3 to 20 carbon atoms, where the straight-chain, branched or cyclic alkyl group may in each case be substituted by one or more $R^1$ radicals and where one or more nonadjacent $CH_2$ groups may be replaced by O, or an aromatic or heteroaromatic ring system which has 5 to 40 aromatic ring atoms and may be substituted in each case by one or more $R^1$ radicals; at the same time, two R' radicals together may also form an aromatic, heteroaromatic, aliphatic or heteroaliphatic ring system;

Ar' is the same or different at each instance and is an aromatic or heteroaromatic ring system which has 5 to 40 aromatic ring atoms and may be substituted by one or more $R^1$ radicals;

$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may be replaced by $Si(R^2)_2$, $C=O$, $NR^2$, O, S or $CONR^2$, or an aromatic or heteroaromatic ring system which has 5 to 40 aromatic ring atoms and may be substituted in each case by one or more $R^2$ radicals; at the same time, two or more $R^1$ radicals together may form a ring system;

$R^2$ is the same or different at each instance and is H, D, F or an aliphatic, aromatic or heteroaromatic organic radical, especially a hydrocarbyl radical, having 1 to 20 carbon atoms, in which one or more hydrogen atoms may also be replaced by F;

m is 0, 1 or 2;

n is the same or different at each instance and is 0, 1, 2, 3 or 4.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An electron-deficient heteroaryl group in the context of the present invention is a heteroaryl group having at least one heteroaromatic six-membered ring having at least two nitrogen atoms or at least one heteroaromatic five-membered ring having at least two heteroatoms, where at least one heteroatom in the five-membered ring is nitrogen and the other heteroatom in the five-membered ring is a substituted nitrogen or oxygen or sulfur. It is possible for further aromatic or heteroaromatic groups to be fused onto this heteroaromatic five- or six-membered ring. In a preferred embodiment of the invention, the electron-deficient heteroaryl group contains at least one heteroaromatic six-membered ring having at least two nitrogen atoms. Examples of electron-deficient heteroaryl groups are pyrimidine, pyrazine, pyridazine, triazine, quinazoline, quinoxaline, benzoquinazoline or benzimidazole. Further electron-deficient heteroaryl groups are detailed more specifically in the description that follows.

An aromatic ring system in the context of this invention contains 6 to 60 carbon atoms in the ring system, preferably 6 to 40 carbon atoms. A heteroaromatic ring system in the context of this invention contains 2 to 60 carbon atoms, preferably 2 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferably, the aromatic ring system is selected from fluorene, 9,9'-spirobifluorene, 9,9-diarylamine or groups in which two or more aryl and/or heteroaryl groups are joined to one another by single bonds.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5 to 60 aromatic ring atoms and may also be substituted in each case by the abovementioned radicals and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

When two R' or $R^1$ radicals together form a ring system, it may be mono- or polycyclic. In this case, the radicals which together form a ring system are preferably adjacent, meaning that these radicals are bonded to the same carbon atom or to carbon atoms bonded directly to one another. When two R' radicals together form a ring system, this gives rise to a spiro system.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

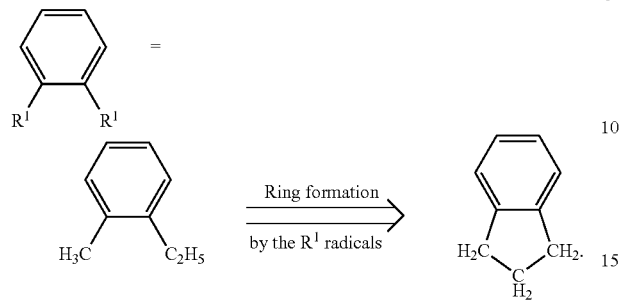

In addition, however, the abovementioned wording shall also be understood to mean that, if one of the two radicals is hydrogen, the second radical binds to the position to which the hydrogen atom was bonded, forming a ring. This shall be illustrated by the following scheme:

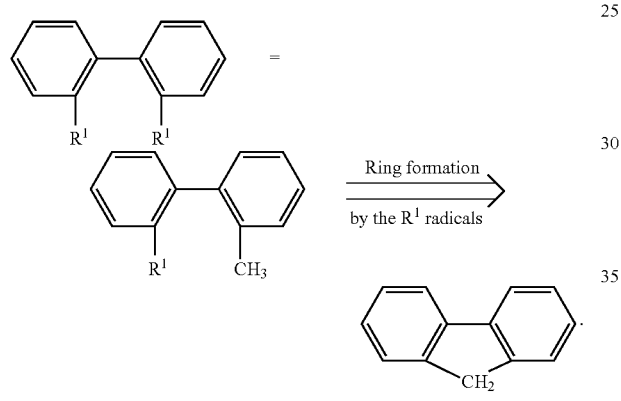

According to the position in which the group of the formula (2) is fused on, the organic electroluminescent device of the invention encompasses at least one compound according to one of the following formulae (3), (4) and (5):

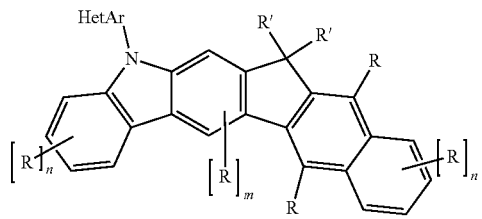

Formula (3)

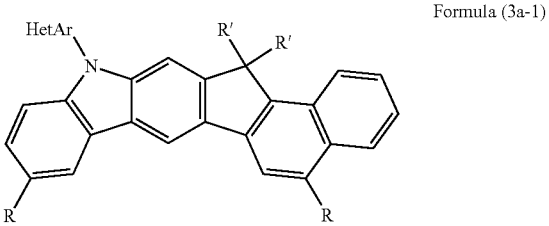

Formula (4)

Formula (5)

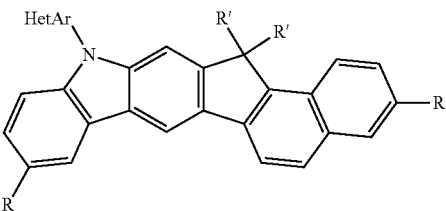

where the symbols and indices used have the definitions given above.

In a preferred embodiment of the invention, the compounds of the formulae (3), (4) and (5) are selected from the compounds of the following formulae (3a-1), (3a-2), (4a-1), (4a-2), (5a-1) and (5a-2):

Formula (3a-1)

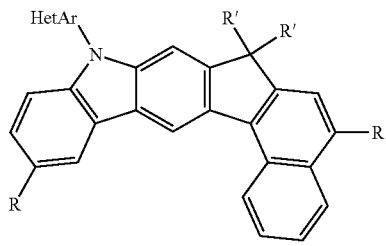

Formula (3a-2)

Formula (4a-1)

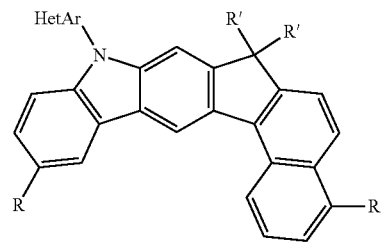

Formula (4a-2)

Formula (5a-1)

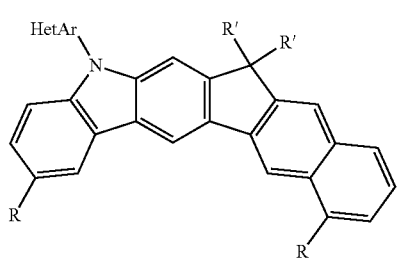

Formula (5a-2)

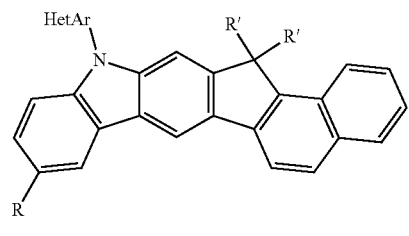

where HetAr, R and R' have the definitions given above.

At the same time, the R radical on the group of the formula (2) is preferably H, and so the compounds of the formulae (3), (4) and (5) are compounds of the following formulae (3b), (4b) and (5b):

Formula (3b)

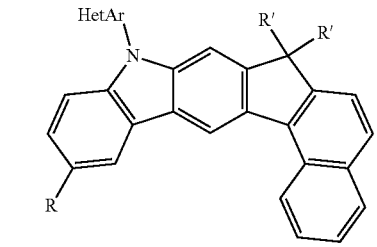

Formula (4b)

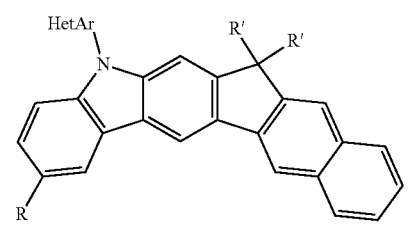

Formula (5b)

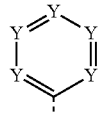

where HetAr, R and R' have the definitions given above.

In a preferred embodiment of the invention, R in the formulae (3b), (4b) and (5b) is carbazolyl substituted by an $R^1$ radical on the nitrogen atom, where $R^1$ is an aromatic or heteroaromatic ring system. The carbazolyl radical here is preferably bonded via the 3 position. In a further preferred embodiment of the invention, the R radical in the formulae (3b), (4b) and (5b) is H, and so preference is given to compounds of the following formulae (3c), (4c) and (5c):

Formula (3c)

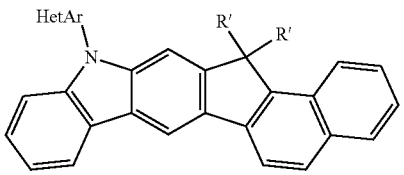

Formula (4c)

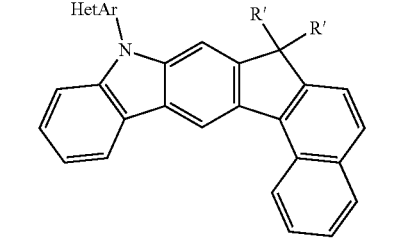

Formula (5c)

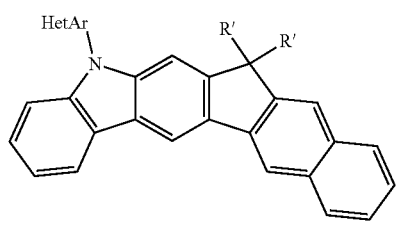

where HetAr and R' have the definitions given above.

Preferred HetAr groups are described hereinafter. As described above, HetAr is an electron-deficient heteroaryl group which has 6 to 14 aromatic ring atoms, has at least two nitrogen atoms, and may be substituted by one or more R radicals. In a preferred embodiment of the invention, HetAr has 6 to 10 aromatic ring atoms, where HetAr may in each case be substituted by one or more R radicals. In a preferred embodiment of the invention, HetAr has exactly two or three nitrogen atoms and no further heteroatoms in the base skeleton.

Preferably, HetAr is selected from the structures of the following formulae (HetAr-1) to (HetAr-8):

(HetAr-1)

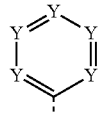

(HetAr-2)

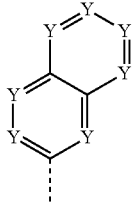

-continued

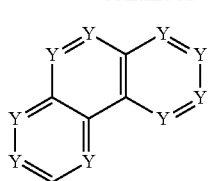
(HetAr-3)

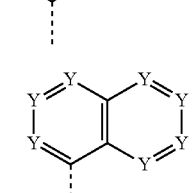
(HetAr-4)

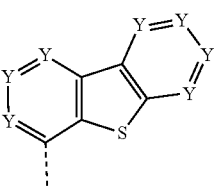
(HetAr-5)

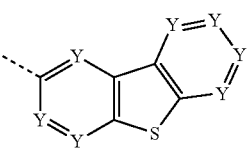
(HetAr-6)

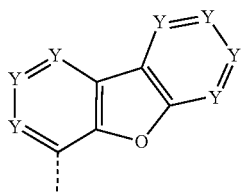
(HetAr-7)

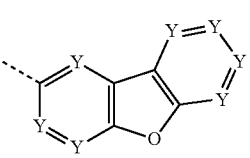
(HetAr-8)

where the dotted bond represents the bond to the nitrogen atom, R has the definitions given above and Y is as follows:

Y is the same or different at each instance and is CR or N, with the proviso that at least two symbols Y and not more than three symbols Y are N.

At the same time, preferably not more than two nitrogen atoms are bonded directly to one another. More preferably, no nitrogen atoms are bonded directly to one another.

It is preferable here for formula (HetAr-1) when it represents a pyrimidine group or a 1,3,5-triazine group. For the formulae (HetAr-2) to (HetAr-8), it is preferable when these have exactly two nitrogen atoms. It is more preferable here for these two nitrogen atoms to be present in the same six-membered ring of the heteroaryl group. More preferably, the formulae (HetAr-2) and (HetAr-4) represent quinazoline groups.

Preference is given to the groups of the formulae (HetAr-1), (HetAr-2) and (HetAr-3), particular preference to the groups of the formulae (HetAr-1) and (HetAr-2) and very particular preference to the groups of the formula (HetAr-2).

Preferred embodiments of the (HetAr-1) group are the groups of the formulae (HetAr-1a) to (HetAr-1d), preferred embodiments of the (HetAr-2) group are the groups of the formula (HetAr-2a), preferred embodiments of the (HetAr-3) group are the groups of the formula (HetAr-3a), preferred embodiments of the (HetAr-4) group are the groups of the formula (HetAr-4a), preferred embodiments of the (HetAr-5) group are the groups of the formula (HetAr-5a), preferred embodiments of the (HetAr-6) group are the groups of the formula (HetAr-6a), preferred embodiments of the (HetAr-7) group are the groups of the formula (HetAr-7a), and preferred embodiments of the (HetAr-8) group are the groups of the formula (HetAr-8a),

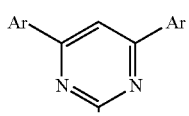
(HetAr-1a)

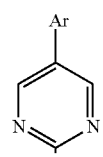
(HetAr-1b)

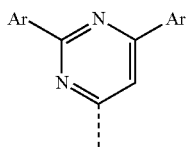
(HetAr-1c)

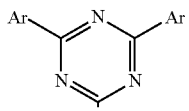
(HetAr-1d)

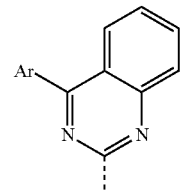
(HetAr-2a)

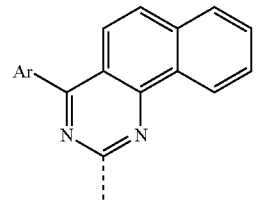
(HetAr-3a)

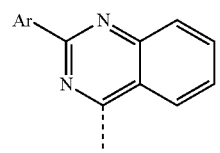
(HetAr-4a)

-continued

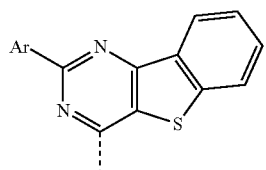
(HetAr-5a)

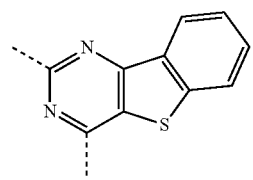
(HetAr-6a)

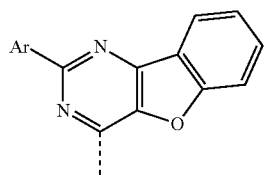
(HetAr-7a)

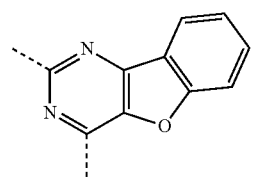
(HetAr-8c)

where Ar is the same or different at each instance and is an aromatic or heteroaromatic ring system which has 5 to 40 aromatic ring atoms and may be substituted by one or more $R^1$ radicals, and the further symbols have the definitions given above.

Particular preference is given to the (HetAr-1d) and (HetAr-2a) groups, especially (HetAr-2a).

Suitable aromatic or heteroaromatic ring systems Ar are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^1$ radicals.

The Ar groups here are preferably independently selected from the groups of the following formulae Ar-1 to Ar-75:

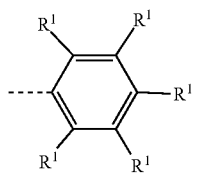
Ar-1

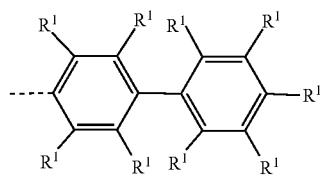
Ar-2

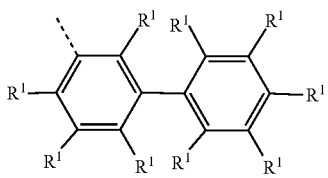
Ar-3

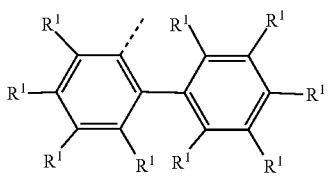
Ar-4

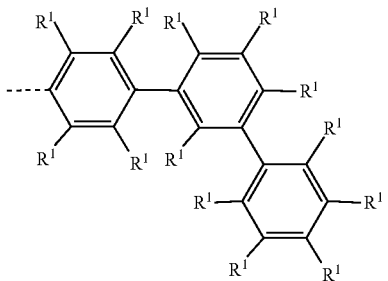
Ar-5

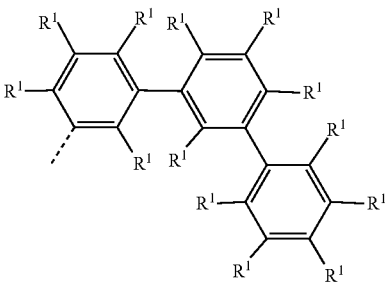
Ar-6

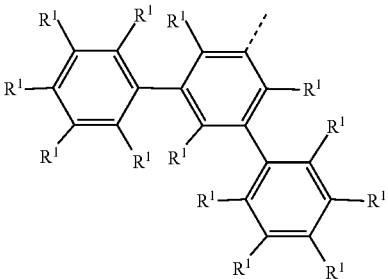
Ar-7

-continued
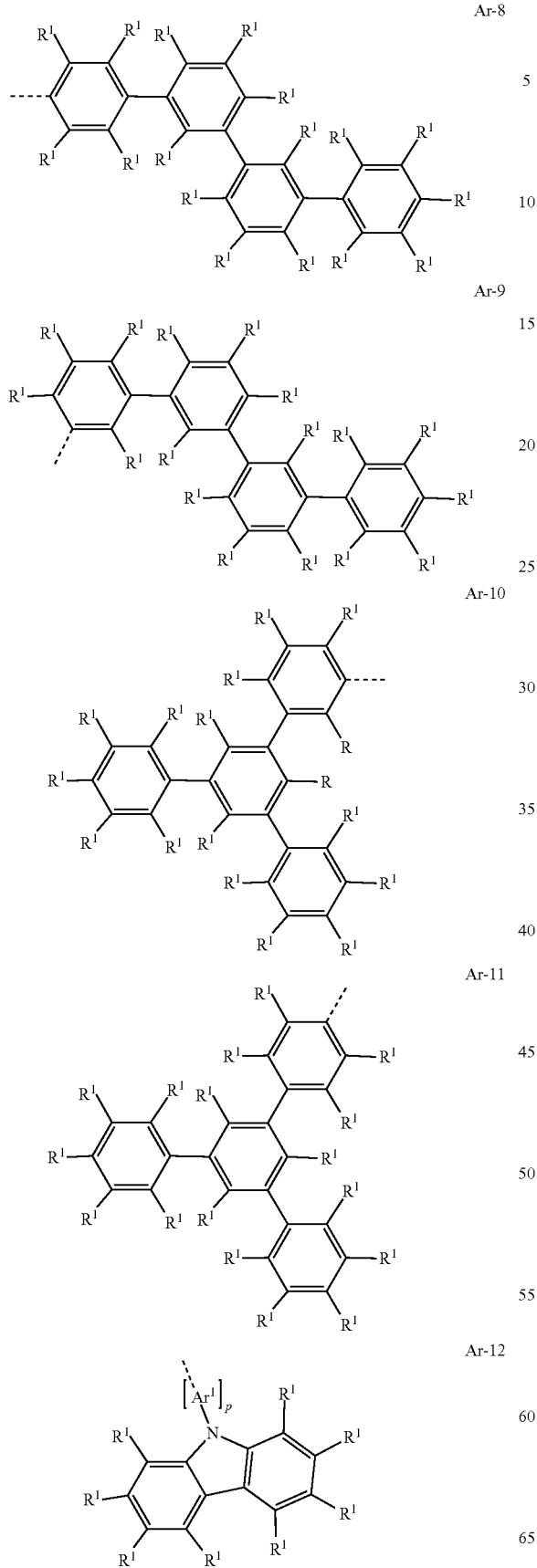
Ar-8
Ar-9
Ar-10
Ar-11
Ar-12
-continued
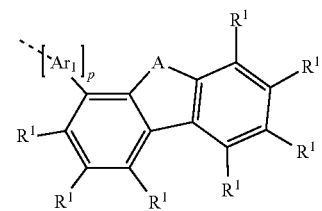
Ar-13
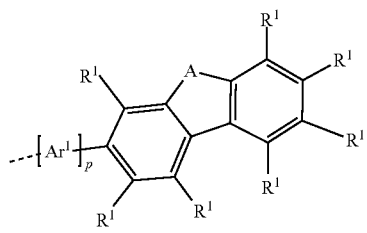
Ar-14
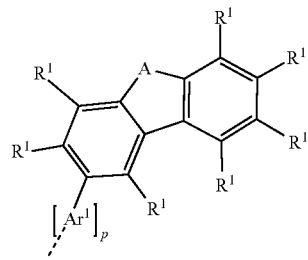
Ar-15
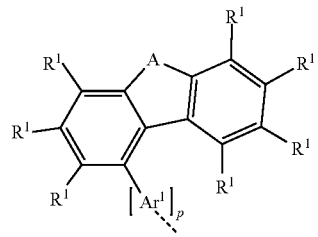
Ar-16
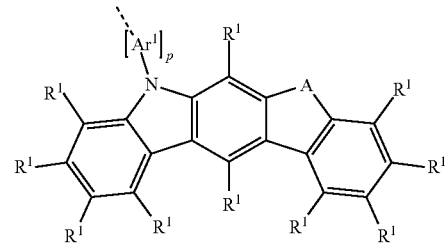
Ar-17
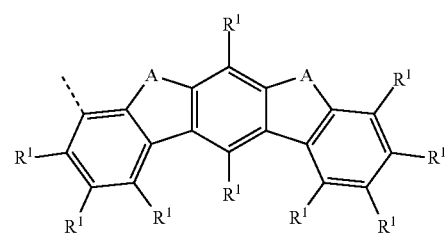
Ar-18

-continued
Ar-19
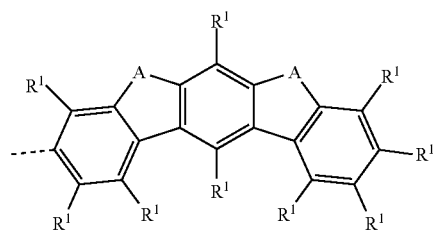
Ar-20
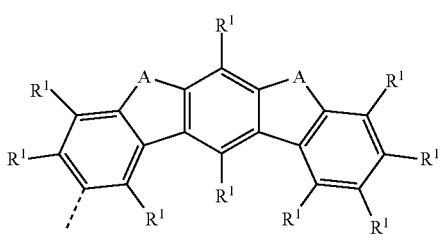
Ar-21
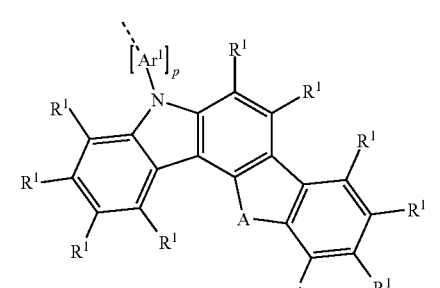
Ar-22
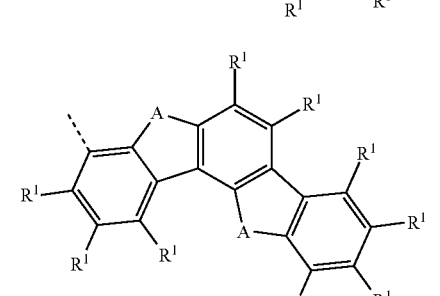
Ar-23
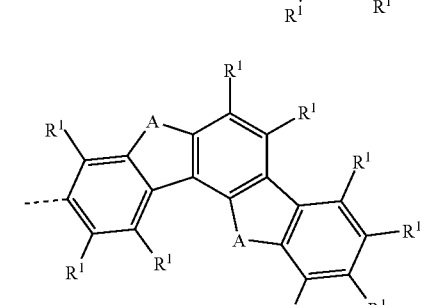
Ar-24
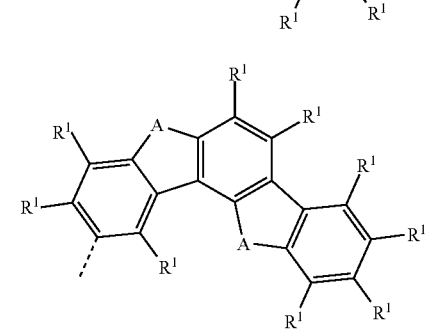
-continued
Ar-25
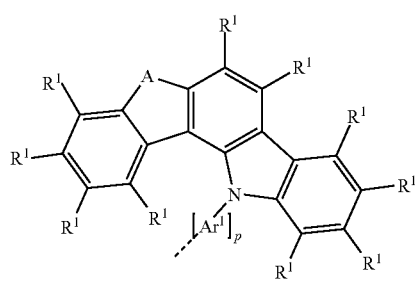
Ar-26
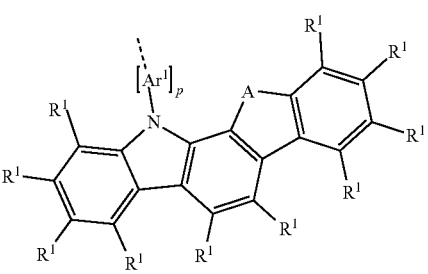
Ar-27
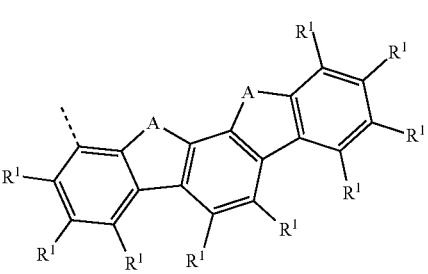
Ar-28
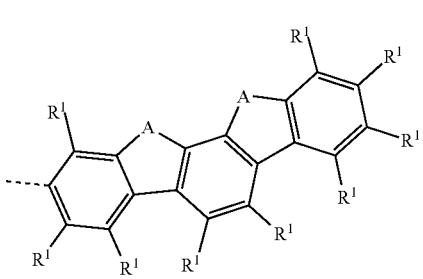
Ar-29
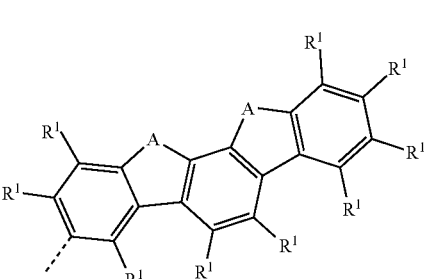
Ar-30
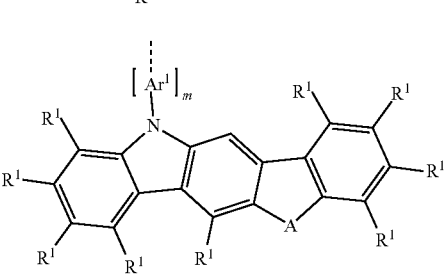

Ar-31
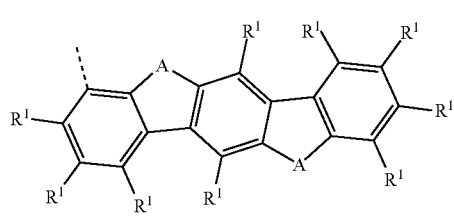
Ar-32
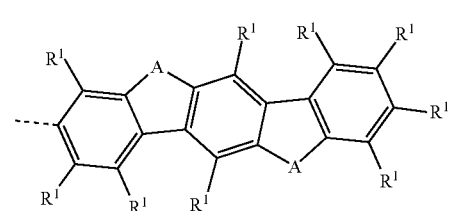
Ar-33
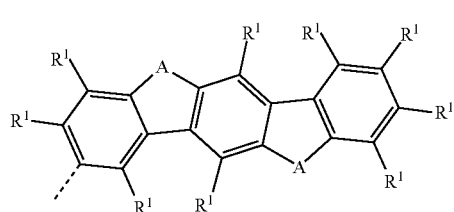
Ar-34
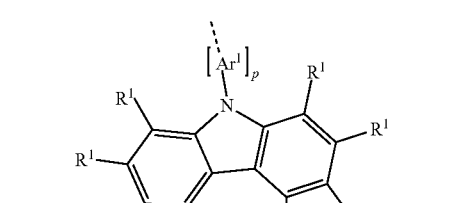
Ar-35
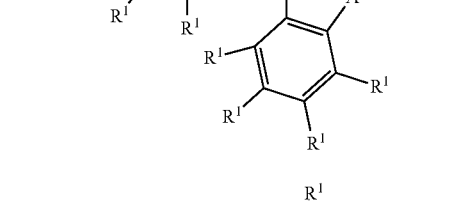
Ar-36
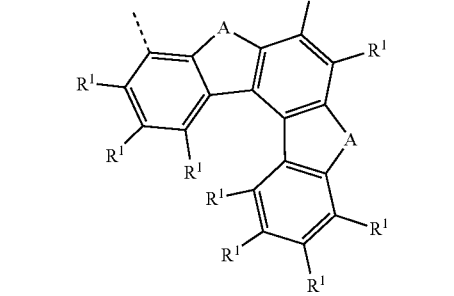
Ar-37
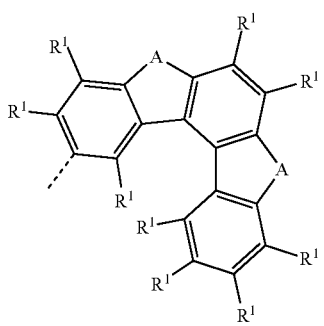
Ar-38
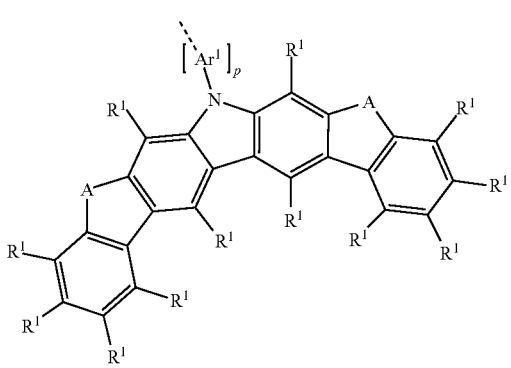
Ar-39
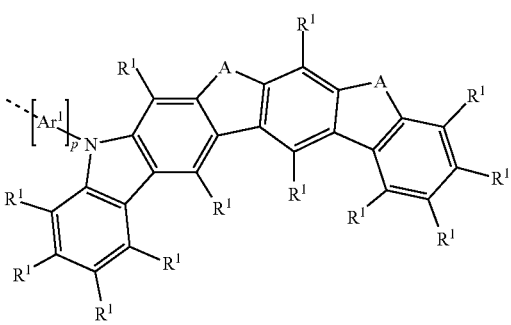
Ar-40
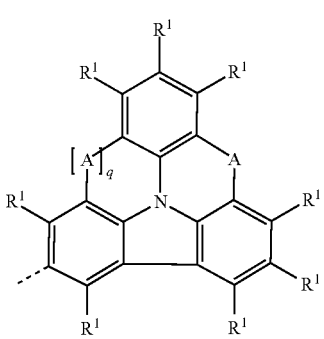

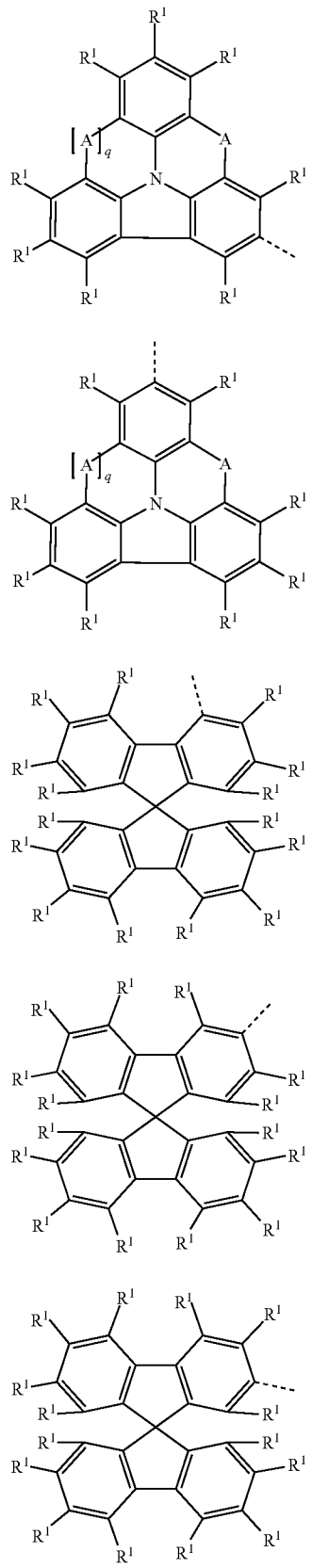
Ar-41
Ar-42
Ar-43
Ar-44
Ar-45
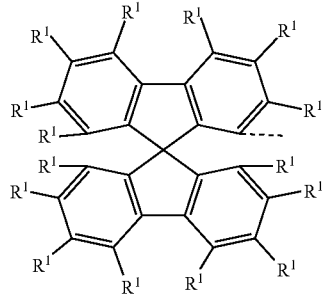
Ar-46
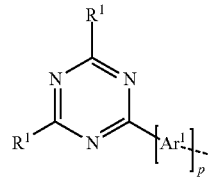
Ar-47
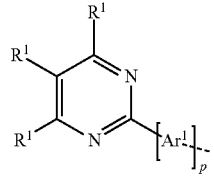
Ar-48
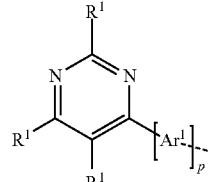
Ar-49
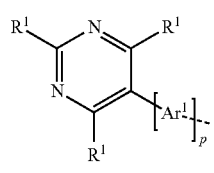
Ar-50
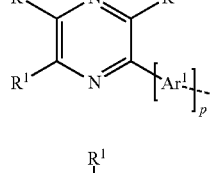
Ar-51
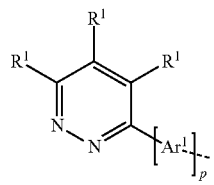
Ar-52
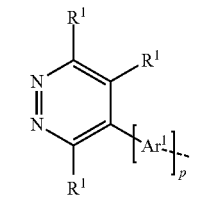
Ar-53

-continued
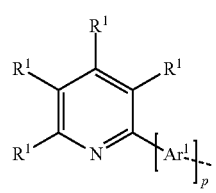
Ar-54
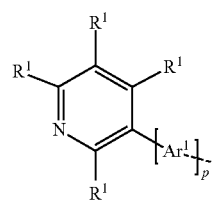
Ar-55
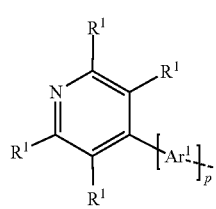
Ar-56
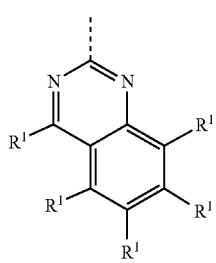
Ar-57
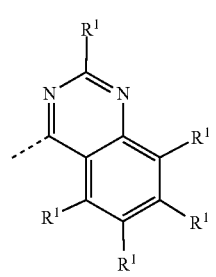
Ar-58
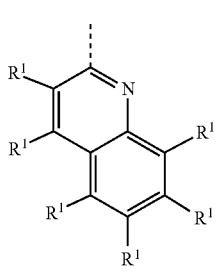
Ar-59
-continued
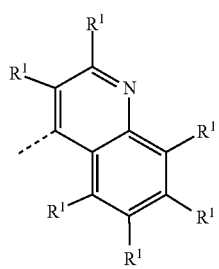
Ar-60
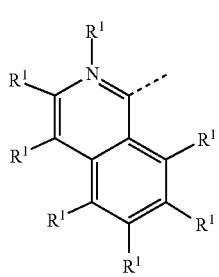
Ar-61
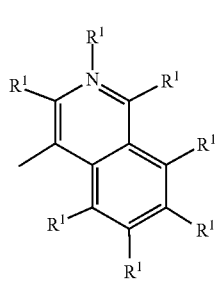
Ar-62
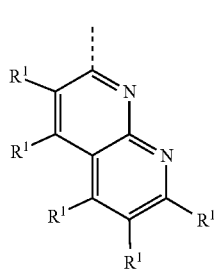
Ar-63
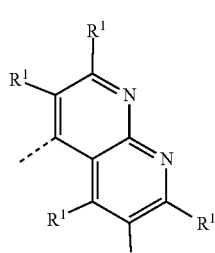
Ar-64
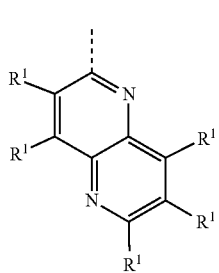
Ar-65

Ar-66 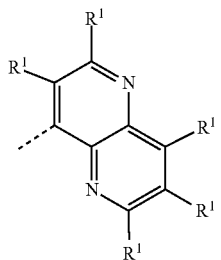

Ar-67 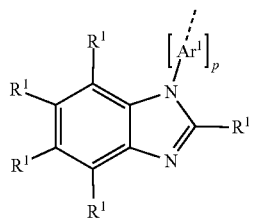

Ar-68 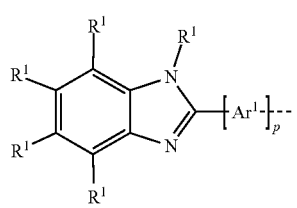

Ar-69 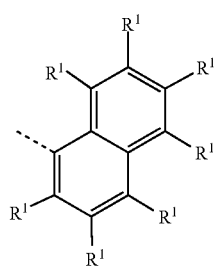

Ar-70 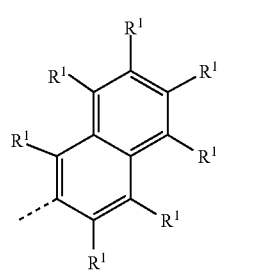

Ar-71 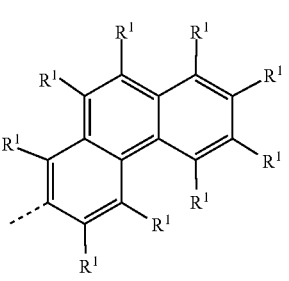

Ar-72 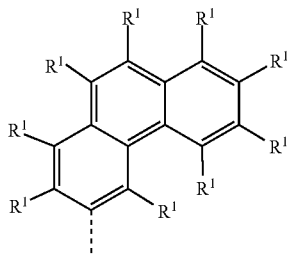

Ar-73 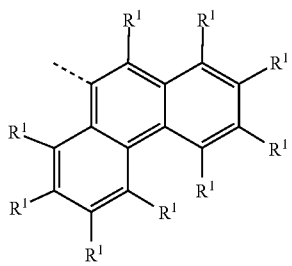

Ar-74 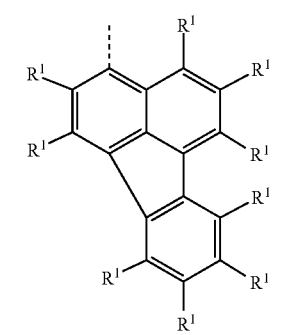

Ar-75 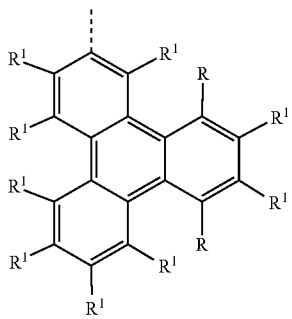

where $R^1$ is as defined above, the dotted bond represents the bond to HetAr and, in addition:

$Ar^1$ is the same or different at each instance and is a bivalent aromatic or heteroaromatic ring system which has 6 to 18 aromatic ring atoms and may be substituted in each case by one or more $R^1$ radicals;

A is the same or different at each instance and is $C(R^1)_2$, $NR^1$, O or S;

p is 0 or 1, where p=0 means that the $Ar^1$ group is absent and that the corresponding aromatic or heteroaromatic group is bonded directly to HetAr;

q is 0 or 1, where q=0 means that no A group is bonded at this position and $R^1$ radicals are bonded to the corresponding carbon atoms instead.

When the abovementioned groups for Ar have two or more A groups, possible options for these include all combinations from the definition of A. Preferred embodiments in that case are those in which one A group is NR$^1$ and the other A group is C(R$^1$)$_2$ or in which both A groups are NR$^1$ or in which both A groups are O.

When A is NR$^1$, the substituent R$^1$ bonded to the nitrogen atom is preferably an aromatic or heteroaromatic ring system which has 5 to 24 aromatic ring atoms and may also be substituted by one or more R$^2$ radicals. In a particularly preferred embodiment, this R$^1$ substituent is the same or different at each instance and is an aromatic or heteroaromatic ring system which has 6 to 24 aromatic ring atoms, especially 6 to 18 aromatic ring atoms, which does not have any fused aryl groups and which does not have any fused heteroaryl groups in which two or more aromatic or heteroaromatic 6-membered ring groups are fused directly to one another, and which may also be substituted in each case by one or more R$^2$ radicals. Preference is given to phenyl, biphenyl, terphenyl and quaterphenyl having bonding patterns as listed above for Ar-1 to Ar-11, where these structures, rather than by R$^1$, may be substituted by one or more R$^2$ radicals, but are preferably unsubstituted. Preference is further given to triazine, pyrimidine and quinazoline as listed above for Ar-47 to Ar-50, Ar-57 and Ar-58, where these structures, rather than by R$^1$, may be substituted by one or more R$^2$ radicals.

When A is C(R$^1$)$_2$, the substituents R$^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system having 5 to 24 aromatic ring atoms, which may also be substituted by one or more R$^2$ radicals. Most preferably, R$^1$ is a methyl group or a phenyl group. In this case, the R$^1$ radicals together may also form a ring system, which leads to a spiro system.

There follows a description of preferred substituents R and R' bonded to the base skeleton of the benzoindenocarbazole.

In a preferred embodiment of the invention, R is the same or different at each instance and is selected from the group consisting of H, D, an aromatic or heteroaromatic ring system which has 6 to 30 aromatic ring atoms and may be substituted by one or more R$^1$ radicals, and an N(Ar')$_2$ group. More preferably, R is the same or different at each instance and is selected from the group consisting of H or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more R$^1$ radicals.

Suitable aromatic or heteroaromatic ring systems R or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position or which, for R, may also be joined via the nitrogen atom, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more R$^1$ radicals. Particular preference is given to the structures Ar-1 to Ar-75 listed above.

Further suitable R groups are groups of the formula —Ar$^4$—N(Ar$^2$)(Ar$^3$) where Ar$^2$, Ar$^3$ and Ar$^4$ are the same or different at each instance and are an aromatic or heteroaromatic ring system which has 5 to 24 aromatic ring atoms and may be substituted in each case by one or more R$^1$ radicals. The total number of aromatic ring atoms in Ar$^2$, Ar$^3$ and Ar$^4$ here is not more than 60 and preferably not more than 40. PIn this case, Ar$^4$ and Ar$^2$ may also be bonded to one another and/or Ar$^2$ and Ar$^3$ to one another by a group selected from C(R$^1$)$_2$, NR$^1$, O and S. Preferably, Ar$^4$ and Ar$^2$ are joined to one another and Ar$^2$ and Ar$^3$ to one another in the respective ortho position to the bond to the nitrogen atom. In a further embodiment of the invention, none of the Ar$^2$, Ar$^3$ and Ar$^4$ groups are bonded to one another. PPreferably, Ar$^4$ is an aromatic or heteroaromatic ring system which has 6 to 24 aromatic ring atoms, preferably 6 to 12 aromatic ring atoms, and may be substituted in each case by one or more R$^1$ radicals. More preferably, Ar$^4$ is selected from the group consisting of ortho-, meta- or para-phenylene or ortho-, meta- or para-biphenyl, each of which may be substituted by one or more R$^1$ radicals, but are preferably unsubstituted. Most preferably, Ar$^4$ is an unsubstituted phenylene group. PPreferably, Ar$^2$ and Ar$^3$ are the same or different at each instance and are an aromatic or heteroaromatic ring system which has 6 to 24 aromatic ring atoms and may be substituted in each case by one or more R$^1$ radicals. Particularly preferred Ar$^2$ and Ar$^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene or triphenylene, each of which may be substituted by one or more R$^1$ radicals. Most preferably, Ar$^2$ and Ar$^3$ are the same or different at each instance and are selected from the group consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene. PIn a preferred embodiment of the invention, R' is the same or different at each instance and is selected from the group consisting of a straight-chain alkyl group having 1 to 6 carbon atoms or a cyclic alkyl group having 3 to 6 carbon atoms, where the alkyl group may be substituted in each case by one or more R$^1$ radicals, or an aromatic or heteroaromatic ring system which has 6 to 24 aromatic ring atoms and may be substituted in each case by one or more R$^1$ radicals; at the same time, two R' radicals together may also form a ring system, giving rise to a spiro system. More preferably, R' is the same or different at each instance and is selected from the group consisting of a straight-chain alkyl group having 1, 2, 3 or 4 carbon atoms or a branched or cyclic alkyl group having 3 to 6 carbon atoms, where the alkyl group may be substituted in each case by one or more R$^1$ radicals, but is preferably unsubstituted, or an aromatic ring system which has 6 to 12 aromatic ring atoms, especially 6 aromatic ring atoms, and may be substituted in each case by one or more preferably nonaromatic $R^1$ radicals, but is preferably unsubstituted; at the same time, two R' radicals together may form a ring system. When two R' radicals together form a ring system, this preferably forms a fluorene structure. Most preferably, R' is the same or different at each instance and is selected from the group consisting of a straight-chain alkyl group having 1, 2, 3 or 4 carbon atoms, or a branched alkyl group having 3 to 6 carbon atoms. PIn a further preferred embodiment of the invention, $R^1$ is the same or different at each instance and is selected from the group consisting of H, D, F, CN, a straight-chain alkyl group having 1 to 10 carbon atoms or a branched or cyclic alkyl group having 3 to 10 carbon atoms, where the alkyl group may be substituted in each case by one or more $R^2$ radicals, or an aromatic or heteroaromatic ring system which has 6 to 24 aromatic ring atoms and may be substituted in each case by one or more $R^2$ radicals. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may in each case be substituted by one or more $R^2$ radicals, but is preferably unsubstituted, or an aromatic or heteroaromatic ring system which has 6 to 13 aromatic ring atoms and may be substituted in each case by one or more $R^2$ radicals, but is preferably unsubstituted. PIn a further preferred embodiment of the invention, $R^2$ is the same or different at each instance and is H, an alkyl group having 1 to 4 carbon atoms or an aryl group having 6 to 10 carbon atoms, which may be substituted by an alkyl group having 1 to 4 carbon atoms, but is preferably unsubstituted. PAt the same time, in compounds of the invention that are processed by vacuum evaporation, the alkyl groups preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta- or para-terphenyl or quaterphenyl or branched terphenyl or quaterphenyl groups.

It is further preferable when the compound does not contain any fused aryl or heteroaryl groups in which more than two six-membered rings are fused directly to one another. An exception to this is formed by phenanthrene, triphenylene and the (HetAr-3) group listed above, which, because of their high triplet energy, may be preferable in spite of the presence of fused aromatic six-membered rings.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds detailed in the following table:

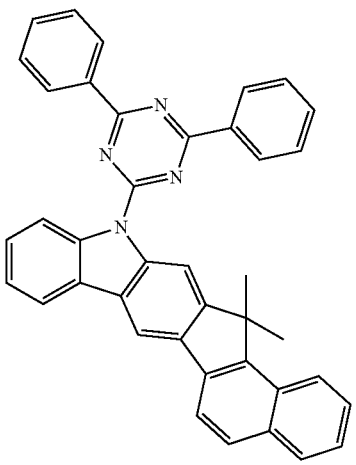 [SMILES: CC1(C)c2cc3c(cc2-c2ccc4ccccc4c21)c1ccccc1n3-c1nc(-c2ccccc2)nc(-c2ccccc2)n1]

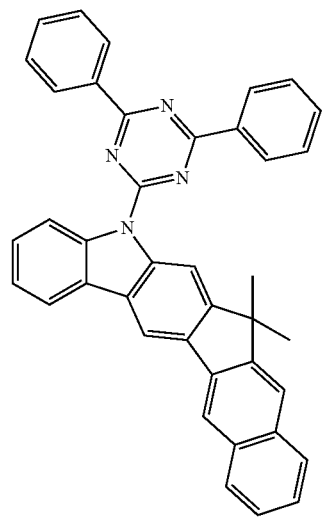 [SMILES: CC1(C)c2cc3ccccc3cc2-c2cc3c4ccccc4n(-c4nc(-c5ccccc5)nc(-c5ccccc5)n4)c3cc21]

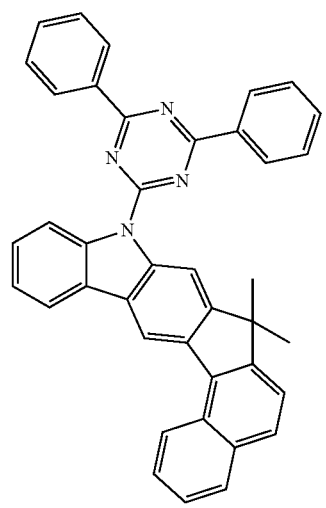 [SMILES: CC1(C)c2cc3c(cc2-c2c1ccc1ccccc21)c1ccccc1n3-c1nc(-c2ccccc2)nc(-c2ccccc2)n1]

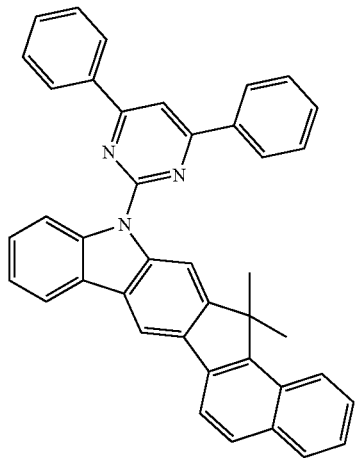 [SMILES: CC1(C)c2cc3c(cc2-c2ccc4ccccc4c21)c1ccccc1n3-c1nc(-c2ccccc2)cc(-c2ccccc2)n1]
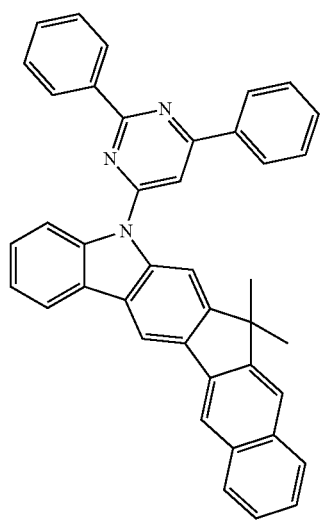 [SMILES: CC1(C)c2cc3ccccc3cc2-c2cc3c4ccccc4n(-c4cc(-c5ccccc5)nc(-c5ccccc5)n4)c3cc21]
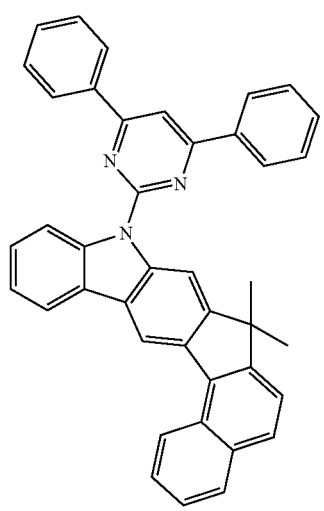 [SMILES: CC1(C)c2cc3c(cc2-c2c1ccc1ccccc21)c1ccccc1n3-c1nc(-c2ccccc2)cc(-c2ccccc2)n1]
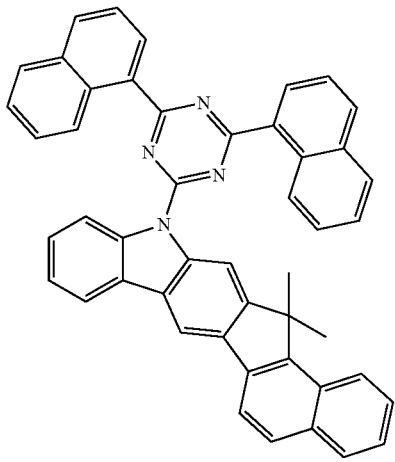 [SMILES: CC1(C)c2cc3c(cc2-c2ccc4ccccc4c21)c1ccccc1n3-c1nc(-c2cccc3ccccc23)nc(-c2cccc3ccccc23)n1]
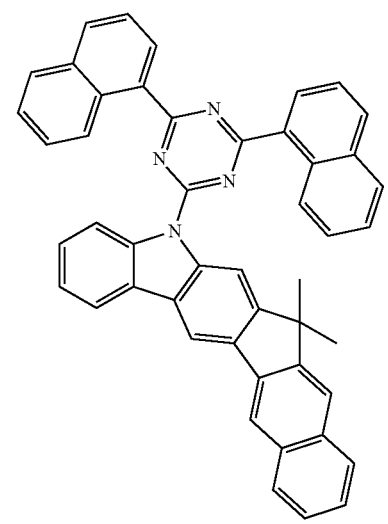 [SMILES: CC1(C)c2cc3ccccc3cc2-c2cc3c4ccccc4n(-c4nc(-c5cccc6ccccc56)nc(-c5cccc6ccccc56)n4)c3cc21]
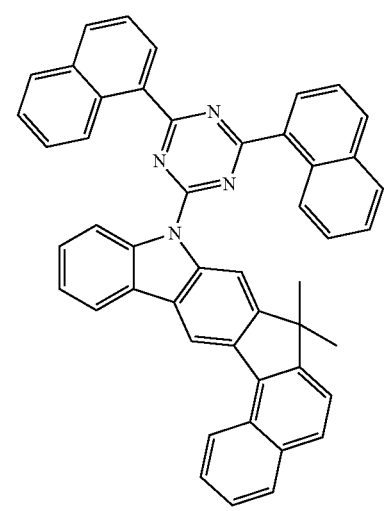 [SMILES: CC1(C)c2cc3c(cc2-c2c1ccc1ccccc21)c1ccccc1n3-c1nc(-c2cccc3ccccc23)nc(-c2cccc3ccccc23)n1]

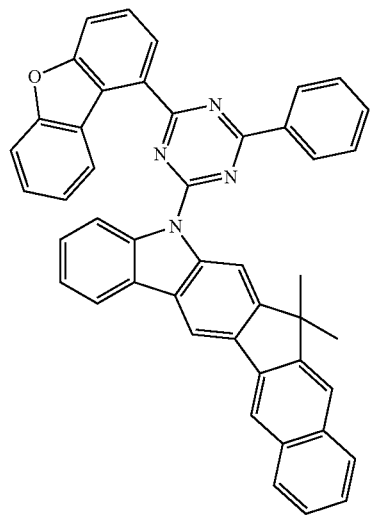 [SMILES: CC1(C)c2cc3ccccc3cc2-c2cc3c4ccccc4n(-c4nc(-c5ccccc5)nc(-c5cccc6oc7ccccc7c56)n4)c3cc21]
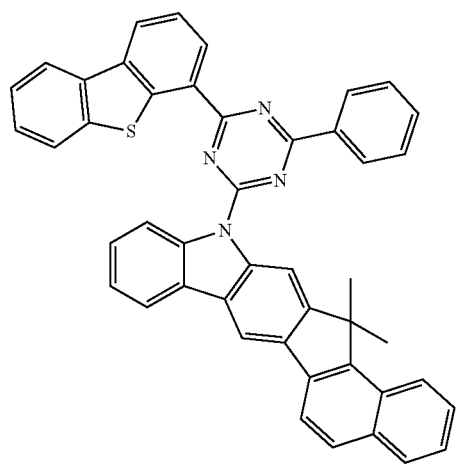 [SMILES: CC1(C)c2cc3c(cc2-c2ccc4ccccc4c21)c1ccccc1n3-c1nc(-c2ccccc2)nc(-c2cccc3c2sc2ccccc23)n1]
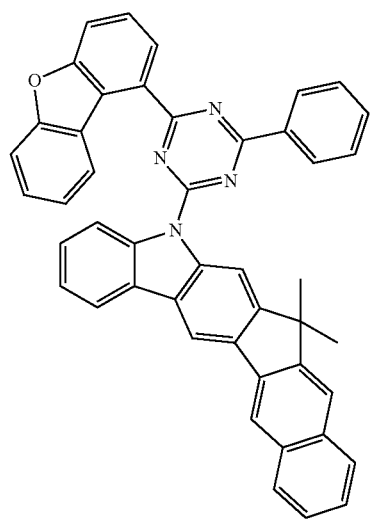 [SMILES: CC1(C)c2cc3ccccc3cc2-c2cc3c4ccccc4n(-c4nc(-c5ccccc5)nc(-c5cccc6oc7ccccc7c56)n4)c3cc21]
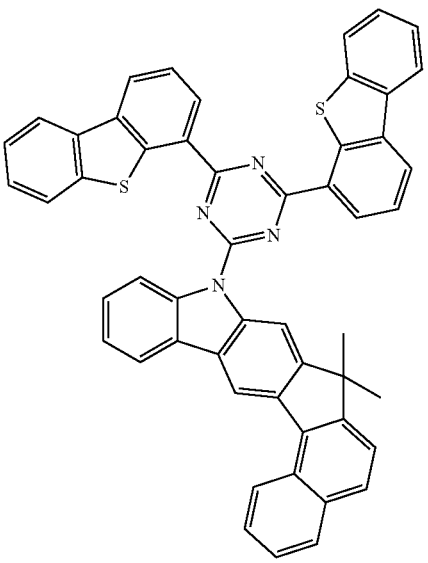 [SMILES: CC1(C)c2cc3c(cc2-c2c1ccc1ccccc21)c1ccccc1n3-c1nc(-c2cccc3c2sc2ccccc23)nc(-c2cccc3c2sc2ccccc23)n1]
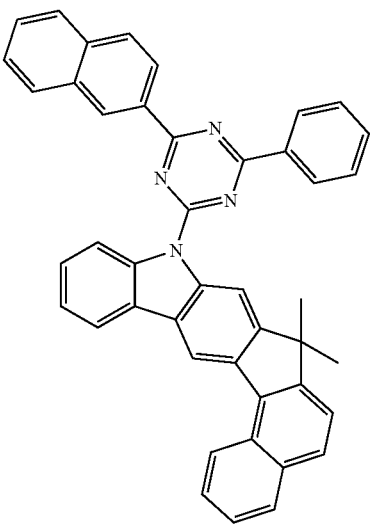 [SMILES: CC1(C)c2cc3c(cc2-c2c1ccc1ccccc21)c1ccccc1n3-c1nc(-c2ccccc2)nc(-c2ccc3ccccc3c2)n1]

-continued
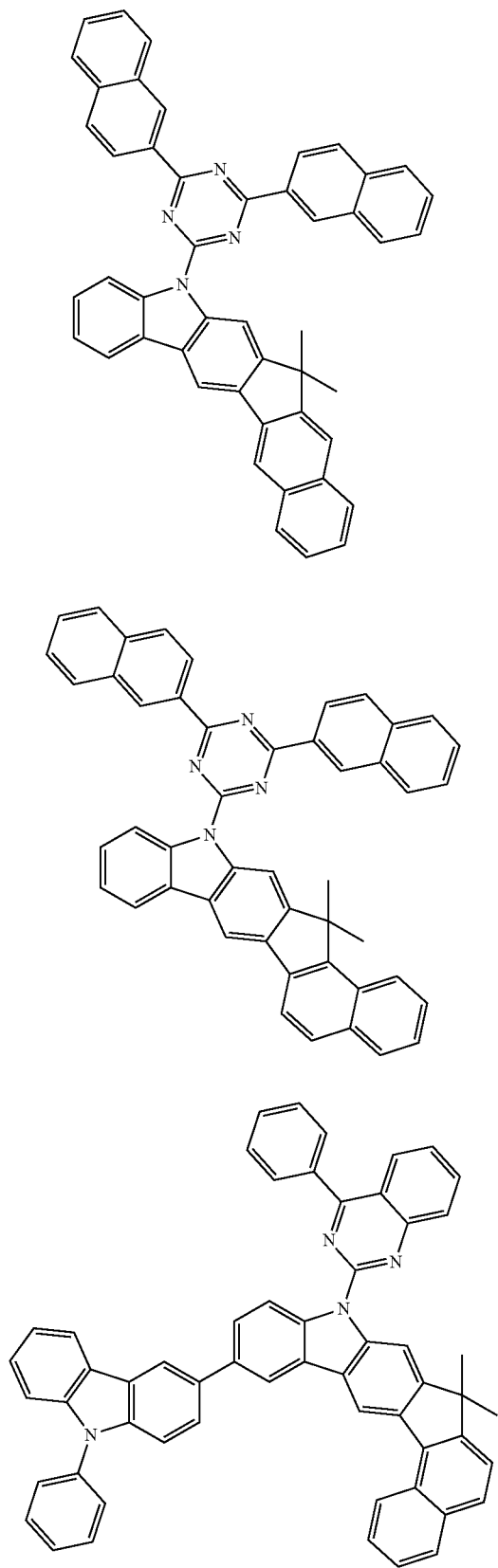
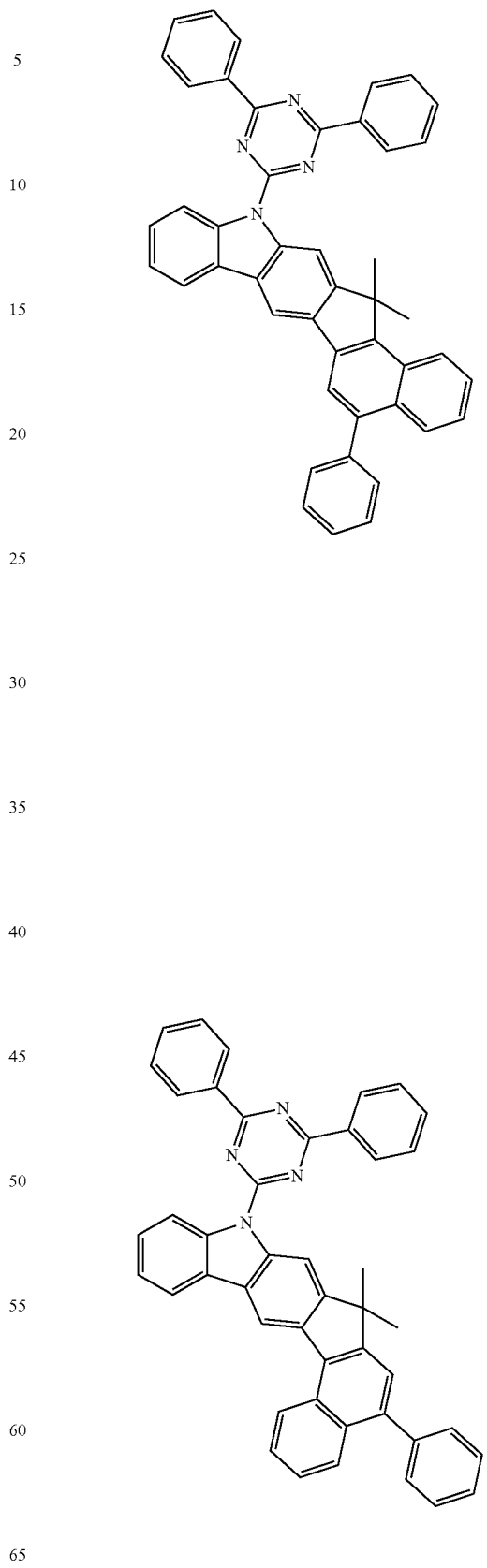

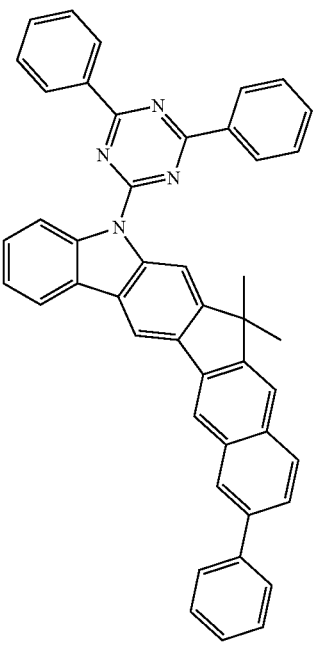 [SMILES: CC1(C)c2cc3ccc(-c4ccccc4)cc3cc2-c2cc3c4ccccc4n(-c4nc(-c5ccccc5)nc(-c5ccccc5)n4)c3cc21]
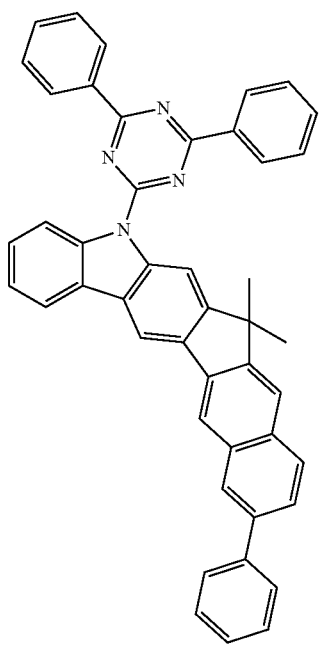
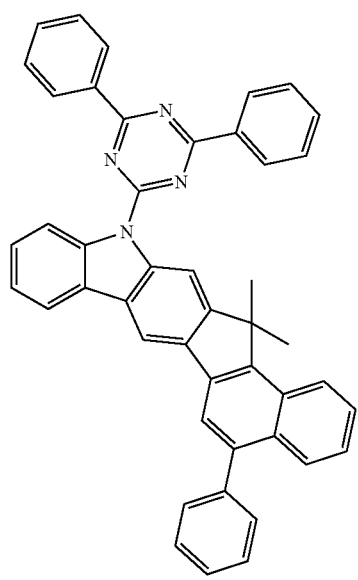 [SMILES: CC1(C)c2cc3c(cc2-c2cc(-c4ccccc4)c4ccccc4c21)c1ccccc1n3-c1nc(-c2ccccc2)nc(-c2ccccc2)n1]
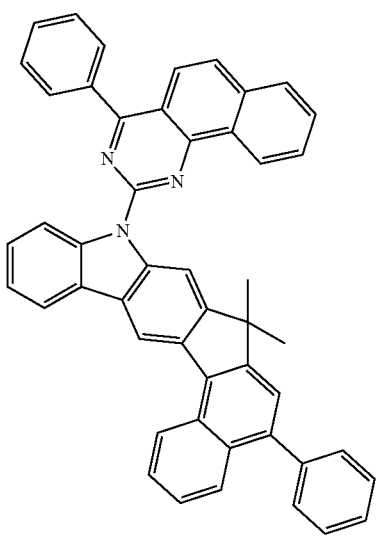 [SMILES: CC1(C)c2cc3c(cc2-c2c1cc(-c1ccccc1)c1ccccc21)c1ccccc1n3-c1nc(-c2ccccc2)c2ccc3ccccc3c2n1]

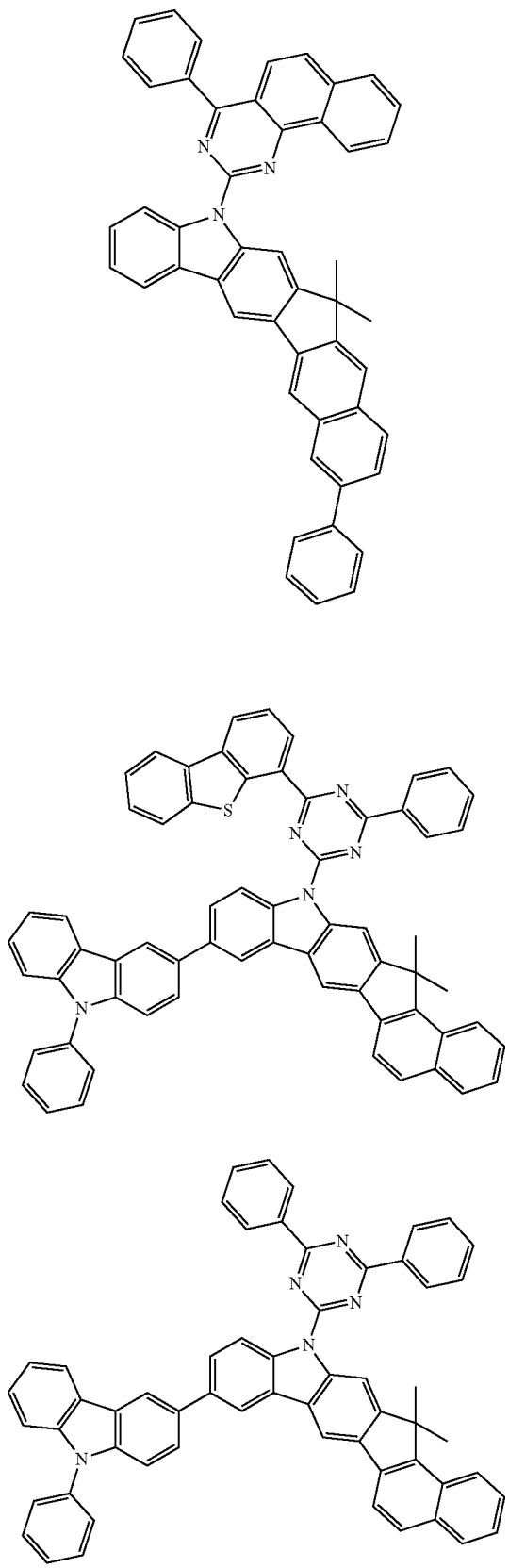
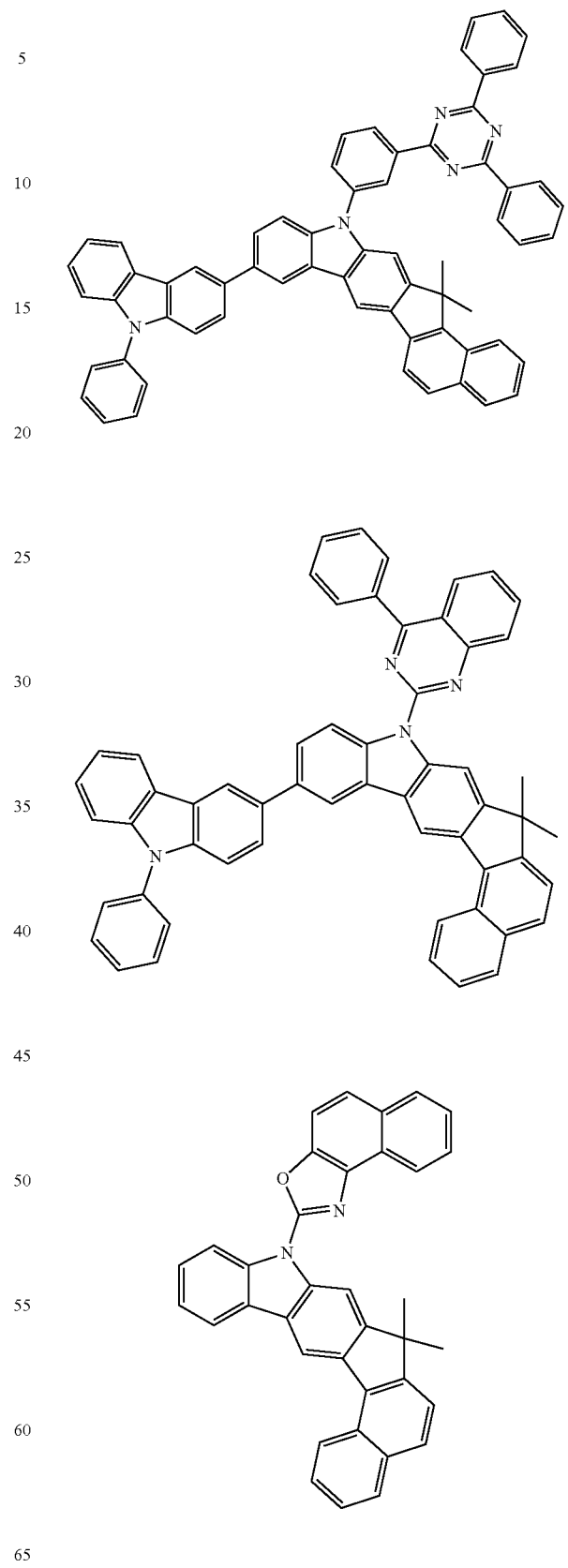

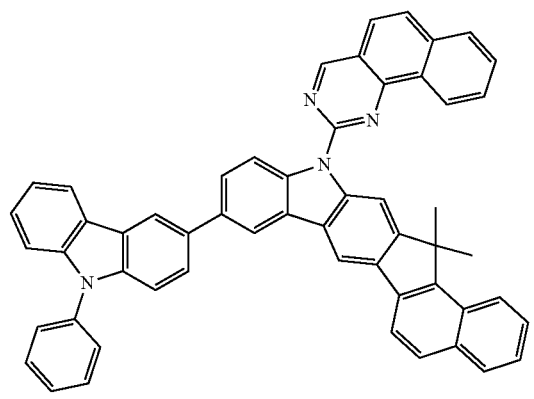 [SMILES: CC1(C)c2cc3c(cc2-c2ccc4ccccc4c21)c1cc(-c2ccc4c(c2)c2ccccc2n4-c2ccccc2)ccc1n3-c1ncc2ccc3ccccc3c2n1]
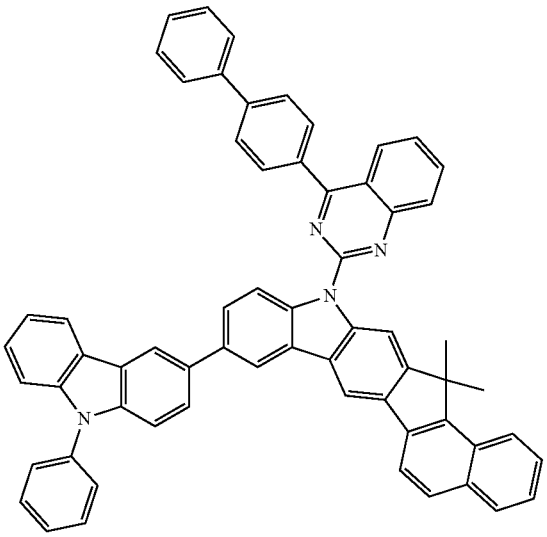
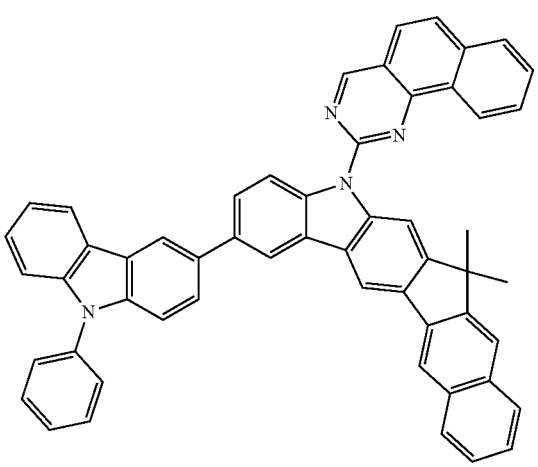 [SMILES: CC1(C)c2cc3ccccc3cc2-c2cc3c4cc(-c5ccc6c(c5)c5ccccc5n6-c5ccccc5)ccc4n(-c4ncc5ccc6ccccc6c5n4)c3cc21]
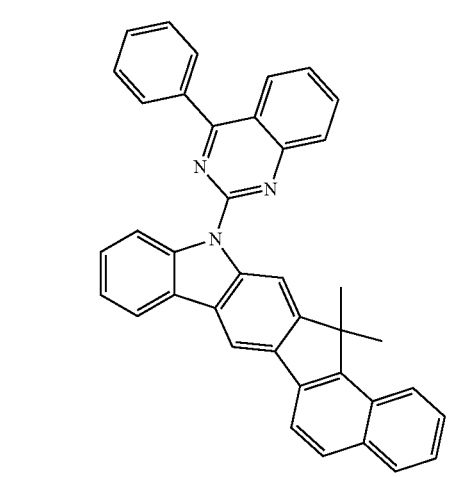
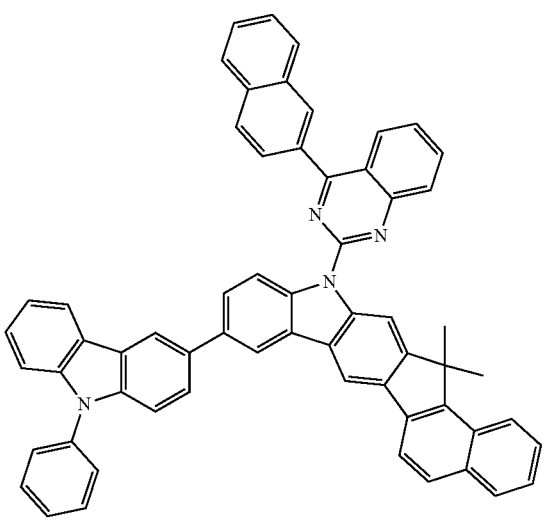 [SMILES: CC1(C)c2cc3c(cc2-c2ccc4ccccc4c21)c1cc(-c2ccc4c(c2)c2ccccc2n4-c2ccccc2)ccc1n3-c1nc(-c2ccc3ccccc3c2)c2ccccc2n1]
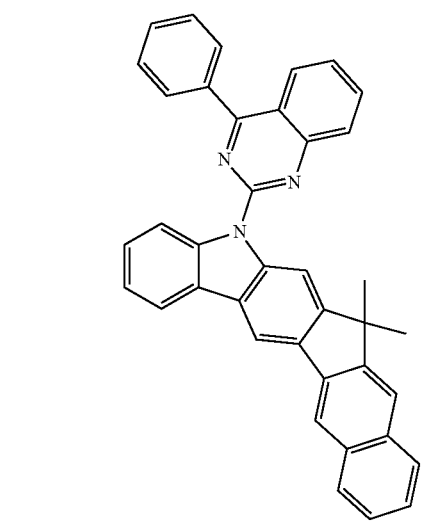 [SMILES: CC1(C)c2cc3ccccc3cc2-c2cc3c4ccccc4n(-c4nc(-c5ccccc5)c5ccccc5n4)c3cc21]

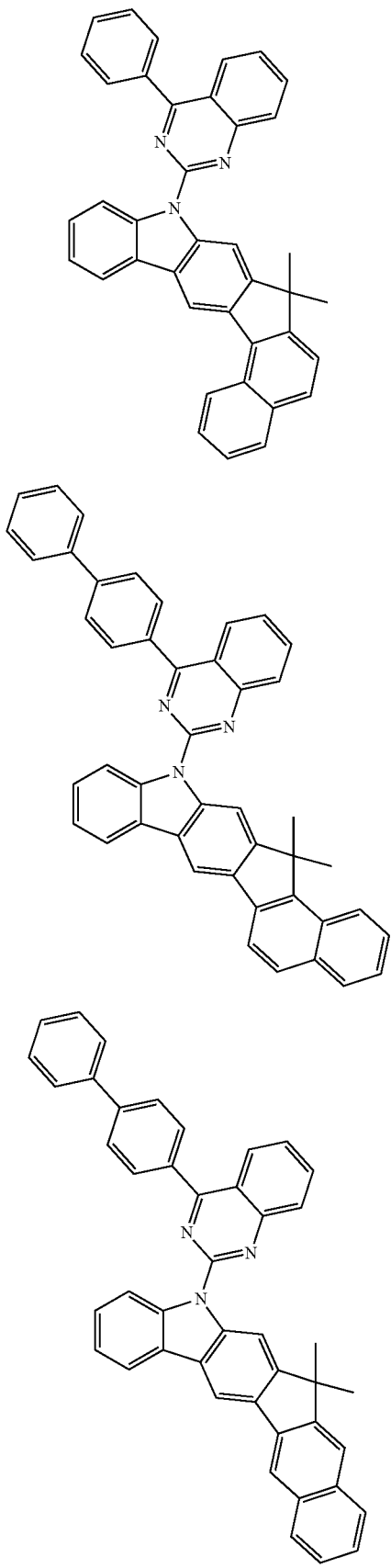
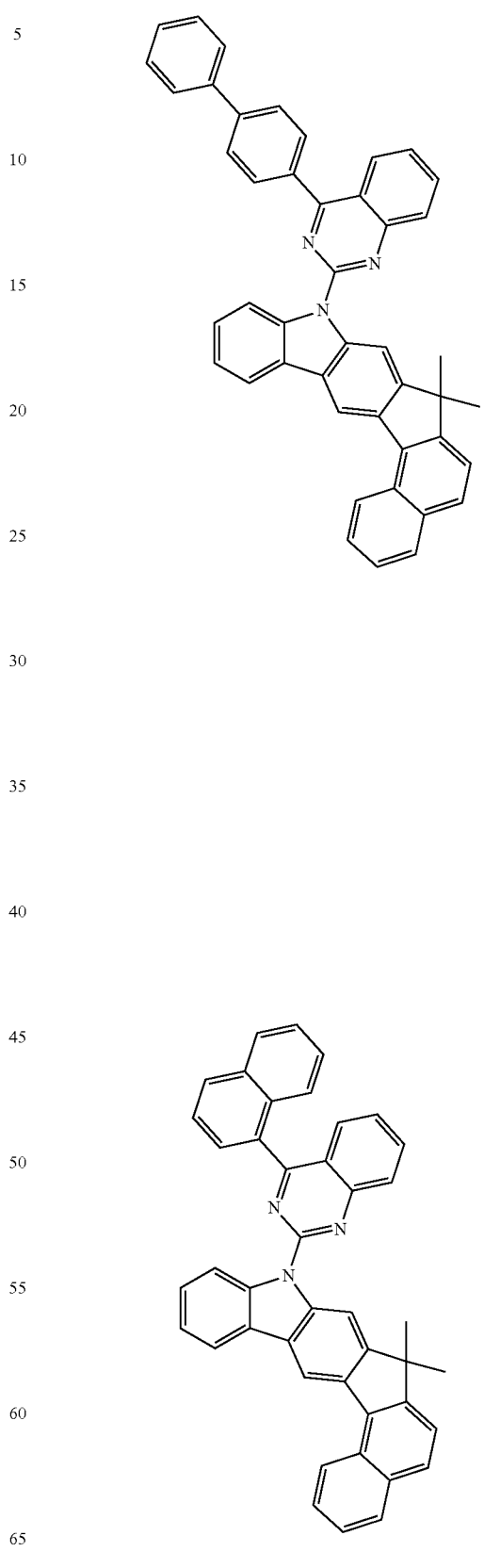

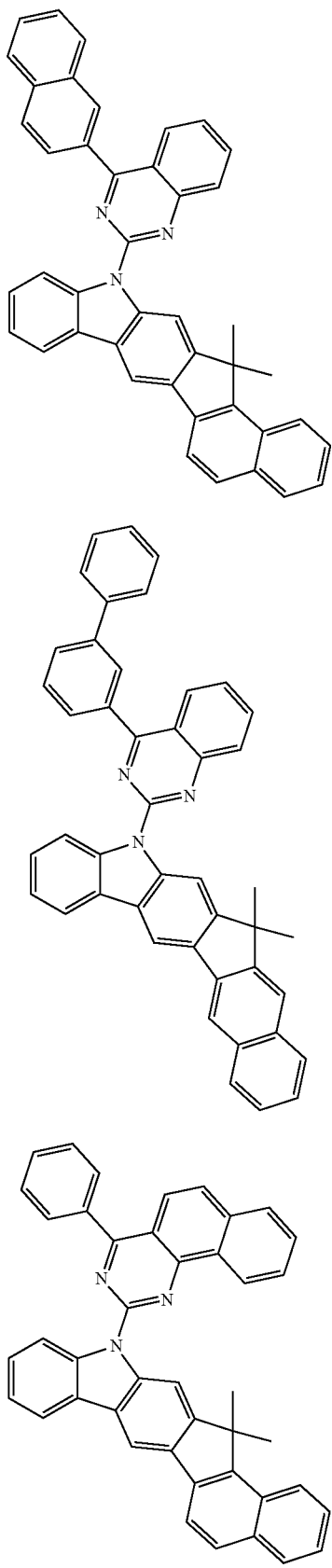
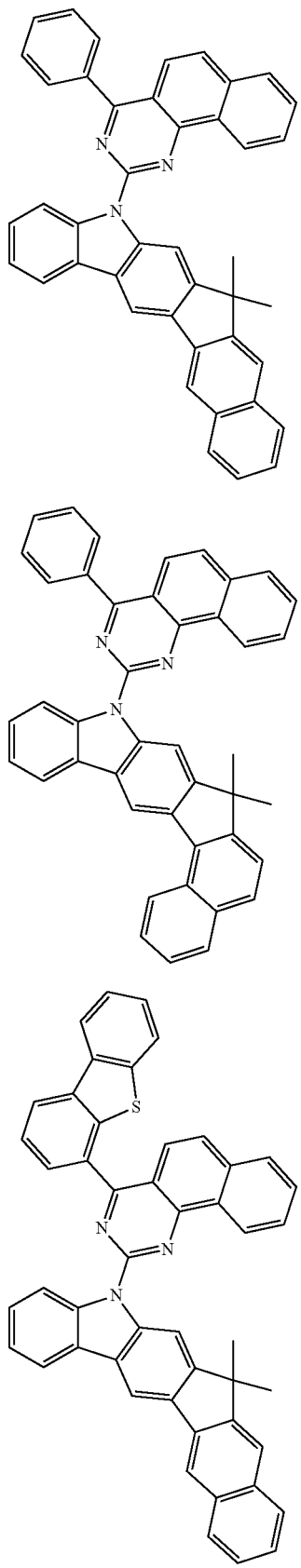

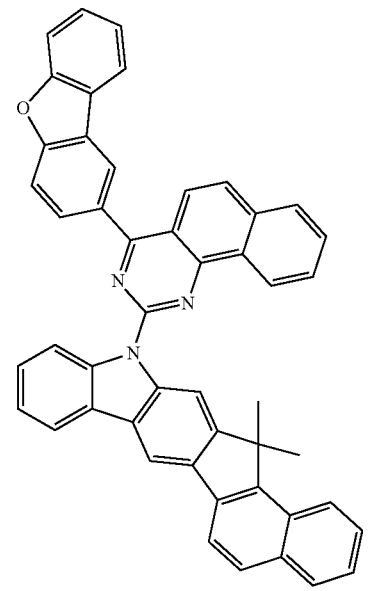 [SMILES: CC1(C)c2cc3c(cc2-c2ccc4ccccc4c21)c1ccccc1n3-c1nc(-c2ccc3oc4ccccc4c3c2)c2ccc3ccccc3c2n1]
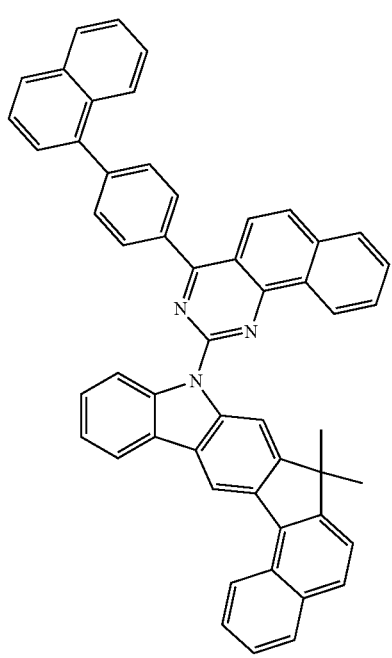 [SMILES: CC1(C)c2cc3c(cc2-c2c1ccc1ccccc21)c1ccccc1n3-c1nc(-c2ccc(-c3cccc4ccccc34)cc2)c2ccc3ccccc3c2n1]
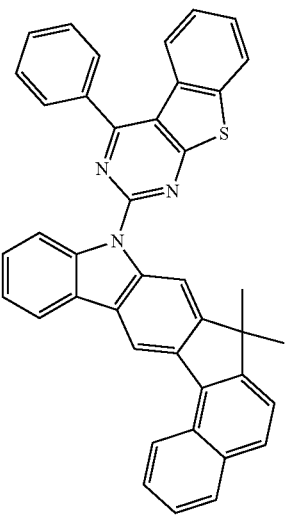 [SMILES: CC1(C)c2cc3c(cc2-c2c1ccc1ccccc21)c1ccccc1n3-c1nc(-c2ccccc2)c2c(n1)sc1ccccc12]
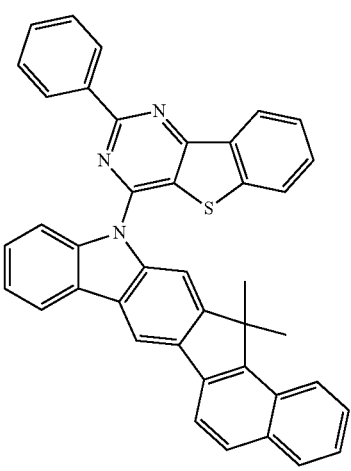 [SMILES: CC1(C)c2cc3c(cc2-c2ccc4ccccc4c21)c1ccccc1n3-c1nc(-c2ccccc2)nc2c1sc1ccccc12]
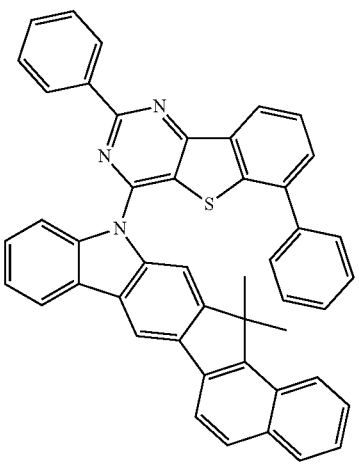 [SMILES: CC1(C)c2cc3c(cc2-c2ccc4ccccc4c21)c1ccccc1n3-c1nc(-c2ccccc2)nc2c1sc1c(-c3ccccc3)cccc12]

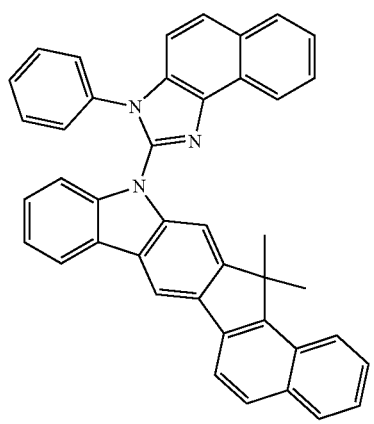 [SMILES: CC1(C)c2cc3c(cc2-c2ccc4ccccc4c21)c1ccccc1n3-c1nc2c3ccccc3ccc2n1-c1ccccc1]
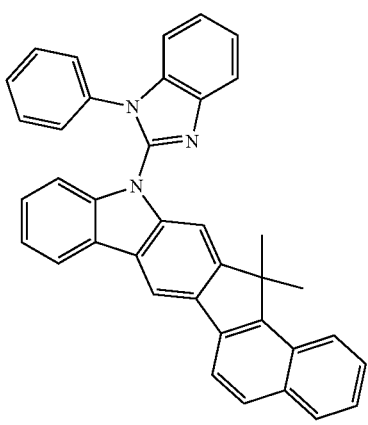
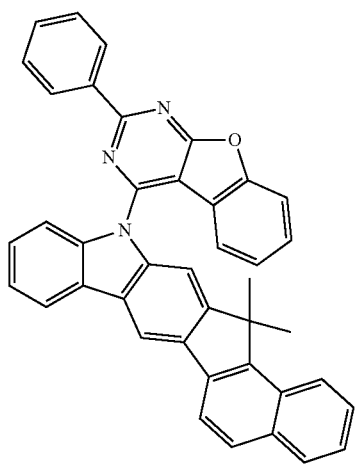 [SMILES: CC1(C)c2cc3c(cc2-c2ccc4ccccc4c21)c1ccccc1n3-c1nc(-c2ccccc2)nc2oc3ccccc3c12]
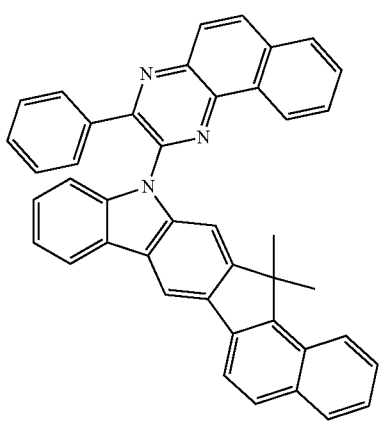
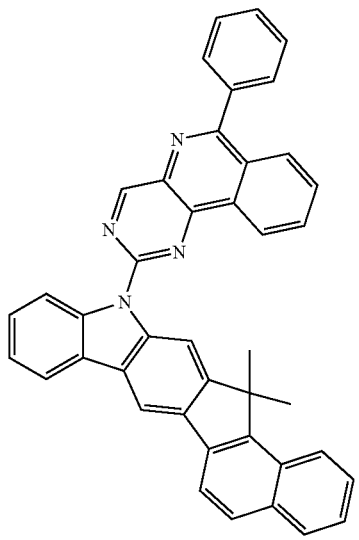 [SMILES: CC1(C)c2cc3c(cc2-c2ccc4ccccc4c21)c1ccccc1n3-c1ncc2nc(-c3ccccc3)c3ccccc3c2n1]
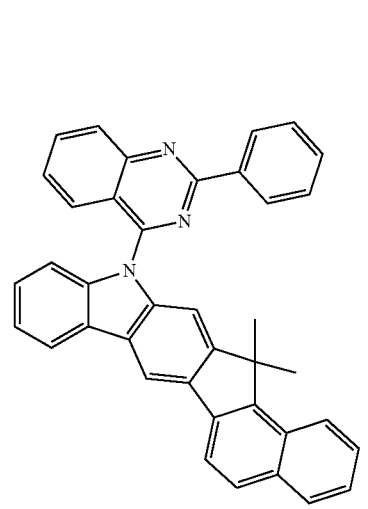 [SMILES: CC1(C)c2cc3c(cc2-c2ccc4ccccc4c21)c1ccccc1n3-c1nc(-c2ccccc2)nc2ccccc12]

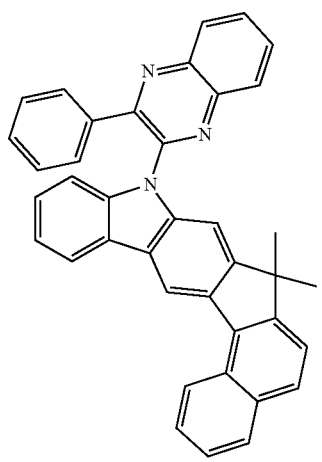 [SMILES: CC1(C)c2cc3c(cc2-c2c1ccc1ccccc21)c1ccccc1n3-c1nc2ccccc2nc1-c1ccccc1]
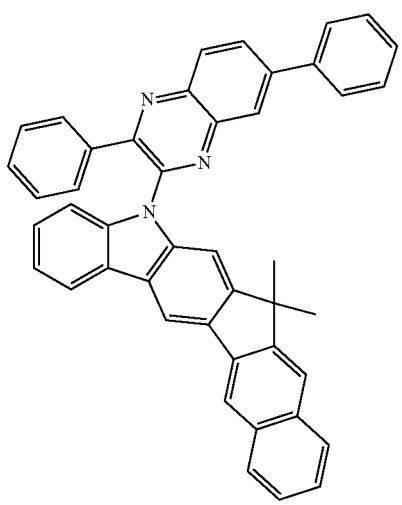
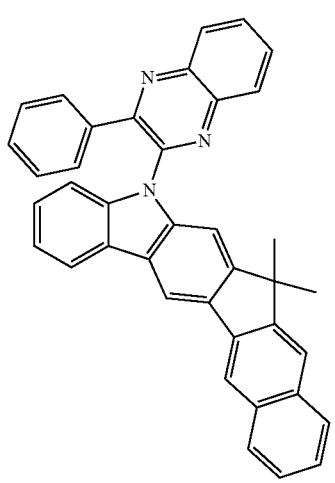 [SMILES: CC1(C)c2cc3ccccc3cc2-c2cc3c4ccccc4n(-c4nc5ccccc5nc4-c4ccccc4)c3cc21]
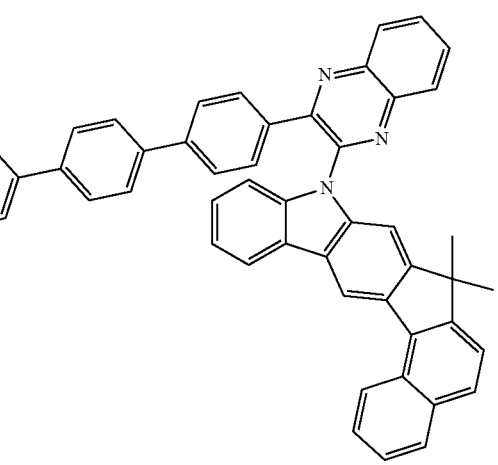
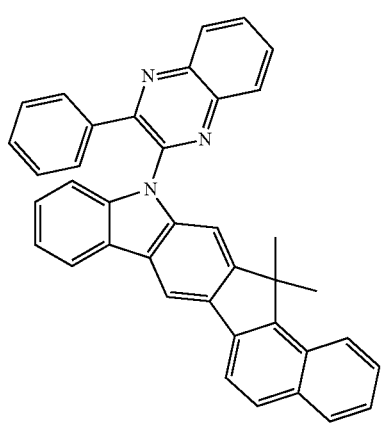 [SMILES: CC1(C)c2cc3c(cc2-c2ccc4ccccc4c21)c1ccccc1n3-c1nc2ccccc2nc1-c1ccccc1]
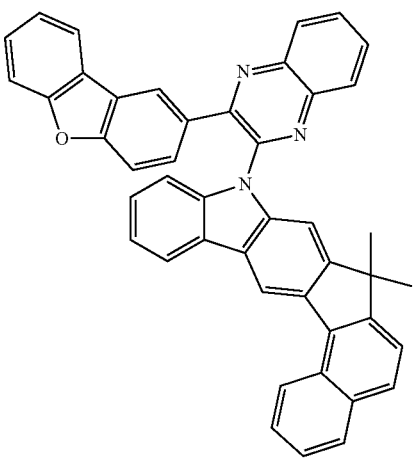 [SMILES: CC1(C)c2cc3c(cc2-c2c1ccc1ccccc21)c1ccccc1n3-c1nc2ccccc2nc1-c1ccc2oc3ccccc3c2c1]

51
-continued
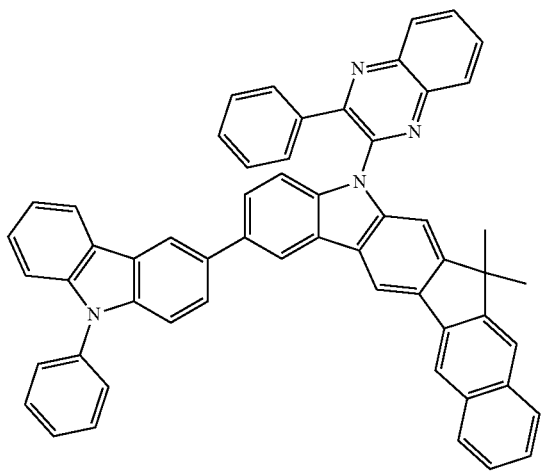 [SMILES: CC1(C)c2cc3ccccc3cc2-c2cc3c4cc(-c5ccc6c(c5)c5ccccc5n6-c5ccccc5)ccc4n(-c4nc5ccccc5nc4-c4ccccc4)c3cc21]
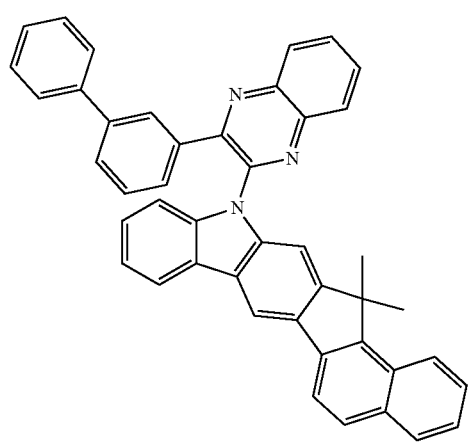 [SMILES: CC1(C)c2cc3c(cc2-c2ccc4ccccc4c21)c1ccccc1n3-c1nc2ccccc2nc1-c1cccc(-c2ccccc2)c1]
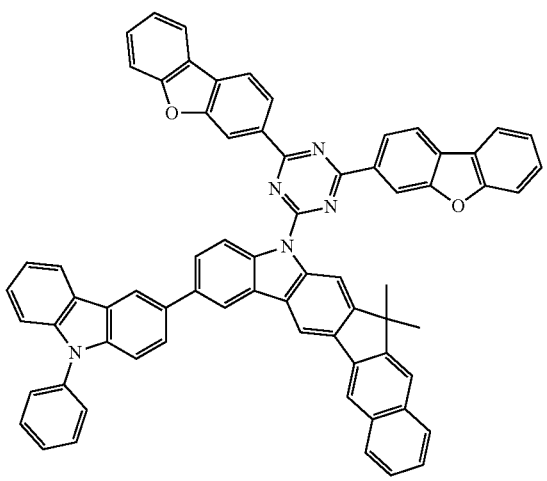 [SMILES: CC1(C)c2cc3ccccc3cc2-c2cc3c4cc(-c5ccc6c(c5)c5ccccc5n6-c5ccccc5)ccc4n(-c4nc(-c5ccc6c(c5)oc5ccccc56)nc(-c5ccc6c(c5)oc5ccccc56)n4)c3cc21]
52
-continued
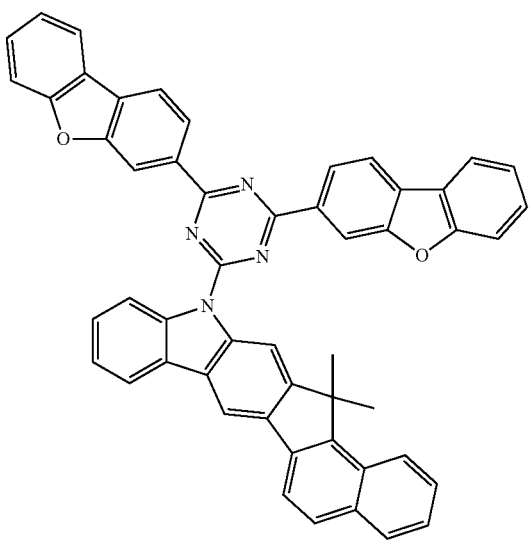 [SMILES: CC1(C)c2cc3c(cc2-c2ccc4ccccc4c21)c1ccccc1n3-c1nc(-c2ccc3c(c2)oc2ccccc23)nc(-c2ccc3c(c2)oc2ccccc23)n1]
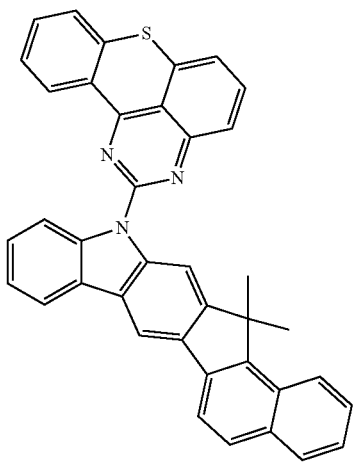 [SMILES: CC1(C)c2cc3c(cc2-c2ccc4ccccc4c21)c1ccccc1n3-c1nc2c3c(cccc3n1)Sc1ccccc1-2]
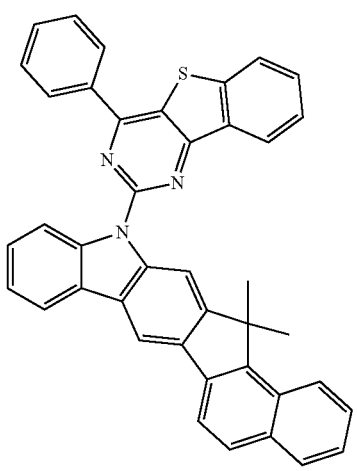 [SMILES: CC1(C)c2cc3c(cc2-c2ccc4ccccc4c21)c1ccccc1n3-c1nc(-c2ccccc2)c2sc3ccccc3c2n1]

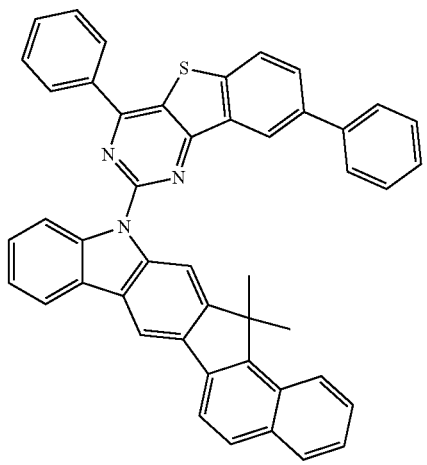 [SMILES: CC1(C)c2cc3c(cc2-c2ccc4ccccc4c21)c1ccccc1n3-c1nc(-c2ccccc2)c2sc3ccc(-c4ccccc4)cc3c2n1]
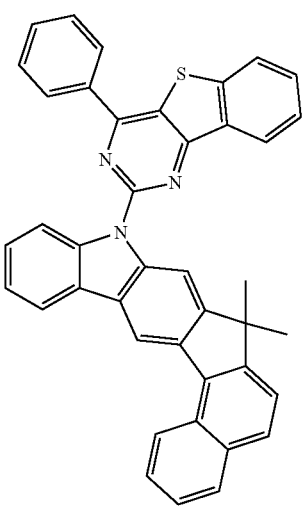
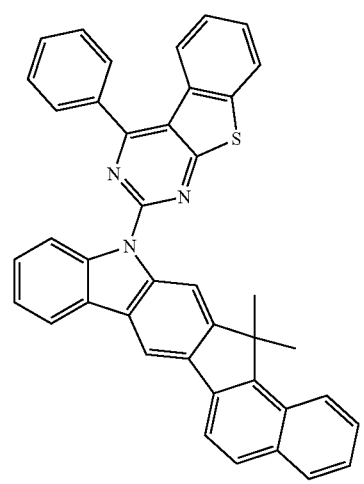 [SMILES: CC1(C)c2cc3c(cc2-c2ccc4ccccc4c21)c1ccccc1n3-c1nc(-c2ccccc2)c2c(n1)sc1ccccc12]
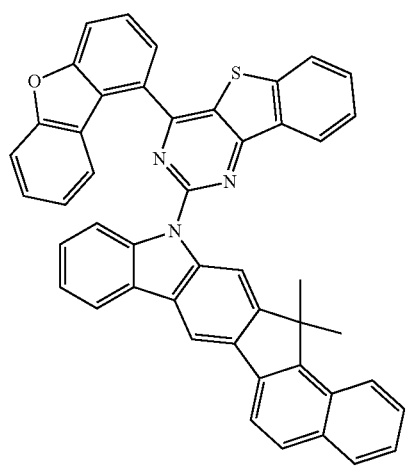
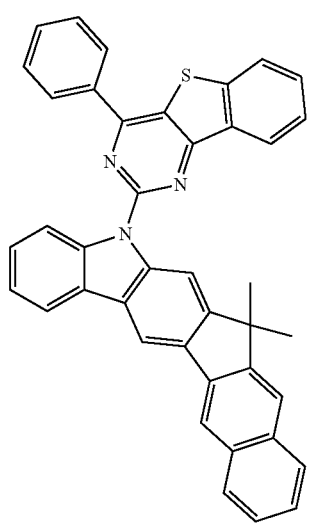 [SMILES: CC1(C)c2cc3ccccc3cc2-c2cc3c4ccccc4n(-c4nc(-c5ccccc5)c5sc6ccccc6c5n4)c3cc21]
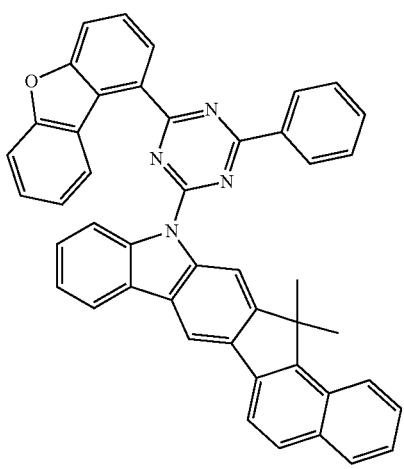 [SMILES: CC1(C)c2cc3c(cc2-c2ccc4ccccc4c21)c1ccccc1n3-c1nc(-c2ccccc2)nc(-c2cccc3oc4ccccc4c23)n1]

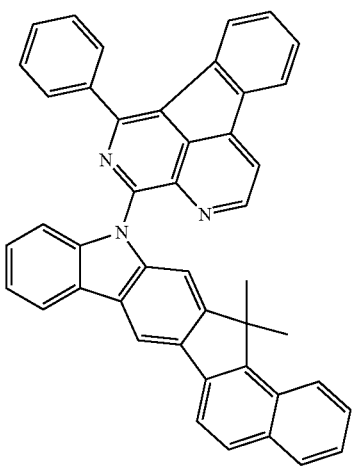 [SMILES: CC1(C)c2cc3c(cc2-c2ccc4ccccc4c21)c1ccccc1n3-c1nc(-c2ccccc2)c2c3c(ccnc13)-c1ccccc1-2]

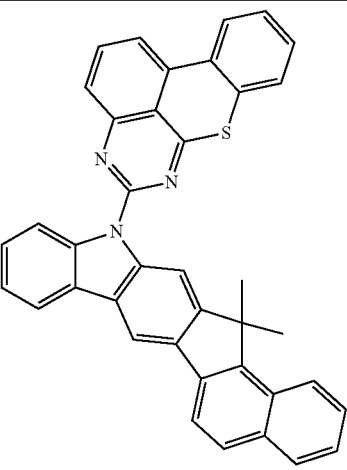

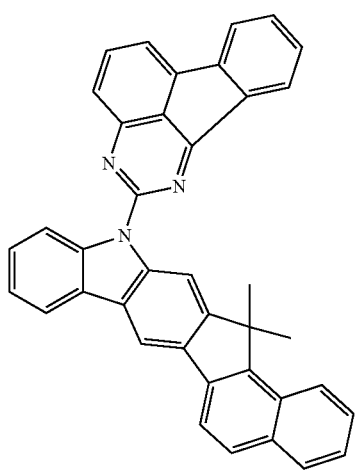 [SMILES: CC1(C)c2cc3c(cc2-c2ccc4ccccc4c21)c1ccccc1n3-c1nc2c3c(cccc3n1)-c1ccccc1-2]

The base structure of the compounds of formula (1) can be prepared by the routes outlined in the schemes which follow. The individual synthesis steps, for example C—C coupling reactions according to Suzuki, C—N coupling reactions according to Hartwig-Buchwald or cyclization reactions, are known in principle to those skilled in the art. Further information relating to the synthesis of the compounds can be found in the synthesis examples. The synthesis of the base structure is shown in Scheme 1. This can be effected by coupling a benzofluorene substituted by a reactive leaving group, for example bromine, with an optionally substituted 2-nitrobenzeneboronic acid, followed by a ring closure reaction. Alternatively, the coupling can be effected with the amino group of an optionally substituted 2-aminochlorobenzene, followed by a ring closure reaction. Scheme 2 shows the introduction of the HetAr group on the nitrogen atom in the base skeleton. It is possible here to introduce an HetAr group substituted by a suitable leaving group, for example chlorine, in a nucleophilic aromatic substitution or in a palladium-catalysed coupling reaction.

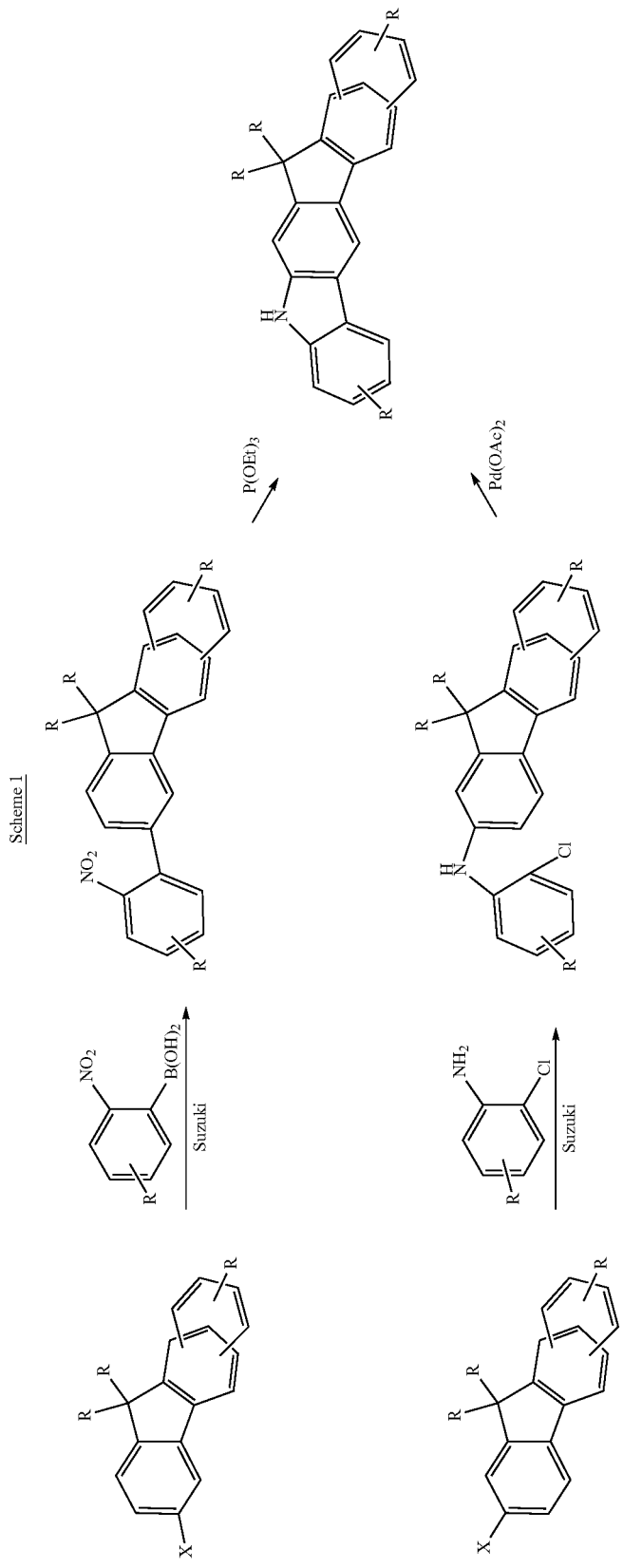

Scheme 2

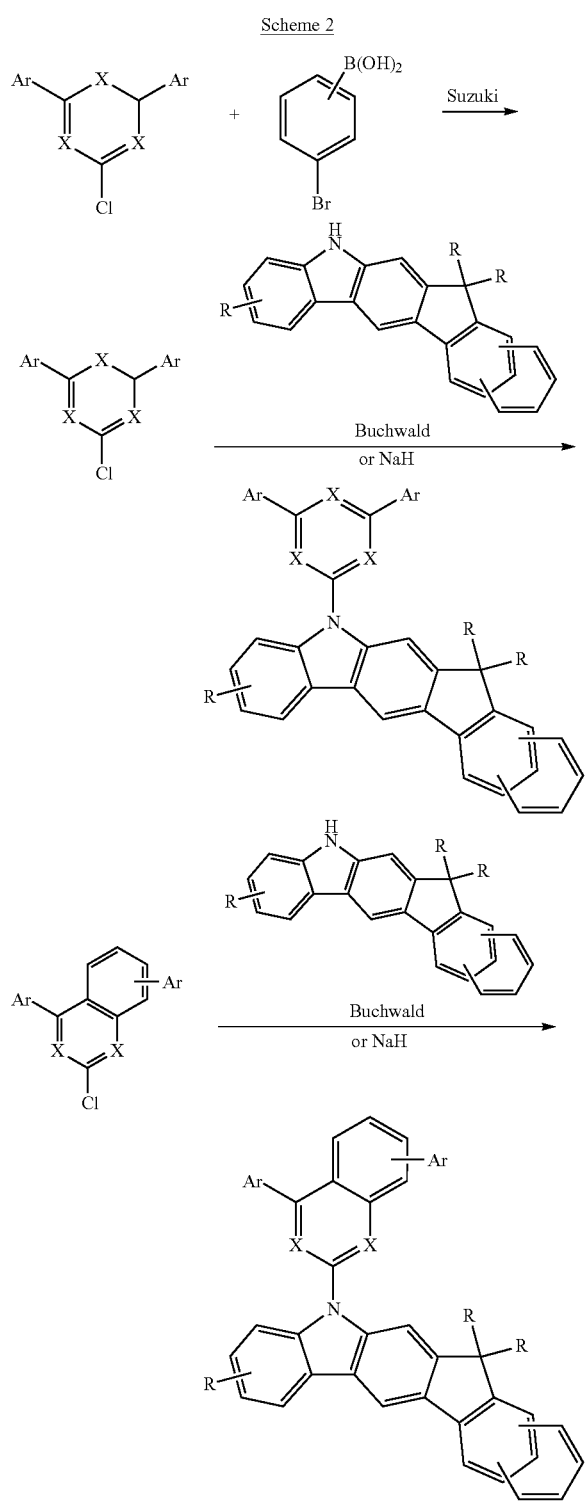

The compound of the formula (1) may also be processed in order to prepare the organic electroluminescent device together with the phosphorescent compound from a liquid phase, for example by spin-coating or by printing methods. For this purpose, formulations of the compounds are required, for example, solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation or a composition comprising at least one compound of formula (1), at least one phosphorescent compound and at least one solvent, especially one of the abovementioned solvents or a mixture of these solvents. The formulation may also contain further organic or inorganic compound, for example one or more further matrix materials. Suitable phosphorescent compounds and further matrix materials are detailed hereinafter.

The present invention further provides for the use of a formulation of the invention for producing an organic electroluminescent device.

The organic electroluminescent device of the invention, as defined above, comprises cathode, anode and at least one emitting layer containing at least one phosphorescent compound and at least one compound of formula (1). Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The electroluminescent device of the invention preferably comprises, as phosphorescent compound, a red-, orange- or yellow-phosphorescing compound, especially a red-phosphorescing compound.

Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

The mixture of the compound of formula (1) and the phosphorescent compound in the emitting layer of the electroluminescent device contains between 99% and 1% by volume, preferably between 98% and 10% by volume, more preferably between 97% and 60% by volume and especially between 95% and 80% by volume of the compound of the formula (1), based on the overall mixture of phosphorescent compound and compound of formula (1). Correspondingly, the mixture contains between 1% and 99% by volume, preferably between 2% and 90% by volume, more preferably between 3% and 40% by volume and especially between 5% and 20% by volume of the phosphorescent compound based on the overall mixture of phosphorescent compound and compound of formula (1). If the electroluminescent device is produced from solution, the same preferred proportions are applicable, in which case the corresponding percentages by weight are used as preferred proportions rather than percentages by volume.

In one embodiment of the invention, the compound of formula (1) is used as the sole matrix material ("single host") for the phosphorescent compound, meaning that the emitting layer of the OLED contains solely the compound of the formula (1) and the phosphorescent compound, but no further compounds. This is a clear advantage over electroluminescent devices containing two or more matrix materials in the emitting layer since such electroluminescent devices can be manufactured much more easily than those containing mixtures of multiple matrix materials. It has been found that, surprisingly, specifically compounds of the formula (1) lead to very good results when these materials are used as the sole matrix material for phosphorescent compounds. It is therefore a preferred embodiment of the invention that the emitting layer consists of exactly one compound of the formula (1) and one or more phosphorescent compounds, preferably exactly one phosphorescent compound.

In a further embodiment of the invention, the emitting layer, apart from the compound of the formula (1) and the phosphorescent compound, contains at least one further matrix material. Suitable matrix materials which can be used in combination with a compound of formula (1) are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, dibenzofuran derivatives, for example according to WO 2015/169412, WO 2016/015810, WO 2016/023608, WO 2017/148564 or WO 2017/148565, or biscarbazoles, for example according to JP 3139321 B2.

It is likewise possible for a further phosphorescent compound which emits at a shorter wavelength than the actual emitter to be present as co-host in the emitting layer. Particularly good results are achieved when the emitter used is a red-phosphorescing compound and the co-host used in combination with the compound of formula (1) is a yellow-phosphorescing compound.

In addition, the co-host used may be a compound that does not take part in charge transport to a significant degree, if at all, as described, for example, in WO 2010/108579. Especially suitable in combination with the compound of formula (1) as co-matrix material are compounds which have a large bandgap and which themselves take part at least not to a significant degree, if any at all, in the charge transport of the emitting layer. Such materials are preferably pure hydrocarbons. Examples of such materials can be found, for example, in WO 2009/124627 or in WO 2010/006680.

Particularly preferred co-host materials which can be used in combination with the compounds of formula (1) are biscarbazole or indenocarbazole derivatives of one of the formulae (6), (7) and (8)

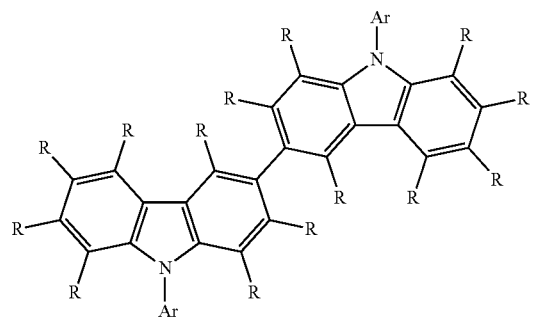

Formula (6)

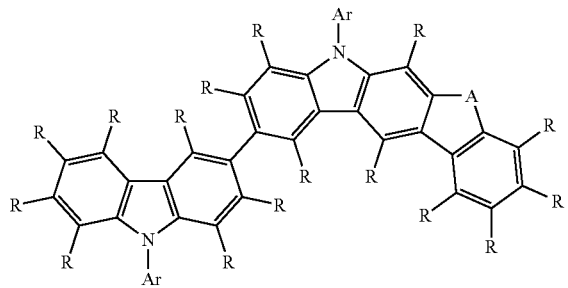

Formula (7)

Formula (8)

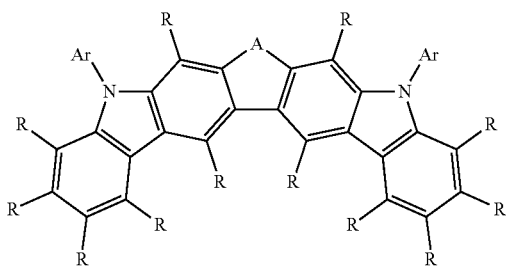

where Ar and A have the definitions given above and R has the definitions given above, but R radicals here may also together form an aromatic or heteroaromatic ring system. In a preferred embodiment of the invention, A is C(R')$_2$.

Preferred embodiments of the compounds of the formulae (6), (7) and (8) are the compounds of the following formulae (6a), (7a) and (8a):

Formula (7a)

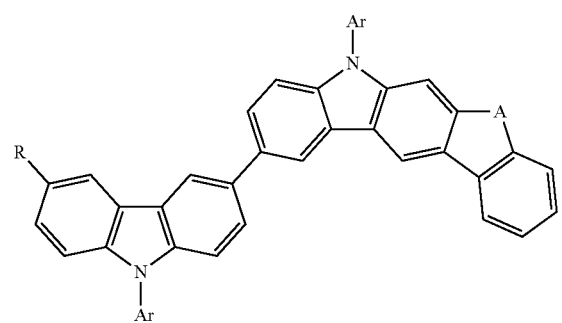

Formula (6a)

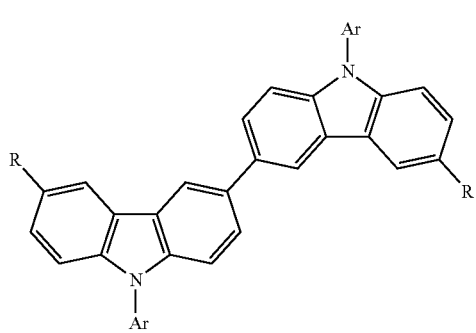

Formula (8a)

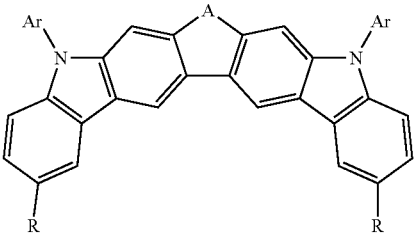

where the symbols used have the definitions given above.

Examples of suitable compounds of formula (6) are the compounds depicted below:

| Structure | CAS-number |
| --- | --- |
| 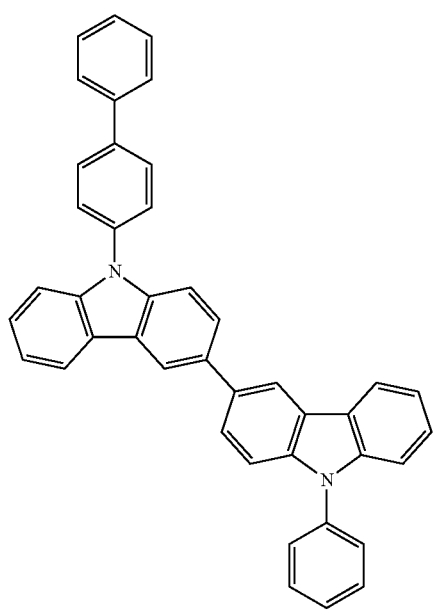 [SMILES: c1ccc(-c2ccc(-n3c4ccccc4c4cc(-c5ccc6c(c5)c5ccccc5n6-c5ccccc5)ccc43)cc2)cc1] | CAS-1454567-05-5 |

| Structure | CAS-number |
|---|---|
| 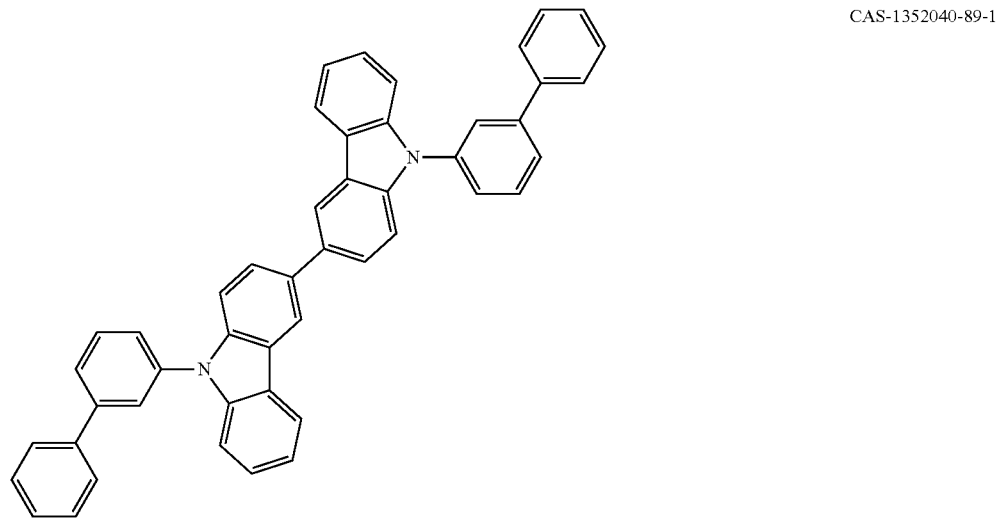 | CAS-1352040-89-1 |
| 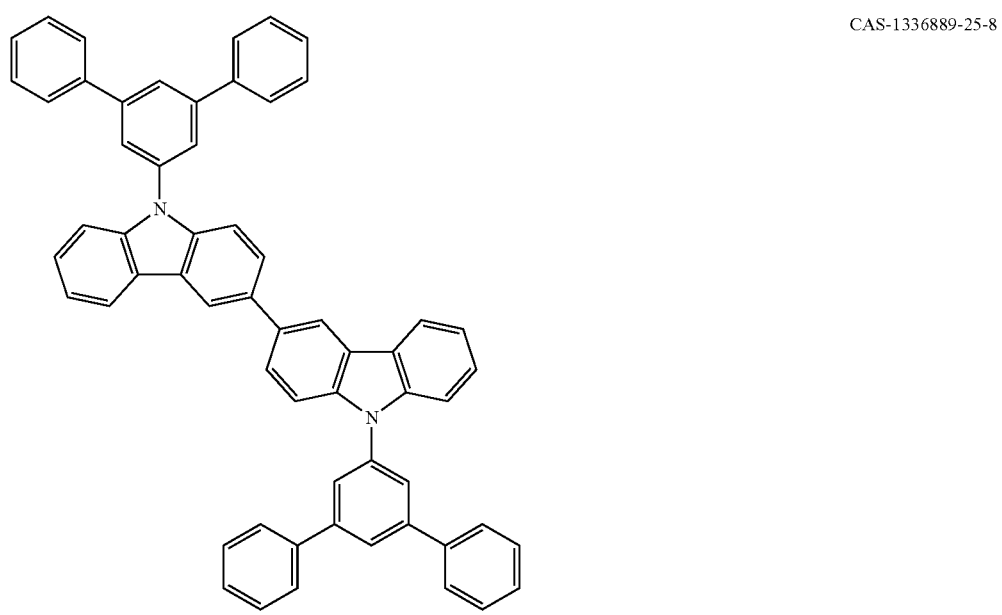 | CAS-1336889-25-8 |

| Structure | CAS-number |
|---|---|
| 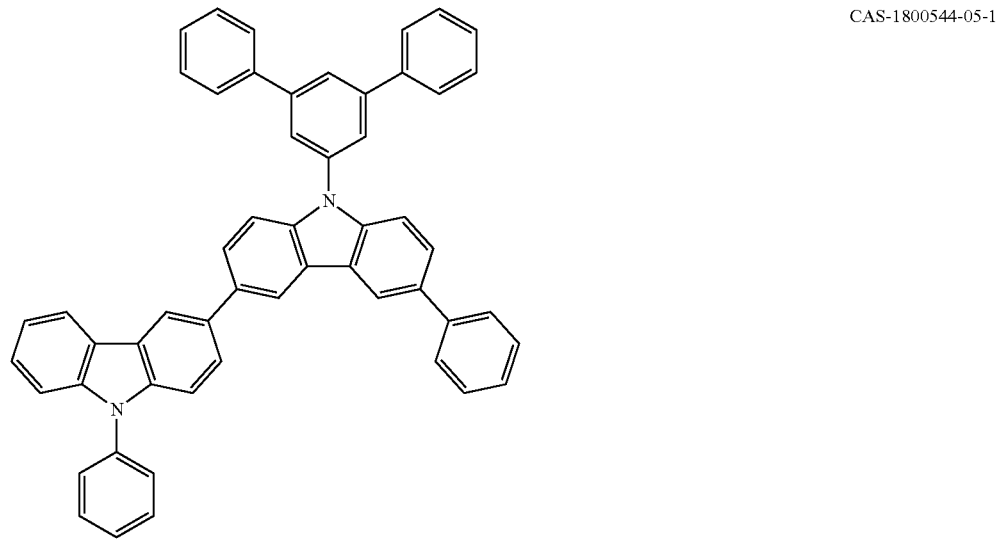 | CAS-1800544-05-1 |
| 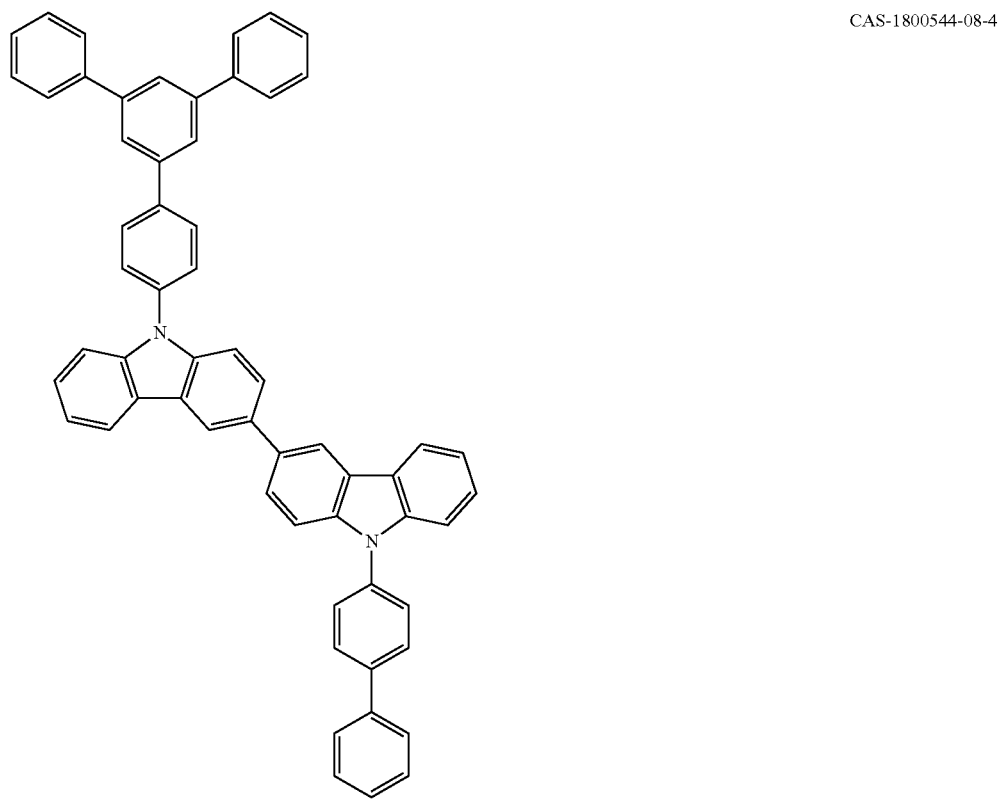 | CAS-1800544-08-4 |

| Structure | CAS-number |
|---|---|
| 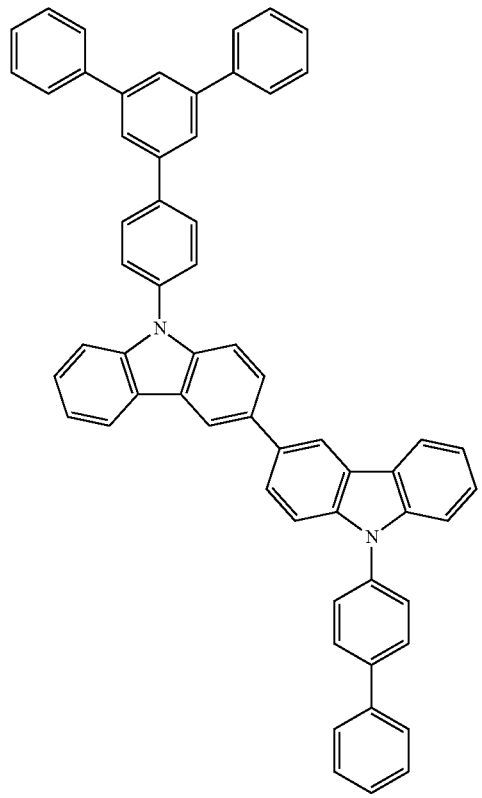 [SMILES: c1ccc(-c2ccc(-n3c4ccccc4c4cc(-c5ccc6c(c5)c5ccccc5n6-c5ccc(-c6cc(-c7ccccc7)cc(-c7ccccc7)c6)cc5)ccc43)cc2)cc1] | CAS-1800544-08-4 |
| 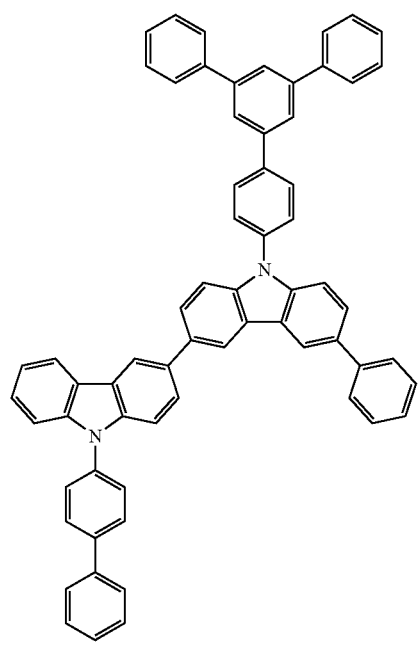 [SMILES: c1ccc(-c2ccc(-n3c4ccccc4c4cc(-c5ccc6c(c5)c5cc(-c7ccccc7)ccc5n6-c5ccc(-c6cc(-c7ccccc7)cc(-c7ccccc7)c6)cc5)ccc43)cc2)cc1] | CAS-1800544-09-5 |

| Structure | CAS-number |
|---|---|
| 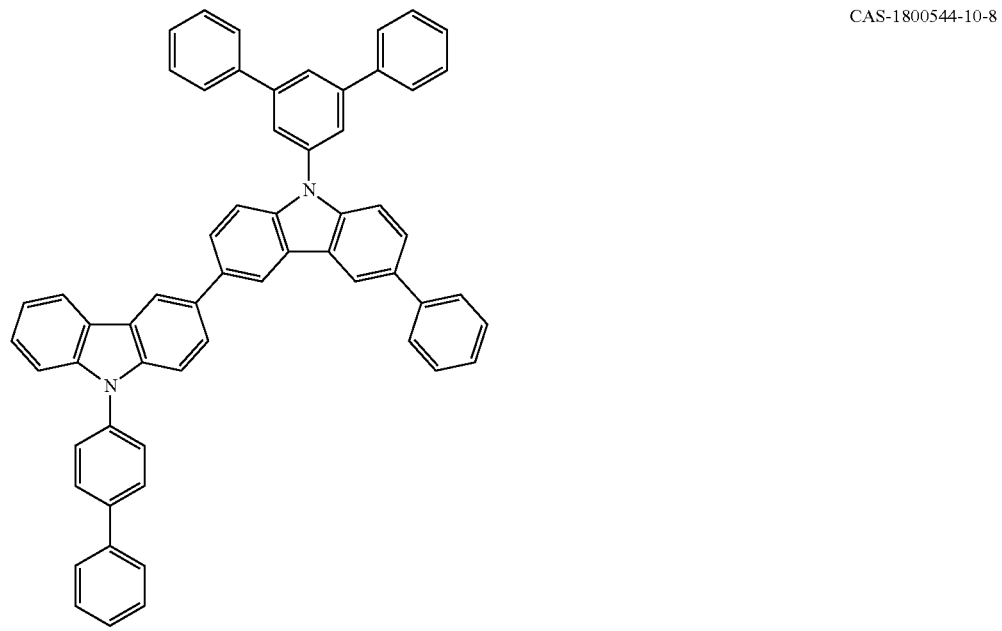 | CAS-1800544-10-8 |
| 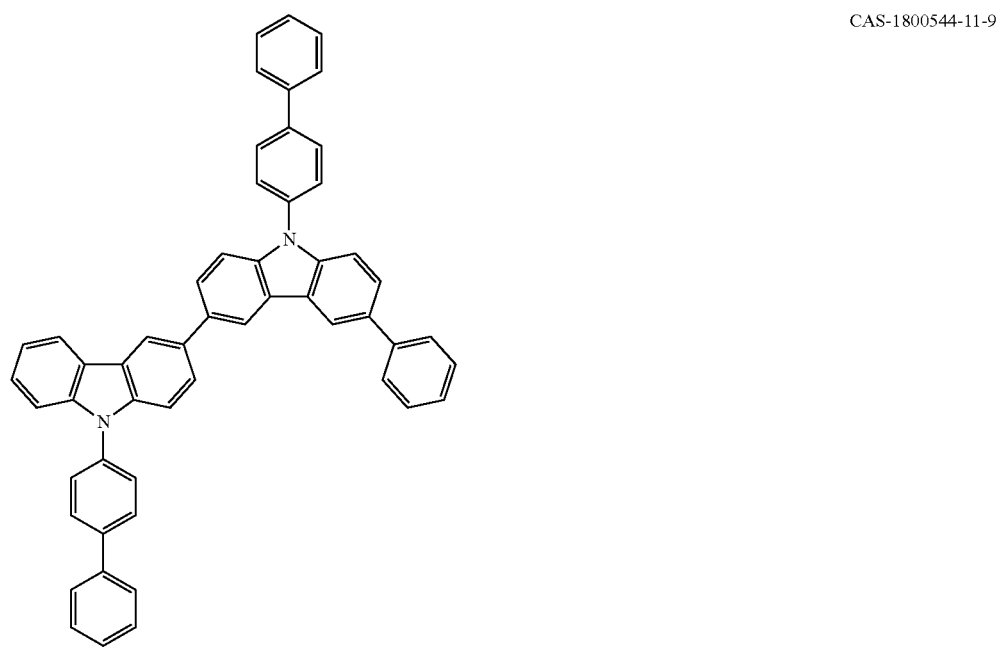 | CAS-1800544-11-9 |

| Structure | CAS-number |
|---|---|
| 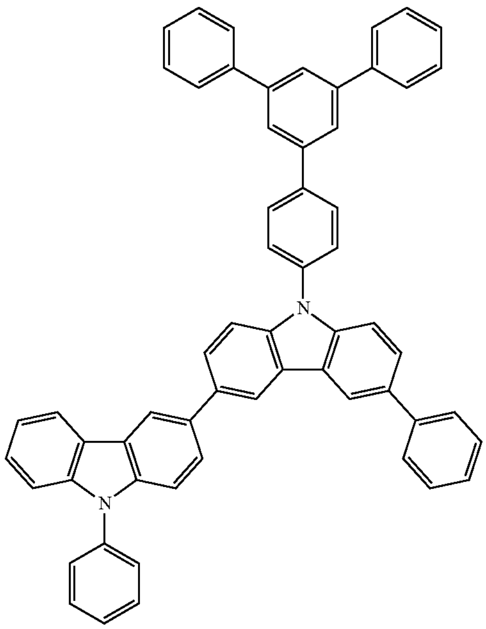 [SMILES: c1ccc(-c2cc(-c3ccccc3)cc(-c3ccc(-n4c5ccc(-c6ccccc6)cc5c5cc(-c6ccc7c(c6)c6ccccc6n7-c6ccccc6)ccc54)cc3)c2)cc1] | CAS-1800544-04-0 |
| 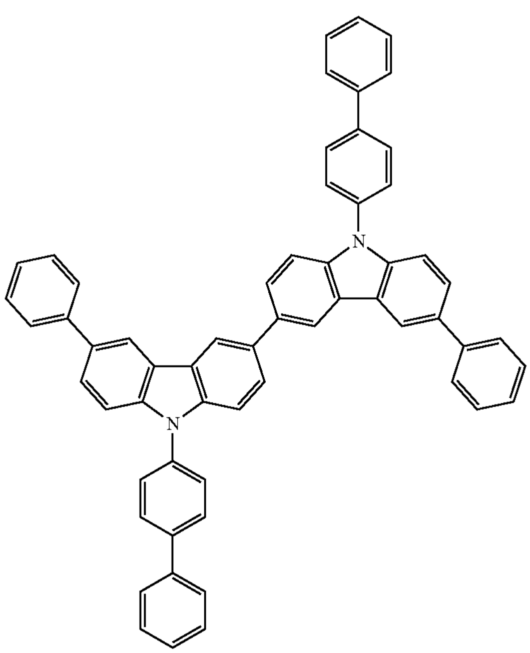 [SMILES: c1ccc(-c2ccc(-n3c4ccc(-c5ccccc5)cc4c4cc(-c5ccc6c(c5)c5cc(-c7ccccc7)ccc5n6-c5ccc(-c6ccccc6)cc5)ccc43)cc2)cc1] | CAS-1842320-52-8 |

| Structure | CAS-number |
|---|---|
| 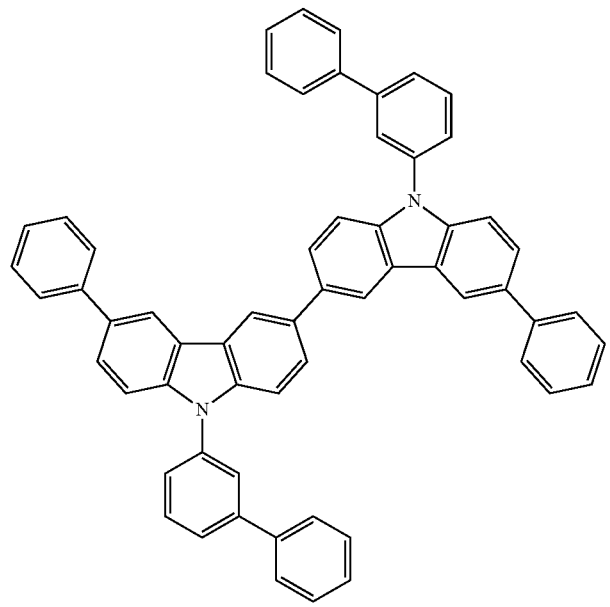 [SMILES: c1ccc(-c2cccc(-n3c4ccc(-c5ccccc5)cc4c4cc(-c5ccc6c(c5)c5cc(-c7ccccc7)ccc5n6-c5cccc(-c6ccccc6)c5)ccc43)c2)cc1] | CAS-1842320-53-9 |
| 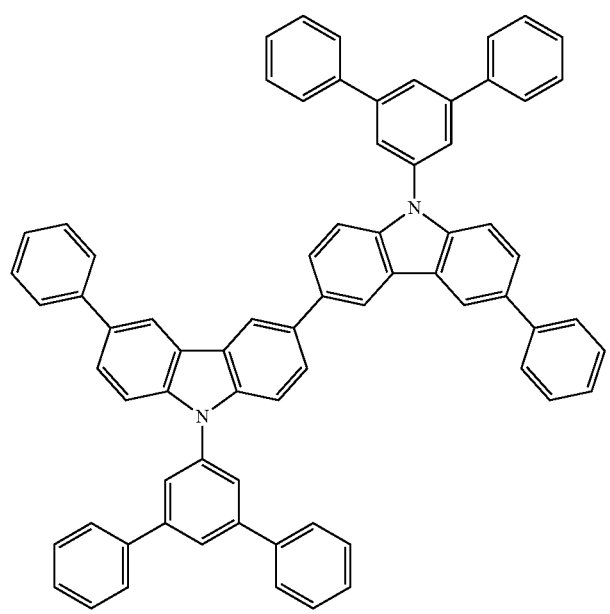 [SMILES: c1ccc(-c2cc(-c3ccccc3)cc(-n3c4ccc(-c5ccccc5)cc4c4cc(-c5ccc6c(c5)c5cc(-c7ccccc7)ccc5n6-c5cc(-c6ccccc6)cc(-c6ccccc6)c5)ccc43)c2)cc1] | CAS-1842320-54-0 |

-continued
| Structure | CAS-number |
|---|---|
| 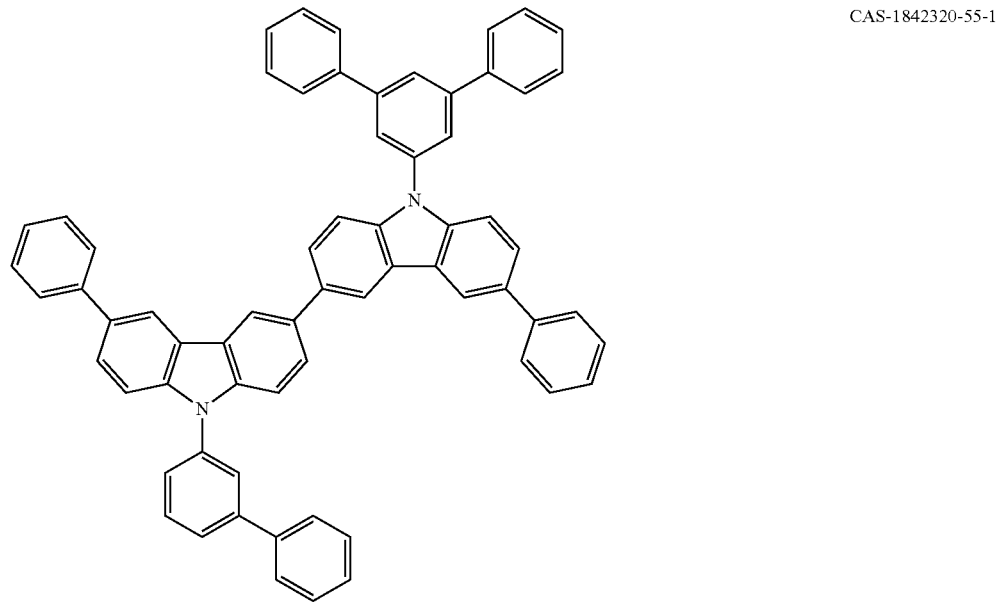 | CAS-1842320-55-1 |
| 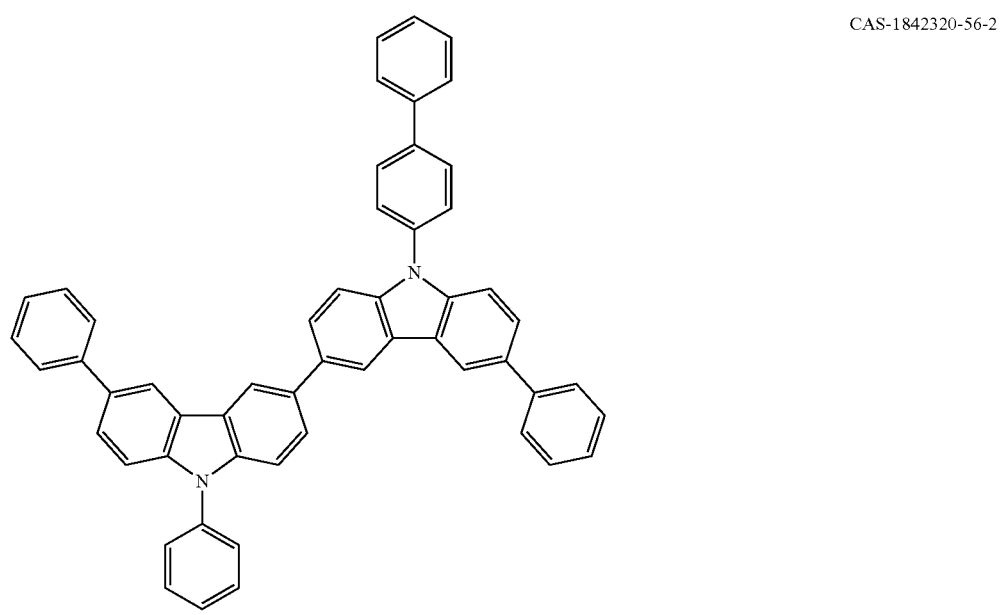 | CAS-1842320-56-2 |

| Structure | CAS-number |
|---|---|
| 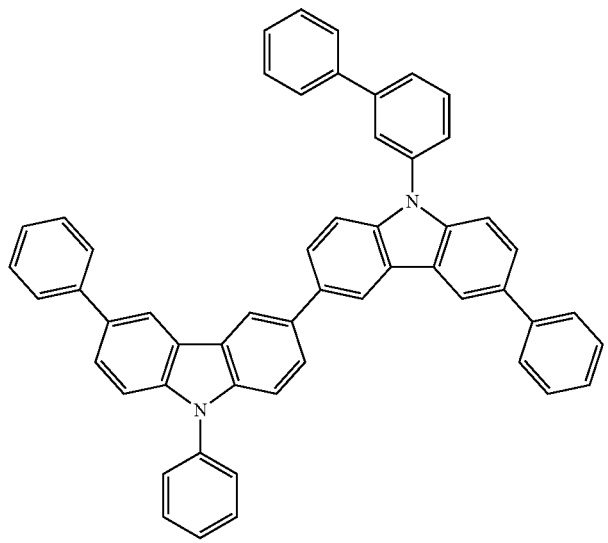 [SMILES: c1ccc(-c2cccc(-n3c4ccc(-c5ccccc5)cc4c4cc(-c5ccc6c(c5)c5cc(-c7ccccc7)ccc5n6-c5ccccc5)ccc43)c2)cc1] | CAS-1842320-57-3 |
| 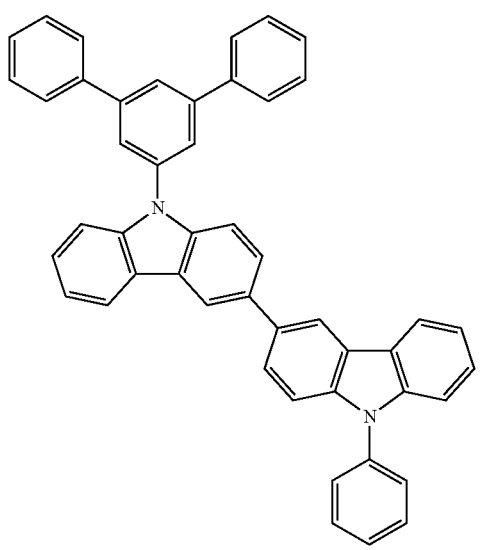 [SMILES: c1ccc(-c2cc(-c3ccccc3)cc(-n3c4ccccc4c4cc(-c5ccc6c(c5)c5ccccc5n6-c5ccccc5)ccc43)c2)cc1] | CAS-1410876-33-3 |
| 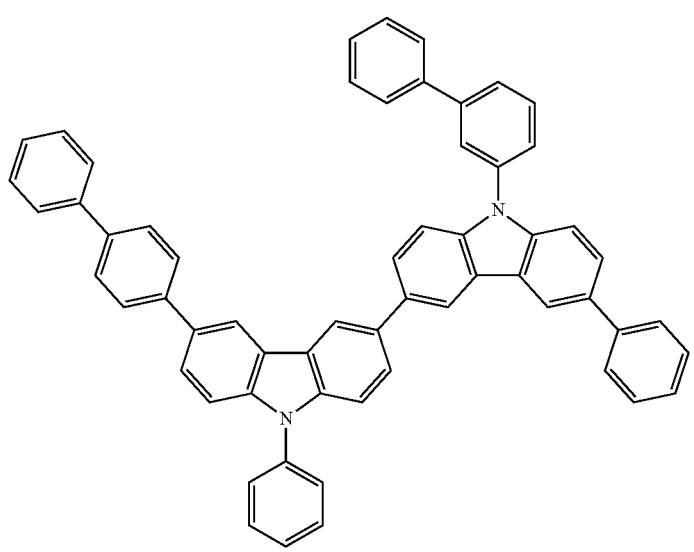 [SMILES: c1ccc(-c2ccc(-c3ccc4c(c3)c3cc(-c5ccc6c(c5)c5cc(-c7ccccc7)ccc5n6-c5cccc(-c6ccccc6)c5)ccc3n4-c3ccccc3)cc2)cc1] | CAS-1842320-58-4 |

| Structure | CAS-number |
|---|---|
| 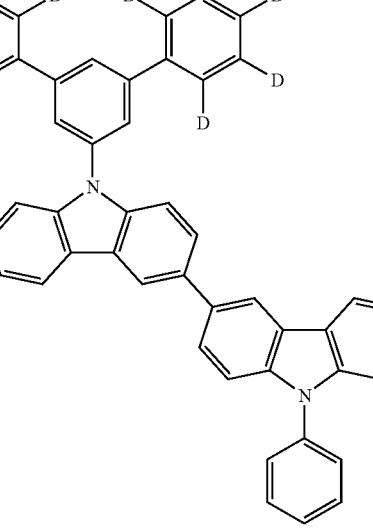 | CAS-1410876-47-9 |
| 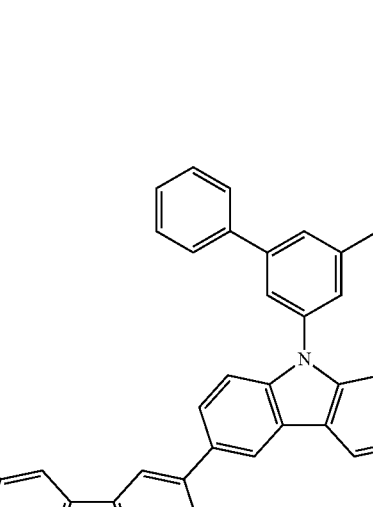 | CAS-1842320-59-5 |

-continued

| Structure | CAS-number |
|---|---|
| 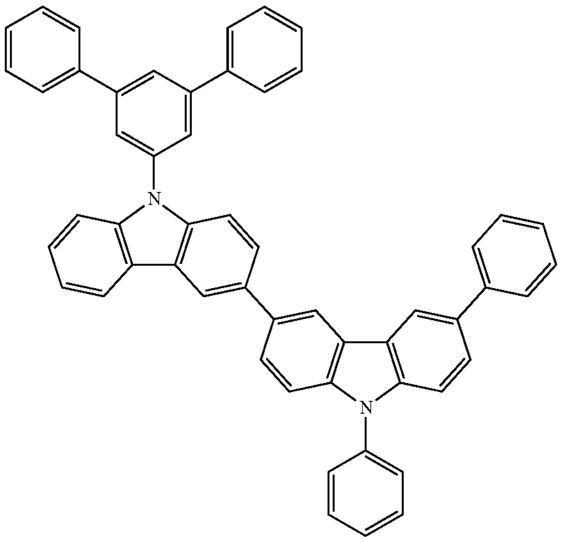 [SMILES: c1ccc(-c2cc(-c3ccccc3)cc(-n3c4ccccc4c4cc(-c5ccc6c(c5)c5cc(-c7ccccc7)ccc5n6-c5ccccc5)ccc43)c2)cc1] | CAS-1848256-38-1 |
| 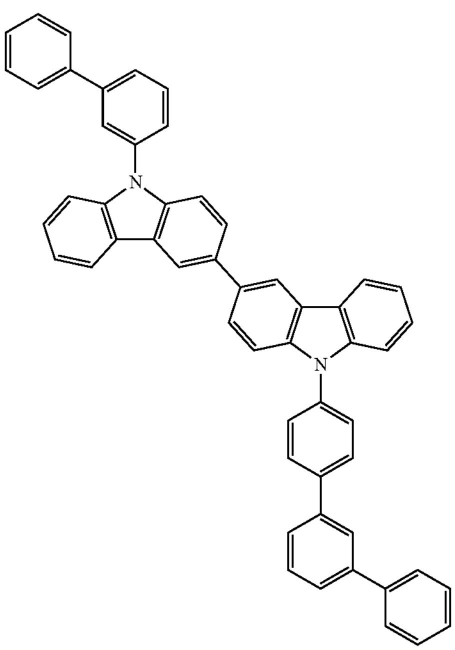 [SMILES: c1ccc(-c2cccc(-c3ccc(-n4c5ccccc5c5cc(-c6ccc7c(c6)c6ccccc6n7-c6cccc(-c7ccccc7)c6)ccc54)cc3)c2)cc1] | CAS-1865661-14-8 |

| Structure | CAS-number |
|---|---|
| 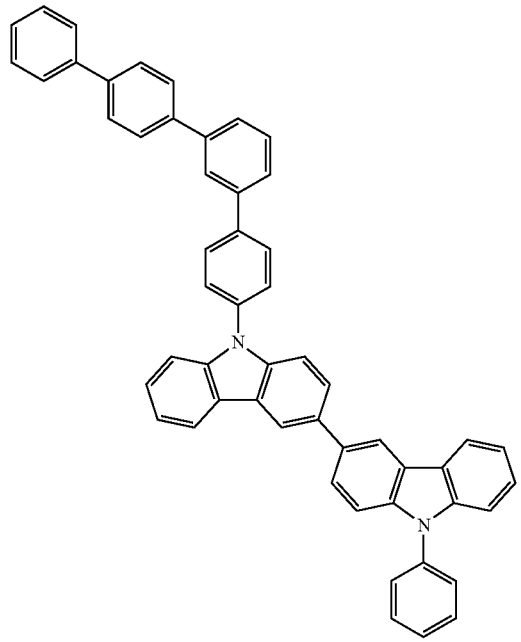 [SMILES: c1ccc(-c2ccc(-c3cccc(-c4ccc(-n5c6ccccc6c6cc(-c7ccc8c(c7)c7ccccc7n8-c7ccccc7)ccc65)cc4)c3)cc2)cc1] | CAS-1870867-25-6 |
| 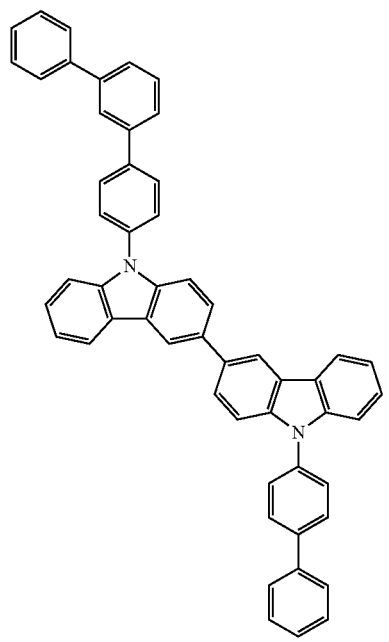 [SMILES: c1ccc(-c2ccc(-n3c4ccccc4c4cc(-c5ccc6c(c5)c5ccccc5n6-c5ccc(-c6cccc(-c7ccccc7)c6)cc5)ccc43)cc2)cc1] | CAS-1884707-32-7 |

| Structure | CAS-number |
|---|---|
| 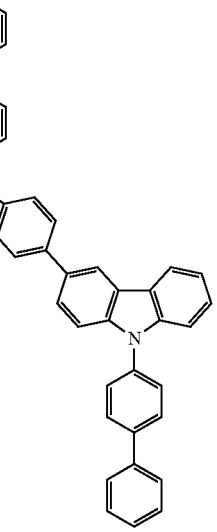 | CAS-1889262-88-7 |
| 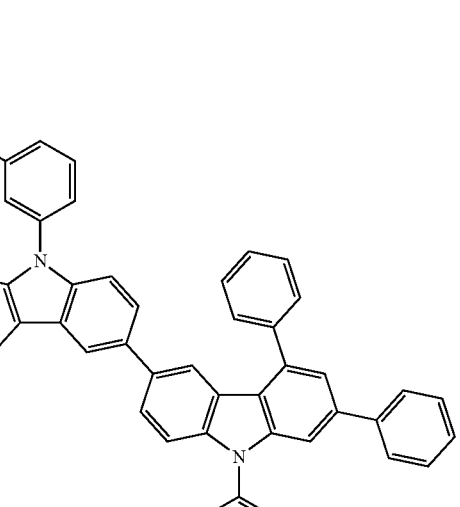 | CAS-2018307-89-4 |

| Structure | CAS-number |
|---|---|
| 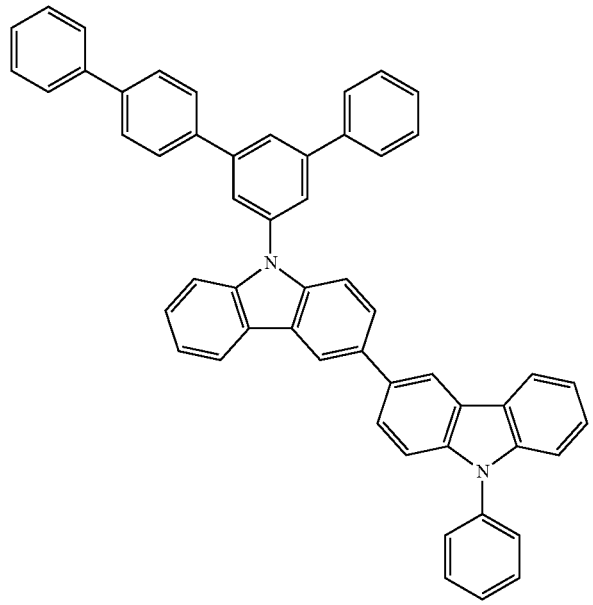 [SMILES: c1ccc(-c2ccc(-c3cc(-c4ccccc4)cc(-n4c5ccccc5c5cc(-c6ccc7c(c6)c6ccccc6n7-c6ccccc6)ccc54)c3)cc2)cc1] | CAS-1454655-29-8 |
| 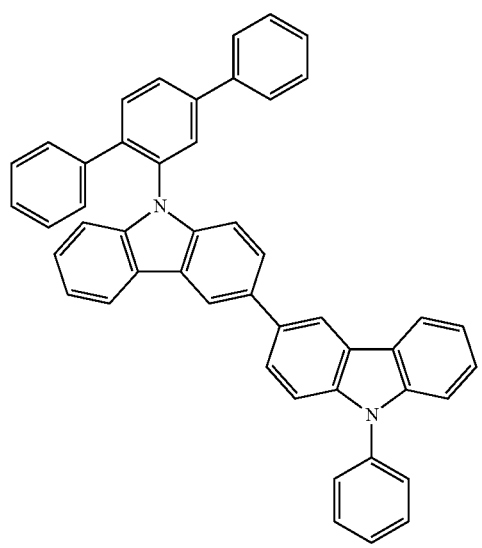 [SMILES: c1ccc(-c2ccc(-c3ccccc3)c(-n3c4ccccc4c4cc(-c5ccc6c(c5)c5ccccc5n6-c5ccccc5)ccc43)c2)cc1] | CAS-1454655-33-4 |

| Structure | CAS-number |
|---|---|
| 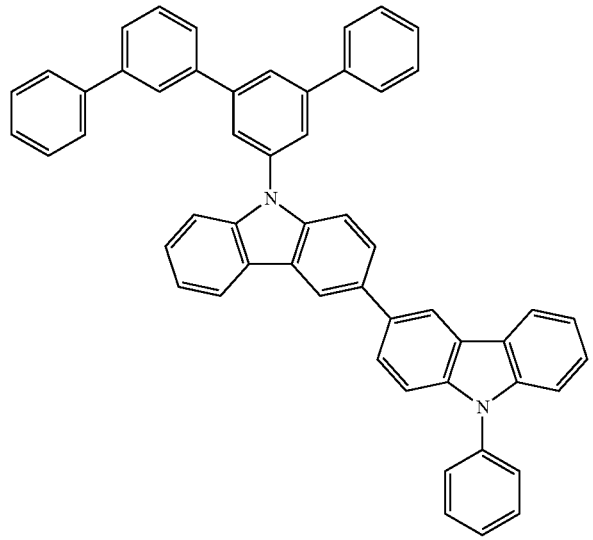 [SMILES: c1ccc(-c2cccc(-c3cc(-c4ccccc4)cc(-n4c5ccccc5c5cc(-c6ccc7c(c6)c6ccccc6n7-c6ccccc6)ccc54)c3)c2)cc1] | CAS-1454660-22-0 |
| 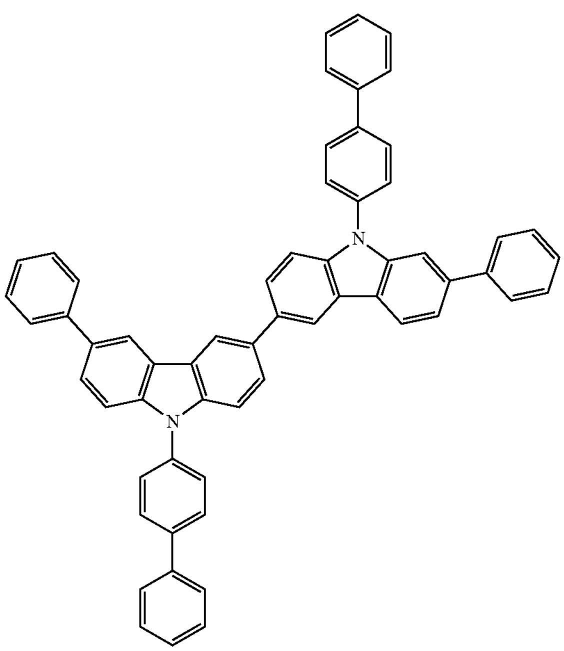 [SMILES: c1ccc(-c2ccc(-n3c4ccc(-c5ccccc5)cc4c4cc(-c5ccc6c(c5)c5ccc(-c7ccccc7)cc5n6-c5ccc(-c6ccccc6)cc5)ccc43)cc2)cc1] | CAS-1907663-27-7 |

| Structure | CAS-number |
|---|---|
| 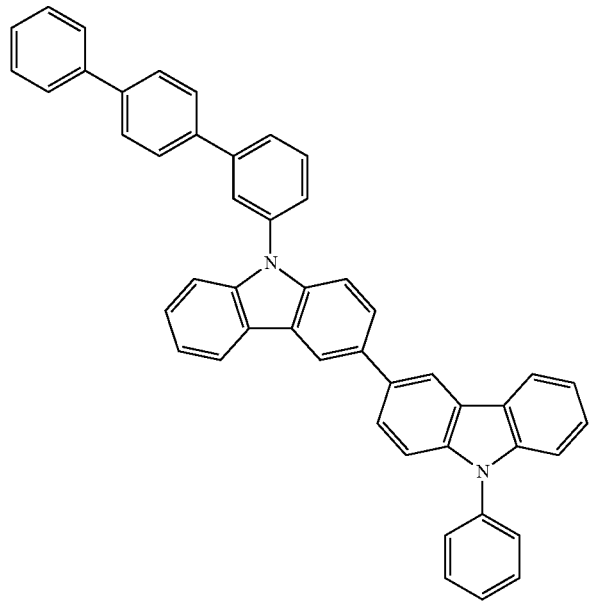 [SMILES: c1ccc(-c2ccc(-c3cccc(-n4c5ccccc5c5cc(-c6ccc7c(c6)c6ccccc6n7-c6ccccc6)ccc54)c3)cc2)cc1] | CAS-1548581-24-3 |
| 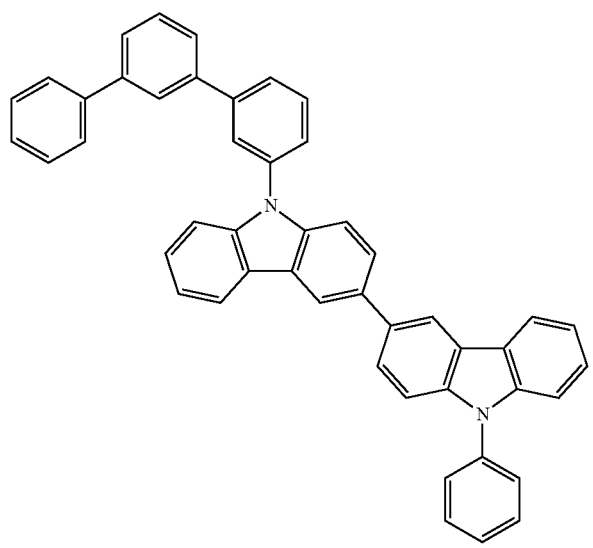 [SMILES: c1ccc(-c2cccc(-c3cccc(-n4c5ccccc5c5cc(-c6ccc7c(c6)c6ccccc6n7-c6ccccc6)ccc54)c3)c2)cc1] | CAS-1548581-27-6 |

| Structure | CAS-number |
|---|---|
| 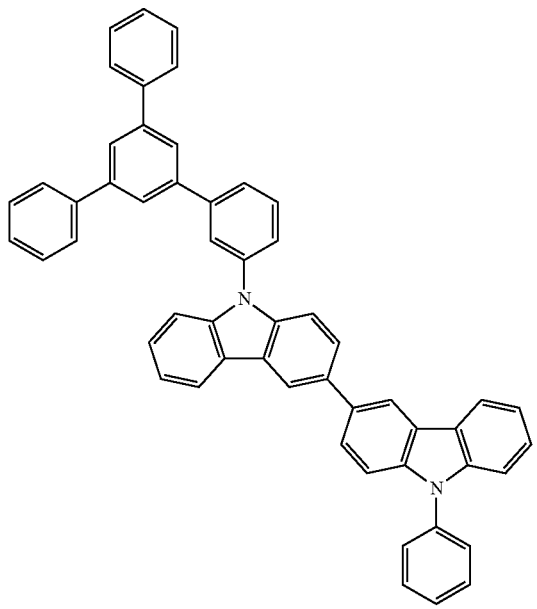 [SMILES: c1ccc(-c2cc(-c3ccccc3)cc(-c3cccc(-n4c5ccccc5c5cc(-c6ccc7c(c6)c6ccccc6n7-c6ccccc6)ccc54)c3)c2)cc1] | CAS-1548581-29-8 |
| 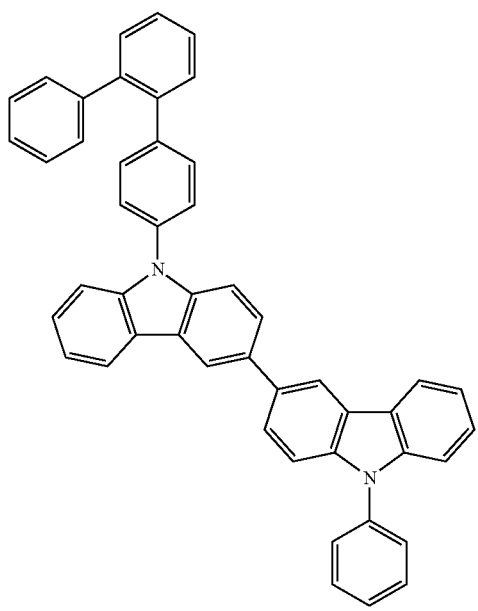 [SMILES: c1ccc(-c2ccccc2-c2ccc(-n3c4ccccc4c4cc(-c5ccc6c(c5)c5ccccc5n6-c5ccccc5)ccc43)cc2)cc1] | CAS-1548581-37-8 |

| Structure | CAS-number |
|---|---|
| 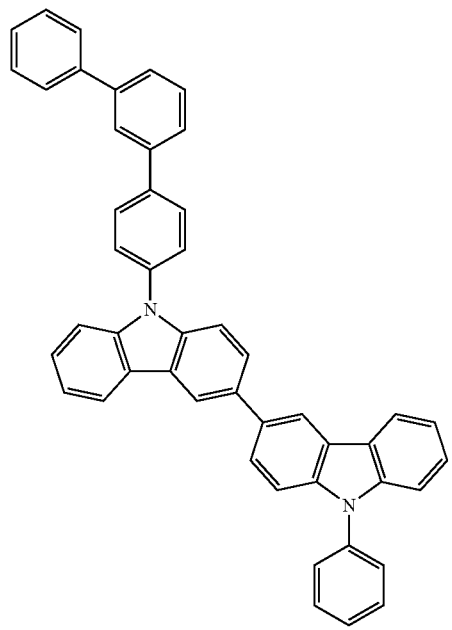 [SMILES: c1ccc(-c2cccc(-c3ccc(-n4c5ccccc5c5cc(-c6ccc7c(c6)c6ccccc6n7-c6ccccc6)ccc54)cc3)c2)cc1] | CAS-1548581-40-3 |
| 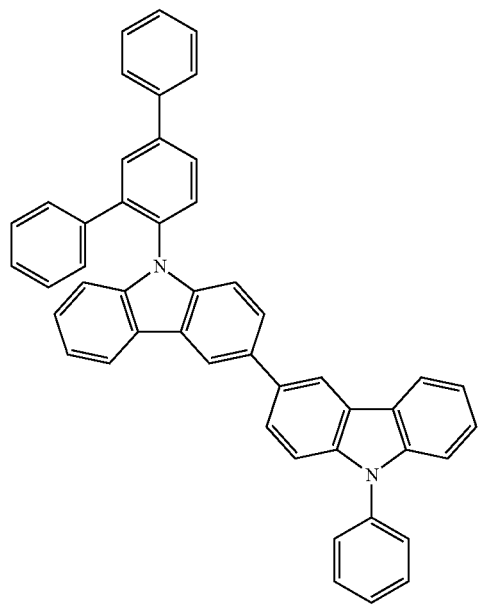 [SMILES: c1ccc(-c2ccc(-n3c4ccccc4c4cc(-c5ccc6c(c5)c5ccccc5n6-c5ccccc5)ccc43)c(-c3ccccc3)c2)cc1] | CAS-1943719-62-7 |

| Structure | CAS-number |
|---|---|
| 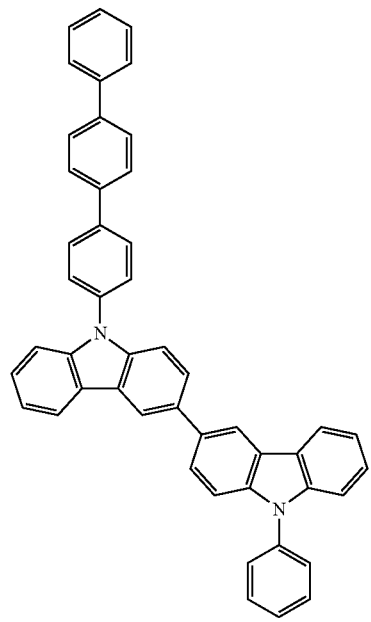 [SMILES: c1ccc(-c2ccc(-c3ccc(-n4c5ccccc5c5cc(-c6ccc7c(c6)c6ccccc6n7-c6ccccc6)ccc54)cc3)cc2)cc1] | CAS-1548581-42-5 |
| 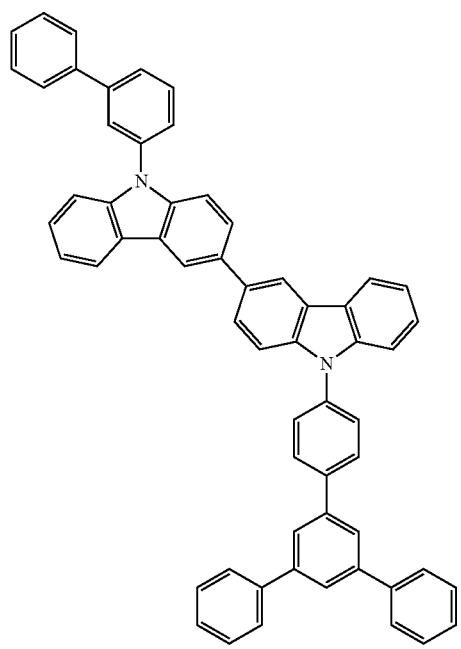 [SMILES: c1ccc(-c2cc(-c3ccccc3)cc(-c3ccc(-n4c5ccccc5c5cc(-c6ccc7c(c6)c6ccccc6n7-c6cccc(-c7ccccc7)c6)ccc54)cc3)c2)cc1] | CAS-1942079-50-6 |

-continued
| Structure | CAS-number |
|---|---|
| 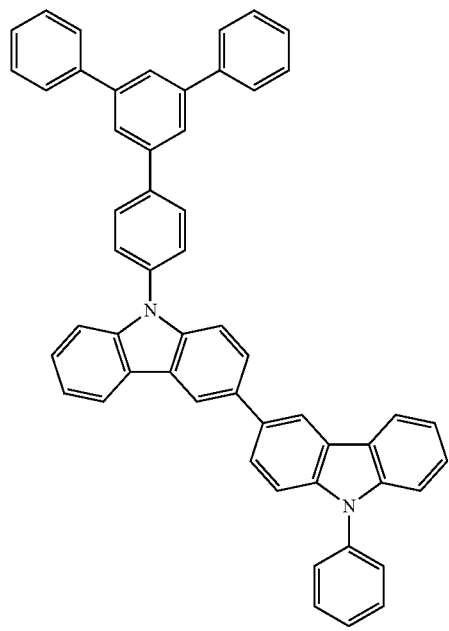 [SMILES: c1ccc(-c2cc(-c3ccccc3)cc(-c3ccc(-n4c5ccccc5c5cc(-c6ccc7c(c6)c6ccccc6n7-c6ccccc6)ccc54)cc3)c2)cc1] | CAS-1548581-44-7 |
| 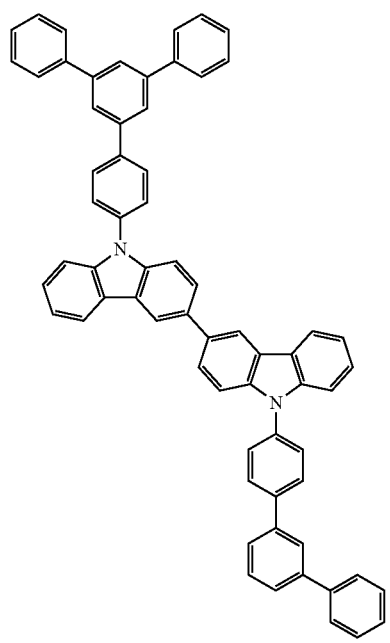 [SMILES: c1ccc(-c2cccc(-c3ccc(-n4c5ccccc5c5cc(-c6ccc7c(c6)c6ccccc6n7-c6ccc(-c7cc(-c8ccccc8)cc(-c8ccccc8)c7)cc6)ccc54)cc3)c2)cc1] | CAS-1942079-51-7 |

| Structure | CAS-number |
|---|---|
| 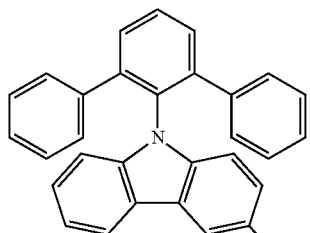 | CAS-1943719-63-8 |
| 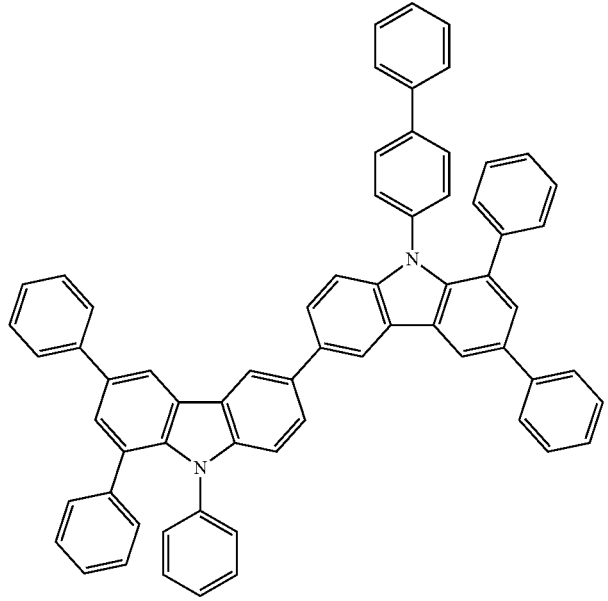 [SMILES: c1ccc(-c2ccc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)cc2)cc1] | CAS-1955476-12-6 |
| 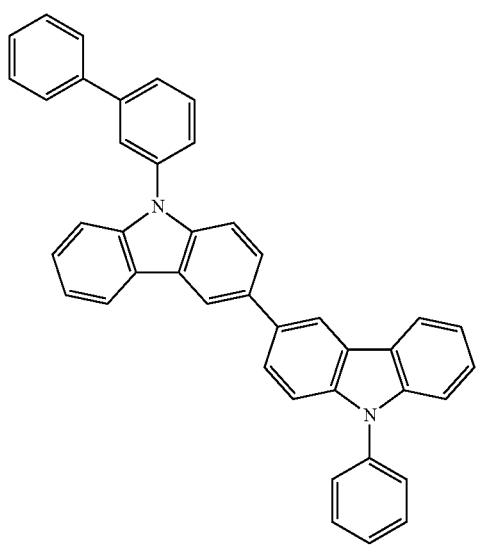 [SMILES: c1ccc(-c2cccc(-n3c4ccccc4c4cc(-c5ccc6c(c5)c5ccccc5n6-c5ccccc5)ccc43)c2)cc1] | CAS-1619966-75-4 |
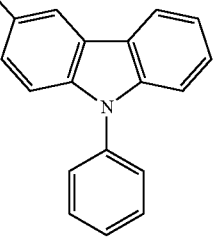

| Structure | CAS-number |
|---|---|
| 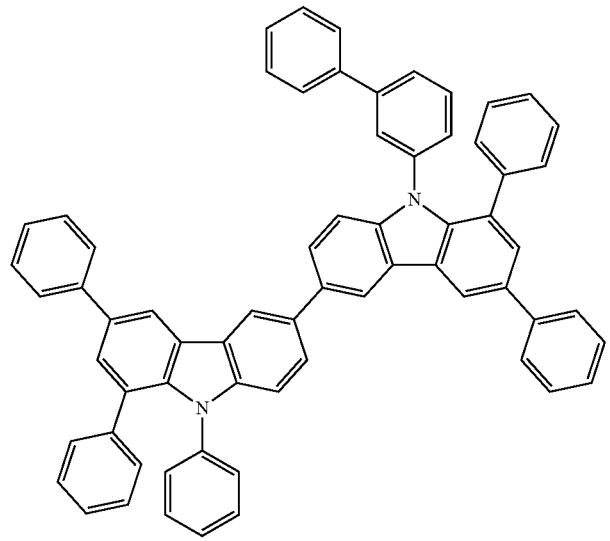 [SMILES: c1ccc(-c2cccc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)c2)cc1] | CAS-1955476-13-7 |
| 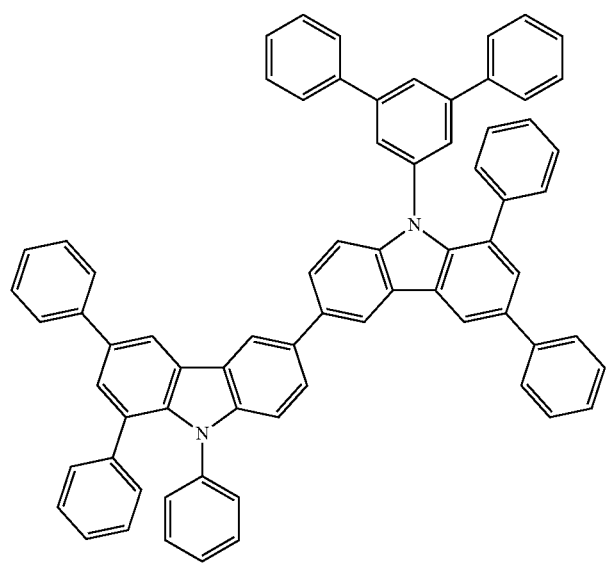 [SMILES: c1ccc(-c2cc(-c3ccccc3)cc(-n3c4ccc(-c5ccc6c(c5)c5cc(-c7ccccc7)cc(-c7ccccc7)c5n6-c5ccccc5)cc4c4cc(-c5ccccc5)cc(-c5ccccc5)c43)c2)cc1] | CAS-1955476-15-9 |

| Structure | CAS-number |
|---|---|
| 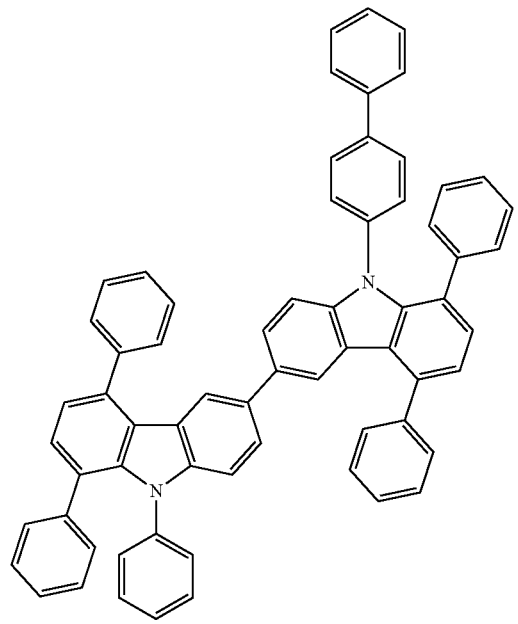 [SMILES: c1ccc(-c2ccc(-n3c4ccc(-c5ccc6c(c5)c5c(-c7ccccc7)ccc(-c7ccccc7)c5n6-c5ccccc5)cc4c4c(-c5ccccc5)ccc(-c5ccccc5)c43)cc2)cc1] | CAS-1955476-28-4 |
| 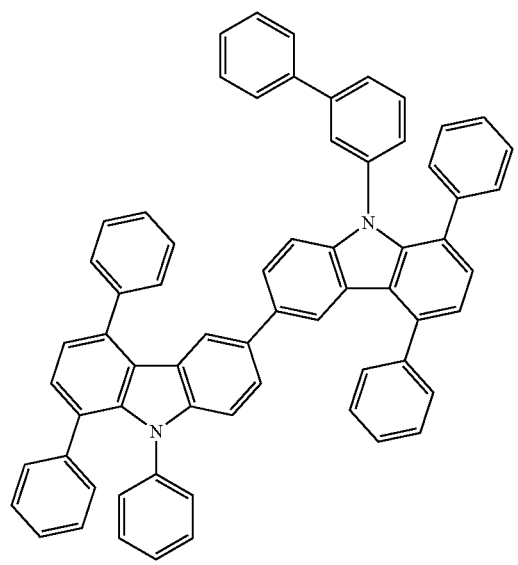 [SMILES: c1ccc(-c2cccc(-n3c4ccc(-c5ccc6c(c5)c5c(-c7ccccc7)ccc(-c7ccccc7)c5n6-c5ccccc5)cc4c4c(-c5ccccc5)ccc(-c5ccccc5)c43)c2)cc1] | CAS-1955476-30-8 |

| Structure | CAS-number |
|---|---|
| 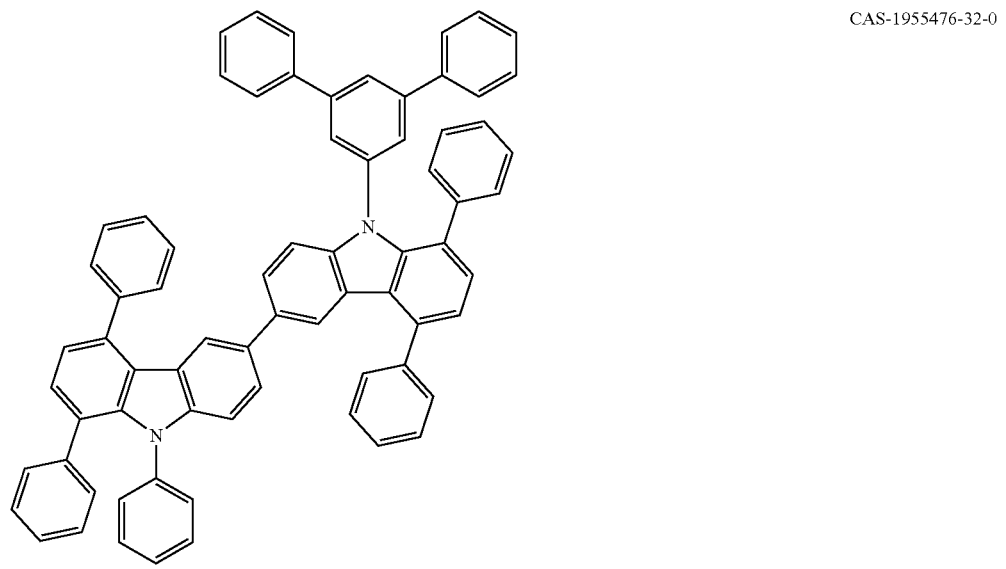 | CAS-1955476-32-0 |
| 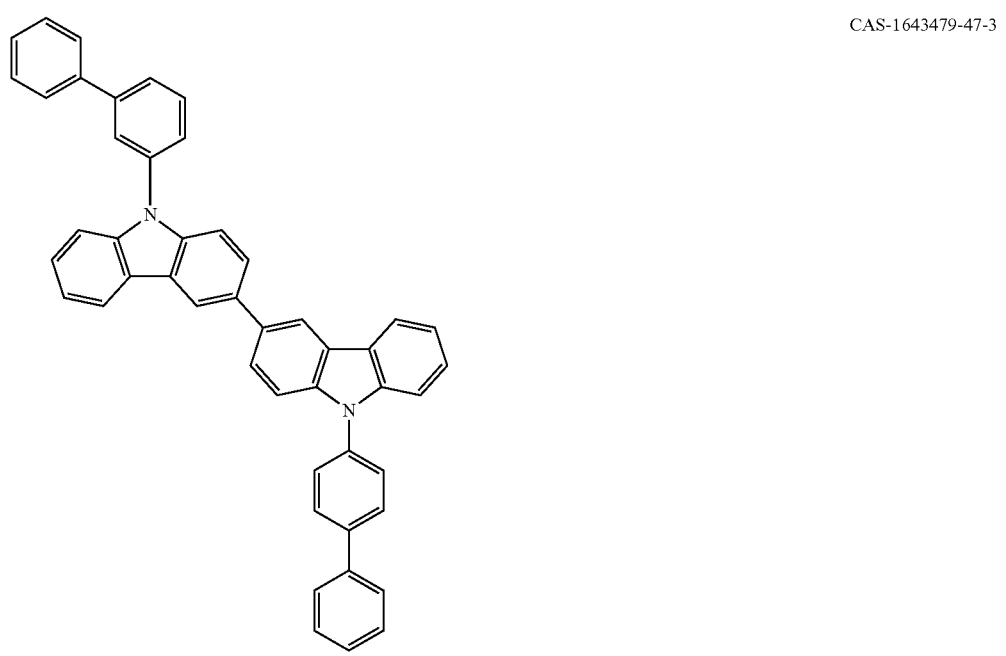 | CAS-1643479-47-3 |

| Structure | CAS-number |
|---|---|
| 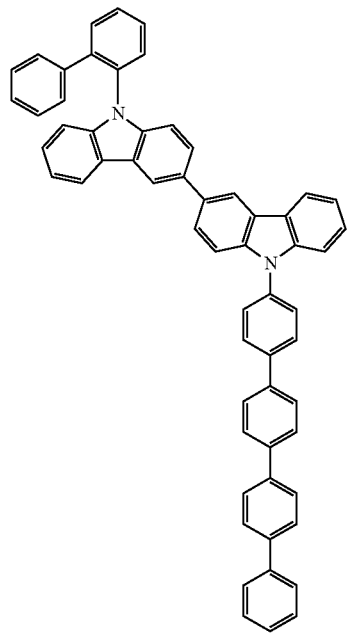 [SMILES: c1ccc(-c2ccc(-c3ccc(-c4ccc(-n5c6ccccc6c6cc(-c7ccc8c(c7)c7ccccc7n8-c7ccccc7-c7ccccc7)ccc65)cc4)cc3)cc2)cc1] | CAS-1973498-04-2 |
| 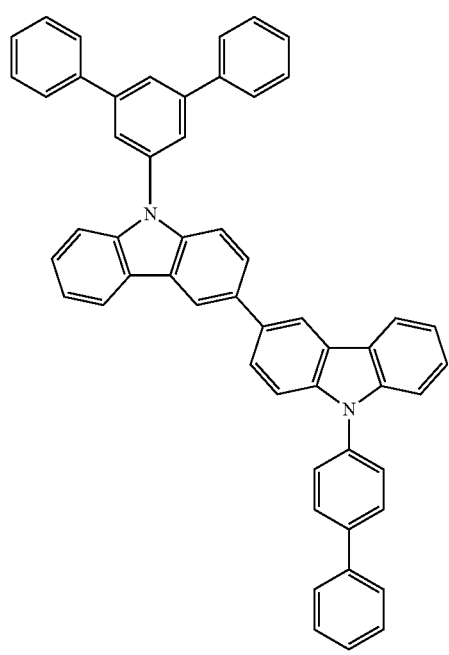 [SMILES: c1ccc(-c2ccc(-n3c4ccccc4c4cc(-c5ccc6c(c5)c5ccccc5n6-c5cc(-c6ccccc6)cc(-c6ccccc6)c5)ccc43)cc2)cc1] | CAS-1643479-49-5 |

| Structure | CAS-number |
|---|---|
| 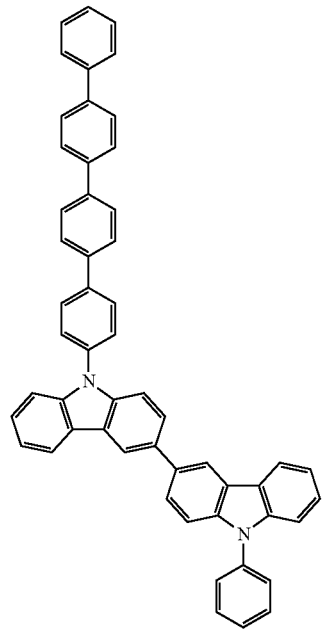 [SMILES: c1ccc(-c2ccc(-c3ccc(-c4ccc(-n5c6ccccc6c6cc(-c7ccc8c(c7)c7ccccc7n8-c7ccccc7)ccc65)cc4)cc3)cc2)cc1] | CAS-1973498-03-1 |
| 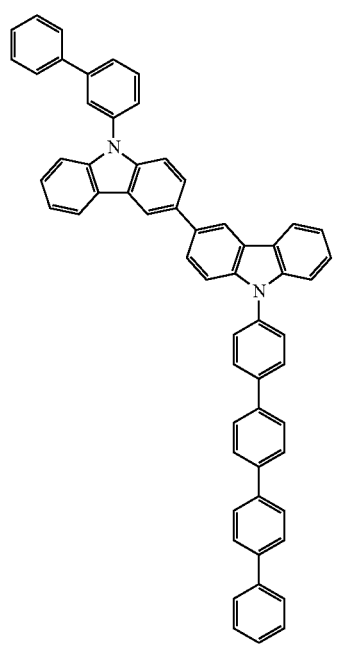 [SMILES: c1ccc(-c2ccc(-c3ccc(-c4ccc(-n5c6ccccc6c6cc(-c7ccc8c(c7)c7ccccc7n8-c7cccc(-c8ccccc8)c7)ccc65)cc4)cc3)cc2)cc1] | CAS-1973498-05-3 |

| Structure | CAS-number |
|---|---|
| 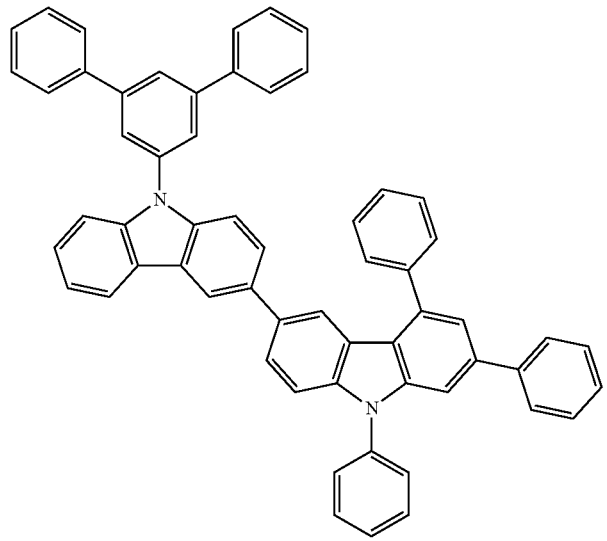 [SMILES: c1ccc(-c2cc(-c3ccccc3)cc(-n3c4ccccc4c4cc(-c5ccc6c(c5)c5c(-c7ccccc7)cc(-c7ccccc7)cc5n6-c5ccccc5)ccc43)c2)cc1] | CAS-2018307-36-1 |
| 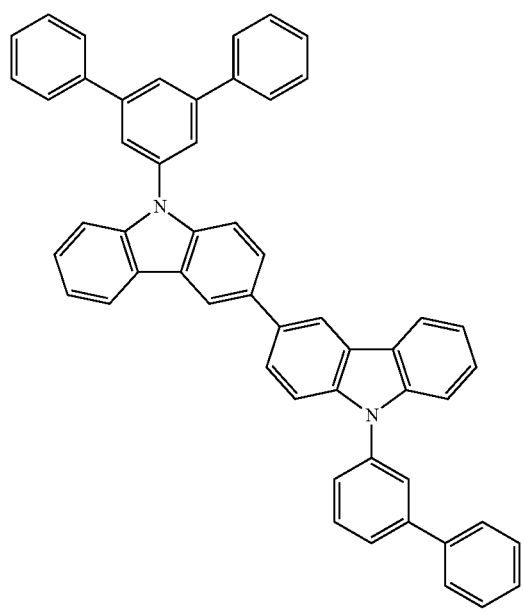 [SMILES: c1ccc(-c2cccc(-n3c4ccccc4c4cc(-c5ccc6c(c5)c5ccccc5n6-c5cc(-c6ccccc6)cc(-c6ccccc6)c5)ccc43)c2)cc1] | CAS-1643479-56-4 |

| Structure | CAS-number |
|---|---|
| 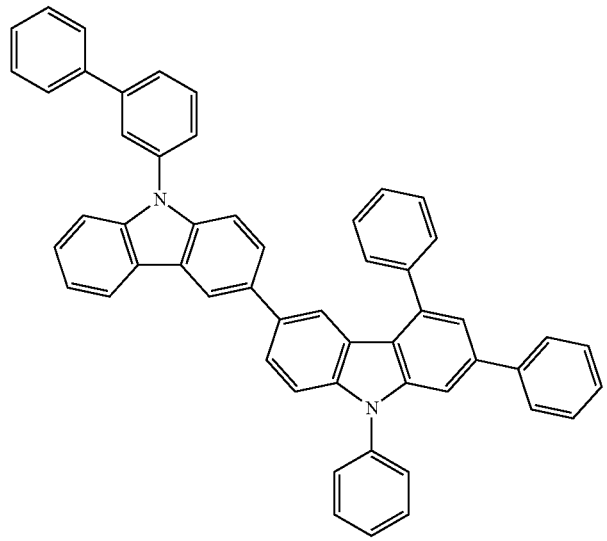 [SMILES: c1ccc(-c2cccc(-n3c4ccccc4c4cc(-c5ccc6c(c5)c5c(-c7ccccc7)cc(-c7ccccc7)cc5n6-c5ccccc5)ccc43)c2)cc1] | CAS-2018307-35-0 |
| 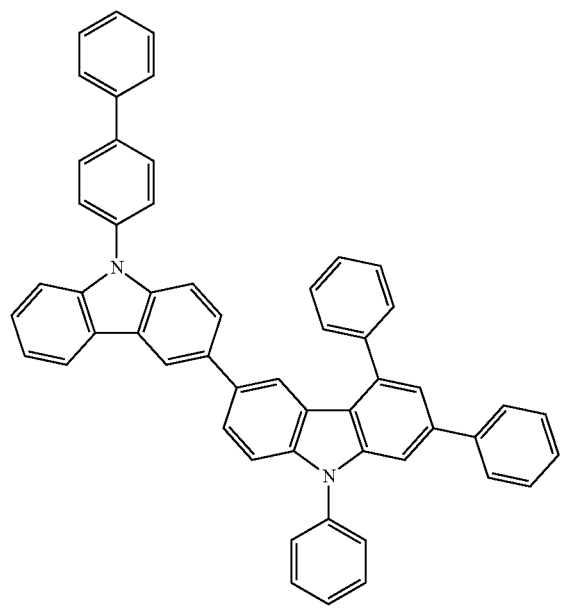 [SMILES: c1ccc(-c2ccc(-n3c4ccccc4c4cc(-c5ccc6c(c5)c5c(-c7ccccc7)cc(-c7ccccc7)cc5n6-c5ccccc5)ccc43)cc2)cc1] | CAS-2018307-37-2 |

| Structure | CAS-number |
|---|---|
| 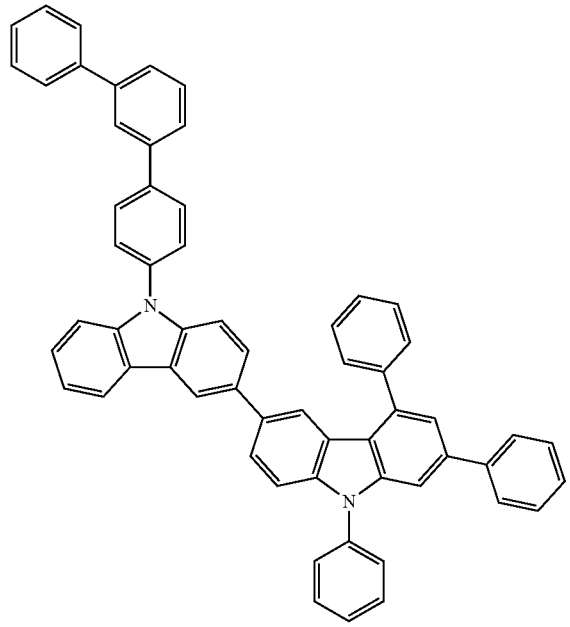 [SMILES: c1ccc(-c2cccc(-c3ccc(-n4c5ccccc5c5cc(-c6ccc7c(c6)c6c(-c8ccccc8)cc(-c8ccccc8)cc6n7-c6ccccc6)ccc54)cc3)c2)cc1] | CAS-2018307-38-3 |
| 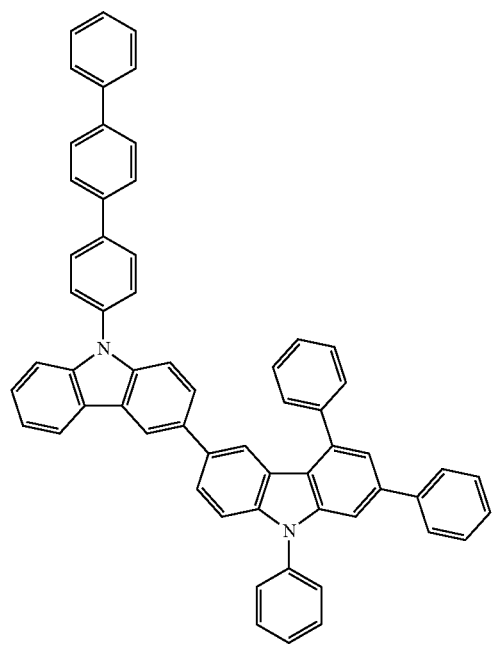 [SMILES: c1ccc(-c2ccc(-c3ccc(-n4c5ccccc5c5cc(-c6ccc7c(c6)c6c(-c8ccccc8)cc(-c8ccccc8)cc6n7-c6ccccc6)ccc54)cc3)cc2)cc1] | CAS-2018307-39-4 |

| Structure | CAS-number |
|---|---|
| 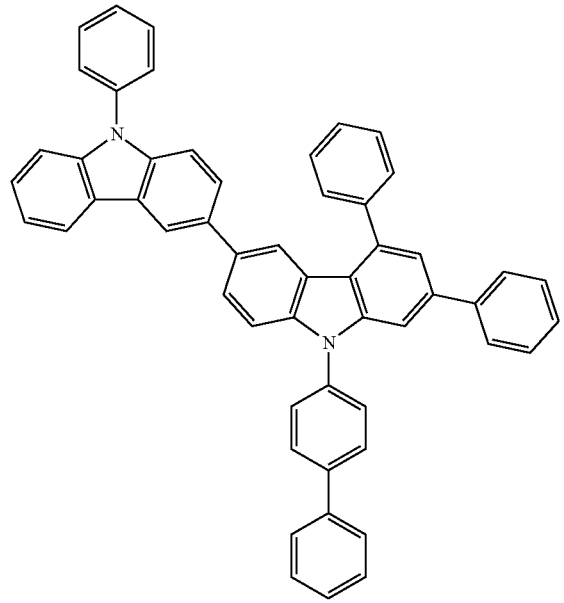 [SMILES: c1ccc(-c2ccc(-n3c4ccc(-c5ccc6c(c5)c5ccccc5n6-c5ccccc5)cc4c4c(-c5ccccc5)cc(-c5ccccc5)cc43)cc2)cc1] | CAS-2018307-77-0 |
| 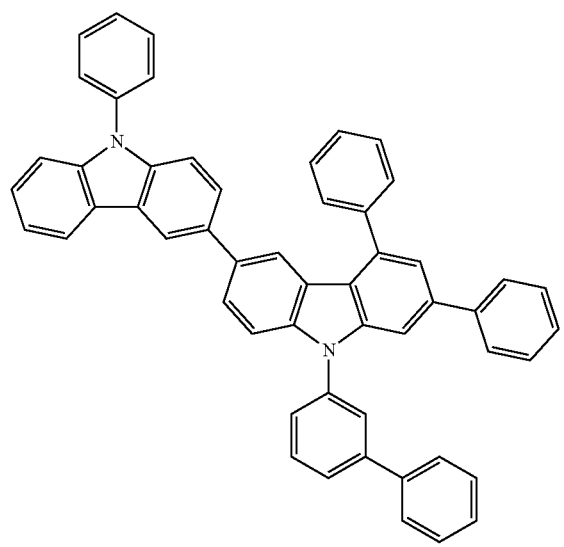 [SMILES: c1ccc(-c2cccc(-n3c4ccc(-c5ccc6c(c5)c5ccccc5n6-c5ccccc5)cc4c4c(-c5ccccc5)cc(-c5ccccc5)cc43)c2)cc1] | CAS-2018307-78-1 |

| Structure | CAS-number |
|---|---|
| 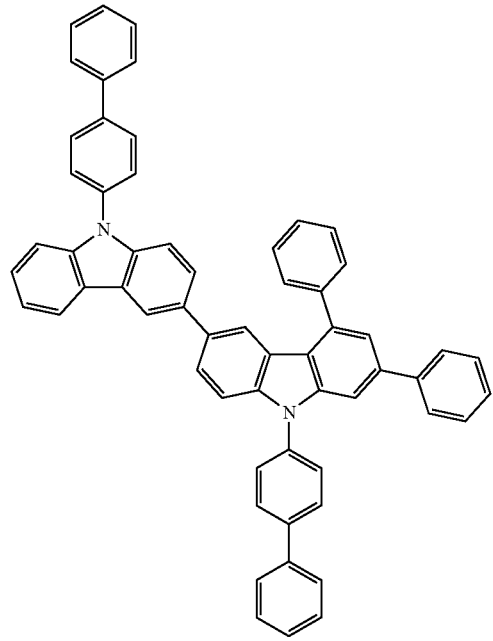 [SMILES: c1ccc(-c2ccc(-n3c4ccccc4c4cc(-c5ccc6c(c5)c5c(-c7ccccc7)cc(-c7ccccc7)cc5n6-c5ccc(-c6ccccc6)cc5)ccc43)cc2)cc1] | CAS-2018307-90-7 |
| 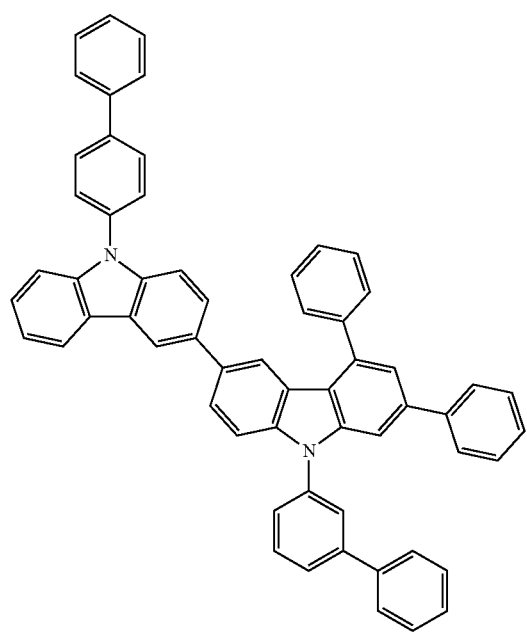 [SMILES: c1ccc(-c2ccc(-n3c4ccccc4c4cc(-c5ccc6c(c5)c5c(-c7ccccc7)cc(-c7ccccc7)cc5n6-c5cccc(-c6ccccc6)c5)ccc43)cc2)cc1] | CAS-2018307-91-8 |

| Structure | CAS-number |
|---|---|
| 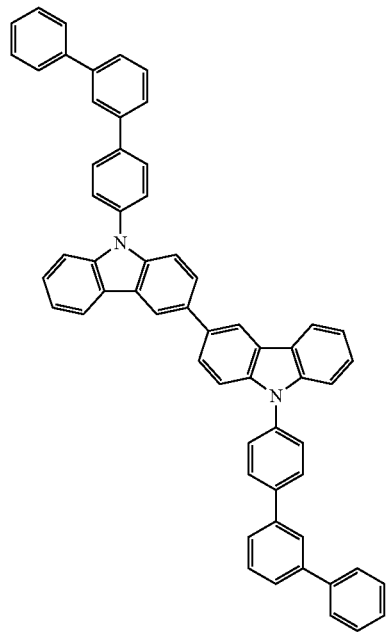 [SMILES: c1ccc(-c2cccc(-c3ccc(-n4c5ccccc5c5cc(-c6ccc7c(c6)c6ccccc6n7-c6ccc(-c7cccc(-c8ccccc8)c7)cc6)ccc54)cc3)c2)cc1] | CAS-1799958-74-9 |
| 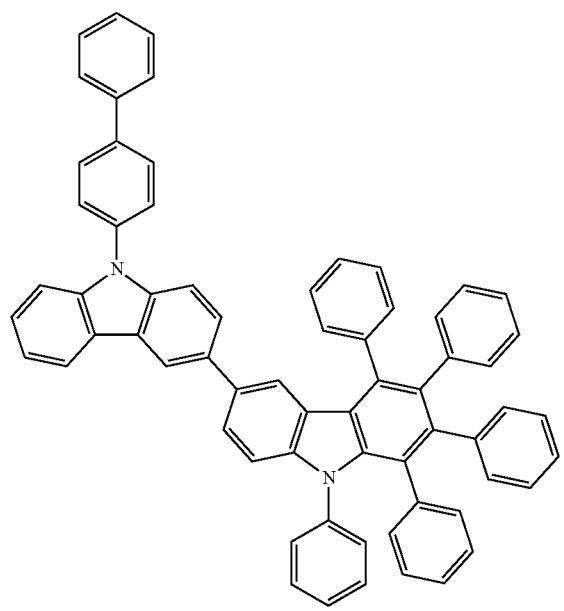 [SMILES: c1ccc(-c2ccc(-n3c4ccccc4c4cc(-c5ccc6c(c5)c5c(-c7ccccc7)c(-c7ccccc7)c(-c7ccccc7)c(-c7ccccc7)c5n6-c5ccccc5)ccc43)cc2)cc1] | CAS-2052160-86-6 |

| Structure | CAS-number |
|---|---|
| 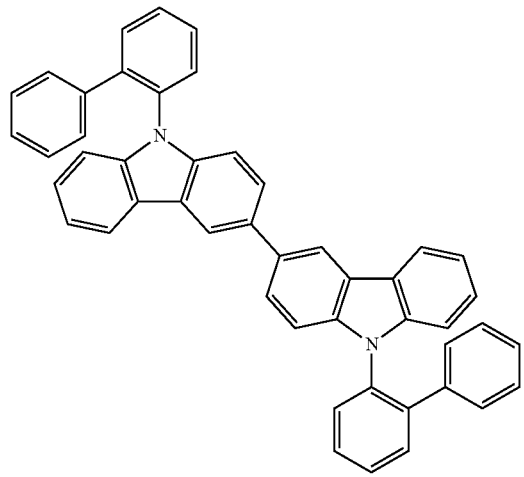 [SMILES: c1ccc(-c2ccccc2-n2c3ccccc3c3cc(-c4ccc5c(c4)c4ccccc4n5-c4ccccc4-c4ccccc4)ccc32)cc1] | CAS-1799958-79-4 |
| 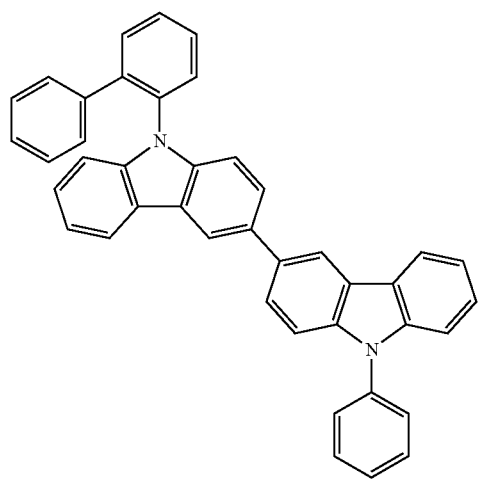 [SMILES: c1ccc(-c2ccccc2-n2c3ccccc3c3cc(-c4ccc5c(c4)c4ccccc4n5-c4ccccc4)ccc32)cc1] | CAS-1799958-76-1 |
| 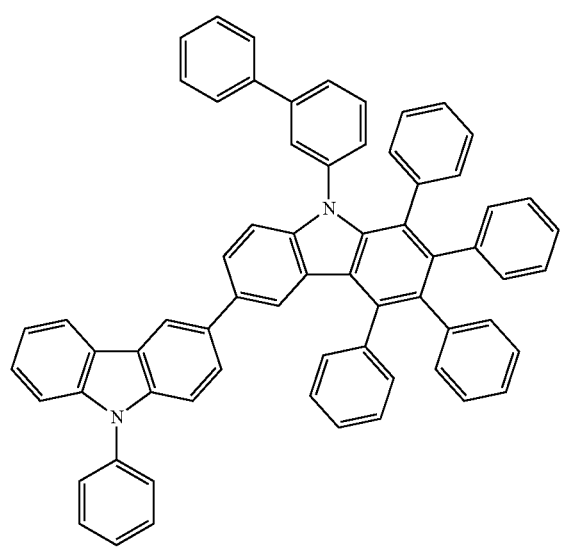 [SMILES: c1ccc(-c2cccc(-n3c4ccc(-c5ccc6c(c5)c5ccccc5n6-c5ccccc5)cc4c4c(-c5ccccc5)c(-c5ccccc5)c(-c5ccccc5)c(-c5ccccc5)c43)c2)cc1] | CAS-2052160-91-3 |

| Structure | CAS-number |
|---|---|
| 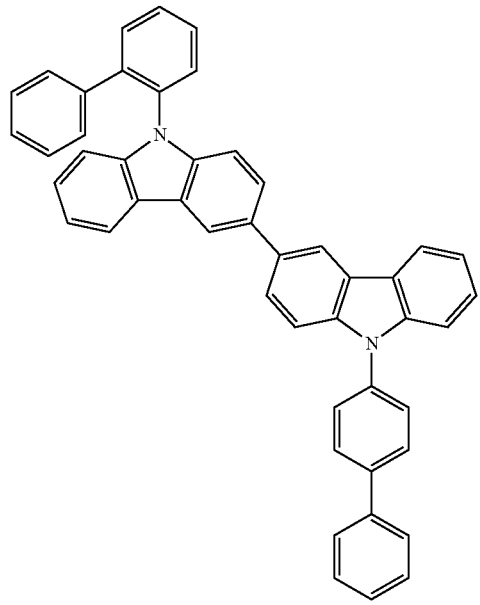 [SMILES: c1ccc(-c2ccc(-n3c4ccccc4c4cc(-c5ccc6c(c5)c5ccccc5n6-c5ccccc5-c5ccccc5)ccc43)cc2)cc1] | CAS-1799958-77-2 |
| 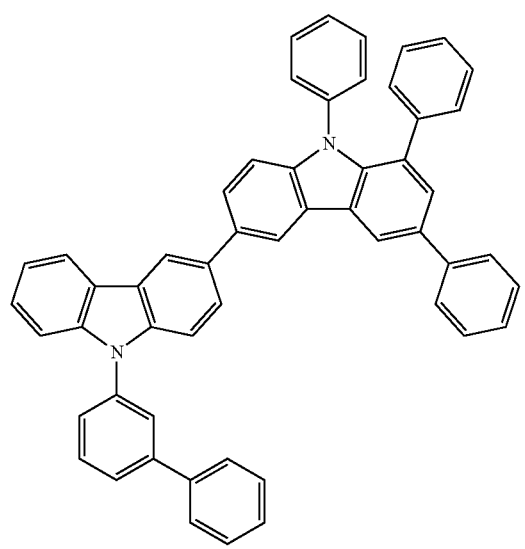 [SMILES: c1ccc(-c2cccc(-n3c4ccccc4c4cc(-c5ccc6c(c5)c5cc(-c7ccccc7)cc(-c7ccccc7)c5n6-c5ccccc5)ccc43)c2)cc1] | CAS-2055848-40-1 |

| Structure | CAS-number |
|---|---|
| 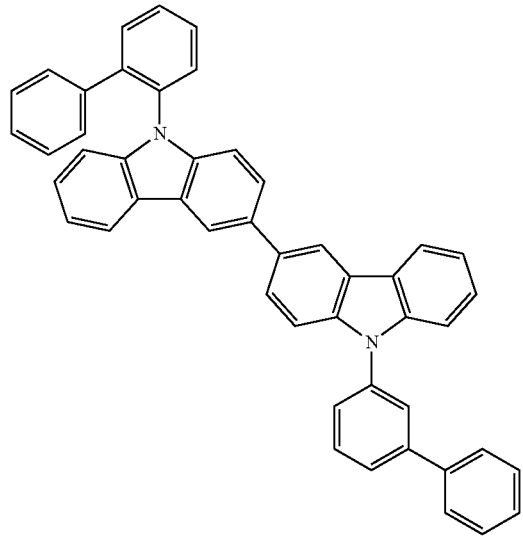 [SMILES: c1ccc(-c2cccc(-n3c4ccccc4c4cc(-c5ccc6c(c5)c5ccccc5n6-c5ccccc5-c5ccccc5)ccc43)c2)cc1] | CAS-1799958-78-3 |
| 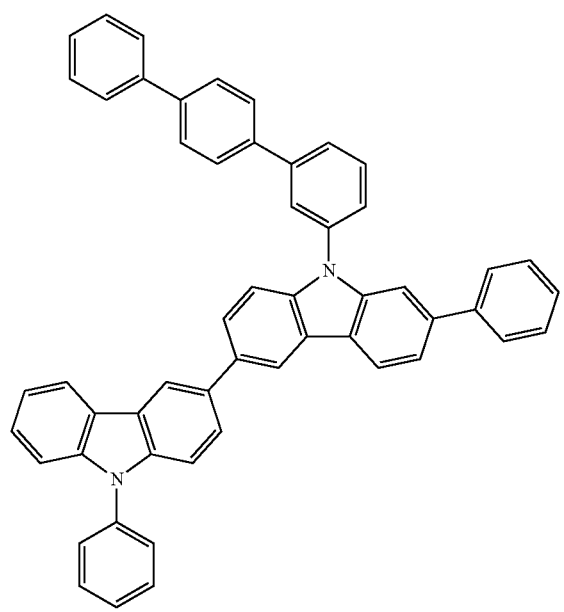 [SMILES: c1ccc(-c2ccc(-c3cccc(-n4c5ccc(-c6ccc7c(c6)c6ccccc6n7-c6ccccc6)cc5c5ccc(-c6ccccc6)cc54)c3)cc2)cc1] | CAS-2057418-19-4 |

| Structure | CAS-number |
|---|---|
| 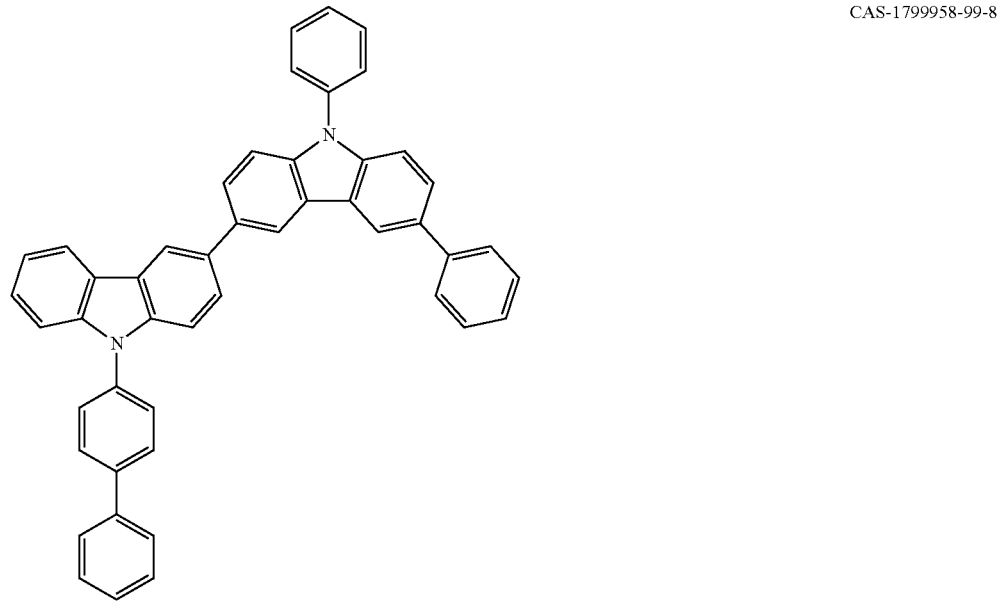 | CAS-1799958-99-8 |
| 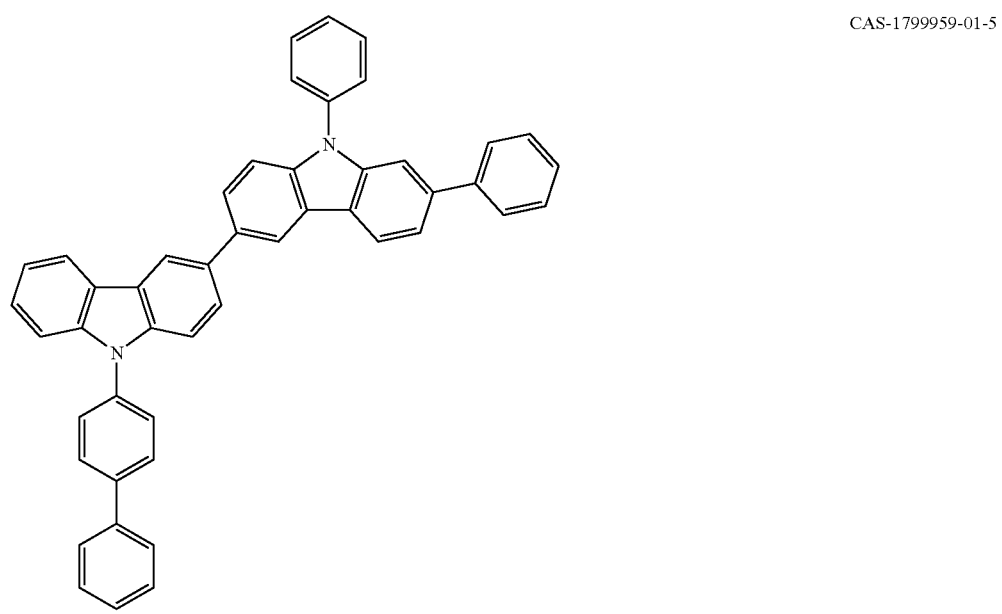 | CAS-1799959-01-5 |

| Structure | CAS-number |
|---|---|
| 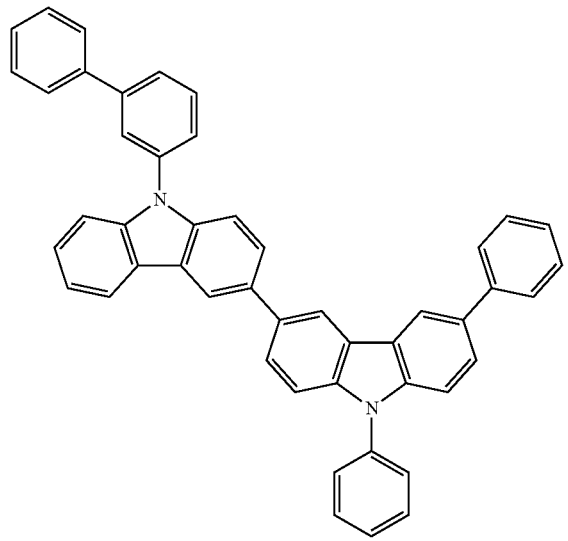 [SMILES: c1ccc(-c2cccc(-n3c4ccccc4c4cc(-c5ccc6c(c5)c5cc(-c7ccccc7)ccc5n6-c5ccccc5)ccc43)c2)cc1] | CAS-1799959-03-7 |
| 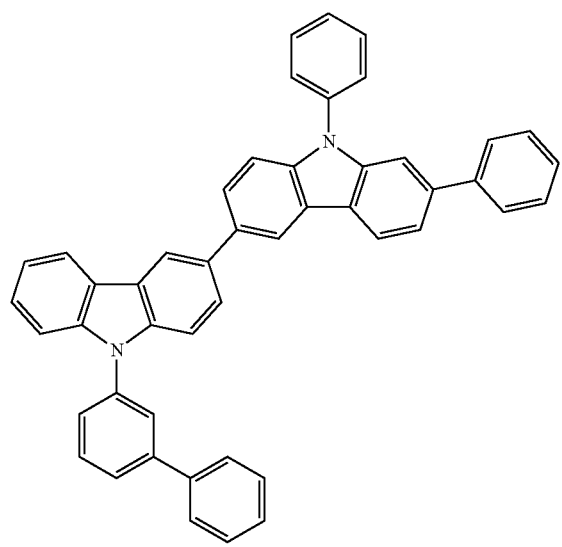 [SMILES: c1ccc(-c2cccc(-n3c4ccccc4c4cc(-c5ccc6c(c5)c5ccc(-c7ccccc7)cc5n6-c5ccccc5)ccc43)c2)cc1] | CAS-1799959-05-9 |

-continued
| Structure | CAS-number |
|---|---|
| 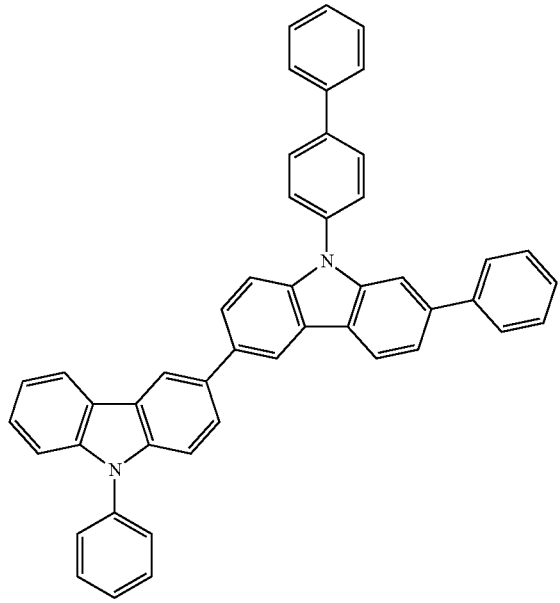 [SMILES: c1ccc(-c2ccc(-n3c4ccc(-c5ccc6c(c5)c5ccccc5n6-c5ccccc5)cc4c4ccc(-c5ccccc5)cc43)cc2)cc1] | CAS-1799959-07-1 |
| 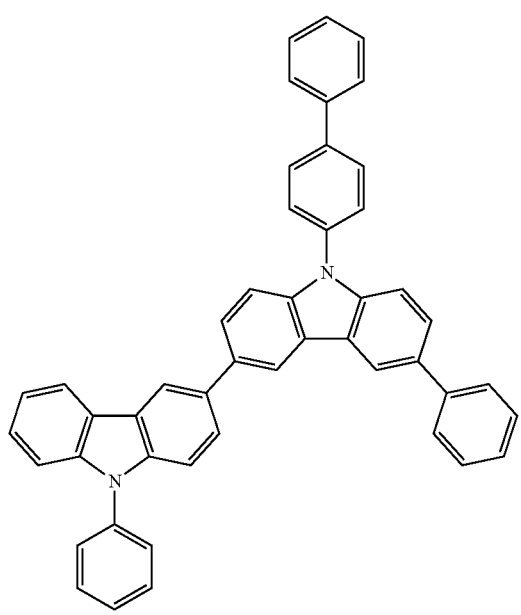 [SMILES: c1ccc(-c2ccc(-n3c4ccc(-c5ccccc5)cc4c4cc(-c5ccc6c(c5)c5ccccc5n6-c5ccccc5)ccc43)cc2)cc1] | CAS-1799959-09-3 |

| Structure | CAS-number |
|---|---|
| 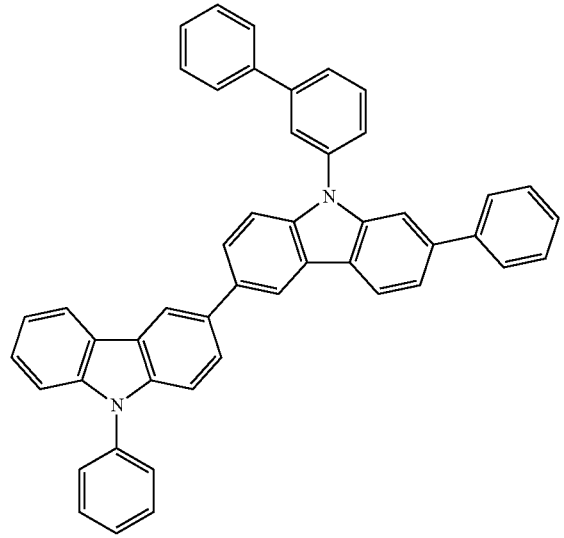 [SMILES: c1ccc(-c2cccc(-n3c4ccc(-c5ccc6c(c5)c5ccccc5n6-c5ccccc5)cc4c4ccc(-c5ccccc5)cc43)c2)cc1] | CAS-1799959-11-7 |
| 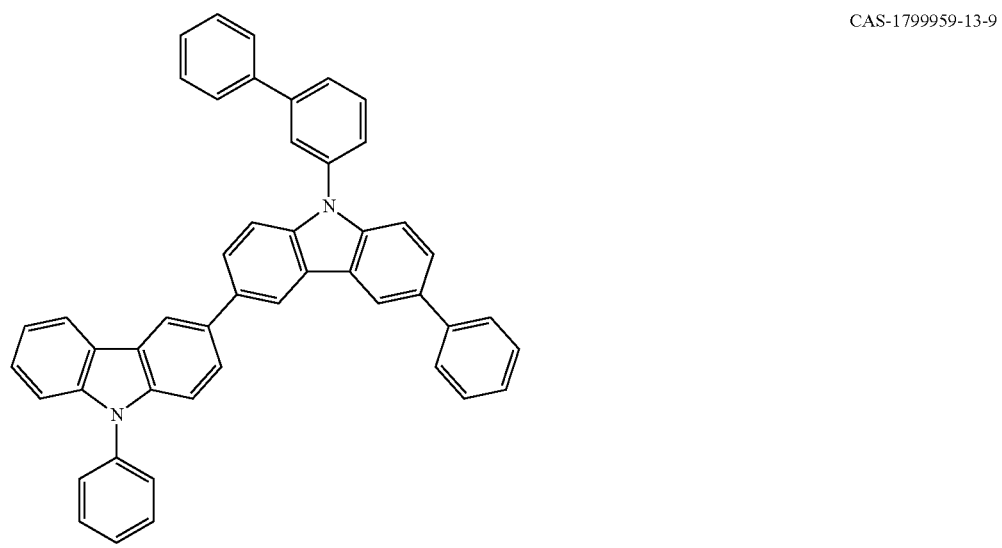 | CAS-1799959-13-9 |
| 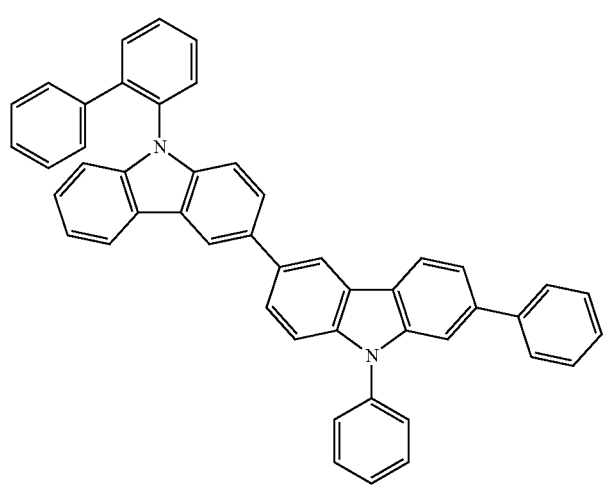 [SMILES: c1ccc(-c2ccc3c4cc(-c5ccc6c(c5)c5ccccc5n6-c5ccccc5-c5ccccc5)ccc4n(-c4ccccc4)c3c2)cc1] | CAS-2085318-61-0 |

| Structure | CAS-number |
|---|---|
| 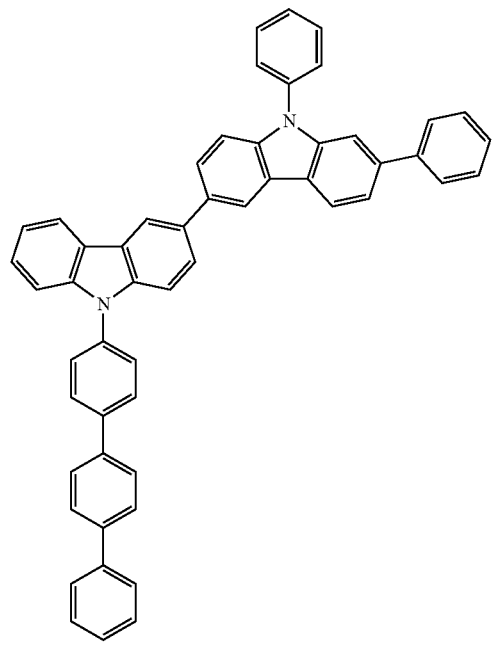 [SMILES: c1ccc(-c2ccc(-c3ccc(-n4c5ccccc5c5cc(-c6ccc7c(c6)c6ccc(-c8ccccc8)cc6n7-c6ccccc6)ccc54)cc3)cc2)cc1] | CAS-2085318-62-1 |
| 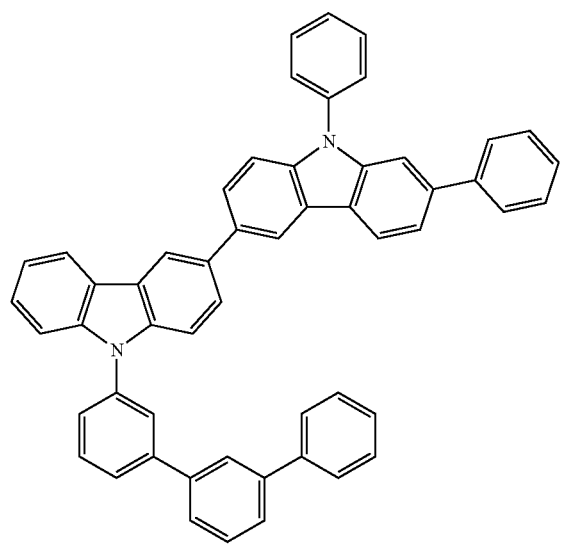 [SMILES: c1ccc(-c2cccc(-c3cccc(-n4c5ccccc5c5cc(-c6ccc7c(c6)c6ccc(-c8ccccc8)cc6n7-c6ccccc6)ccc54)c3)c2)cc1] | CAS-2085318-64-3 |

| Structure | CAS-number |
|---|---|
| 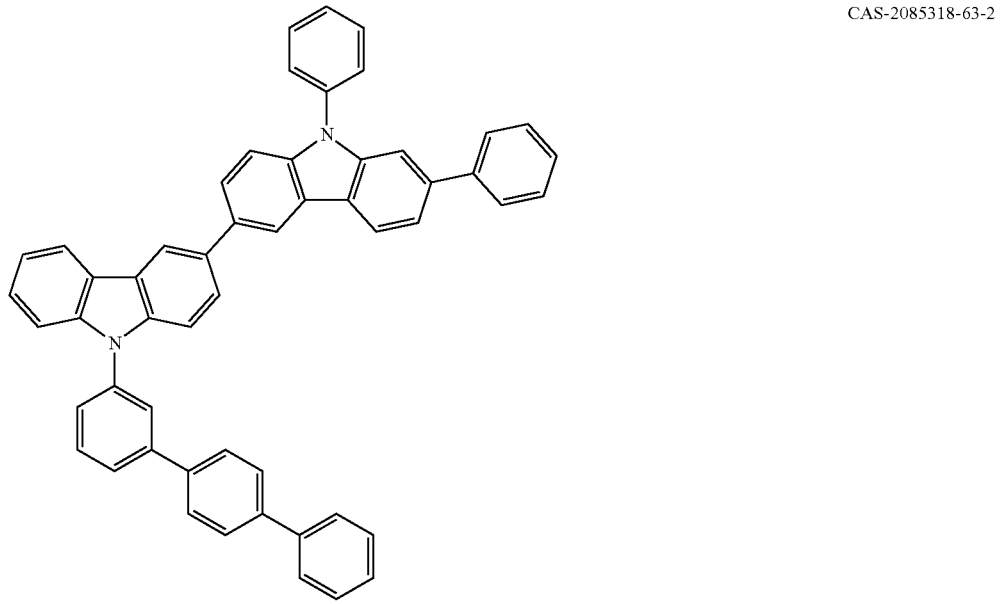 | CAS-2085318-63-2 |
| 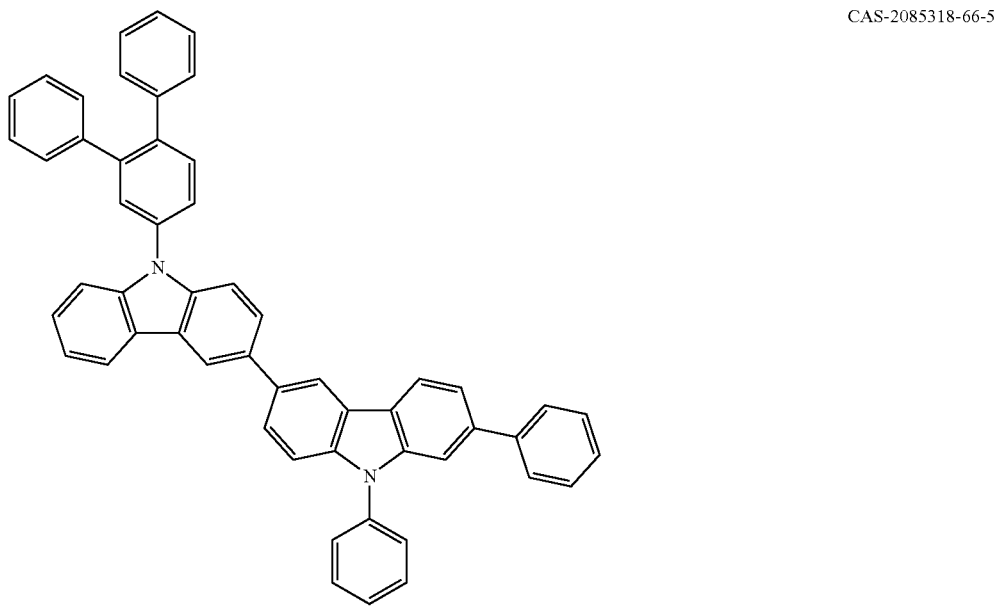 | CAS-2085318-66-5 |

| Structure | CAS-number |
|---|---|
| 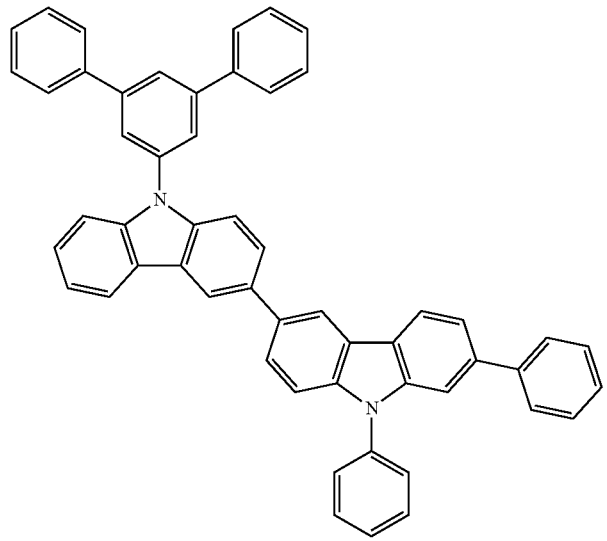 [SMILES: c1ccc(-c2cc(-c3ccccc3)cc(-n3c4ccccc4c4cc(-c5ccc6c(c5)c5ccc(-c7ccccc7)cc5n6-c5ccccc5)ccc43)c2)cc1] | CAS-2085318-65-4 |
| 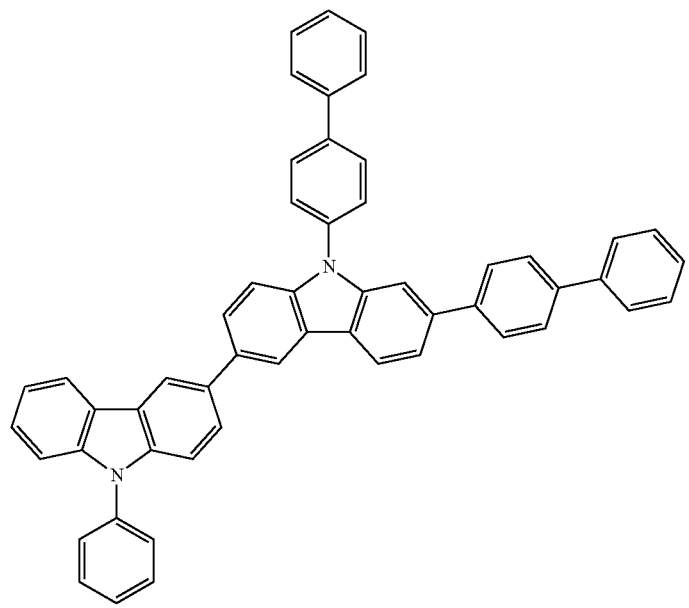 [SMILES: c1ccc(-c2ccc(-c3ccc4c5cc(-c6ccc7c(c6)c6ccccc6n7-c6ccccc6)ccc5n(-c5ccc(-c6ccccc6)cc5)c4c3)cc2)cc1] | CAS-2085318-77-8 |

| Structure | CAS-number |
|---|---|
| 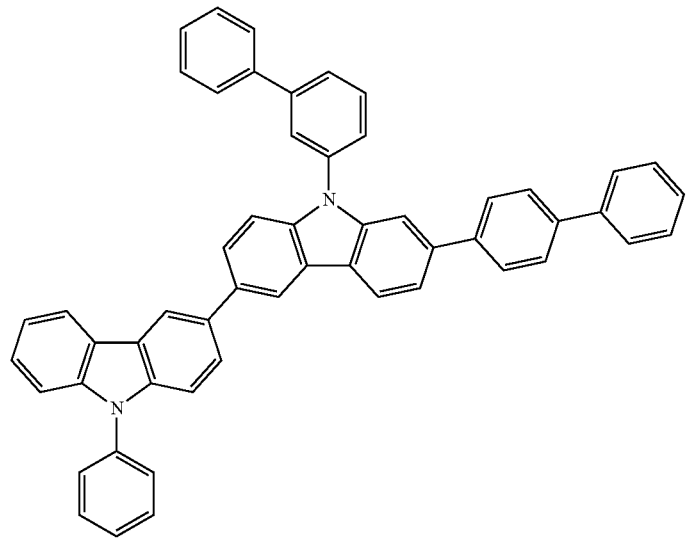 [SMILES: c1ccc(-c2ccc(-c3ccc4c5cc(-c6ccc7c(c6)c6ccccc6n7-c6ccccc6)ccc5n(-c5cccc(-c6ccccc6)c5)c4c3)cc2)cc1] | CAS-2085318-78-9 |
| 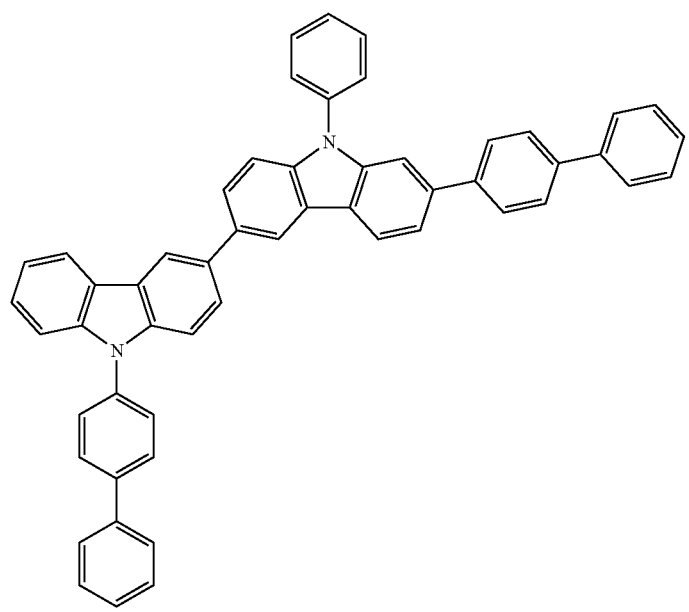 [SMILES: c1ccc(-c2ccc(-c3ccc4c5cc(-c6ccc7c(c6)c6ccccc6n7-c6ccc(-c7ccccc7)cc6)ccc5n(-c5ccccc5)c4c3)cc2)cc1] | CAS-2085318-79-0 |

| Structure | CAS-number |
|---|---|
| 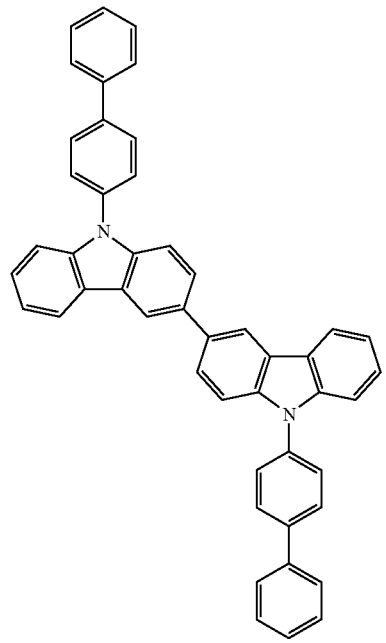 [SMILES: c1ccc(-c2ccc(-n3c4ccccc4c4cc(-c5ccc6c(c5)c5ccccc5n6-c5ccc(-c6ccccc6)cc5)ccc43)cc2)cc1] | CAS-57102-51-9 |
| 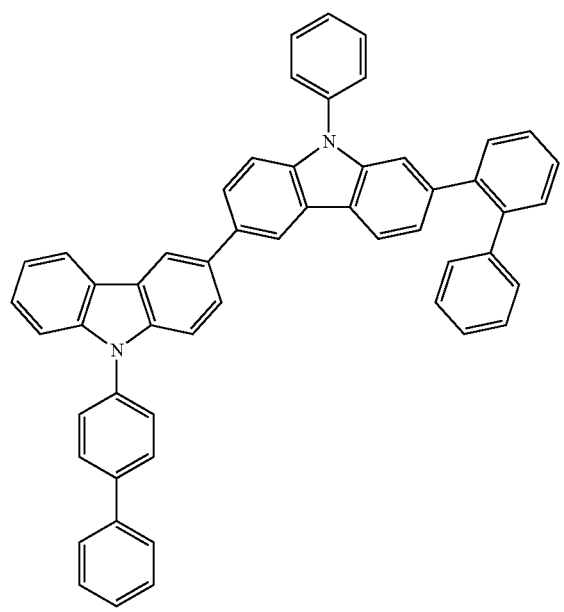 [SMILES: c1ccc(-c2ccc(-n3c4ccccc4c4cc(-c5ccc6c(c5)c5ccc(-c7ccccc7-c7ccccc7)cc5n6-c5ccccc5)ccc43)cc2)cc1] | CAS-2085318-81-4 |

| Structure | CAS-number |
|---|---|
| 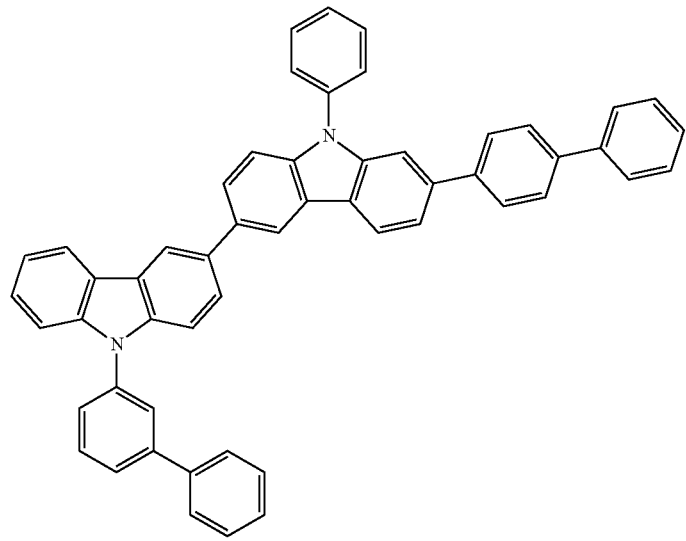 [SMILES: c1ccc(-c2ccc(-c3ccc4c5cc(-c6ccc7c(c6)c6ccccc6n7-c6cccc(-c7ccccc7)c6)ccc5n(-c5ccccc5)c4c3)cc2)cc1] | CAS-2085318-80-3 |
| 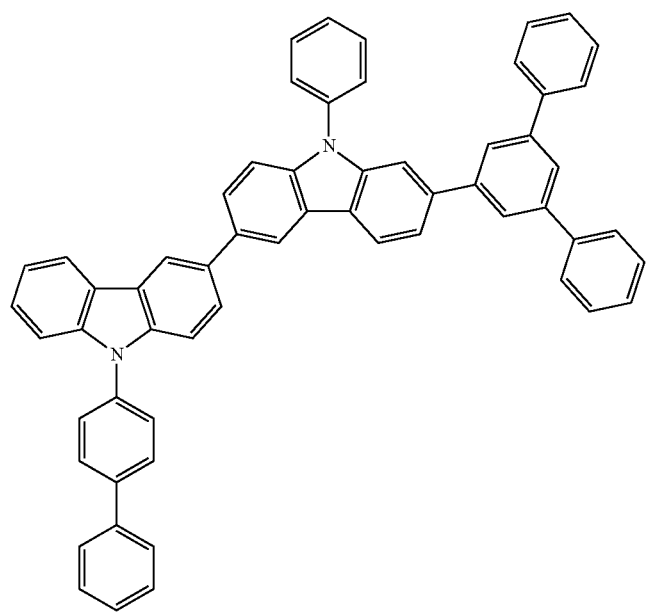 [SMILES: c1ccc(-c2ccc(-n3c4ccccc4c4cc(-c5ccc6c(c5)c5ccc(-c7cc(-c8ccccc8)cc(-c8ccccc8)c7)cc5n6-c5ccccc5)ccc43)cc2)cc1] | CAS-2085318-83-6 |

| Structure | CAS-number |
|---|---|
| 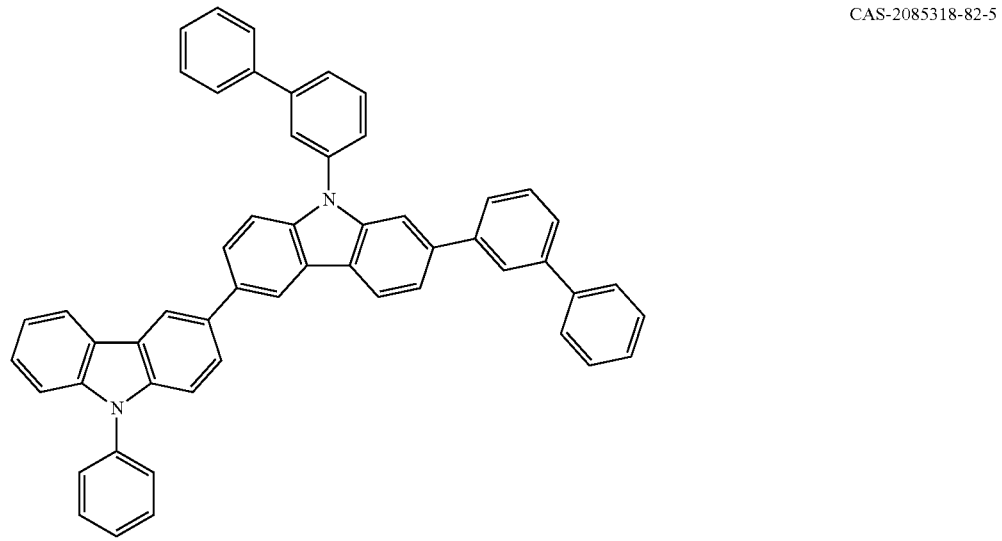 | CAS-2085318-82-5 |
| 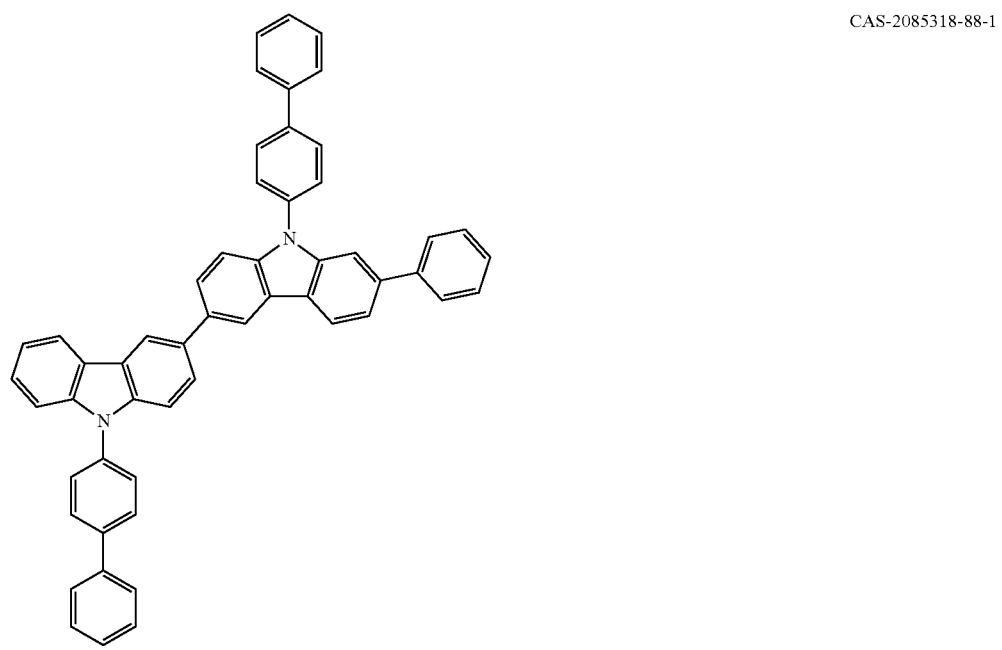 | CAS-2085318-88-1 |

| Structure | CAS-number |
|---|---|
| 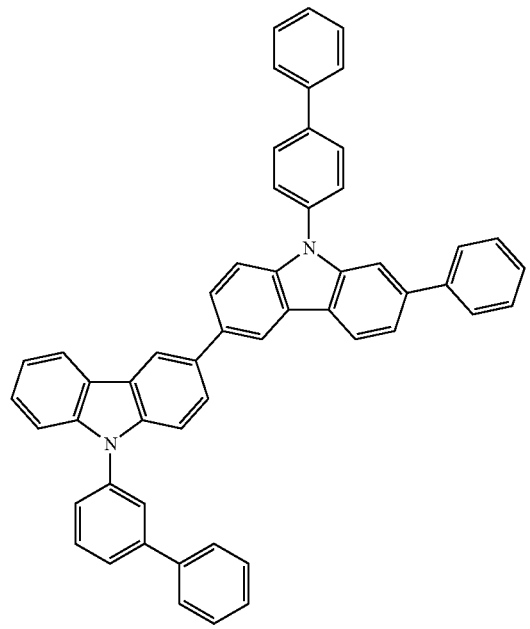 [SMILES: c1ccc(-c2ccc(-n3c4ccc(-c5ccc6c(c5)c5ccccc5n6-c5cccc(-c6ccccc6)c5)cc4c4ccc(-c5ccccc5)cc43)cc2)cc1] | CAS-2085318-87-0 |
| 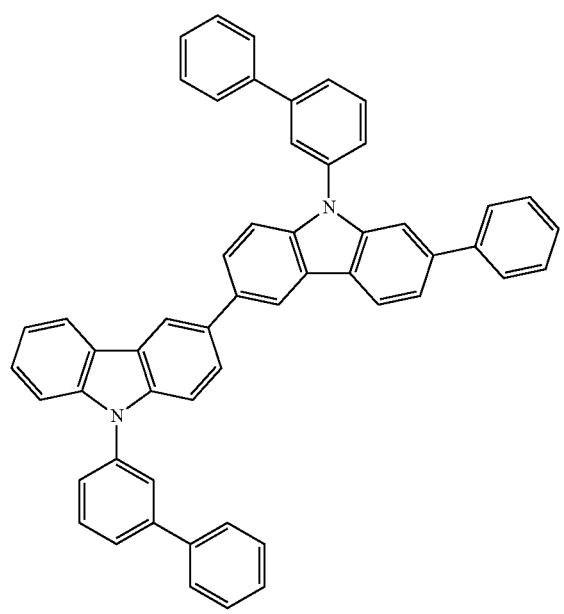 [SMILES: c1ccc(-c2cccc(-n3c4ccccc4c4cc(-c5ccc6c(c5)c5ccc(-c7ccccc7)cc5n6-c5cccc(-c6ccccc6)c5)ccc43)c2)cc1] | CAS-2085318-92-7 |

| Structure | CAS-number |
|---|---|
| 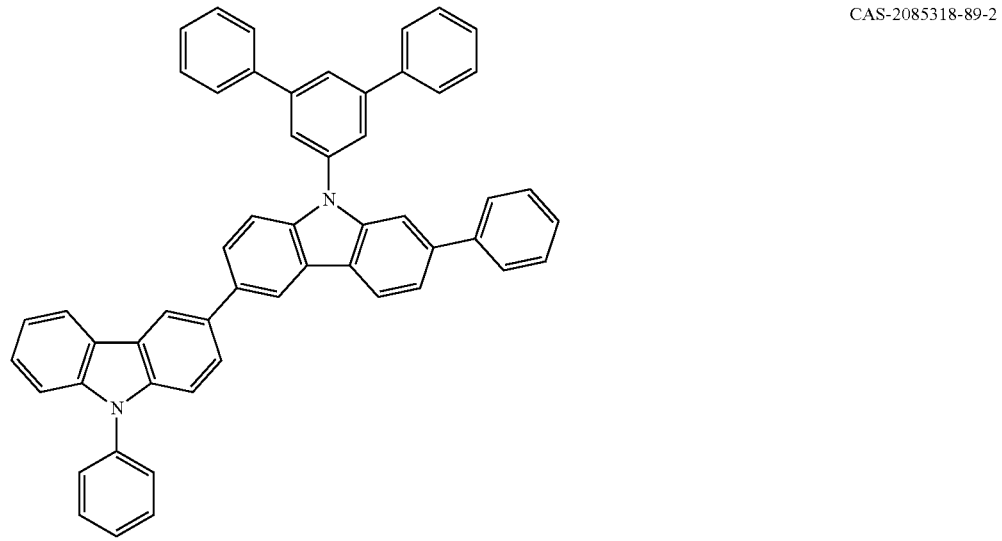 | CAS-2085318-89-2 |
| 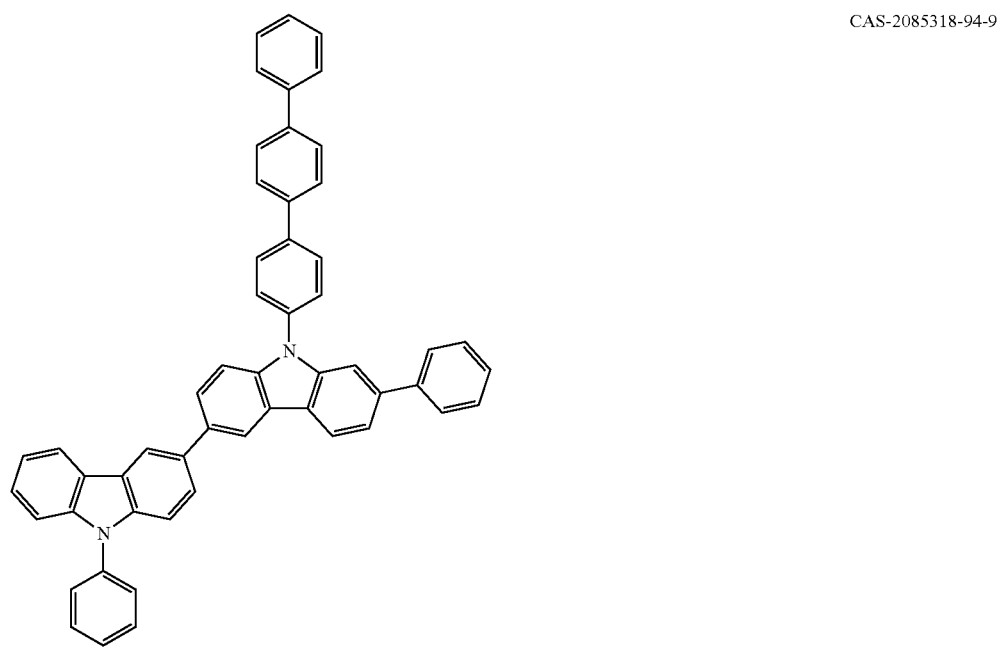 | CAS-2085318-94-9 |

| Structure | CAS-number |
|---|---|
| 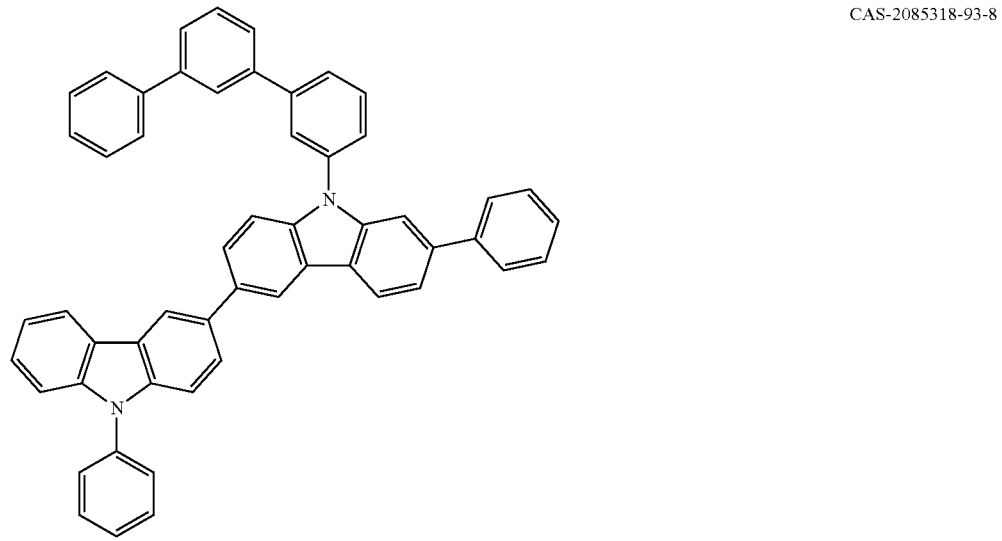 | CAS-2085318-93-8 |
| 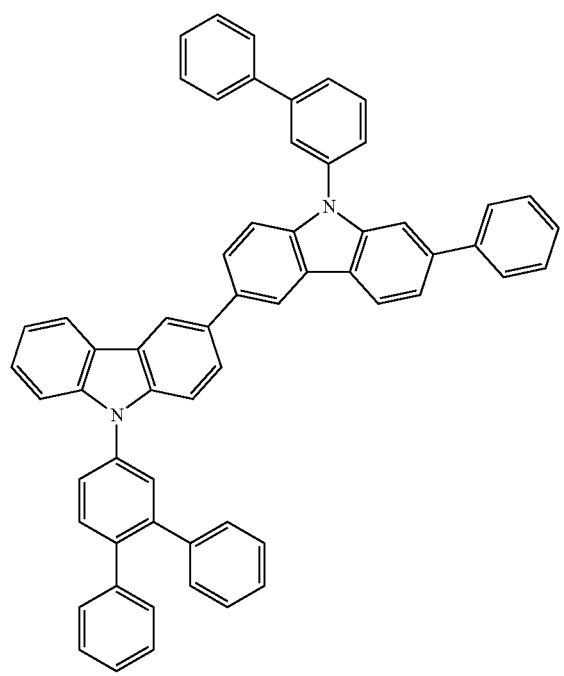 [SMILES: c1ccc(-c2cccc(-n3c4ccc(-c5ccc6c(c5)c5ccccc5n6-c5ccc(-c6ccccc6)c(-c6ccccc6)c5)cc4c4ccc(-c5ccccc5)cc43)c2)cc1] | CAS-2085318-98-3 |

| Structure | CAS-number |
|---|---|
| 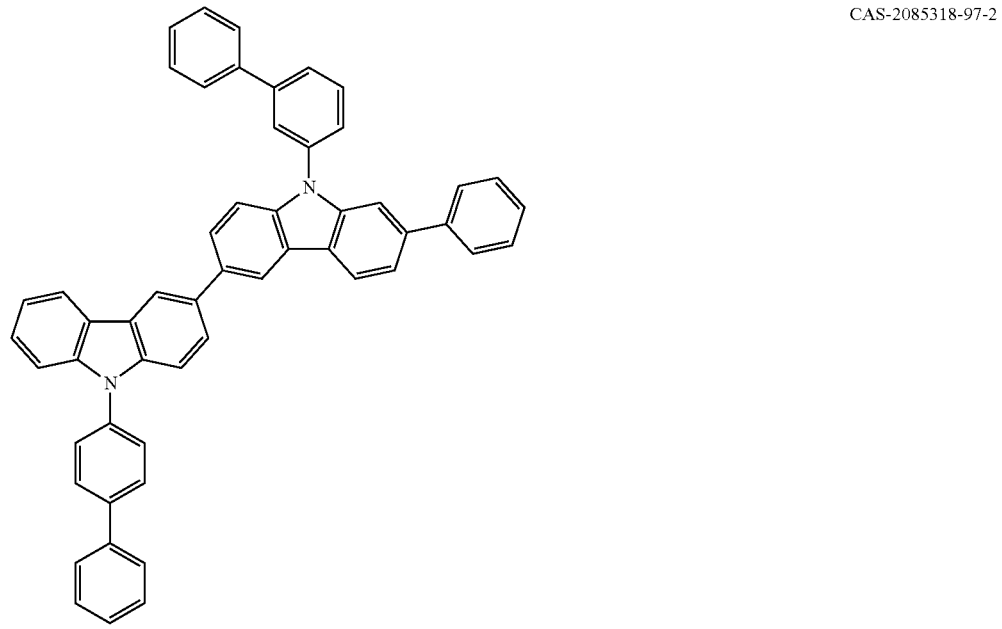 | CAS-2085318-97-2 |
| 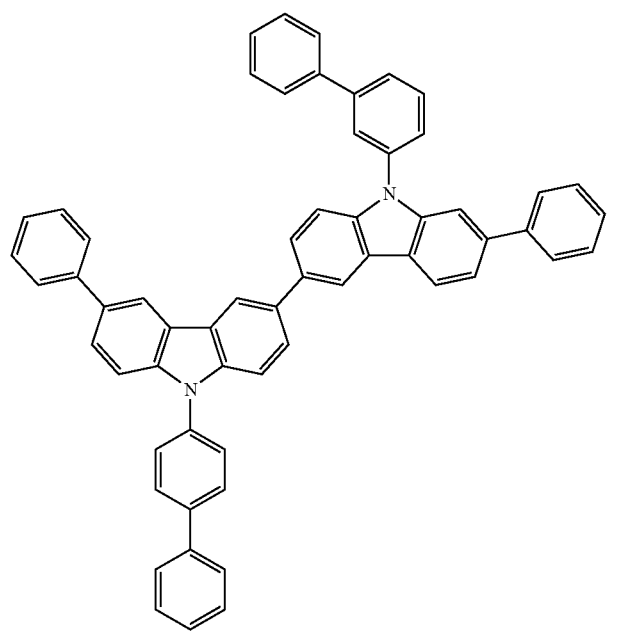 [SMILES: c1ccc(-c2ccc(-n3c4ccc(-c5ccccc5)cc4c4cc(-c5ccc6c(c5)c5ccc(-c7ccccc7)cc5n6-c5cccc(-c6ccccc6)c5)ccc43)cc2)cc1] | CAS-2085319-00-0 |

| Structure | CAS-number |
|---|---|
| 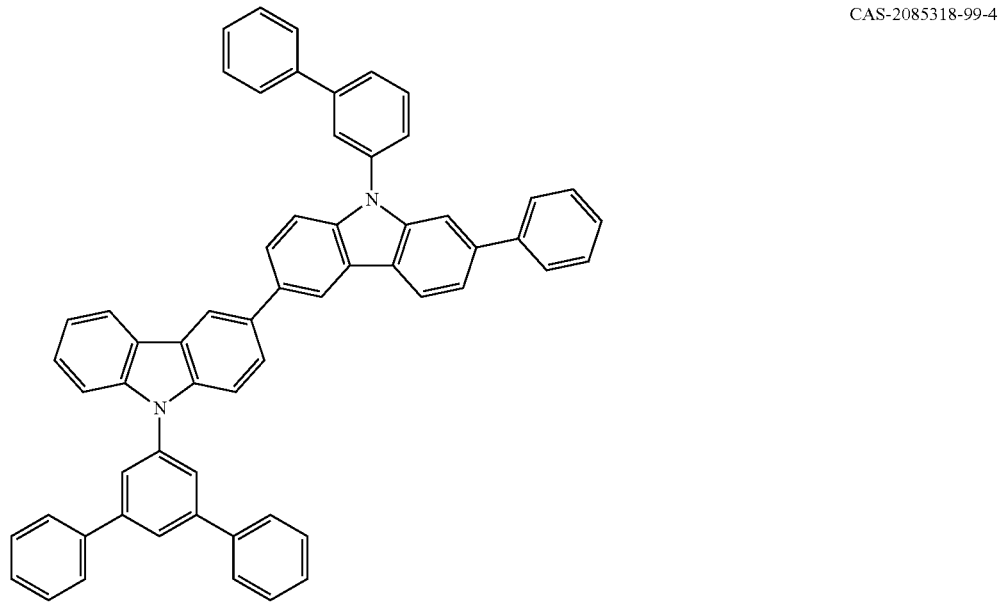 | CAS-2085318-99-4 |
| 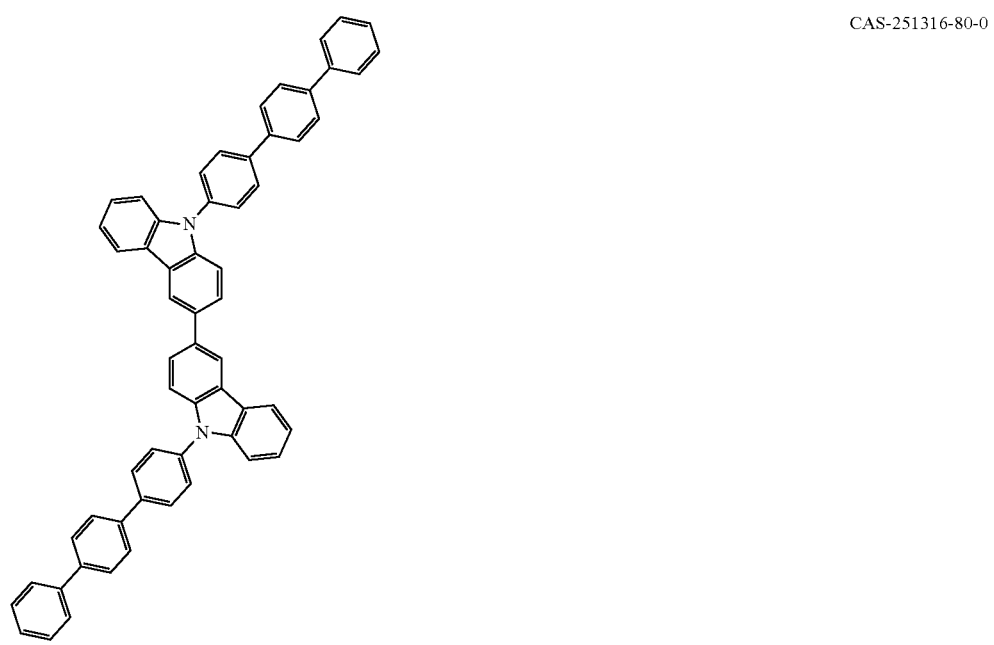 | CAS-251316-80-0 |

| Structure | CAS-number |
|---|---|
| 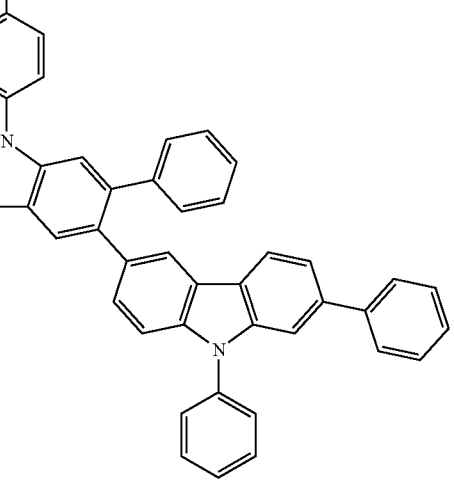 | CAS-2085319-17-9 |
| 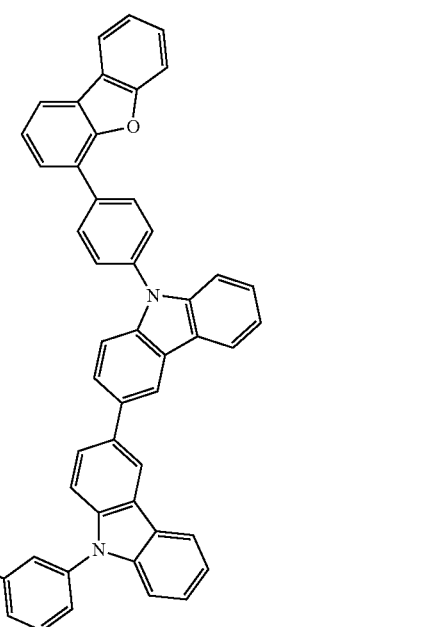 | |
| 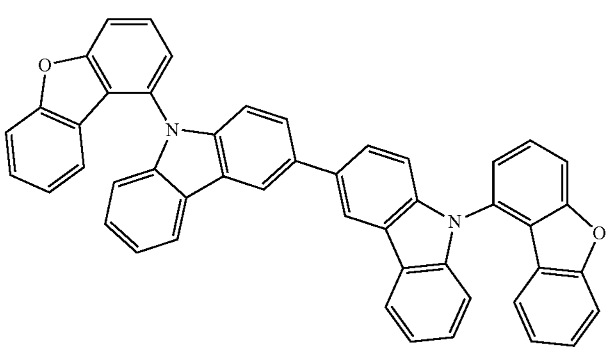 [SMILES: c1ccc2c(c1)oc1cccc(-n3c4ccccc4c4cc(-c5ccc6c(c5)c5ccccc5n6-c5cccc6oc7ccccc7c56)ccc43)c12] | CAS-1427160-09-5 |

| Structure | CAS-number |
|---|---|
| 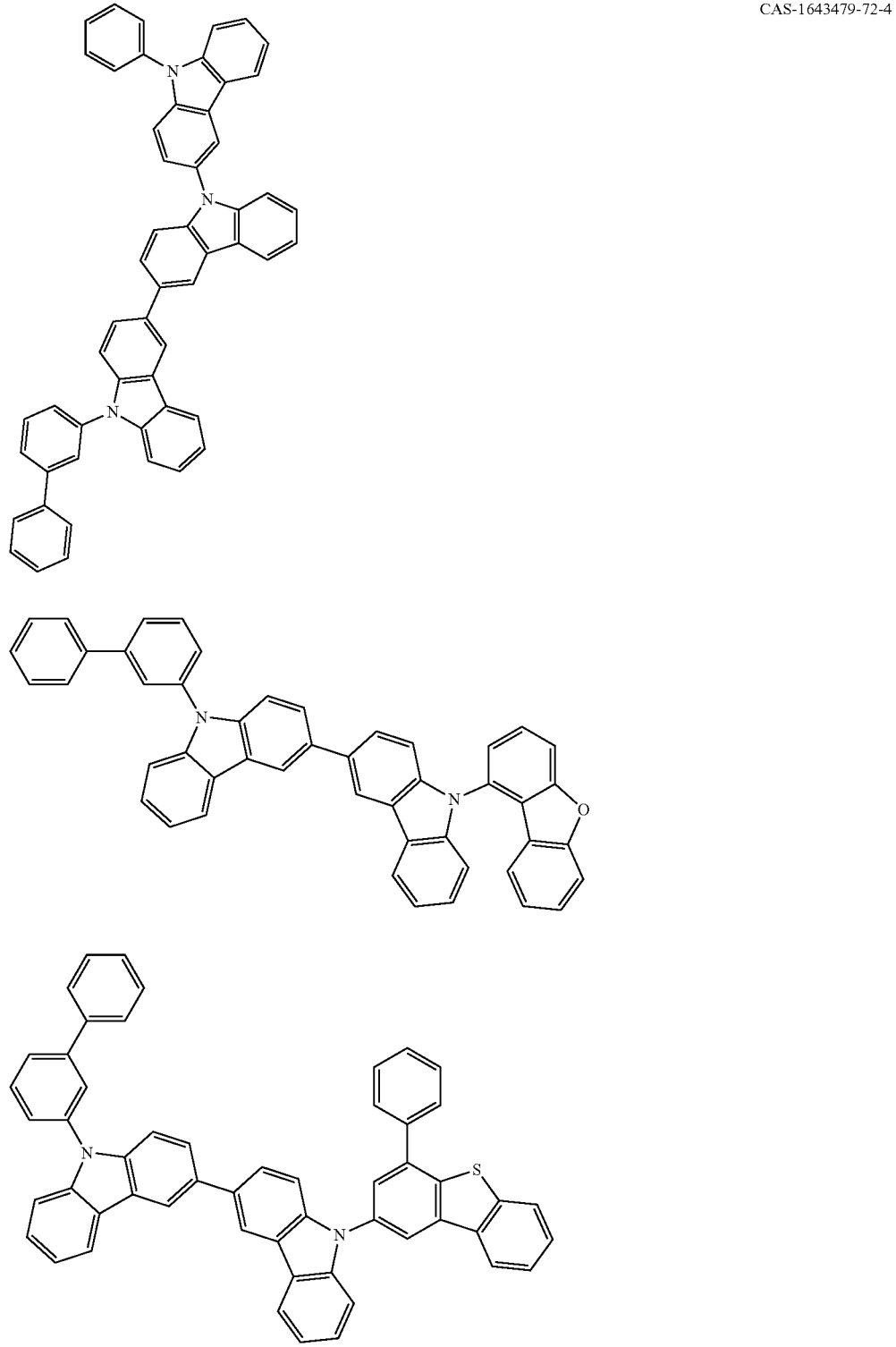 | CAS-1643479-72-4 |

| Structure | CAS-number |
|---|---|
| 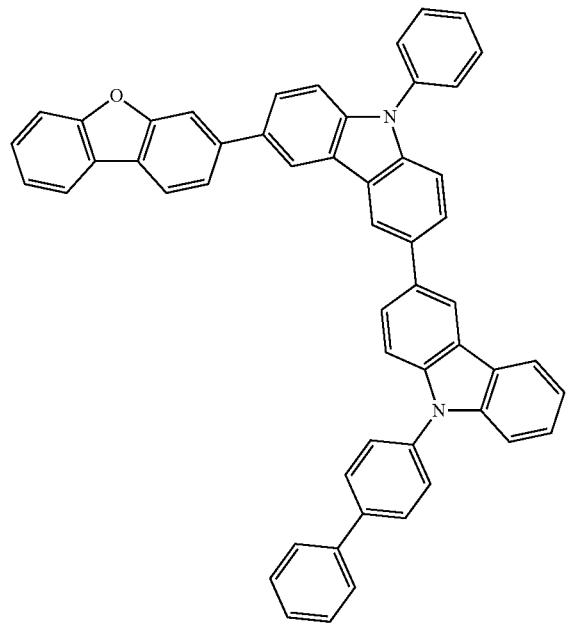 [SMILES: c1ccc(-c2ccc(-n3c4ccccc4c4cc(-c5ccc6c(c5)c5cc(-c7ccc8c(c7)oc7ccccc78)ccc5n6-c5ccccc5)ccc43)cc2)cc1] | CAS-1799959-65-1 |
| 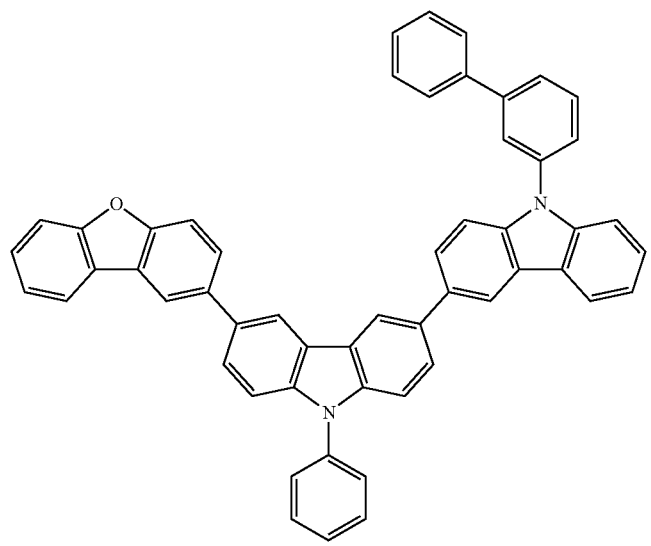 [SMILES: c1ccc(-c2cccc(-n3c4ccccc4c4cc(-c5ccc6c(c5)c5cc(-c7ccc8oc9ccccc9c8c7)ccc5n6-c5ccccc5)ccc43)c2)cc1] | CAS-1799959-74-2 |
| 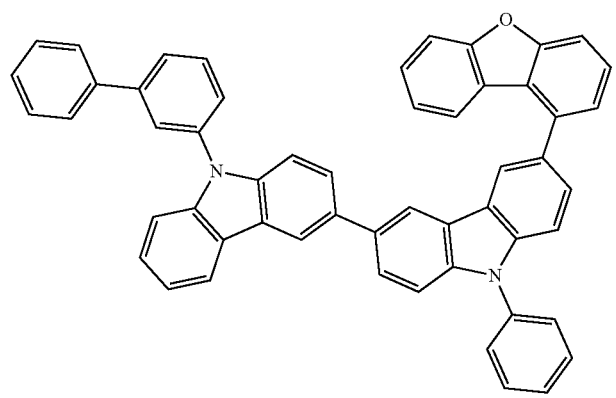 [SMILES: c1ccc(-c2cccc(-n3c4ccccc4c4cc(-c5ccc6c(c5)c5cc(-c7cccc8oc9ccccc9c78)ccc5n6-c5ccccc5)ccc43)c2)cc1] | CAS-1799959-75-3 |

| Structure | CAS-number |
|---|---|
| 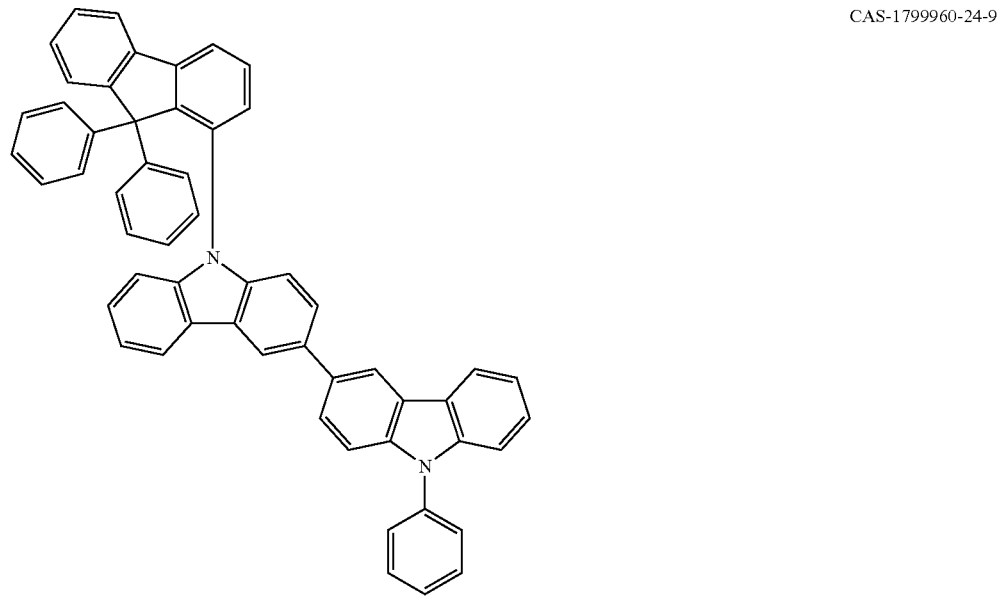 | CAS-1799960-24-9 |
| 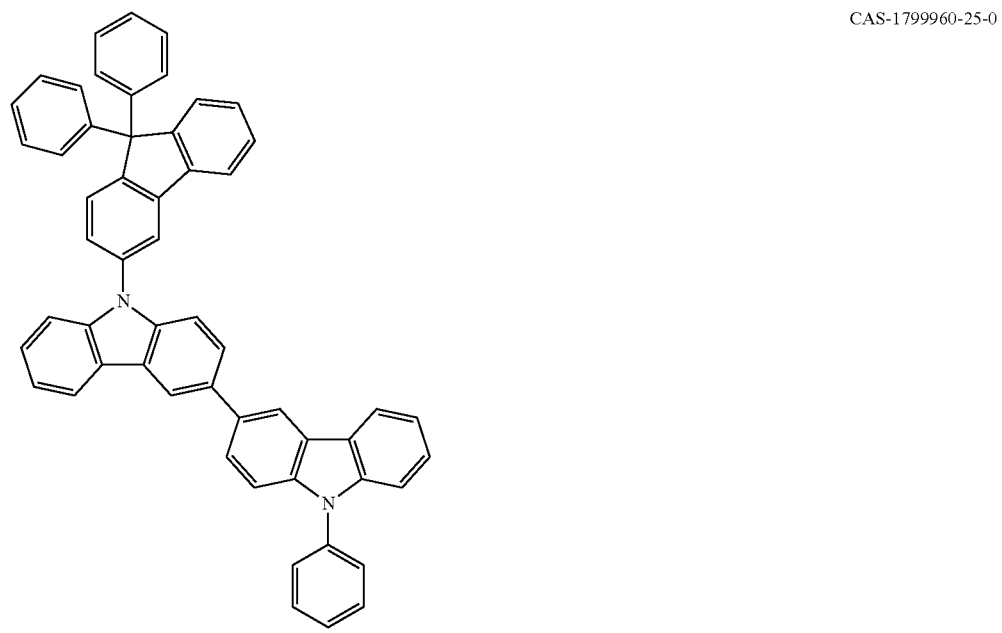 | CAS-1799960-25-0 |

| Structure | CAS-number |
|---|---|
| 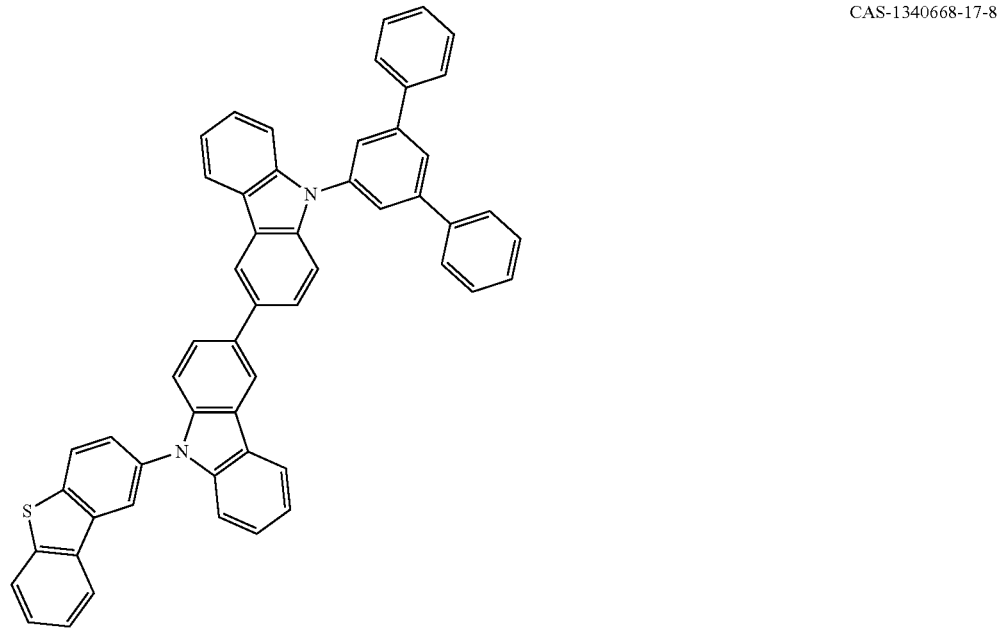 | CAS-1340668-17-8 |
| 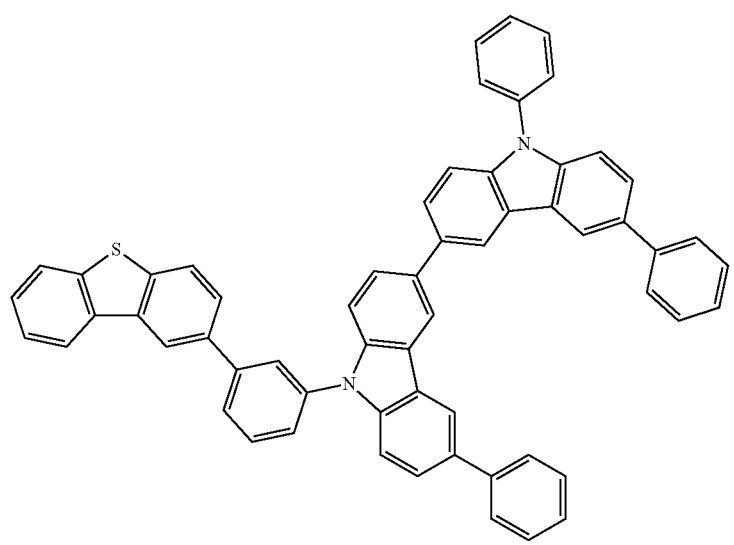 [SMILES: c1ccc(-c2ccc3c(c2)c2cc(-c4ccc5c(c4)c4cc(-c6ccccc6)ccc4n5-c4cccc(-c5ccc6sc7ccccc7c6c5)c4)ccc2n3-c2ccccc2)cc1] | CAS-1340668-19-0 |

| Structure | CAS-number |
|---|---|
| 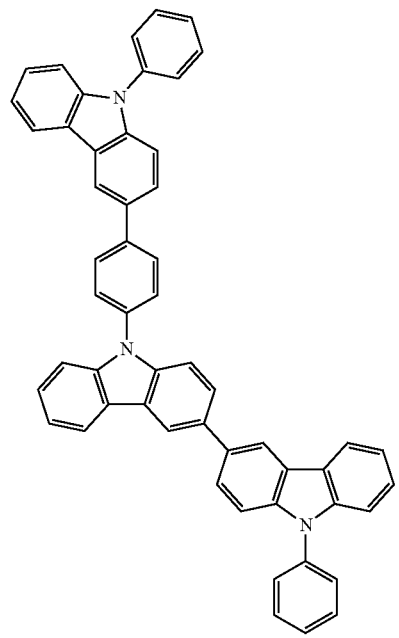 [SMILES: c1ccc(-n2c3ccccc3c3cc(-c4ccc(-n5c6ccccc6c6cc(-c7ccc8c(c7)c7ccccc7n8-c7ccccc7)ccc65)cc4)ccc32)cc1] | CAS-1289556-24-6 |
| 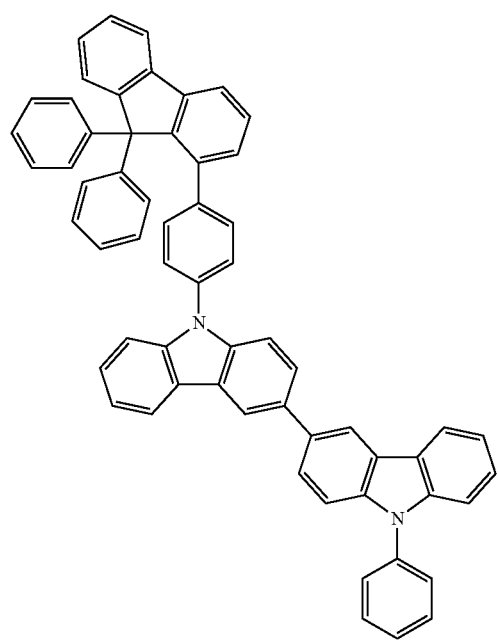 [SMILES: c1ccc(-n2c3ccccc3c3cc(-c4ccc5c(c4)c4ccccc4n5-c4ccc(-c5cccc6c5C(c5ccccc5)(c5ccccc5)c5ccccc5-6)cc4)ccc32)cc1] | CAS-1799960-56-7 |

| Structure | CAS-number |
|---|---|
| 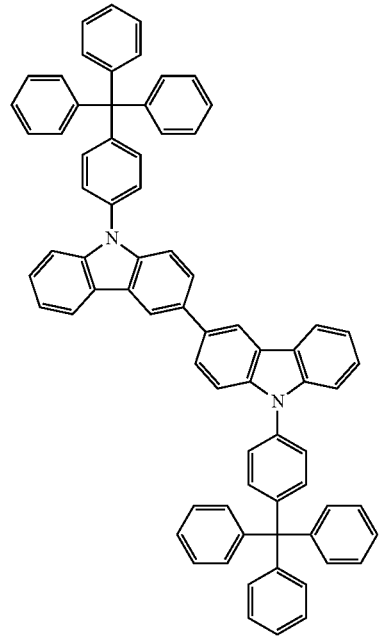 [SMILES: c1ccc(C(c2ccccc2)(c2ccccc2)c2ccc(-n3c4ccccc4c4cc(-c5ccc6c(c5)c5ccccc5n6-c5ccc(C(c6ccccc6)(c6ccccc6)c6ccccc6)cc5)ccc43)cc2)cc1] | CAS-1336889-27-0 |
| 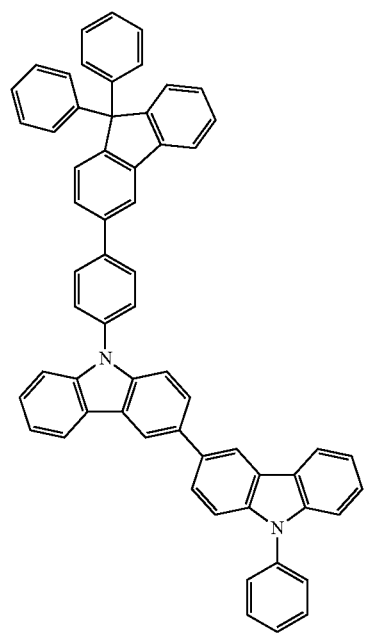 [SMILES: c1ccc(-n2c3ccccc3c3cc(-c4ccc5c(c4)c4ccccc4n5-c4ccc(-c5ccc6c(c5)-c5ccccc5C6(c5ccccc5)c5ccccc5)cc4)ccc32)cc1] | CAS-1799960-58-9 |

| Structure | CAS-number |
|---|---|
| 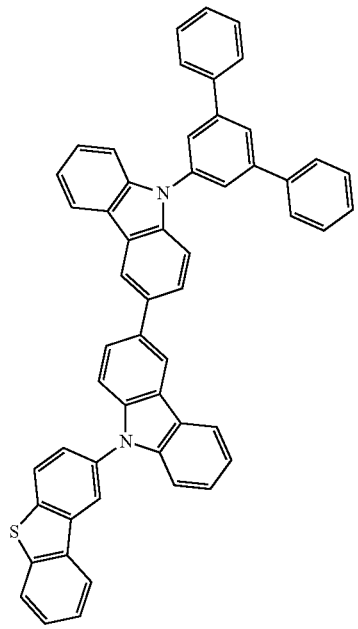 [SMILES: c1ccc(-c2cc(-c3ccccc3)cc(-n3c4ccccc4c4cc(-c5ccc6c(c5)c5ccccc5n6-c5ccc6sc7ccccc7c6c5)ccc43)c2)cc1] | CAS-1340668-17-8 |
| 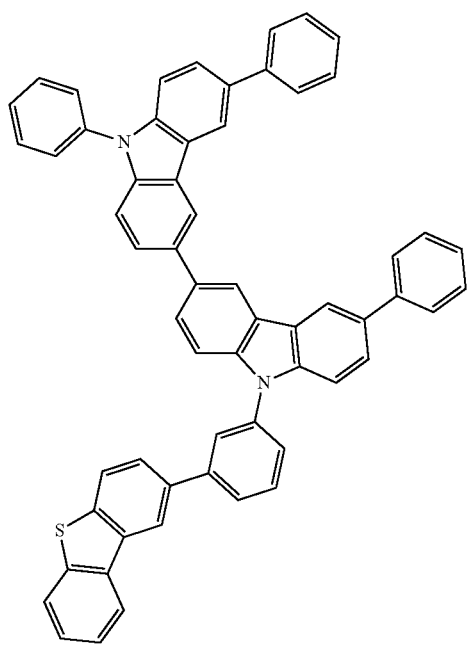 [SMILES: c1ccc(-c2ccc3c(c2)c2cc(-c4ccc5c(c4)c4cc(-c6ccccc6)ccc4n5-c4cccc(-c5ccc6sc7ccccc7c6c5)c4)ccc2n3-c2ccccc2)cc1] | CAS-1340668-19-0 |

| Structure | CAS-number |
|---|---|
| 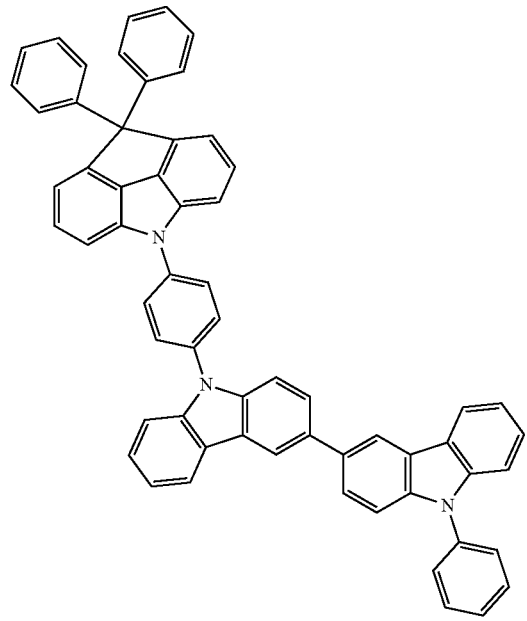 [SMILES: c1ccc(-n2c3ccccc3c3cc(-c4ccc5c(c4)c4ccccc4n5-c4ccc(-n5c6cccc7c6c6c(cccc65)C7(c5ccccc5)c5ccccc5)cc4)ccc32)cc1] | CAS-1812208-18-6 |
| 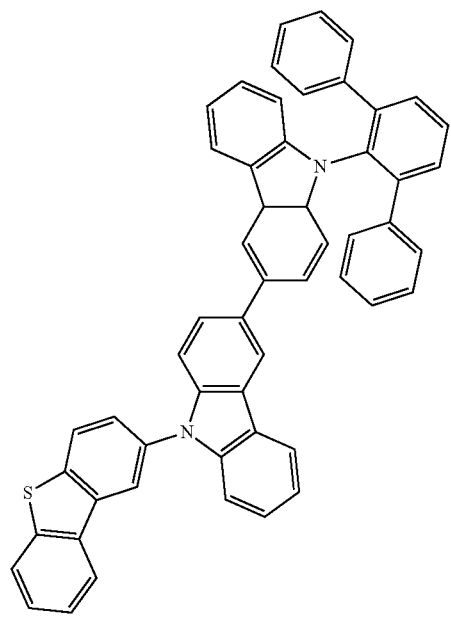 [SMILES: C1=CC2C(C=C1c1ccc3c(c1)c1ccccc1n3-c1ccc3sc4ccccc4c3c1)c1ccccc1N2c1c(-c2ccccc2)cccc1-c1ccccc1] | CAS-1340668-35-0 |

| Structure | CAS-number |
|---|---|
| 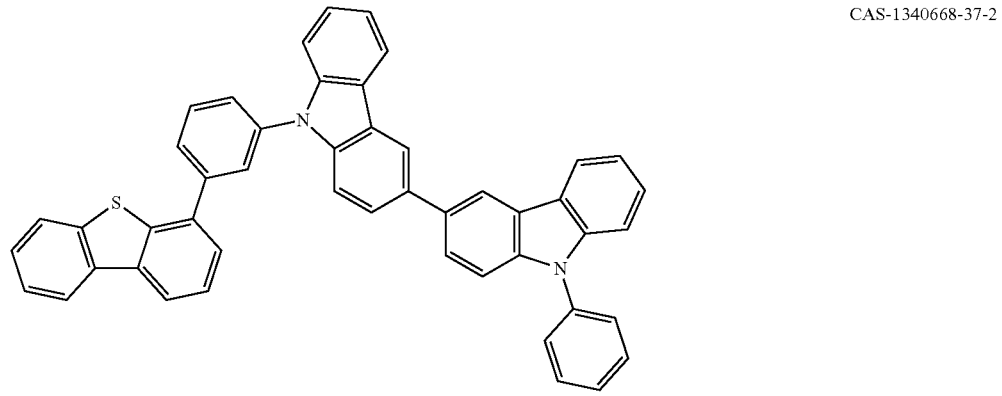 | CAS-1340668-37-2 |
| 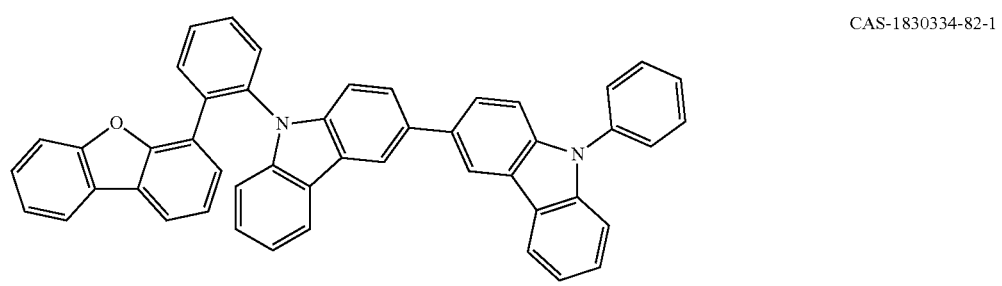 | CAS-1830334-82-1 |
| 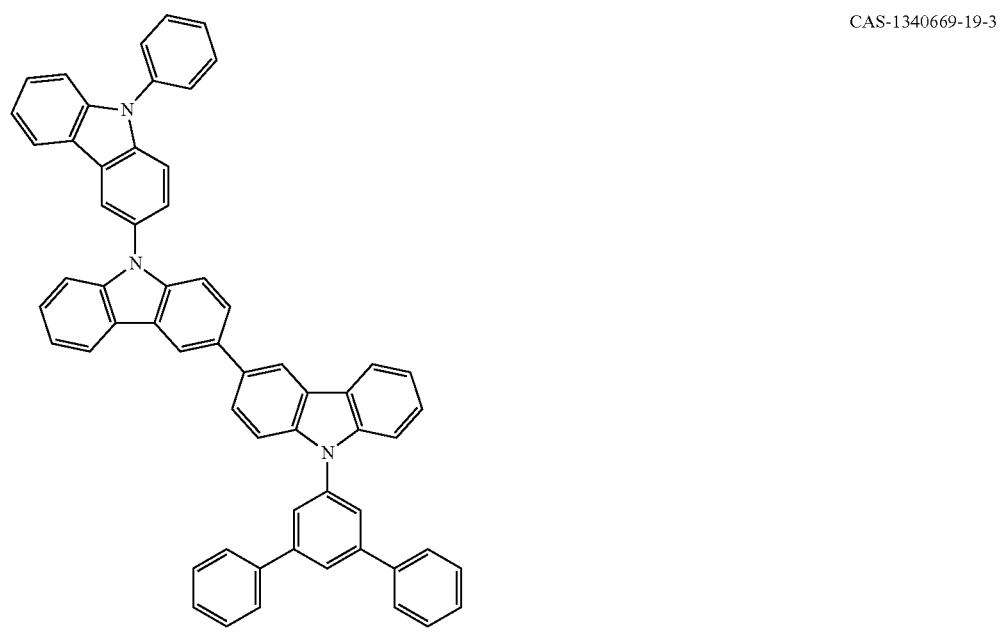 | CAS-1340669-19-3 |

-continued
| Structure | CAS-number |
|---|---|
| 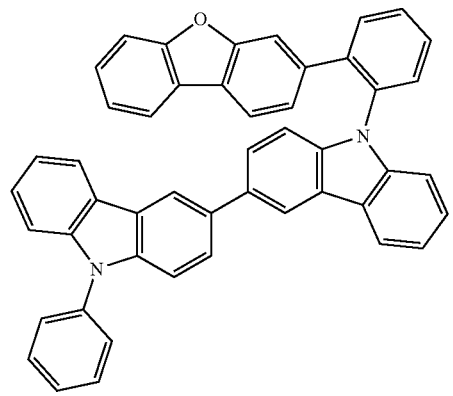 [SMILES: c1ccc(-n2c3ccccc3c3cc(-c4ccc5c(c4)c4ccccc4n5-c4ccccc4-c4ccc5c(c4)oc4ccccc45)ccc32)cc1] | CAS-1830334-85-4 |
| 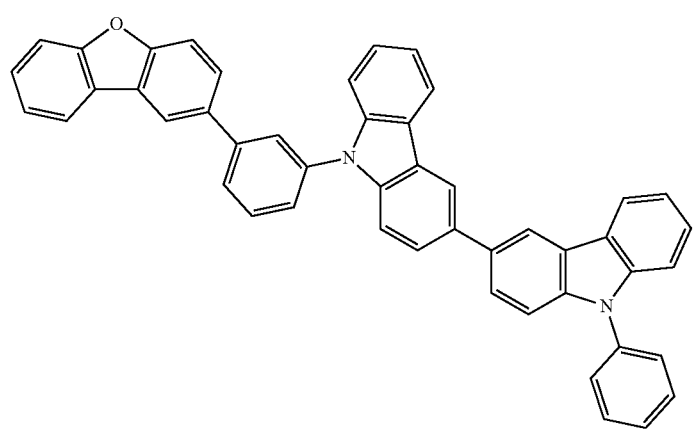 | CAS-1830334-94-5 |
| 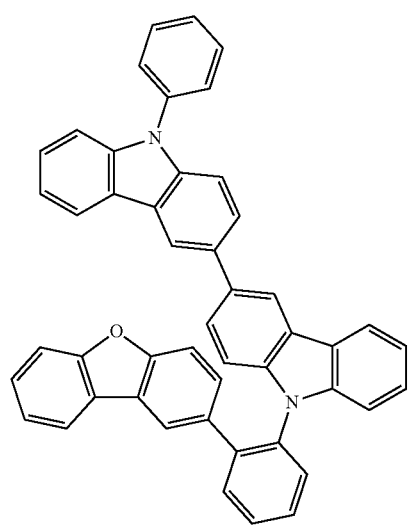 | CAS-1830334-88-7 |

| Structure | CAS-number |
|---|---|
| 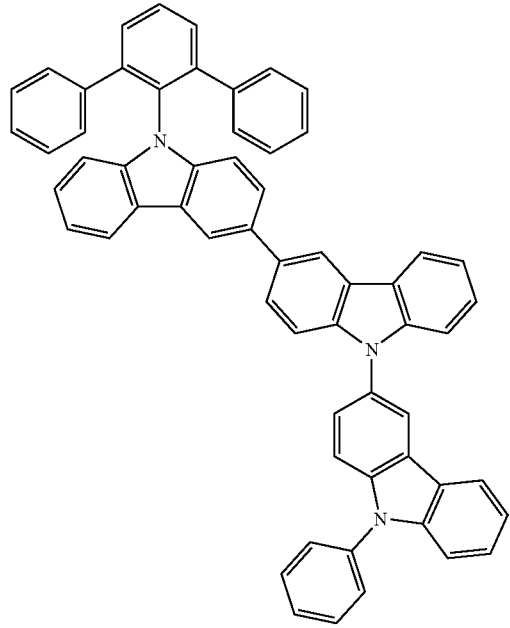 [SMILES: c1ccc(-c2cccc(-c3ccccc3)c2-n2c3ccccc3c3cc(-c4ccc5c(c4)c4ccccc4n5-c4ccc5c(c4)c4ccccc4n5-c4ccccc4)ccc32)cc1] | CAS-1340669-32-0 |
| 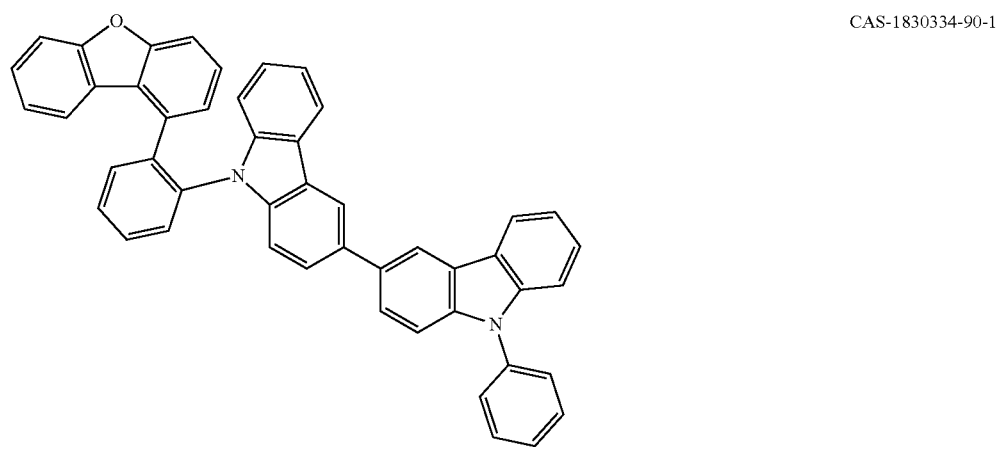 | CAS-1830334-90-1 |
| 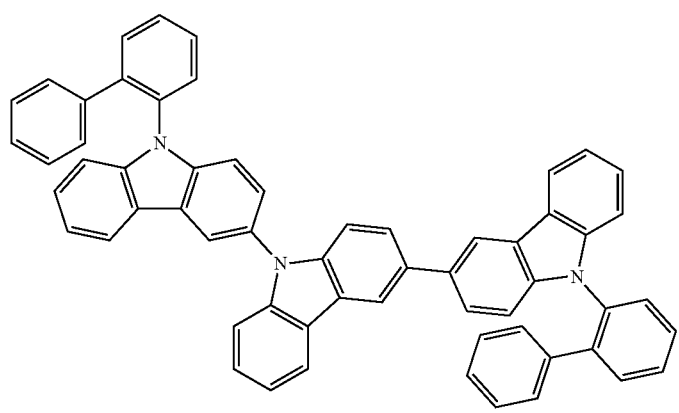 [SMILES: c1ccc(-c2ccccc2-n2c3ccccc3c3cc(-c4ccc5c(c4)c4ccccc4n5-c4ccc5c(c4)c4ccccc4n5-c4ccccc4-c4ccccc4)ccc32)cc1] | CAS-1340669-33-1 |

| Structure | CAS-number |
|---|---|
| 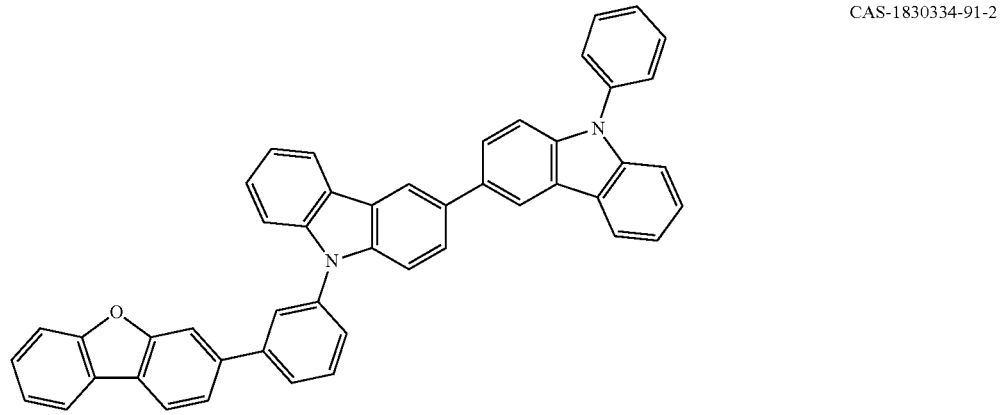 | CAS-1830334-91-2 |
| 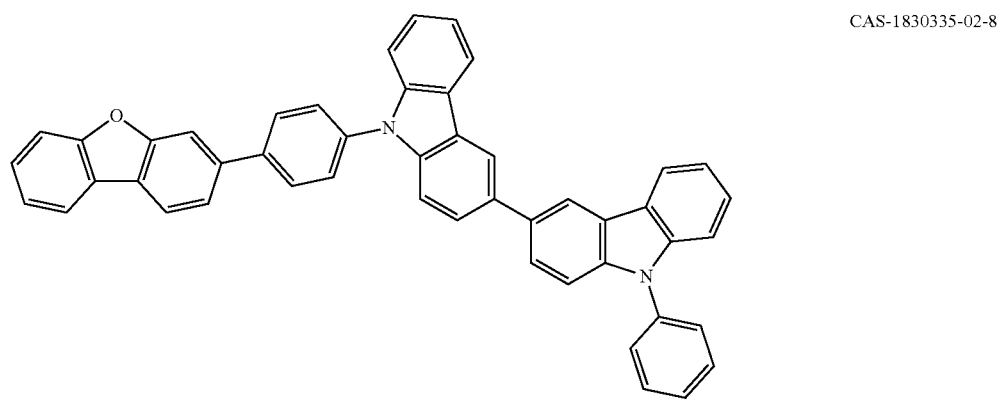 | CAS-1830335-02-8 |
| 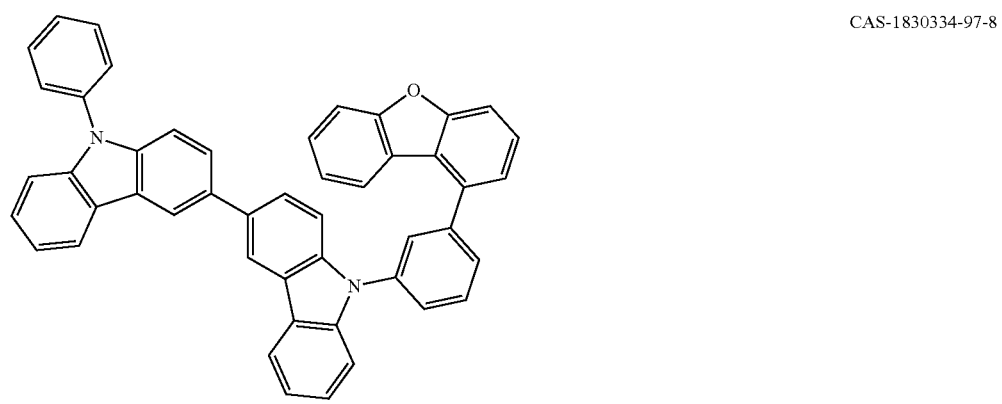 | CAS-1830334-97-8 |
| 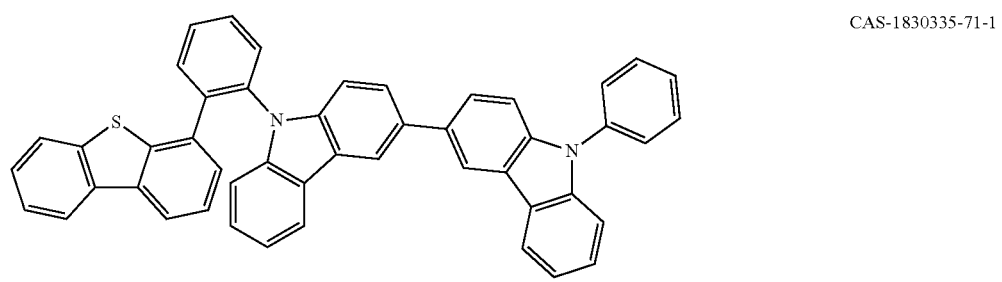 | CAS-1830335-71-1 |

| Structure | CAS-number |
|---|---|
| 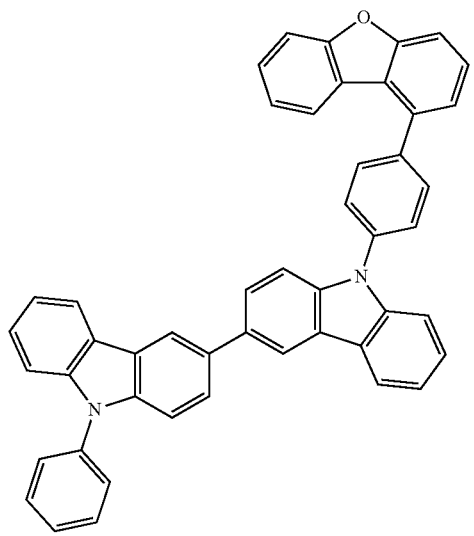 [SMILES: c1ccc(-n2c3ccccc3c3cc(-c4ccc5c(c4)c4ccccc4n5-c4ccc(-c5cccc6oc7ccccc7c56)cc4)ccc32)cc1] | CAS-1830335-07-3 |
| 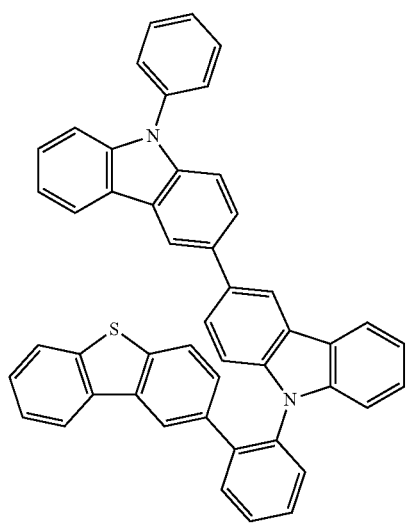 [SMILES: c1ccc(-n2c3ccccc3c3cc(-c4ccc5c(c4)c4ccccc4n5-c4ccccc4-c4ccc5sc6ccccc6c5c4)ccc32)cc1] | CAS-1830335-76-6 |
| 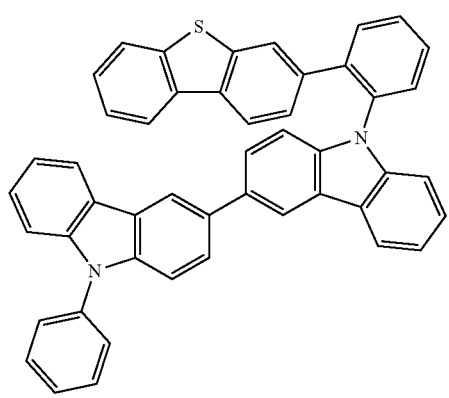 [SMILES: c1ccc(-n2c3ccccc3c3cc(-c4ccc5c(c4)c4ccccc4n5-c4ccccc4-c4ccc5c(c4)sc4ccccc45)ccc32)cc1] | CAS-1830335-72-2 |

| Structure | CAS-number |
|---|---|
| 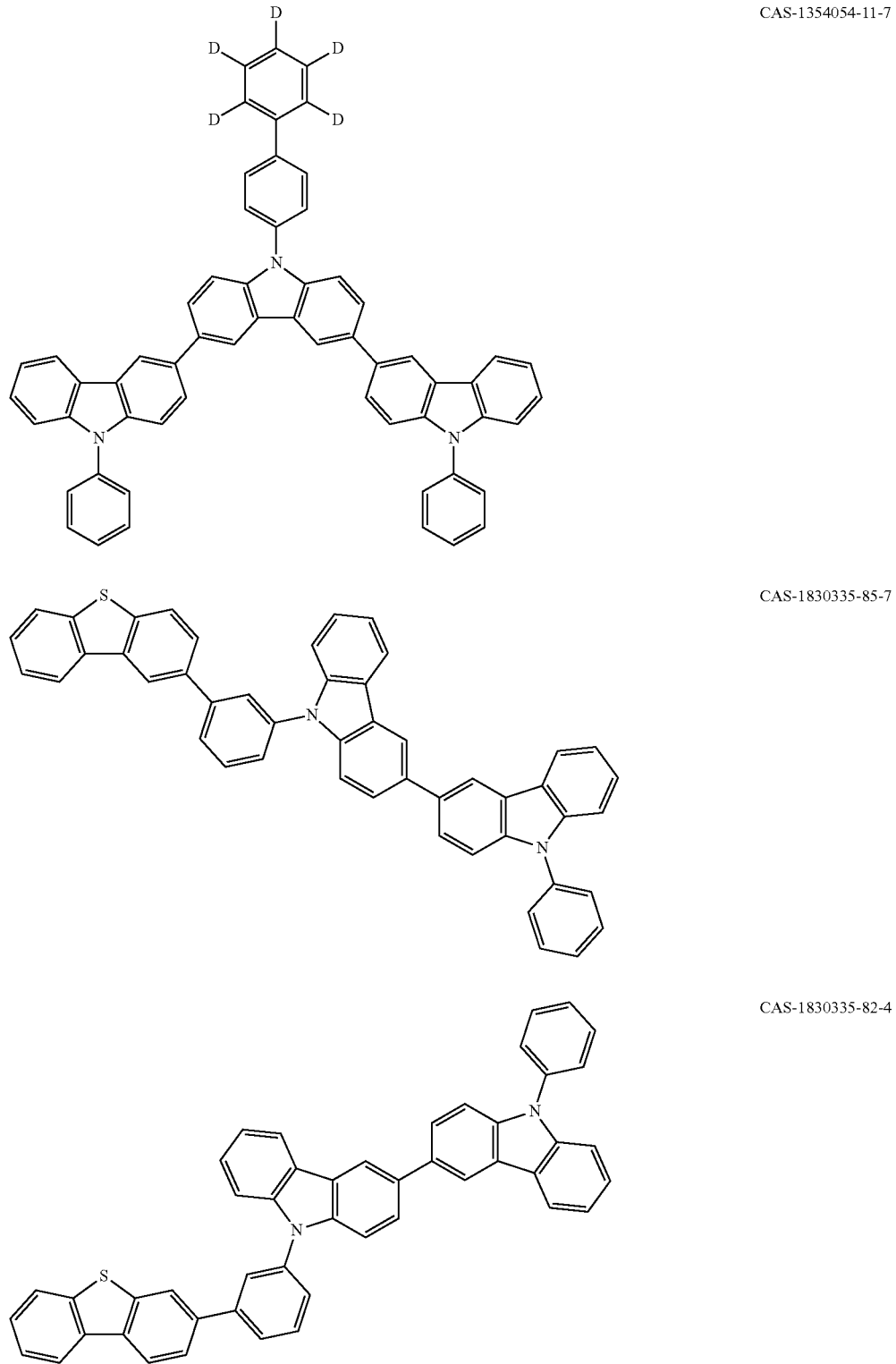 | CAS-1354054-11-7 |
| 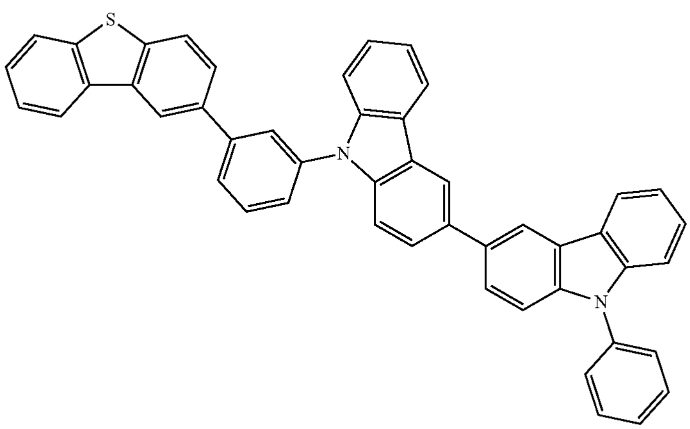 | CAS-1830335-85-7 |
| 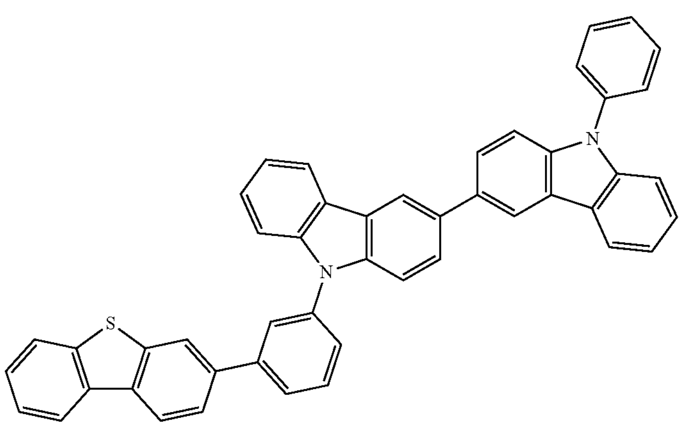 | CAS-1830335-82-4 |

| Structure | CAS-number |
|---|---|
| 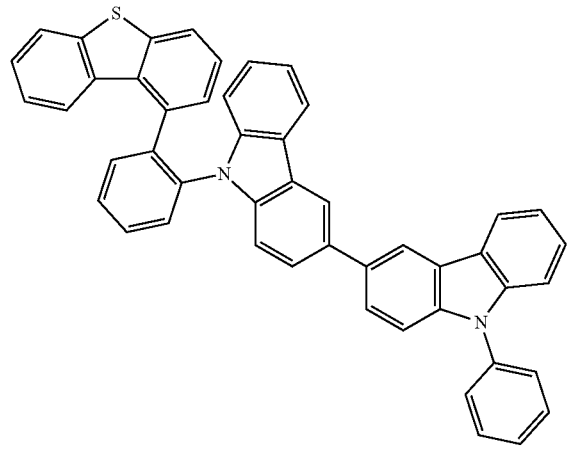 [SMILES: c1ccc(-n2c3ccccc3c3cc(-c4ccc5c(c4)c4ccccc4n5-c4ccccc4-c4cccc5sc6ccccc6c45)ccc32)cc1] | CAS-1830335-79-9 |
| 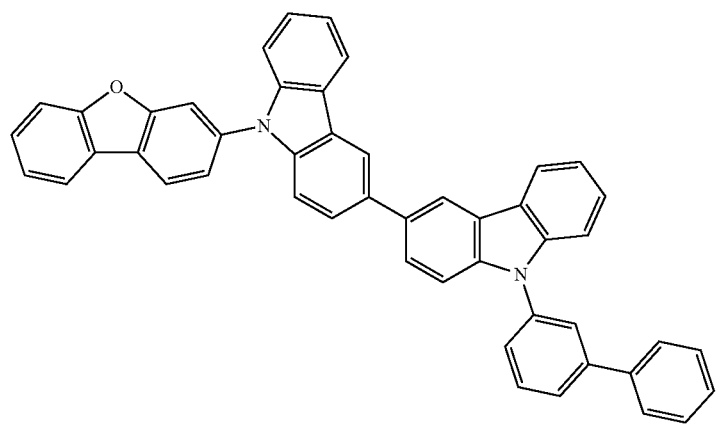 [SMILES: c1ccc(-c2cccc(-n3c4ccccc4c4cc(-c5ccc6c(c5)c5ccccc5n6-c5ccc6c(c5)oc5ccccc56)ccc43)c2)cc1] | CAS-1830339-40-6 |
| 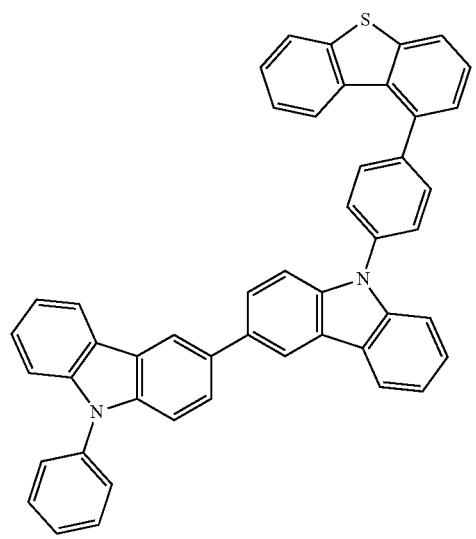 [SMILES: c1ccc(-n2c3ccccc3c3cc(-c4ccc5c(c4)c4ccccc4n5-c4ccc(-c5cccc6sc7ccccc7c56)cc4)ccc32)cc1] | CAS-1830335-95-9 |

| Structure | CAS-number |
|---|---|
| 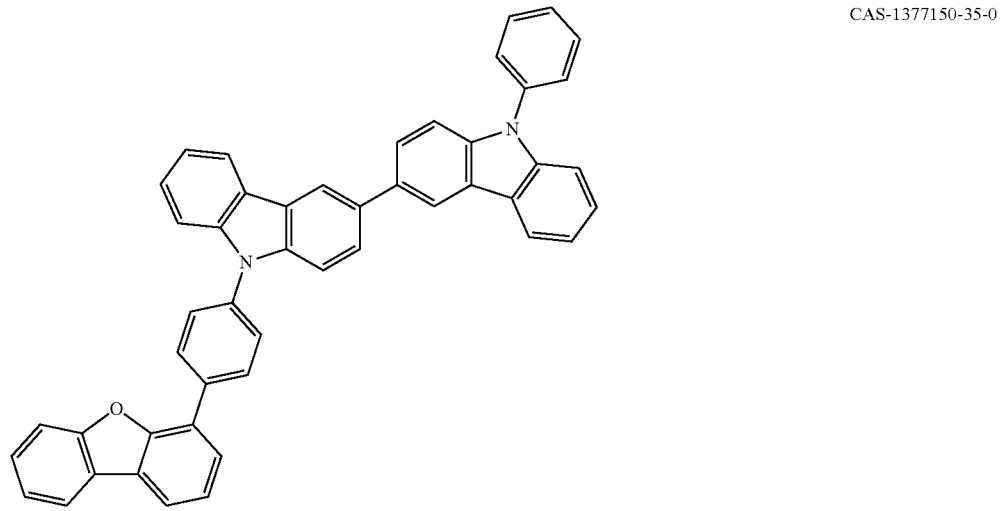 | CAS-1377150-35-0 |
| 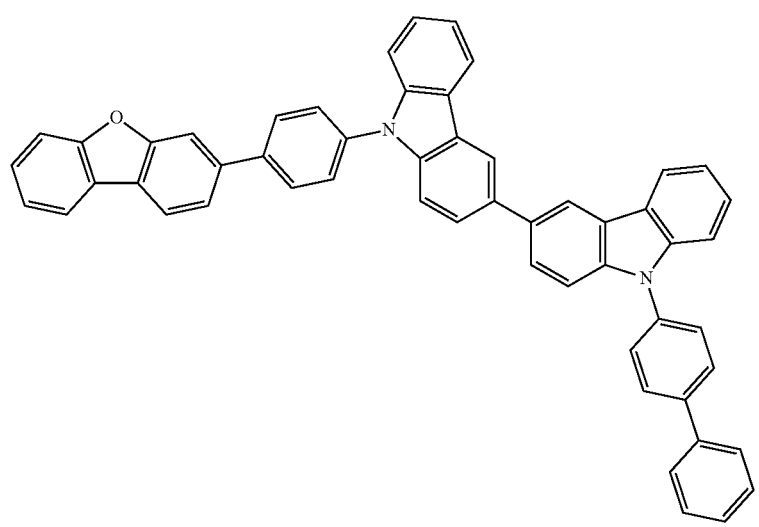 [SMILES: c1ccc(-c2ccc(-n3c4ccccc4c4cc(-c5ccc6c(c5)c5ccccc5n6-c5ccc(-c6ccc7c(c6)oc6ccccc67)cc5)ccc43)cc2)cc1] | CAS-1830339-41-7 |

-continued
| Structure | CAS-number |
|---|---|
| 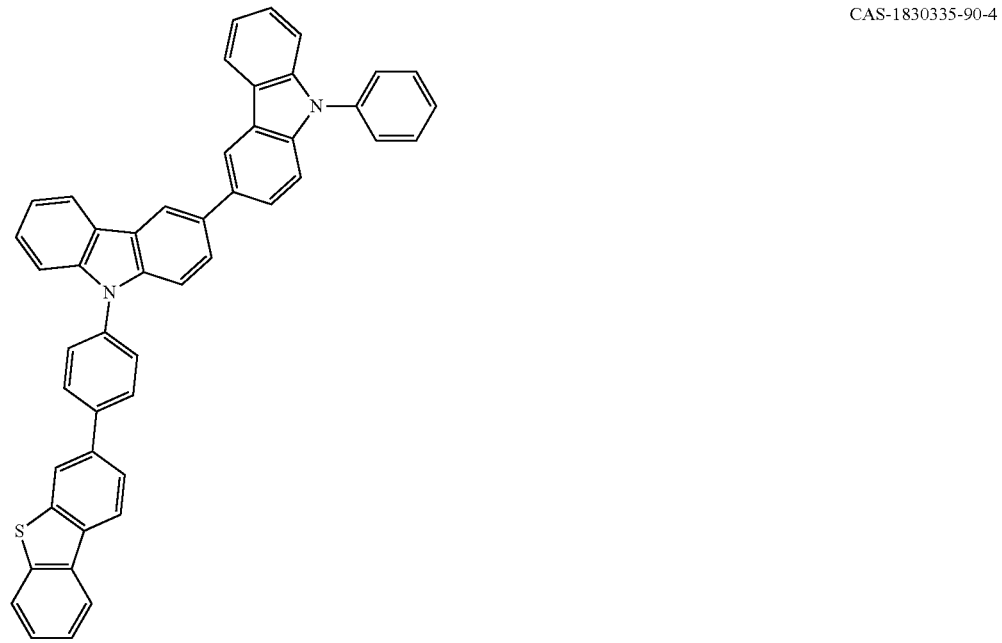 | CAS-1830335-90-4 |
| 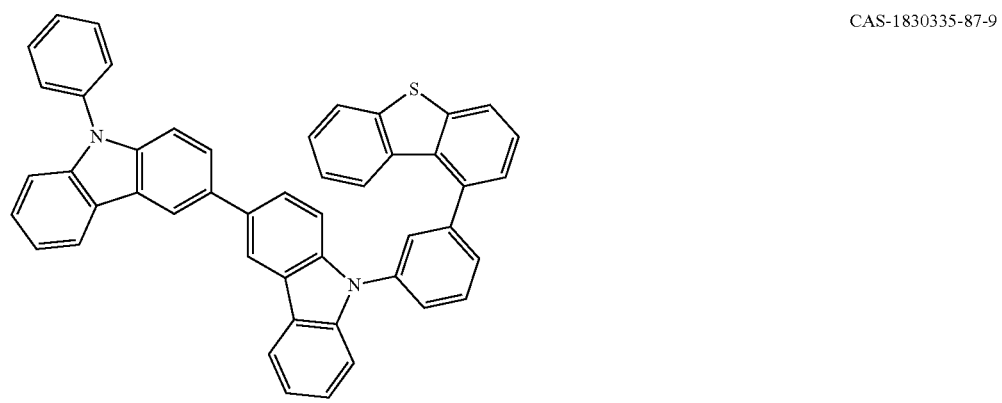 | CAS-1830335-87-9 |
| 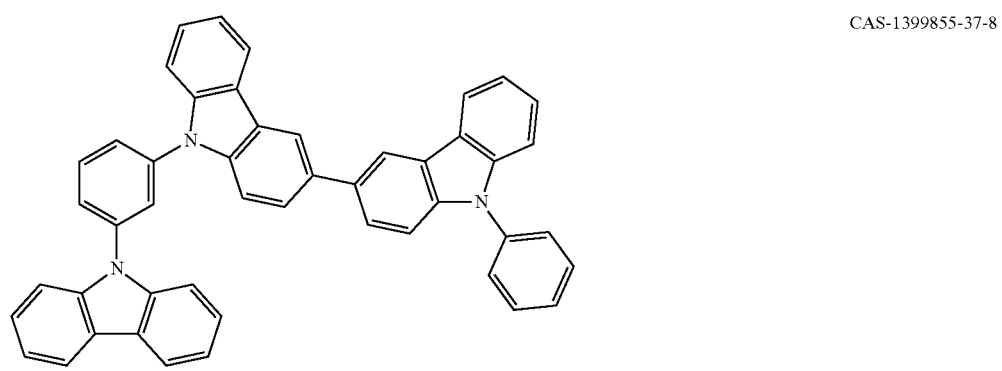 | CAS-1399855-37-8 |

| Structure | CAS-number |
|---|---|
| 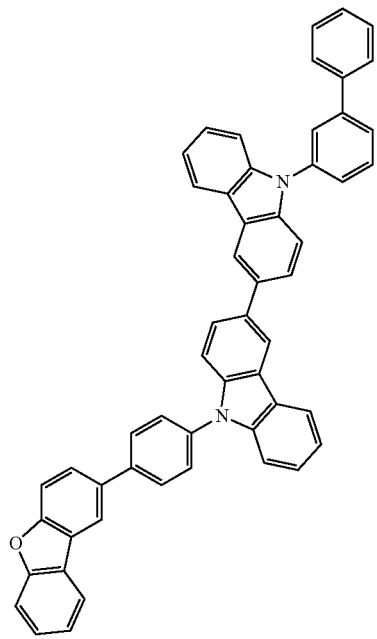 [SMILES: c1ccc(-c2cccc(-n3c4ccccc4c4cc(-c5ccc6c(c5)c5ccccc5n6-c5ccc(-c6ccc7oc8ccccc8c7c6)cc5)ccc43)c2)cc1] | CAS-1830339-42-8 |
| 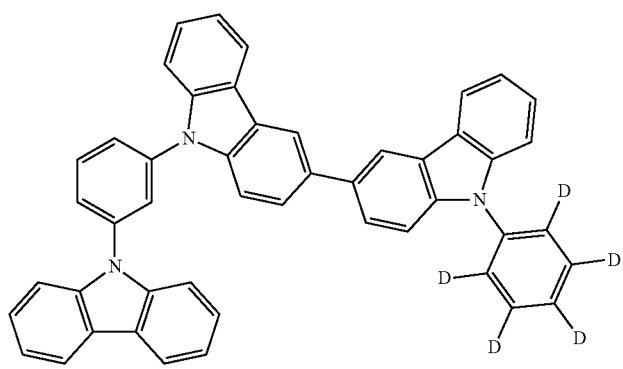 [SMILES: [2H]c1c([2H])c([2H])c(-n2c3ccccc3c3cc(-c4ccc5c(c4)c4ccccc4n5-c4cccc(-n5c6ccccc6c6ccccc65)c4)ccc32)c([2H])c1[2H]] | CAS-1399855-38-9 |
| 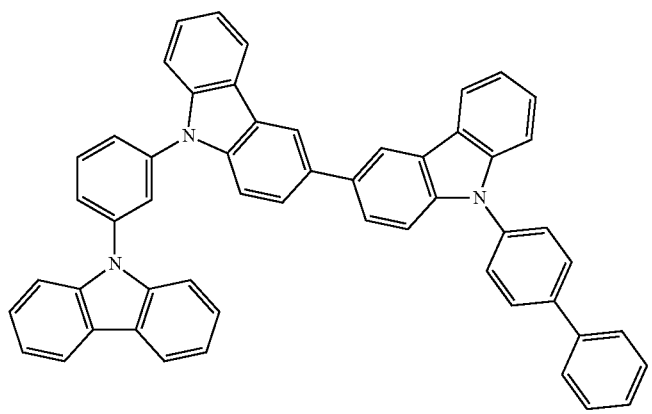 [SMILES: c1ccc(-c2ccc(-n3c4ccccc4c4cc(-c5ccc6c(c5)c5ccccc5n6-c5cccc(-n6c7ccccc7c7ccccc76)c5)ccc43)cc2)cc1] | CAS-1399855-39-0 |

| Structure | CAS-number |
|---|---|
| 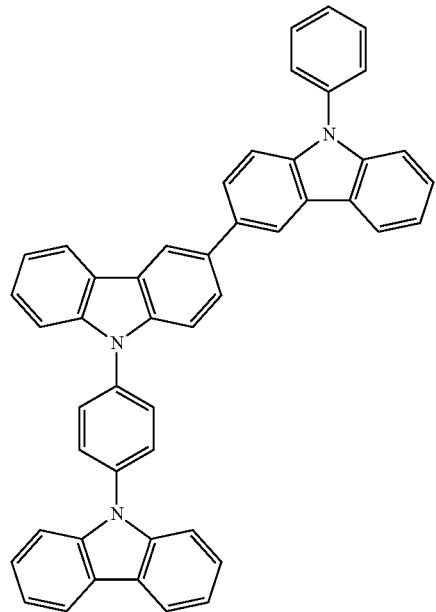 [SMILES: c1ccc(-n2c3ccccc3c3cc(-c4ccc5c(c4)c4ccccc4n5-c4ccc(-n5c6ccccc6c6ccccc65)cc4)ccc32)cc1] | CAS-1399855-46-9 |
| 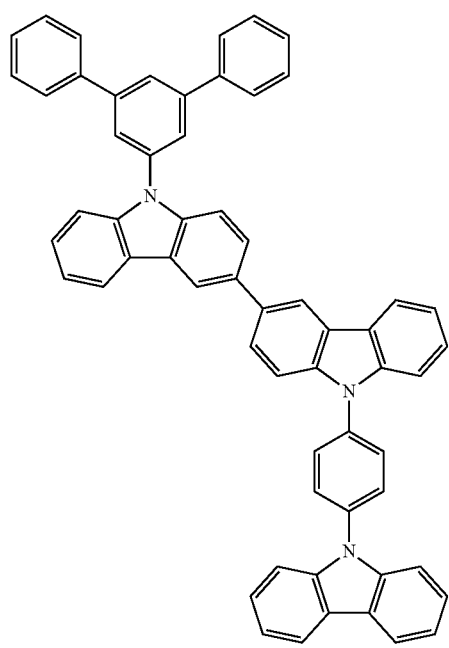 [SMILES: c1ccc(-c2cc(-c3ccccc3)cc(-n3c4ccccc4c4cc(-c5ccc6c(c5)c5ccccc5n6-c5ccc(-n6c7ccccc7c7ccccc76)cc5)ccc43)c2)cc1] | CAS-1399855-47-0 |

| Structure | CAS-number |
|---|---|
| 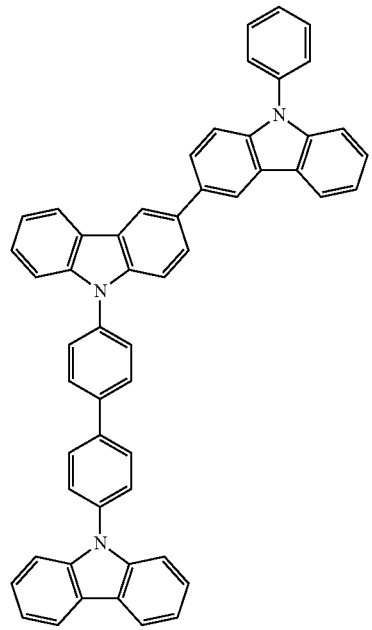 [SMILES: c1ccc(-n2c3ccccc3c3cc(-c4ccc5c(c4)c4ccccc4n5-c4ccc(-c5ccc(-n6c7ccccc7c7ccccc76)cc5)cc4)ccc32)cc1] | CAS-1413936-92-1 |
| 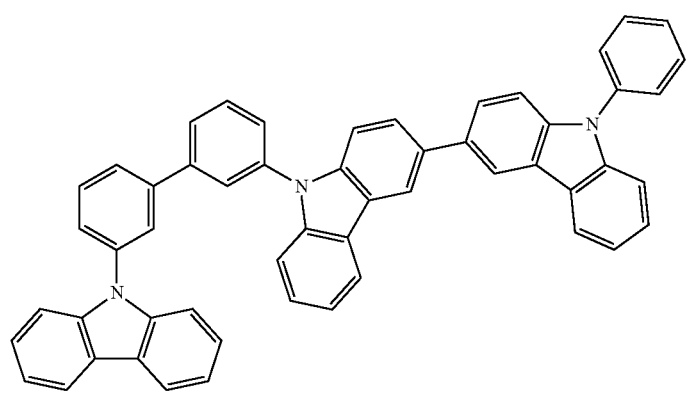 [SMILES: c1ccc(-n2c3ccccc3c3cc(-c4ccc5c(c4)c4ccccc4n5-c4cccc(-c5cccc(-n6c7ccccc7c7ccccc76)c5)c4)ccc32)cc1] | CAS-1413936-95-4 |

| Structure | CAS-number |
|---|---|
| 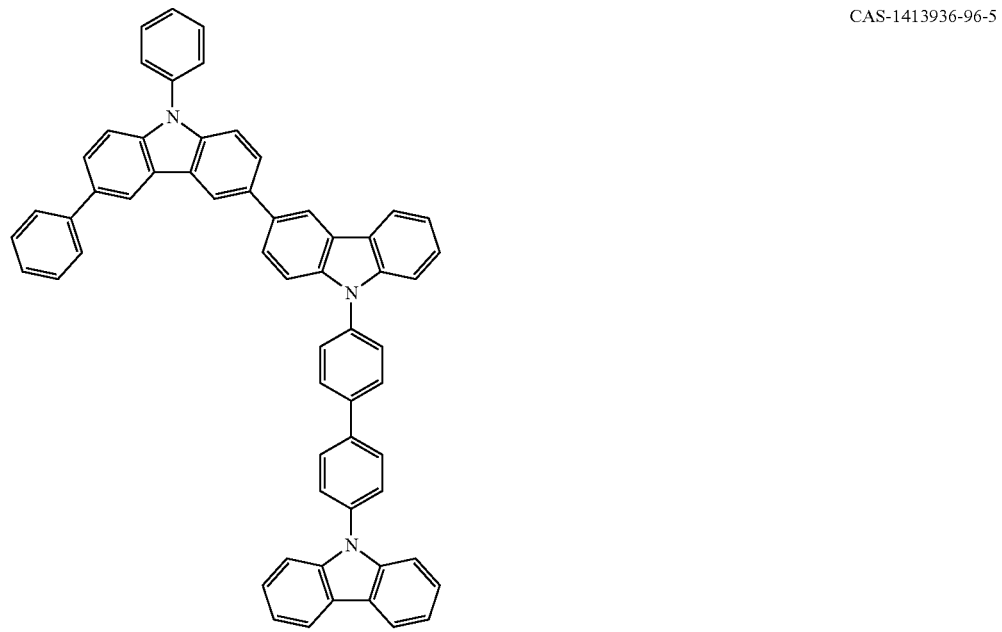 | CAS-1413936-96-5 |
| 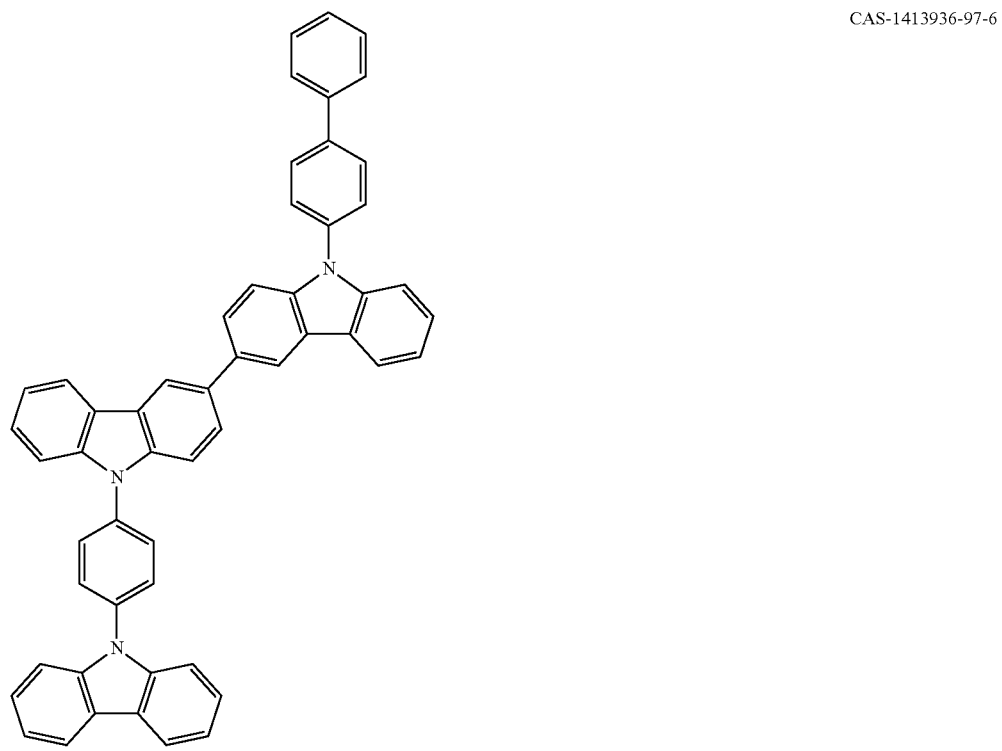 | CAS-1413936-97-6 |

-continued
| Structure | CAS-number |
|---|---|
| 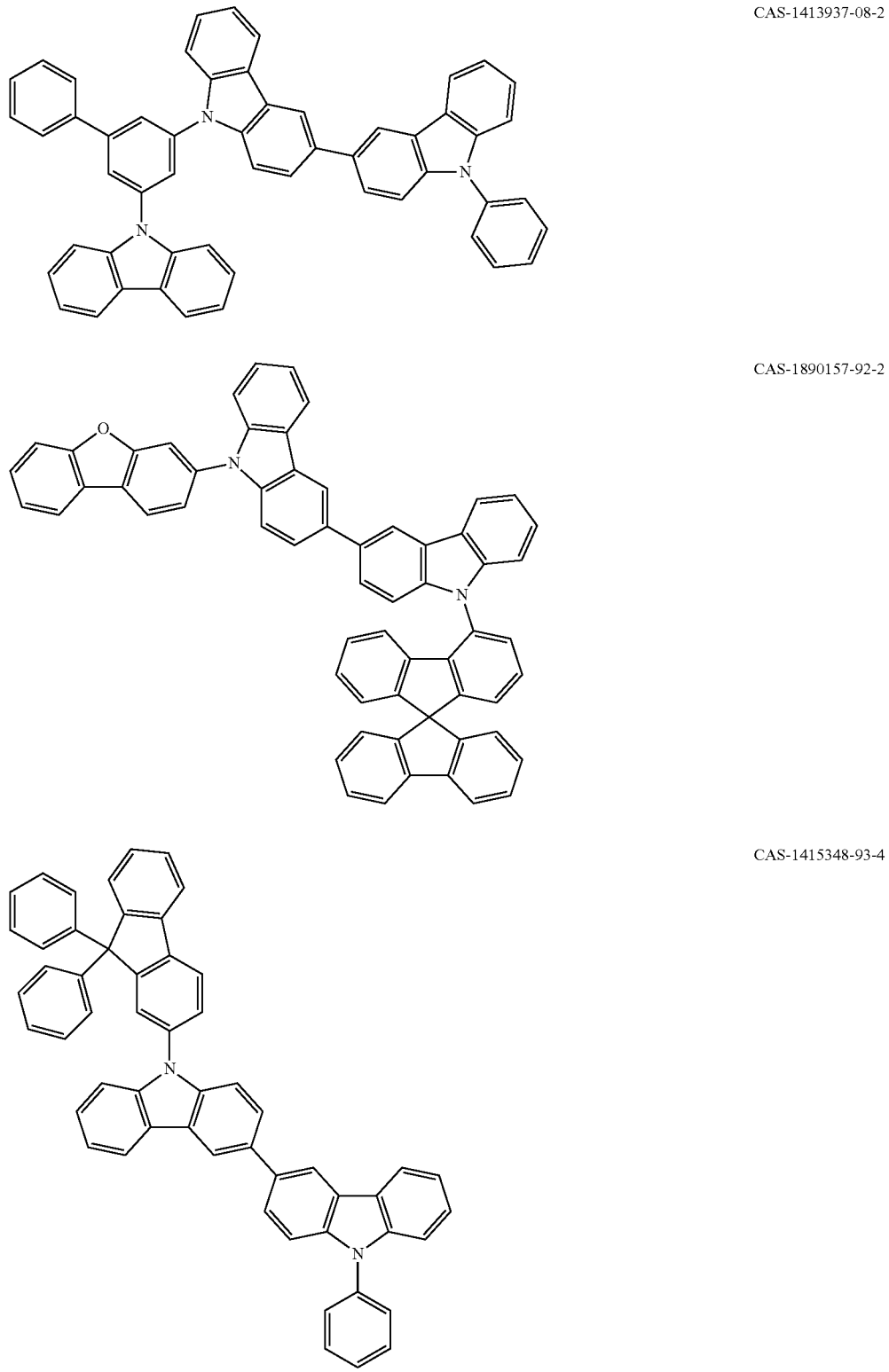 | CAS-1413937-08-2 |
| 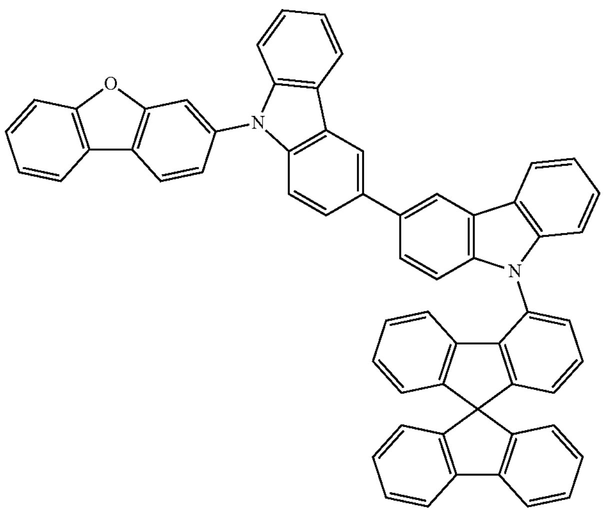 [SMILES: c1ccc2c(c1)-c1ccccc1C21c2ccccc2-c2c(-n3c4ccccc4c4cc(-c5ccc6c(c5)c5ccccc5n6-c5ccc6c(c5)oc5ccccc56)ccc43)cccc21] | CAS-1890157-92-2 |
| 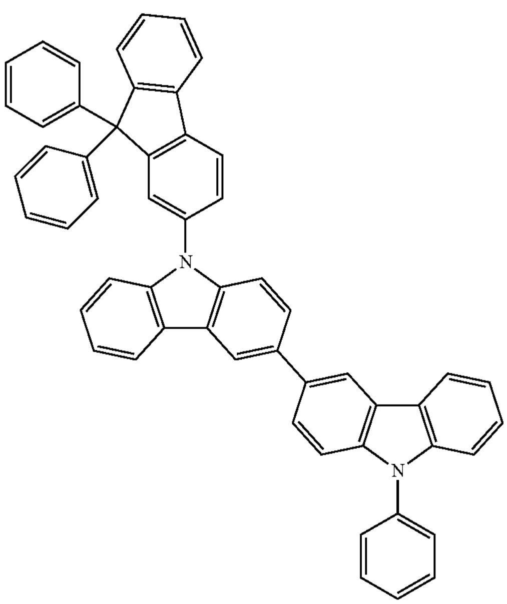 [SMILES: c1ccc(-n2c3ccccc3c3cc(-c4ccc5c(c4)c4ccccc4n5-c4ccc5c(c4)C(c4ccccc4)(c4ccccc4)c4ccccc4-5)ccc32)cc1] | CAS-1415348-93-4 |

| Structure | CAS-number |
|---|---|
| 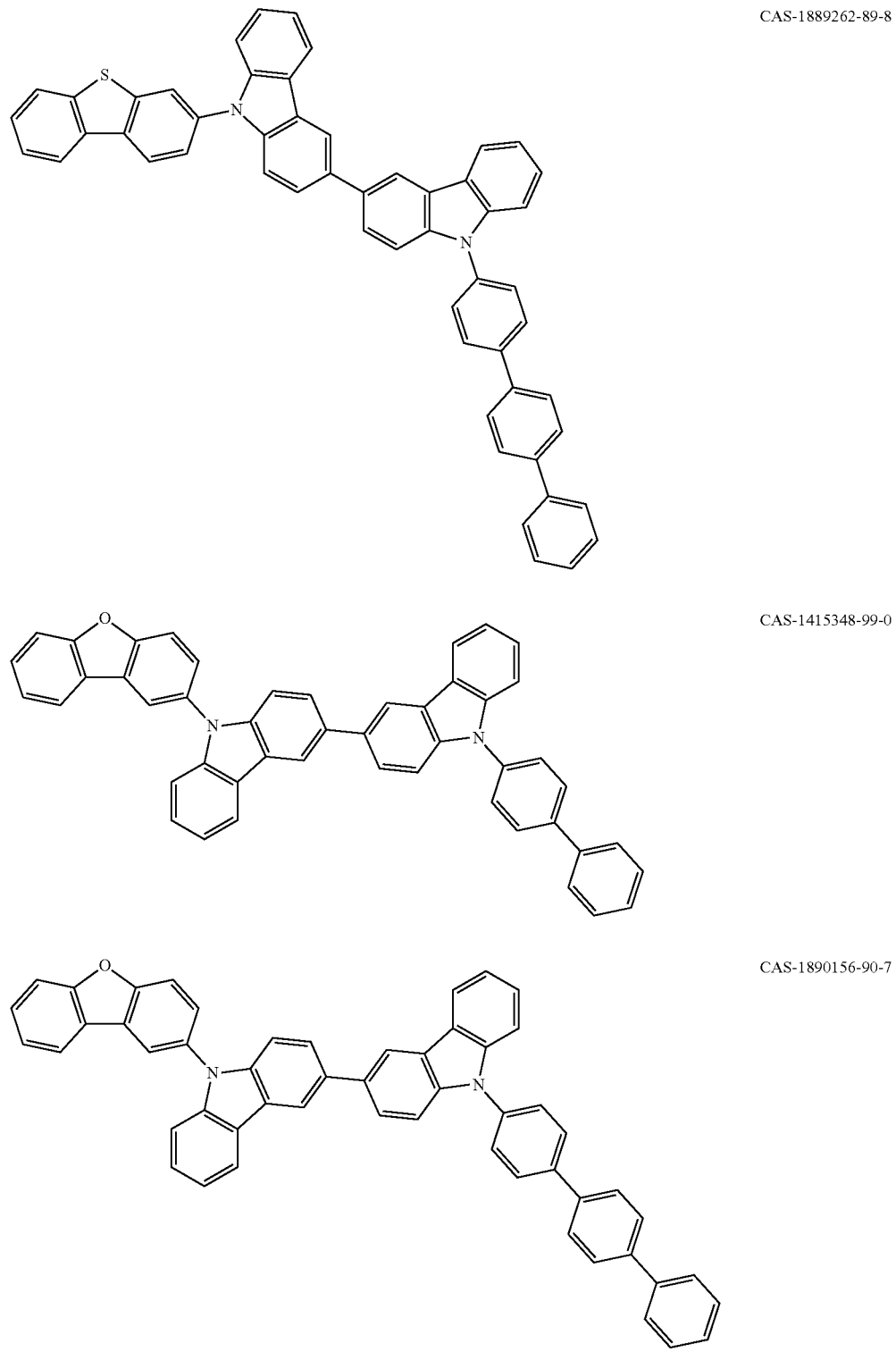 | CAS-1889262-89-8 |
| 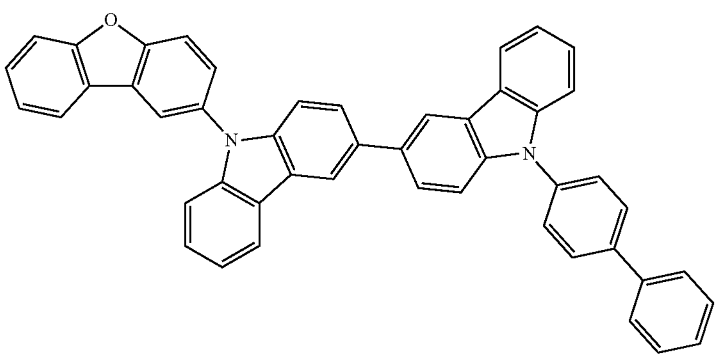 [SMILES: c1ccc(-c2ccc(-n3c4ccccc4c4cc(-c5ccc6c(c5)c5ccccc5n6-c5ccc6oc7ccccc7c6c5)ccc43)cc2)cc1] | CAS-1415348-99-0 |
| 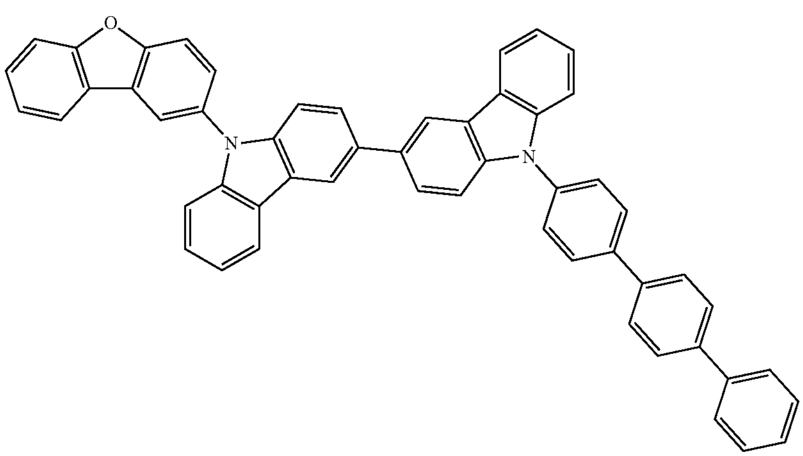 [SMILES: c1ccc(-c2ccc(-c3ccc(-n4c5ccccc5c5cc(-c6ccc7c(c6)c6ccccc6n7-c6ccc7oc8ccccc8c7c6)ccc54)cc3)cc2)cc1] | CAS-1890156-90-7 |

| Structure | CAS-number |
|---|---|
| 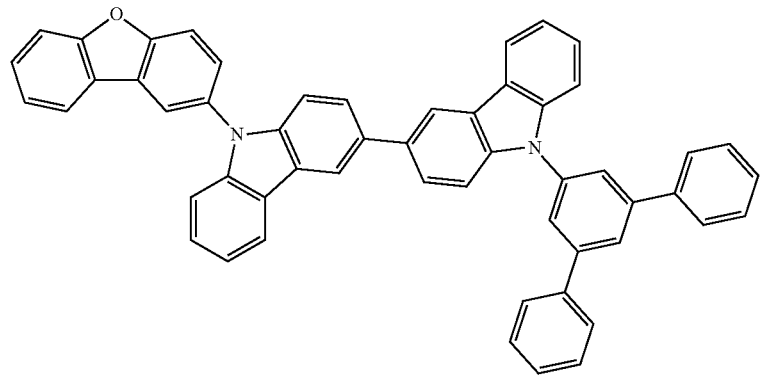 [SMILES: c1ccc(-c2cc(-c3ccccc3)cc(-n3c4ccccc4c4cc(-c5ccc6c(c5)c5ccccc5n6-c5ccc6oc7ccccc7c6c5)ccc43)c2)cc1] | CAS-1415349-00-6 |
| 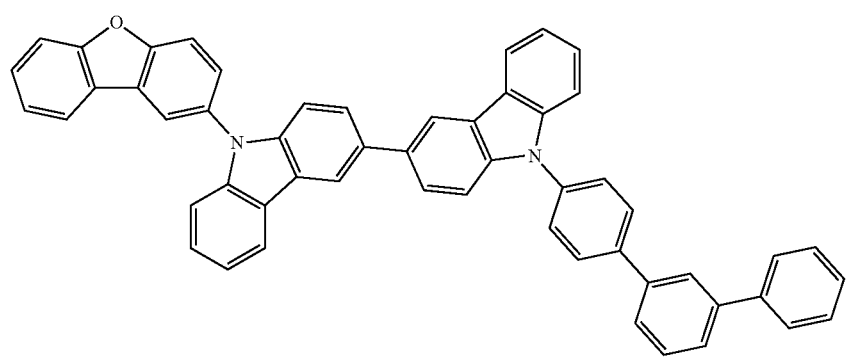 [SMILES: c1ccc(-c2cccc(-c3ccc(-n4c5ccccc5c5cc(-c6ccc7c(c6)c6ccccc6n7-c6ccc7oc8ccccc8c7c6)ccc54)cc3)c2)cc1] | CAS-1890156-91-8 |
| 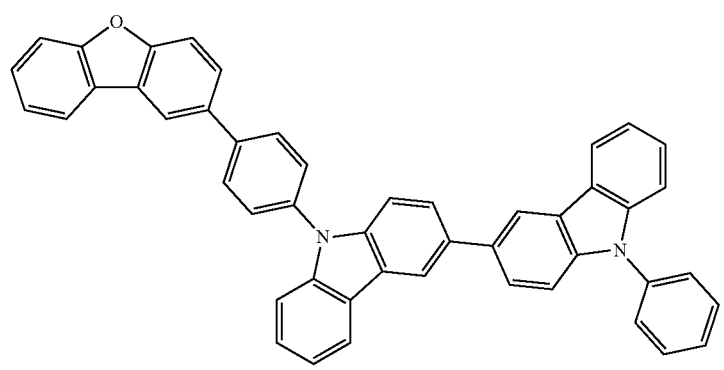 [SMILES: c1ccc(-n2c3ccccc3c3cc(-c4ccc5c(c4)c4ccccc4n5-c4ccc(-c5ccc6oc7ccccc7c6c5)cc4)ccc32)cc1] | CAS-1415349-01-7 |
| 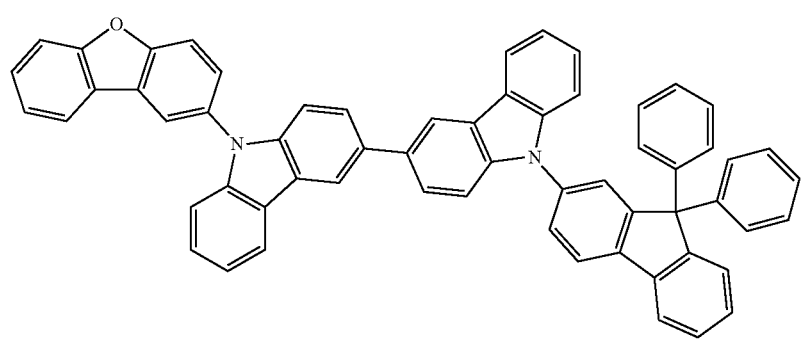 [SMILES: c1ccc(C2(c3ccccc3)c3ccccc3-c3ccc(-n4c5ccccc5c5cc(-c6ccc7c(c6)c6ccccc6n7-c6ccc7oc8ccccc8c7c6)ccc54)cc32)cc1] | CAS-1890157-12-6 |

| Structure | CAS-number |
|---|---|
| 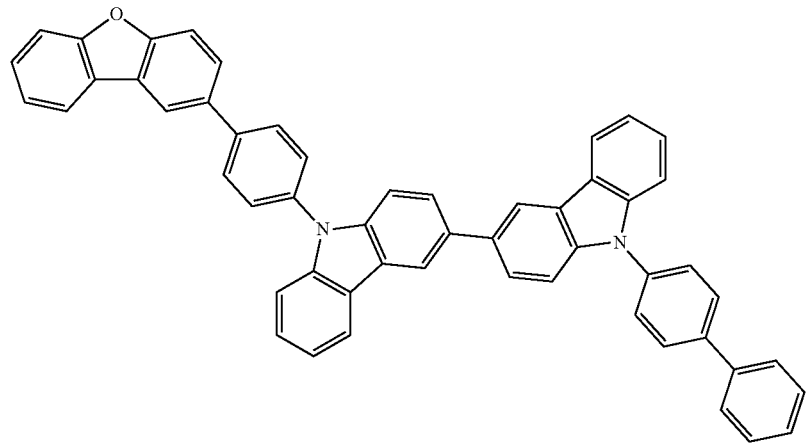 [SMILES: c1ccc(-c2ccc(-n3c4ccccc4c4cc(-c5ccc6c(c5)c5ccccc5n6-c5ccc(-c6ccc7oc8ccccc8c7c6)cc5)ccc43)cc2)cc1] | CAS-1415349-02-8 |
| 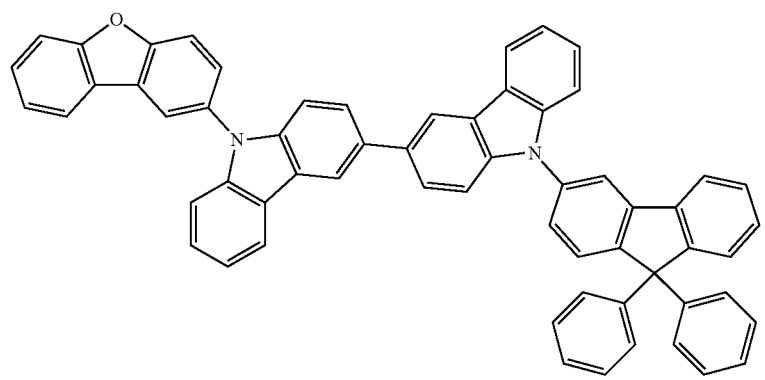 [SMILES: c1ccc(C2(c3ccccc3)c3ccccc3-c3cc(-n4c5ccccc5c5cc(-c6ccc7c(c6)c6ccccc6n7-c6ccc7oc8ccccc8c7c6)ccc54)ccc32)cc1] | CAS-1890157-13-7 |
| 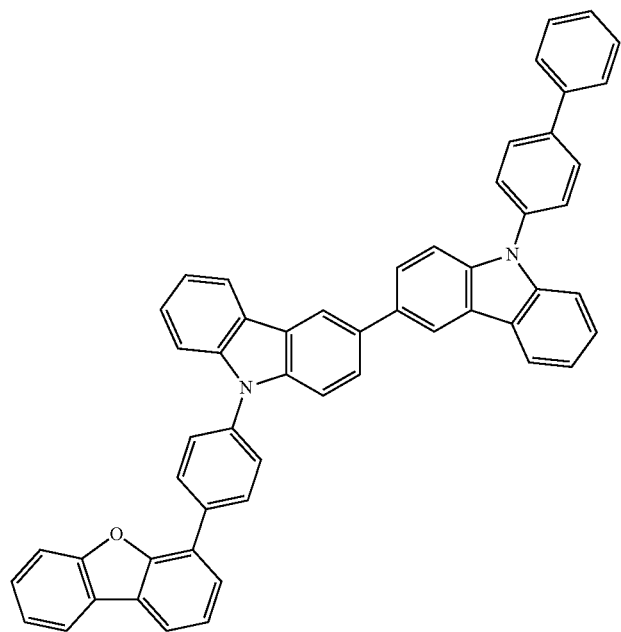 [SMILES: c1ccc(-c2ccc(-n3c4ccccc4c4cc(-c5ccc6c(c5)c5ccccc5n6-c5ccc(-c6cccc7c6oc6ccccc67)cc5)ccc43)cc2)cc1] | CAS-1415349-03-9 |

| Structure | CAS-number |
|---|---|
| 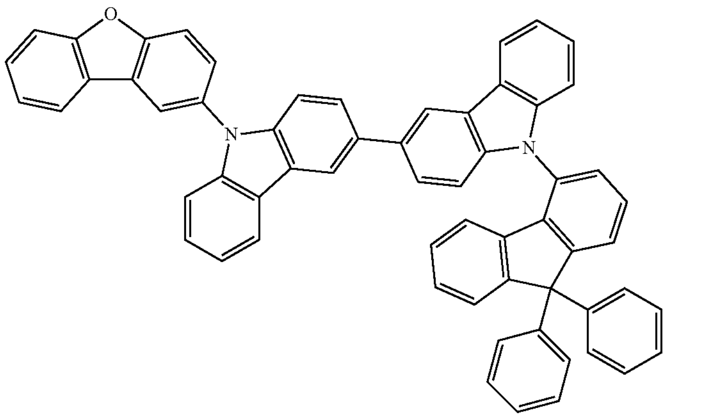 [SMILES: c1ccc(C2(c3ccccc3)c3ccccc3-c3c(-n4c5ccccc5c5cc(-c6ccc7c(c6)c6ccccc6n7-c6ccc7oc8ccccc8c7c6)ccc54)cccc32)cc1] | CAS-1890157-14-8 |
| 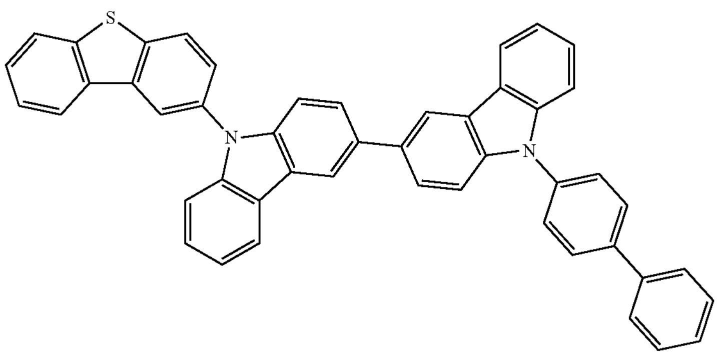 [SMILES: c1ccc(-c2ccc(-n3c4ccccc4c4cc(-c5ccc6c(c5)c5ccccc5n6-c5ccc6sc7ccccc7c6c5)ccc43)cc2)cc1] | CAS-1415349-04-0 |
| 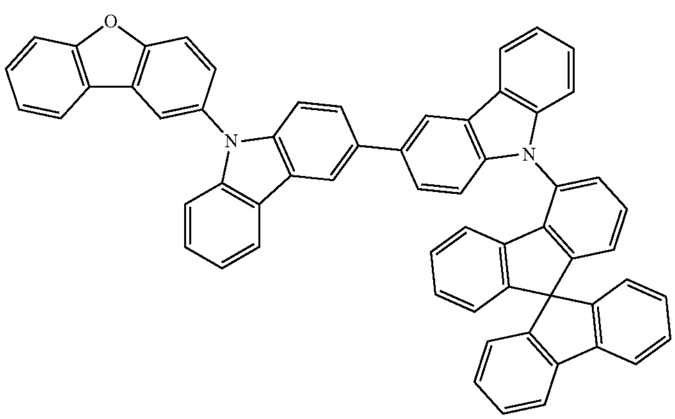 [SMILES: c1ccc2c(c1)-c1ccccc1C21c2ccccc2-c2c(-n3c4ccccc4c4cc(-c5ccc6c(c5)c5ccccc5n6-c5ccc6oc7ccccc7c6c5)ccc43)cccc21] | CAS-1890157-37-5 |
| 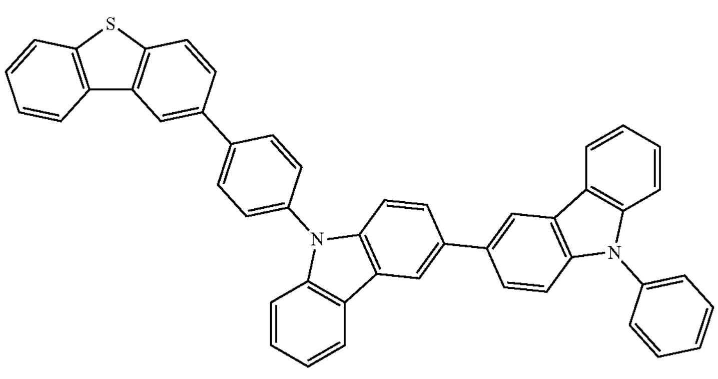 [SMILES: c1ccc(-n2c3ccccc3c3cc(-c4ccc5c(c4)c4ccccc4n5-c4ccc(-c5ccc6sc7ccccc7c6c5)cc4)ccc32)cc1] | CAS-1415349-05-1 |

-continued
| Structure | CAS-number |
|---|---|
| 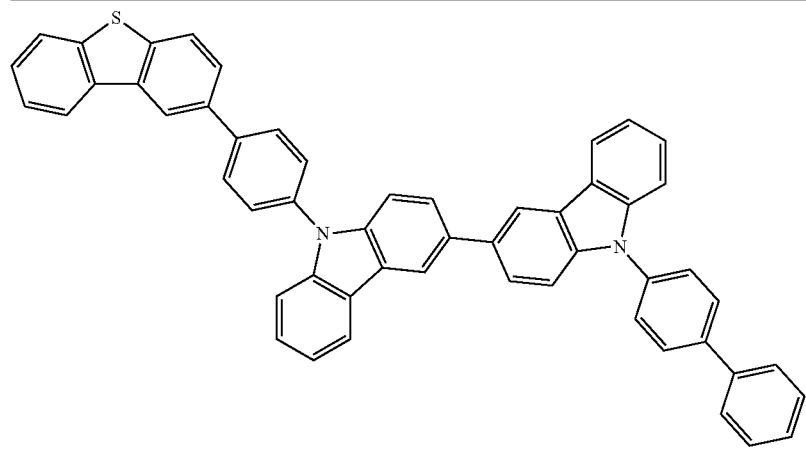 [SMILES: c1ccc(-c2ccc(-n3c4ccccc4c4cc(-c5ccc6c(c5)c5ccccc5n6-c5ccc(-c6ccc7sc8ccccc8c7c6)cc5)ccc43)cc2)cc1] | CAS-1415349-06-2 |
| 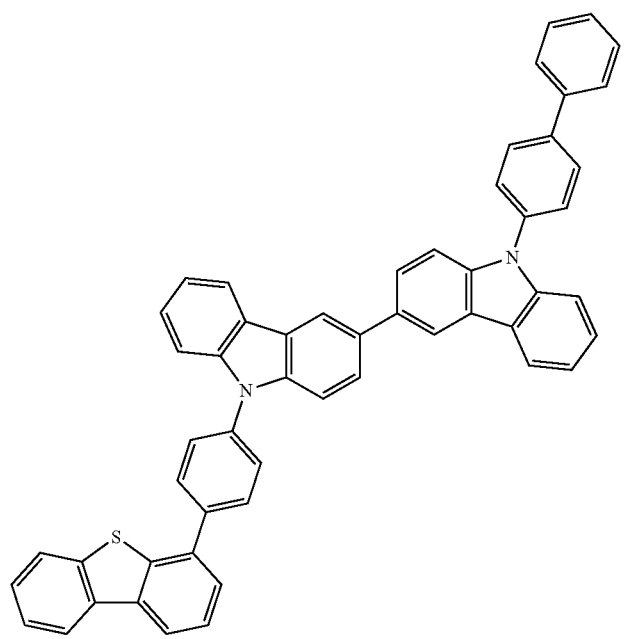 | CAS-1415349-07-3 |
| 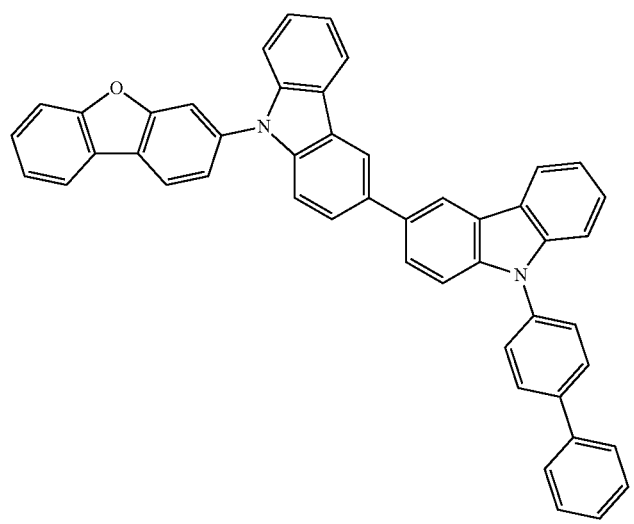 [SMILES: c1ccc(-c2ccc(-n3c4ccccc4c4cc(-c5ccc6c(c5)c5ccccc5n6-c5ccc6c(c5)oc5ccccc56)ccc43)cc2)cc1] | CAS-1890157-41-1 |

| Structure | CAS-number |
|---|---|
| 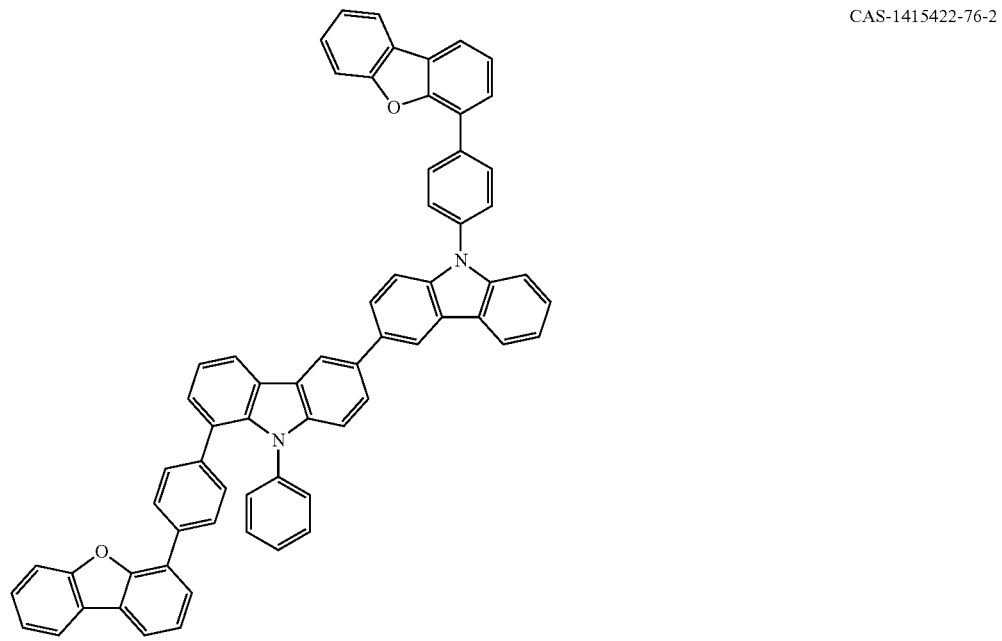 | CAS-1415422-76-2 |
| 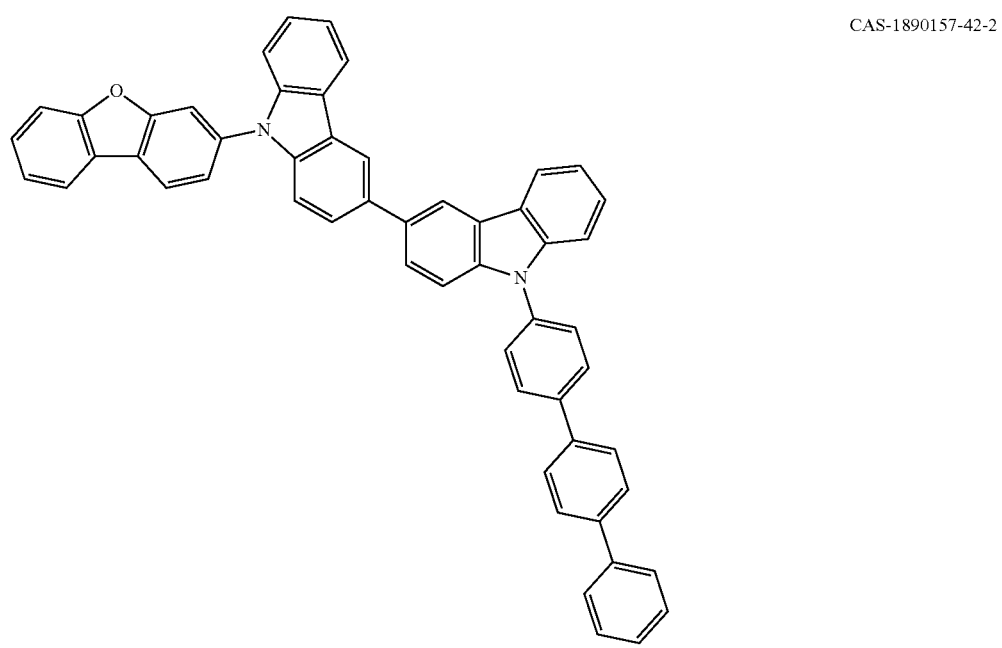 | CAS-1890157-42-2 |

| Structure | CAS-number |
|---|---|
| 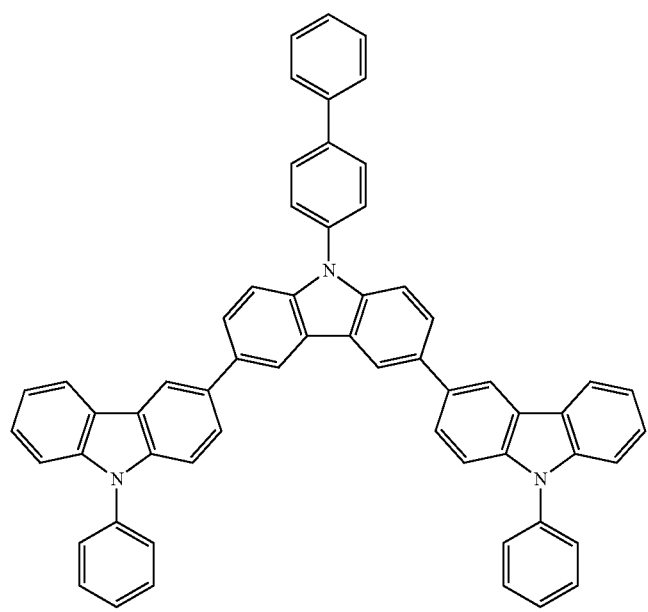 [SMILES: c1ccc(-c2ccc(-n3c4ccc(-c5ccc6c(c5)c5ccccc5n6-c5ccccc5)cc4c4cc(-c5ccc6c(c5)c5ccccc5n6-c5ccccc5)ccc43)cc2)cc1] | CAS-1422451-46-4 |
| 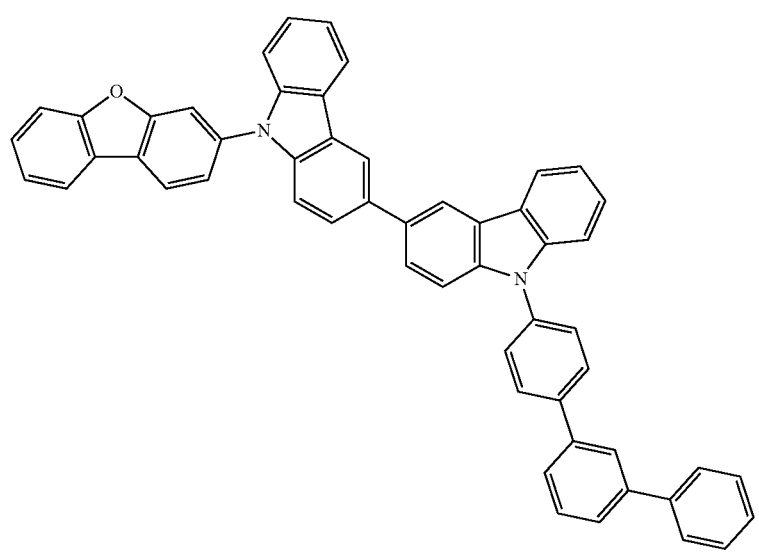 [SMILES: c1ccc(-c2cccc(-c3ccc(-n4c5ccccc5c5cc(-c6ccc7c(c6)c6ccccc6n7-c6ccc7c(c6)oc6ccccc67)ccc54)cc3)c2)cc1] | CAS-1890157-43-3 |

| Structure | CAS-number |
|---|---|
| 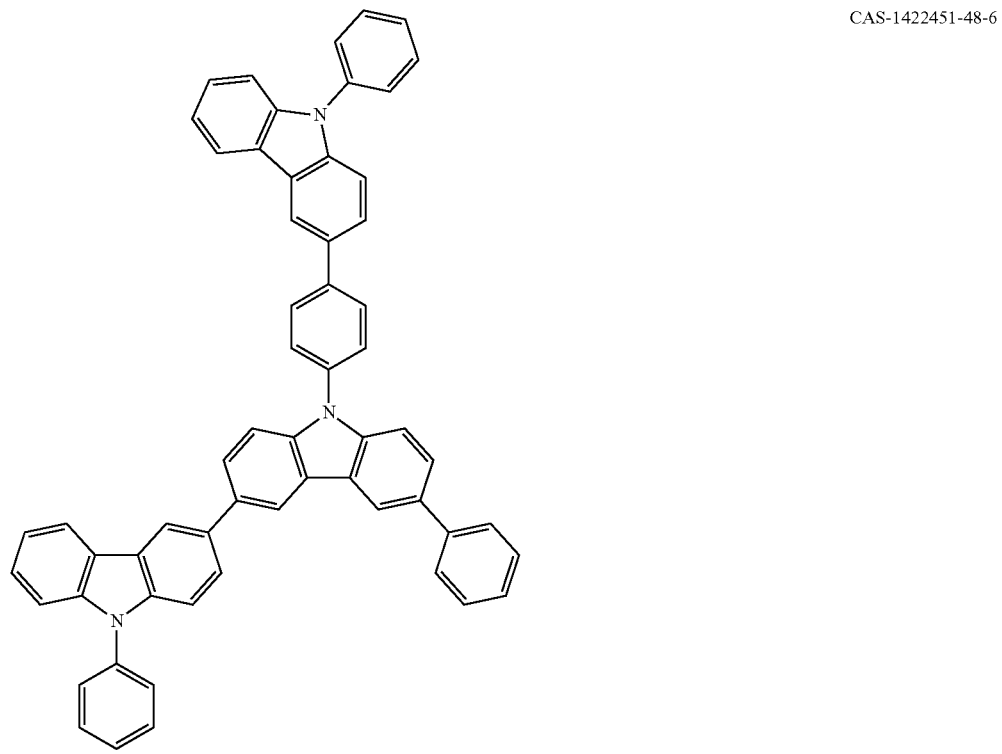 | CAS-1422451-48-6 |
| 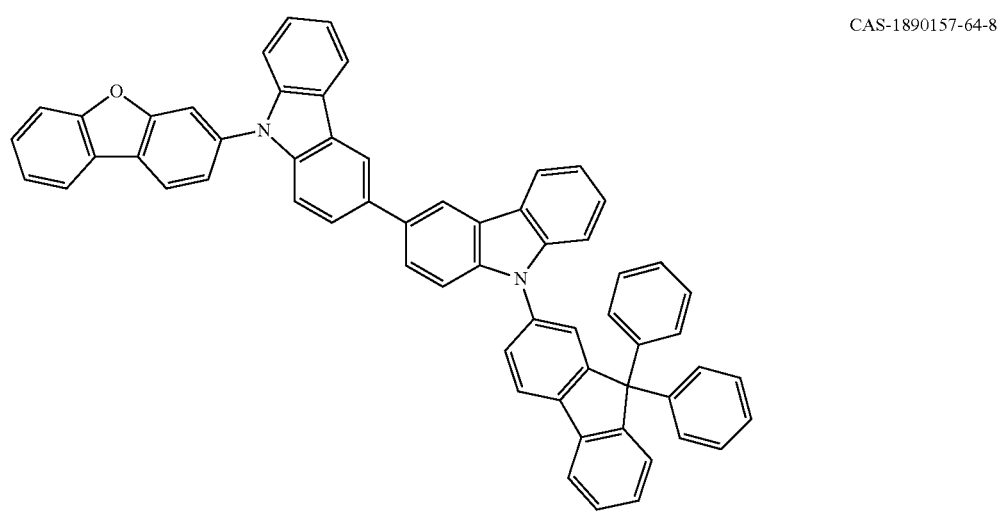 | CAS-1890157-64-8 |

| Structure | CAS-number |
|---|---|
| 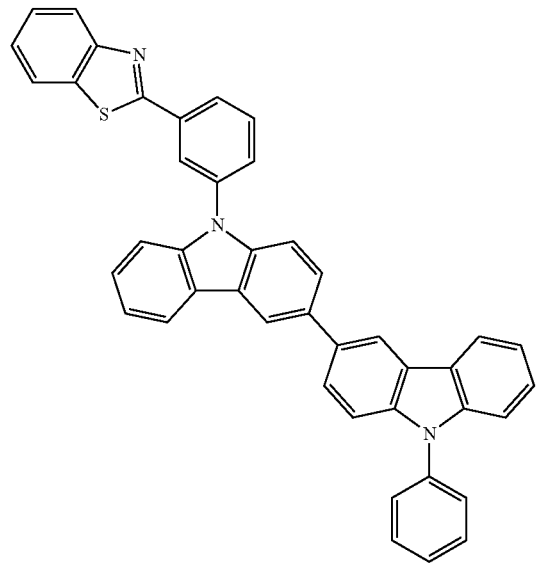 [SMILES: c1ccc(-n2c3ccccc3c3cc(-c4ccc5c(c4)c4ccccc4n5-c4cccc(-c5nc6ccccc6s5)c4)ccc32)cc1] | CAS-1445952-53-3 |
| 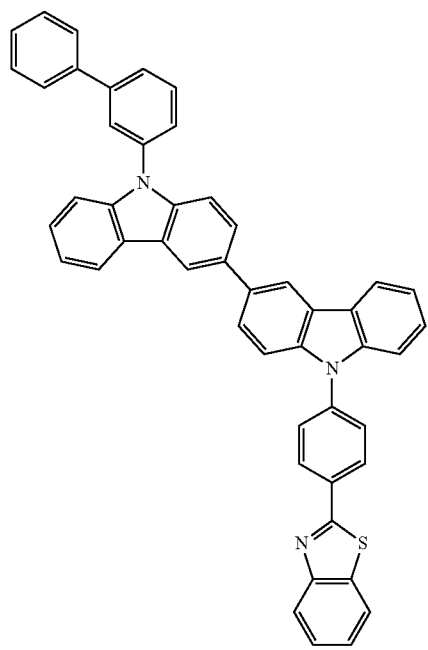 [SMILES: c1ccc(-c2cccc(-n3c4ccccc4c4cc(-c5ccc6c(c5)c5ccccc5n6-c5ccc(-c6nc7ccccc7s6)cc5)ccc43)c2)cc1] | CAS-1445952-58-8 |

| Structure | CAS-number |
|---|---|
| 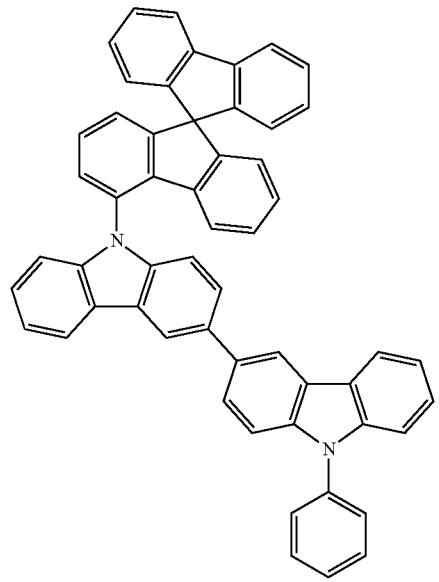 [SMILES: c1ccc(-n2c3ccccc3c3cc(-c4ccc5c(c4)c4ccccc4n5-c4cccc5c4-c4ccccc4C54c5ccccc5-c5ccccc54)ccc32)cc1] | CAS-1450933-86-4 |
| 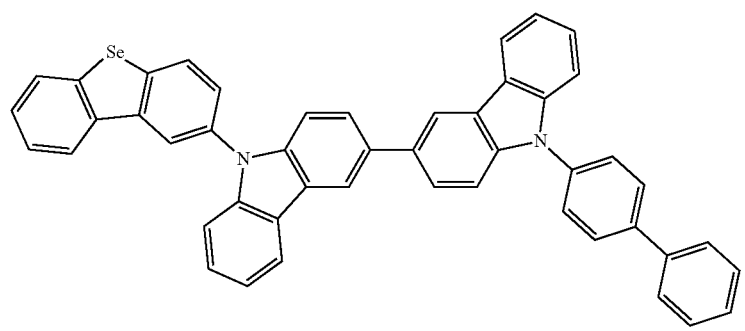 [SMILES: c1ccc(-c2ccc(-n3c4ccccc4c4cc(-c5ccc6c(c5)c5ccccc5n6-c5ccc6[se]c7ccccc7c6c5)ccc43)cc2)cc1] | CAS-1894194-07-0 |
| 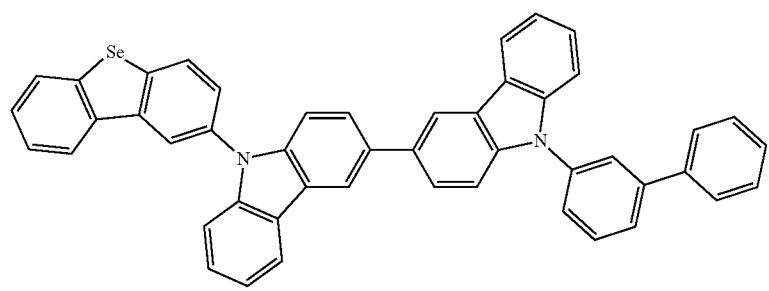 [SMILES: c1ccc(-c2cccc(-n3c4ccccc4c4cc(-c5ccc6c(c5)c5ccccc5n6-c5ccc6[se]c7ccccc7c6c5)ccc43)c2)cc1] | CAS-1894194-09-2 |

| Structure | CAS-number |
|---|---|
| 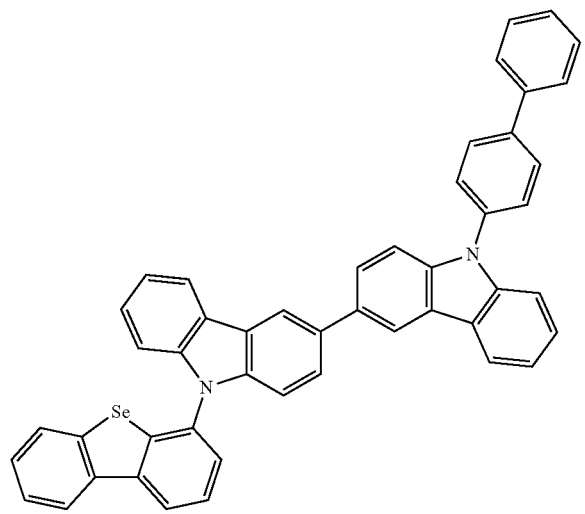 | CAS-1894194-08-1 |
| 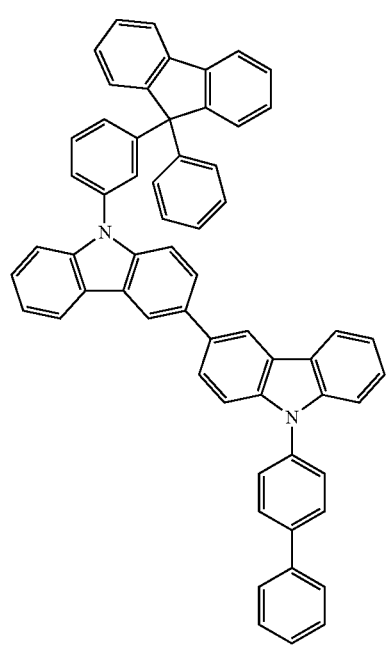 [SMILES: c1ccc(-c2ccc(-n3c4ccccc4c4cc(-c5ccc6c(c5)c5ccccc5n6-c5cccc(C6(c7ccccc7)c7ccccc7-c7ccccc76)c5)ccc43)cc2)cc1] | CAS-1919031-93-8 |

| Structure | CAS-number |
|---|---|
| 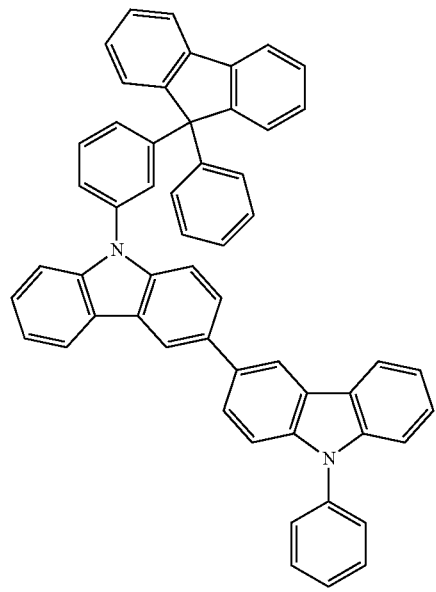 [SMILES: c1ccc(-n2c3ccccc3c3cc(-c4ccc5c(c4)c4ccccc4n5-c4cccc(C5(c6ccccc6)c6ccccc6-c6ccccc65)c4)ccc32)cc1] | CAS-1919031-92-7 |
| 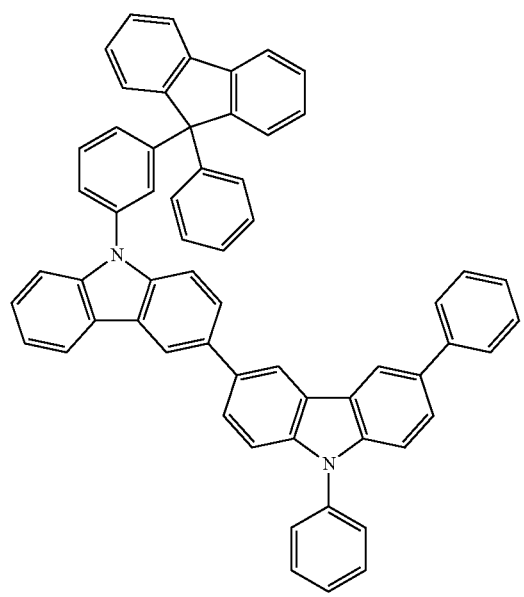 [SMILES: c1ccc(-c2ccc3c(c2)c2cc(-c4ccc5c(c4)c4ccccc4n5-c4cccc(C5(c6ccccc6)c6ccccc6-c6ccccc65)c4)ccc2n3-c2ccccc2)cc1] | CAS-1919031-95-0 |

-continued
| Structure | CAS-number |
|---|---|
| 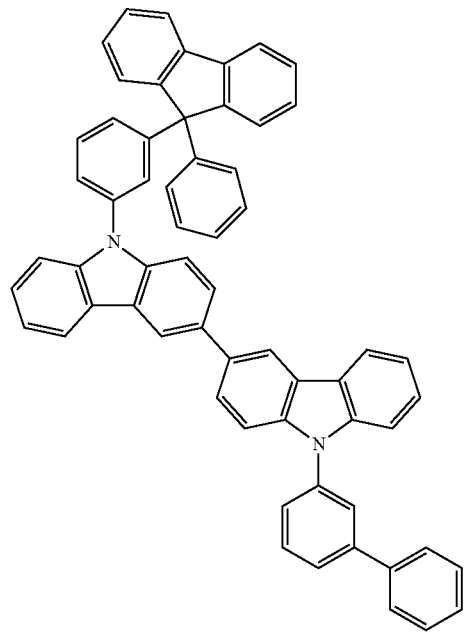 [SMILES: c1ccc(-c2cccc(-n3c4ccccc4c4cc(-c5ccc6c(c5)c5ccccc5n6-c5cccc(C6(c7ccccc7)c7ccccc7-c7ccccc76)c5)ccc43)c2)cc1] | CAS-1919031-94-9 |
| 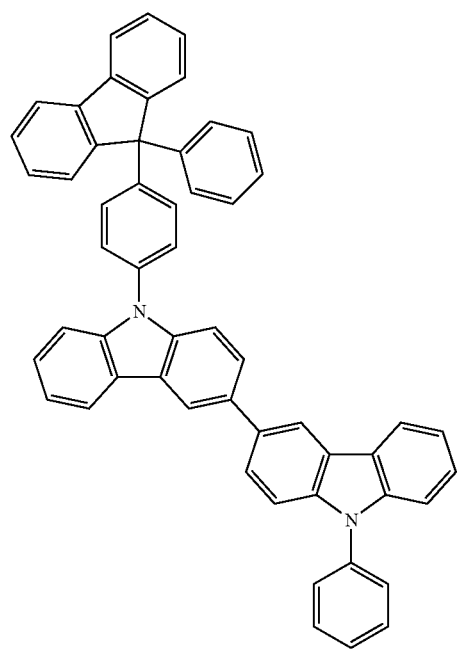 [SMILES: c1ccc(-n2c3ccccc3c3cc(-c4ccc5c(c4)c4ccccc4n5-c4ccc(C5(c6ccccc6)c6ccccc6-c6ccccc65)cc4)ccc32)cc1] | CAS-1919031-97-2 |

| Structure | CAS-number |
|---|---|
| 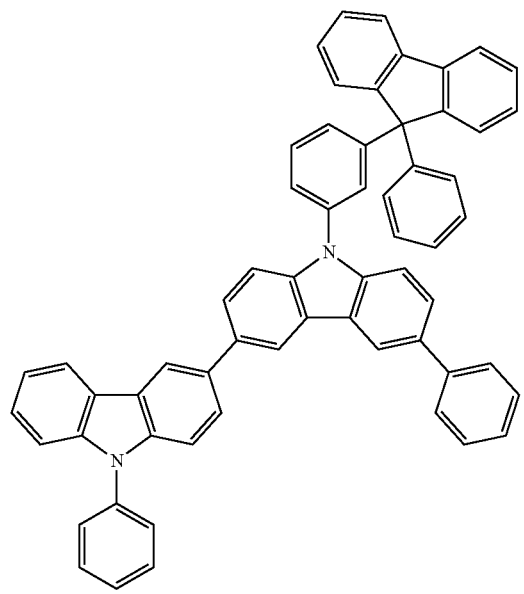 [SMILES: c1ccc(-c2ccc3c(c2)c2cc(-c4ccc5c(c4)c4ccccc4n5-c4ccccc4)ccc2n3-c2cccc(C3(c4ccccc4)c4ccccc4-c4ccccc43)c2)cc1] | CAS-1919031-96-1 |
| 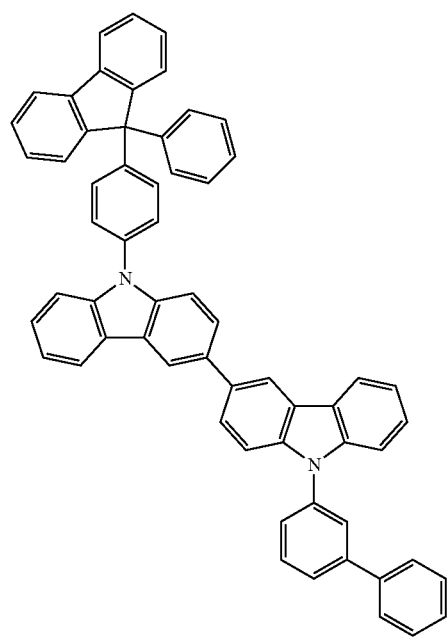 [SMILES: c1ccc(-c2cccc(-n3c4ccccc4c4cc(-c5ccc6c(c5)c5ccccc5n6-c5ccc(C6(c7ccccc7)c7ccccc7-c7ccccc76)cc5)ccc43)c2)cc1] | CAS-1919031-99-4 |

| Structure | CAS-number |
|---|---|
| 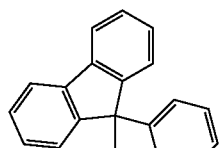 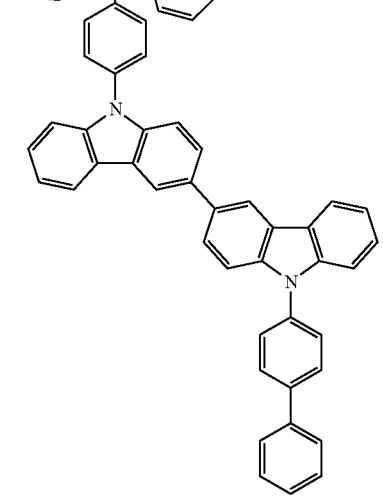 | CAS-1919031-98-3 |
| 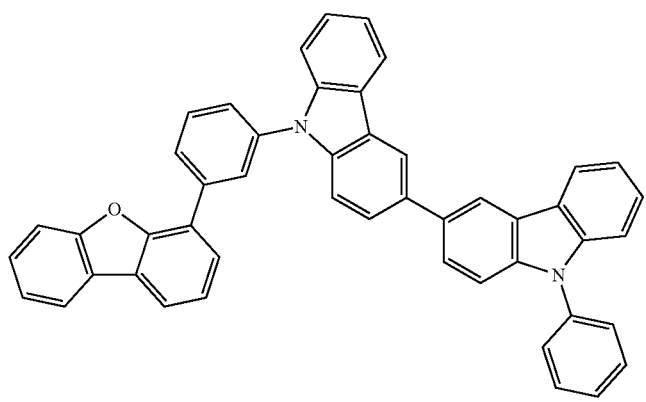 [SMILES: c1ccc(-n2c3ccccc3c3cc(-c4ccc5c(c4)c4ccccc4n5-c4cccc(-c5cccc6c5oc5ccccc56)c4)ccc32)cc1] | CAS-1598389-98-0 |
| 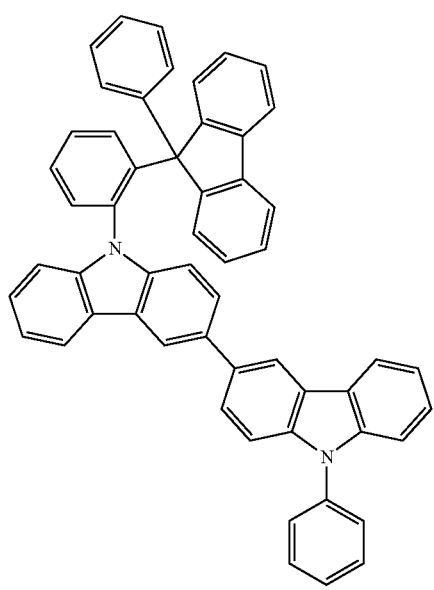 [SMILES: c1ccc(-n2c3ccccc3c3cc(-c4ccc5c(c4)c4ccccc4n5-c4ccccc4C4(c5ccccc5)c5ccccc5-c5ccccc54)ccc32)cc1] | CAS-1919032-02-2 |

| Structure | CAS-number |
|---|---|
| 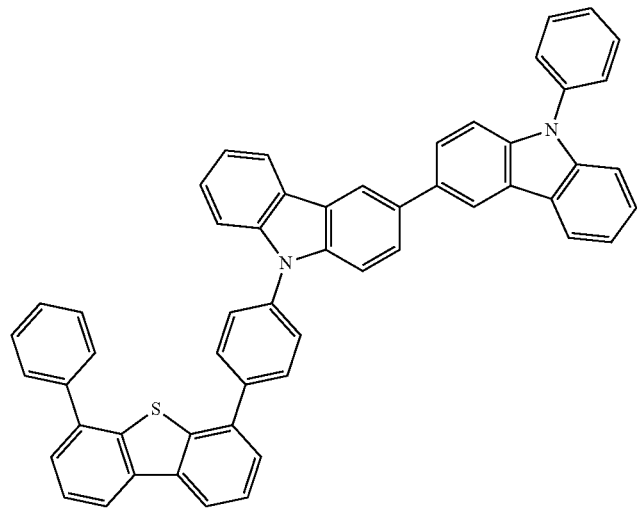 | CAS-1604034-14-1 |
| 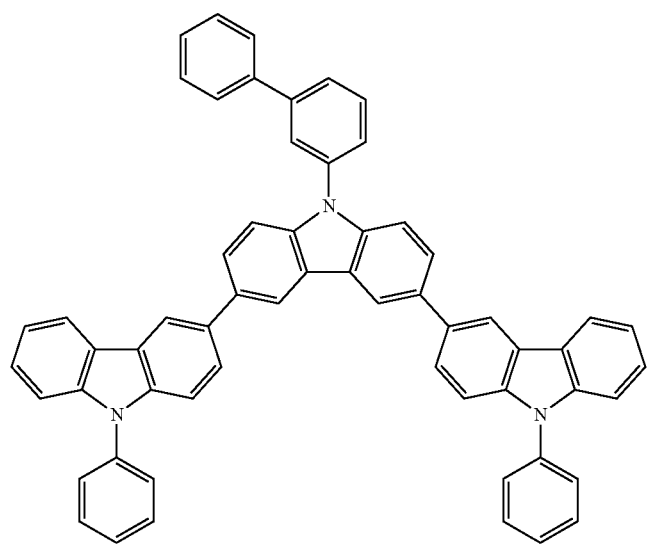 [SMILES: c1ccc(-c2cccc(-n3c4ccc(-c5ccc6c(c5)c5ccccc5n6-c5ccccc5)cc4c4cc(-c5ccc6c(c5)c5ccccc5n6-c5ccccc5)ccc43)c2)cc1] | CAS-1943719-67-2 |
| 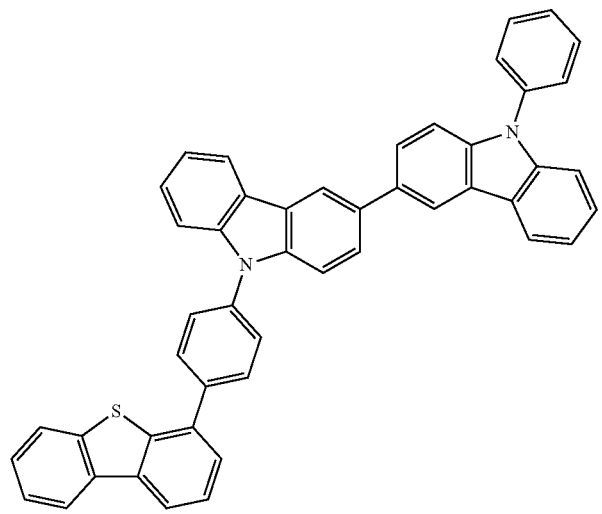 [SMILES: c1ccc(-n2c3ccccc3c3cc(-c4ccc5c(c4)c4ccccc4n5-c4ccc(-c5cccc6c5sc5ccccc56)cc4)ccc32)cc1] | CAS-1604034-02-7 |

| Structure | CAS-number |
|---|---|
| 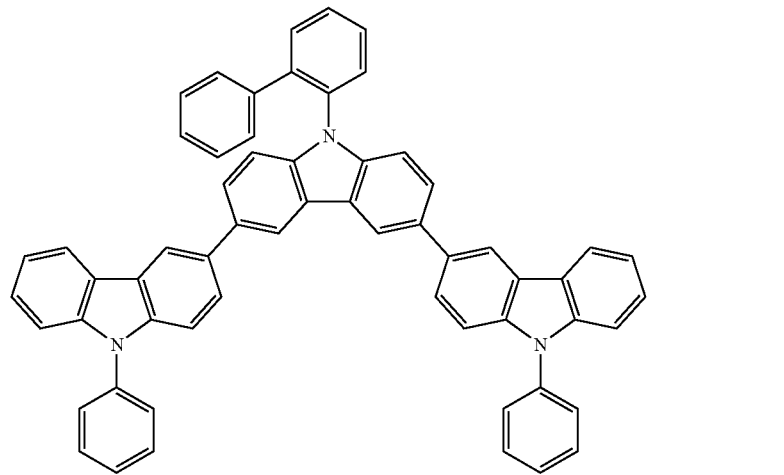 [SMILES: c1ccc(-c2ccccc2-n2c3ccc(-c4ccc5c(c4)c4ccccc4n5-c4ccccc4)cc3c3cc(-c4ccc5c(c4)c4ccccc4n5-c4ccccc4)ccc32)cc1] | CAS-1943719-70-7 |
| 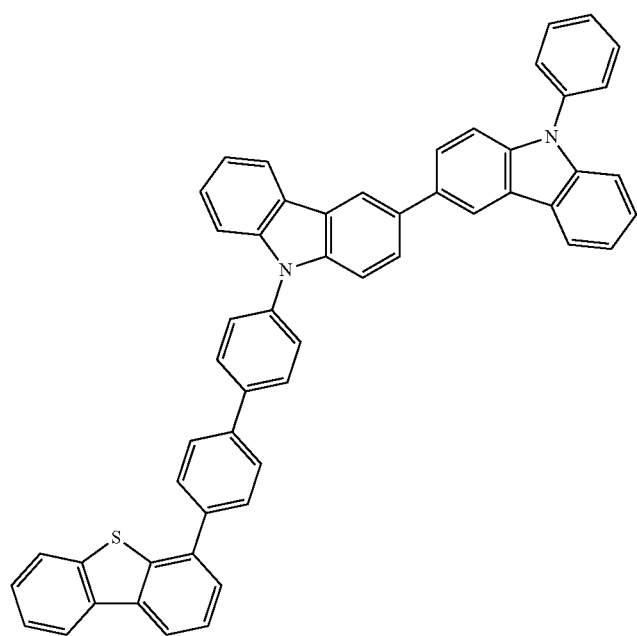 [SMILES: c1ccc(-n2c3ccccc3c3cc(-c4ccc5c(c4)c4ccccc4n5-c4ccc(-c5ccc(-c6cccc7c6sc6ccccc67)cc5)cc4)ccc32)cc1] | CAS-1604034-07-2 |

-continued
| Structure | CAS-number |
|---|---|
| 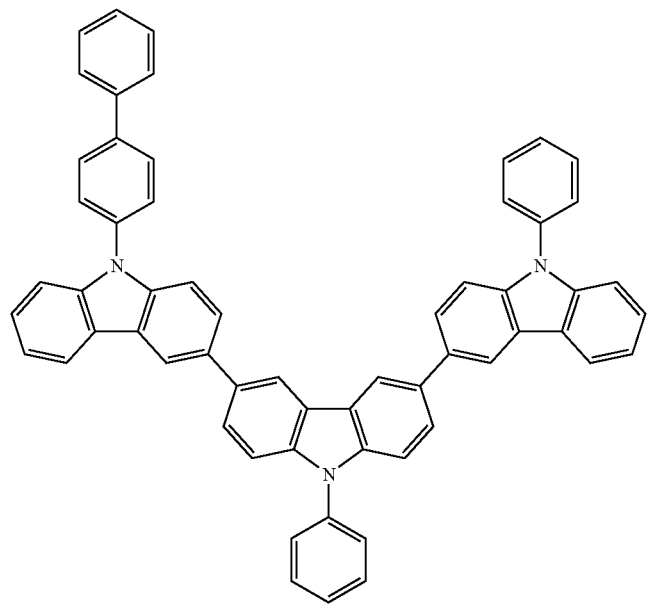 [SMILES: c1ccc(-c2ccc(-n3c4ccccc4c4cc(-c5ccc6c(c5)c5cc(-c7ccc8c(c7)c7ccccc7n8-c7ccccc7)ccc5n6-c5ccccc5)ccc43)cc2)cc1] | CAS-1943719-71-8 |
| 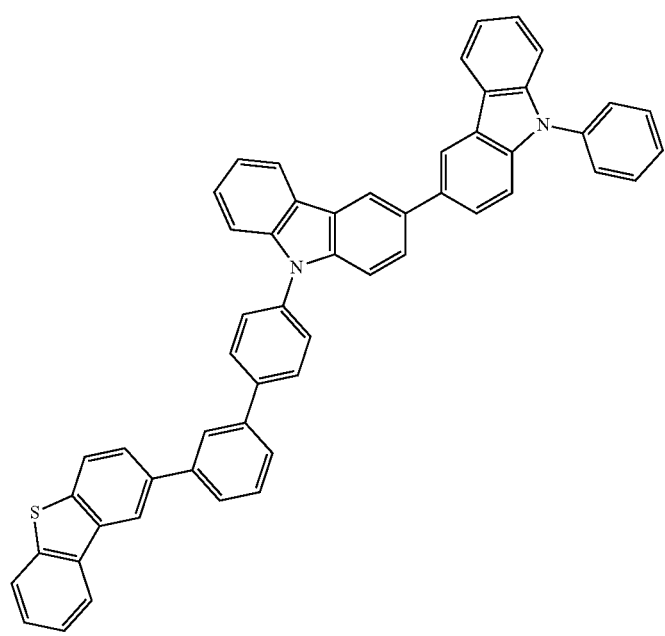 [SMILES: c1ccc(-n2c3ccccc3c3cc(-c4ccc5c(c4)c4ccccc4n5-c4ccc(-c5cccc(-c6ccc7sc8ccccc8c7c6)c5)cc4)ccc32)cc1] | CAS-1604034-12-9 |

| Structure | CAS-number |
|---|---|
| 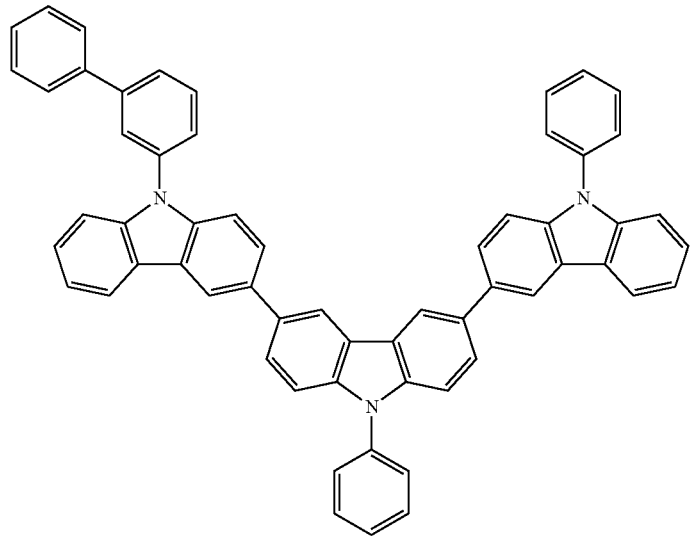 [SMILES: c1ccc(-c2cccc(-n3c4ccccc4c4cc(-c5ccc6c(c5)c5cc(-c7ccc8c(c7)c7ccccc7n8-c7ccccc7)ccc5n6-c5ccccc5)ccc43)c2)cc1] | CAS-1943719-72-9 |
| 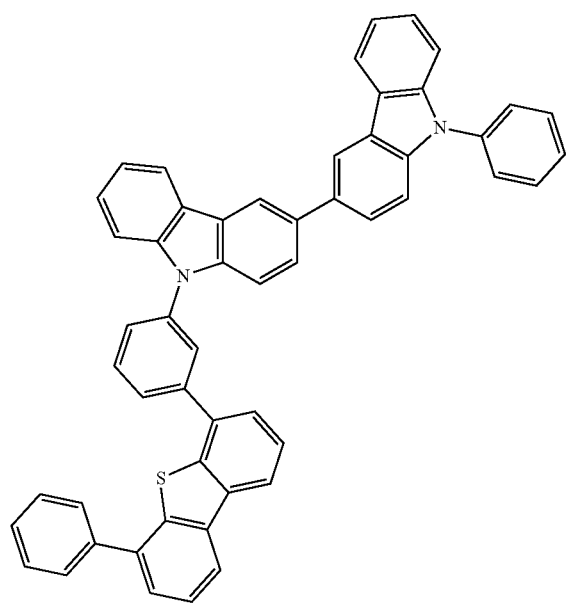 [SMILES: c1ccc(-c2cccc3c2sc2c(-c4cccc(-n5c6ccccc6c6cc(-c7ccc8c(c7)c7ccccc7n8-c7ccccc7)ccc65)c4)cccc23)cc1] | CAS-1622931-00-3 |

-continued
| Structure | CAS-number |
|---|---|
| 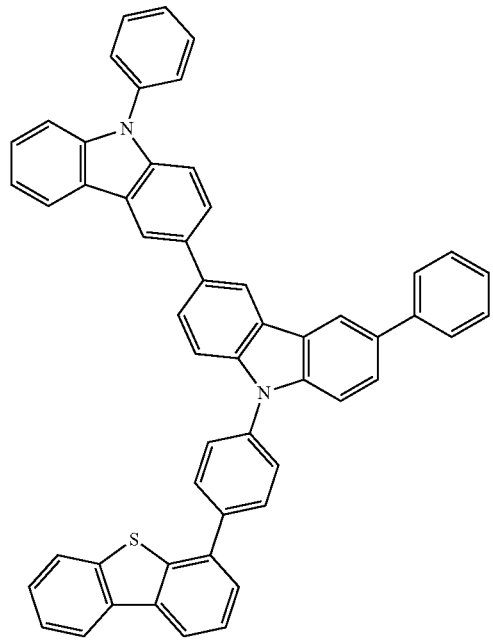 [SMILES: c1ccc(-c2ccc3c(c2)c2cc(-c4ccc5c(c4)c4ccccc4n5-c4ccccc4)ccc2n3-c2ccc(-c3cccc4c3sc3ccccc34)cc2)cc1] | CAS-1604034-15-2 |
| 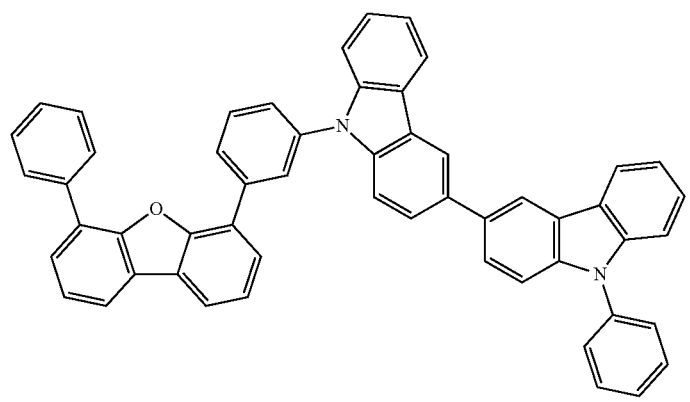 [SMILES: c1ccc(-c2cccc3c2oc2c(-c4cccc(-n5c6ccccc6c6cc(-c7ccc8c(c7)c7ccccc7n8-c7ccccc7)ccc65)c4)cccc23)cc1] | CAS-1622931-01-4 |
| 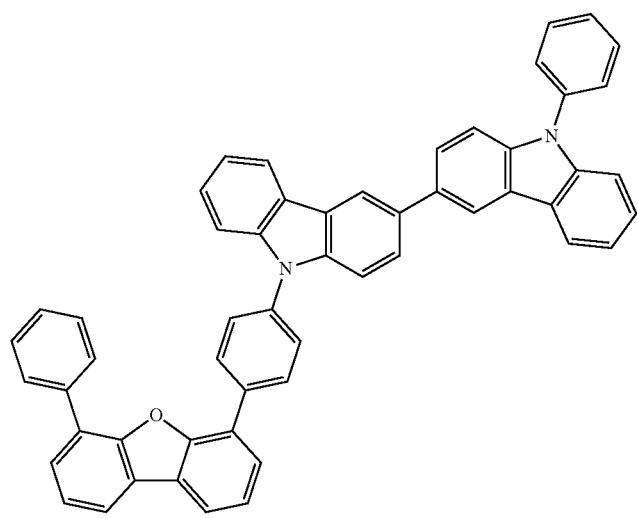 [SMILES: c1ccc(-c2cccc3c2oc2c(-c4ccc(-n5c6ccccc6c6cc(-c7ccc8c(c7)c7ccccc7n8-c7ccccc7)ccc65)cc4)cccc23)cc1] | CAS-1622931-04-7 |

| Structure | CAS-number |
|---|---|
| 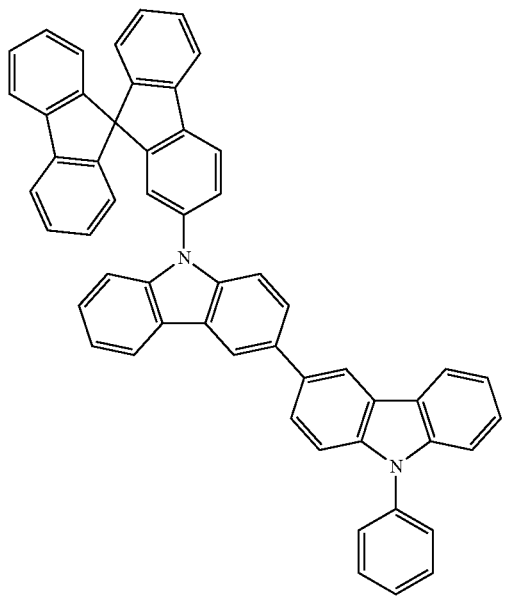 [SMILES: c1ccc(-n2c3ccccc3c3cc(-c4ccc5c(c4)c4ccccc4n5-c4ccc5c(c4)C4(c6ccccc6-c6ccccc64)c4ccccc4-5)ccc32)cc1] | CAS-1630029-28-5 |
| 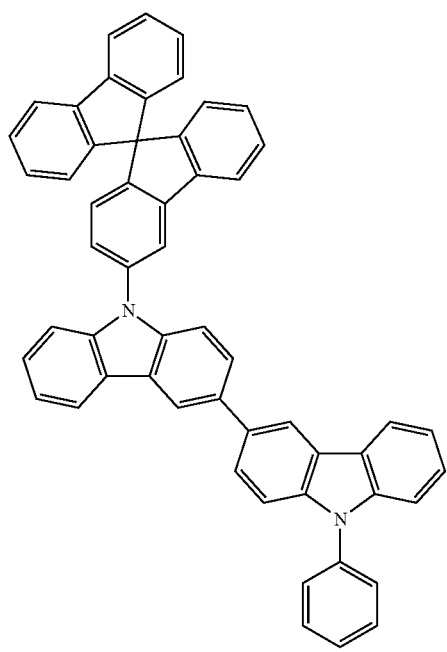 [SMILES: c1ccc(-n2c3ccccc3c3cc(-c4ccc5c(c4)c4ccccc4n5-c4ccc5c(c4)-c4ccccc4C54c5ccccc5-c5ccccc54)ccc32)cc1] | CAS-1630029-29-6 |

| Structure | CAS-number |
|---|---|
| 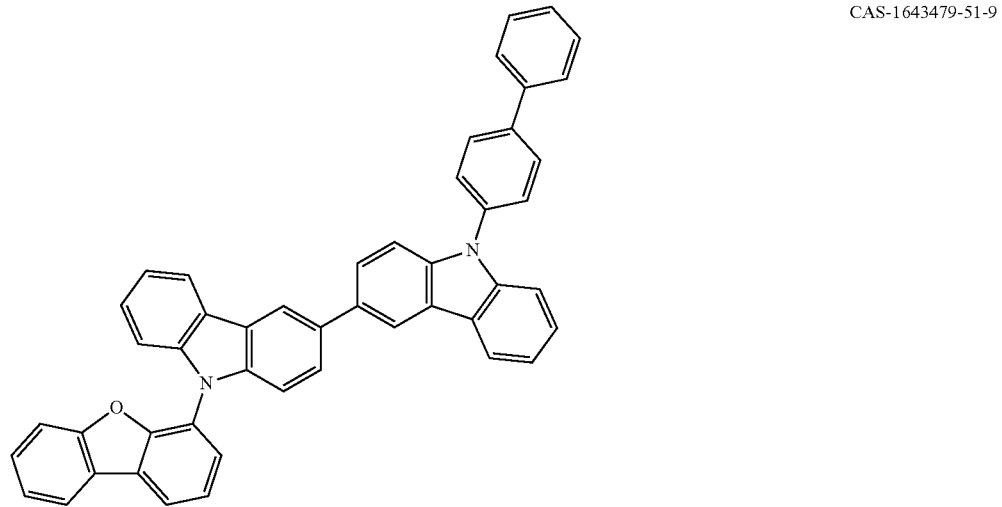 | CAS-1643479-51-9 |
| 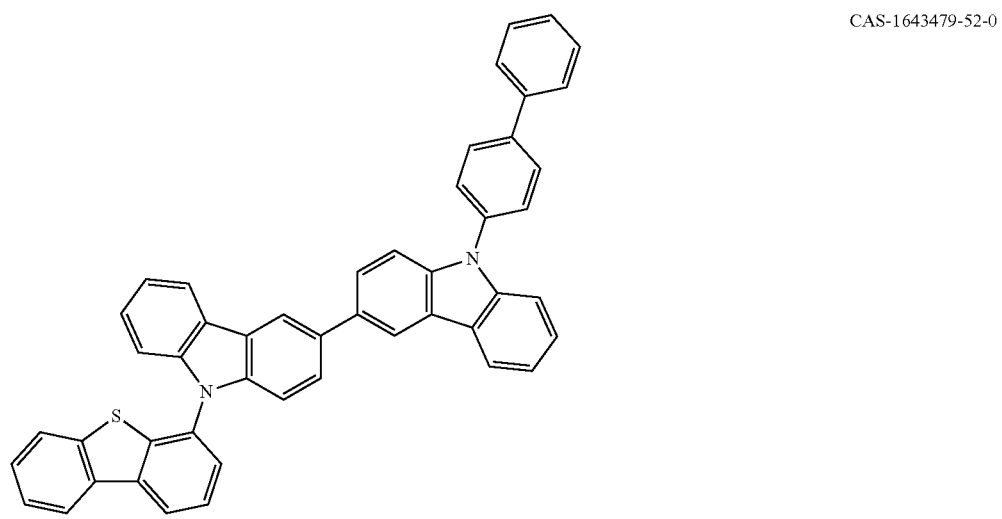 | CAS-1643479-52-0 |

| Structure | CAS-number |
|---|---|
| 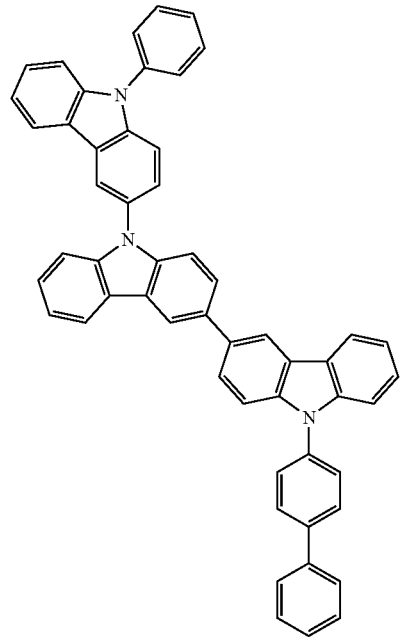 [SMILES: c1ccc(-c2ccc(-n3c4ccccc4c4cc(-c5ccc6c(c5)c5ccccc5n6-c5ccc6c(c5)c5ccccc5n6-c5ccccc5)ccc43)cc2)cc1] | CAS-1643479-54-2 |
| 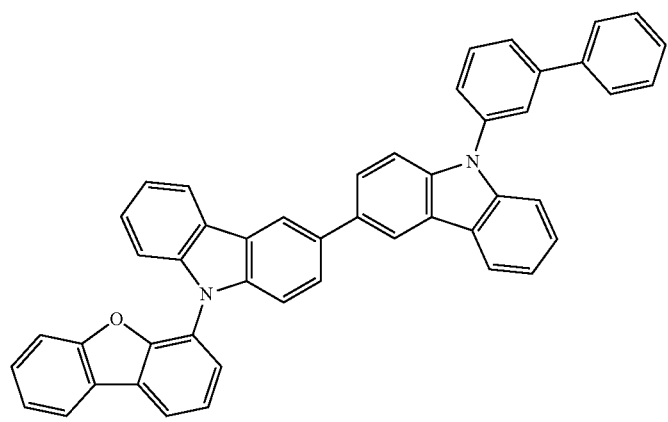 [SMILES: c1ccc(-c2cccc(-n3c4ccccc4c4cc(-c5ccc6c(c5)c5ccccc5n6-c5cccc6c5oc5ccccc56)ccc43)c2)cc1] | CAS-1643479-59-7 |
| 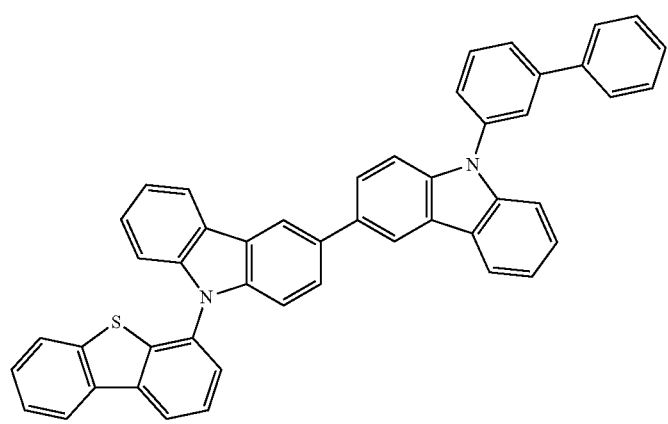 [SMILES: c1ccc(-c2cccc(-n3c4ccccc4c4cc(-c5ccc6c(c5)c5ccccc5n6-c5cccc6c5sc5ccccc56)ccc43)c2)cc1] | CAS-1643479-62-2 |

| Structure | CAS-number |
|---|---|
| 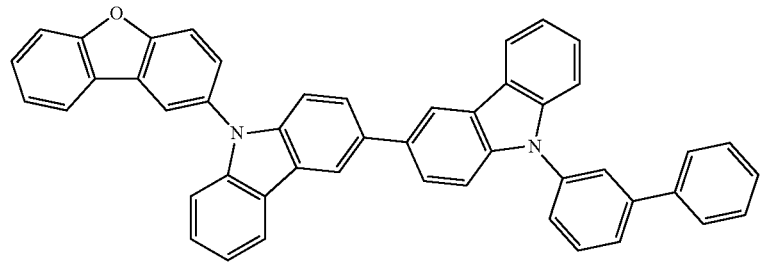 [SMILES: c1ccc(-c2cccc(-n3c4ccccc4c4cc(-c5ccc6c(c5)c5ccccc5n6-c5ccc6oc7ccccc7c6c5)ccc43)c2)cc1] | CAS-1643479-68-8 |
| 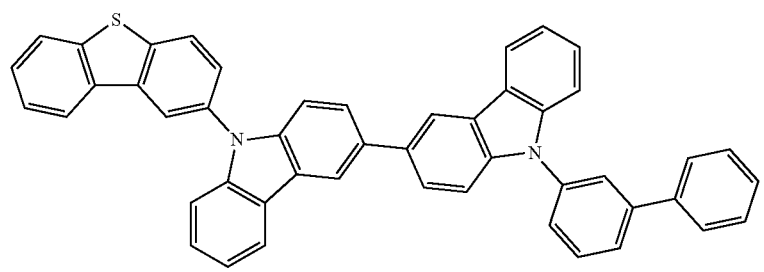 | CAS-1643479-69-9 |
| 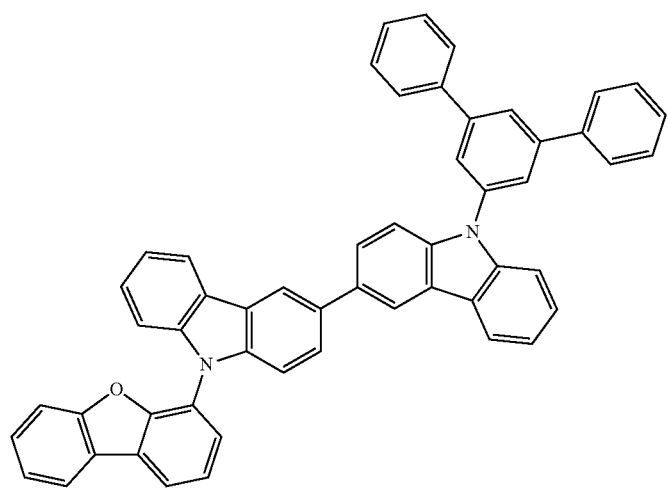 [SMILES: c1ccc(-c2cc(-c3ccccc3)cc(-n3c4ccccc4c4cc(-c5ccc6c(c5)c5ccccc5n6-c5cccc6c5oc5ccccc56)ccc43)c2)cc1] | CAS-1643479-74-6 |

| Structure | CAS-number |
|---|---|
| 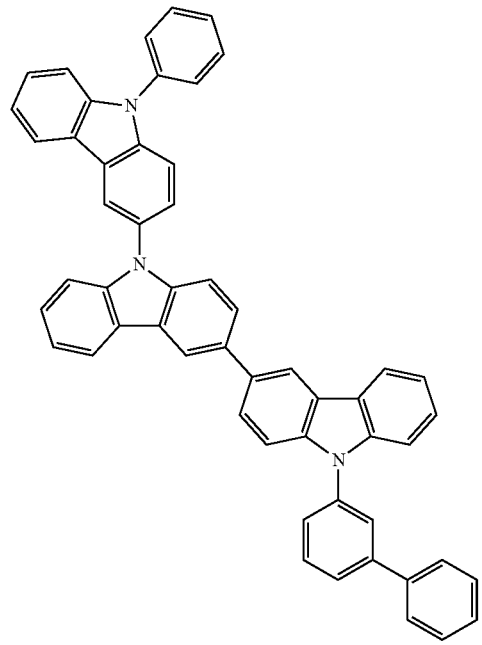 [SMILES: c1ccc(-c2cccc(-n3c4ccccc4c4cc(-c5ccc6c(c5)c5ccccc5n6-c5ccc6c(c5)c5ccccc5n6-c5ccccc5)ccc43)c2)cc1] | CAS-1643479-72-4 |
| 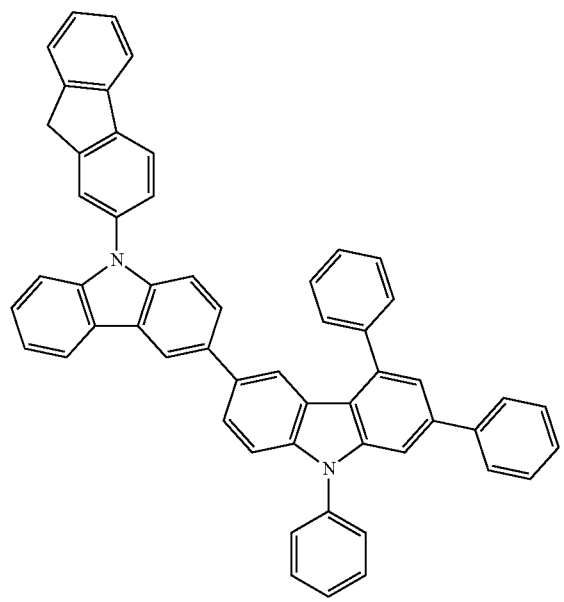 [SMILES: c1ccc(-c2cc(-c3ccccc3)c3c4cc(-c5ccc6c(c5)c5ccccc5n6-c5ccc6c(c5)Cc5ccccc5-6)ccc4n(-c4ccccc4)c3c2)cc1] | CAS-2018307-43-0 |

| Structure | CAS-number |
|---|---|
| 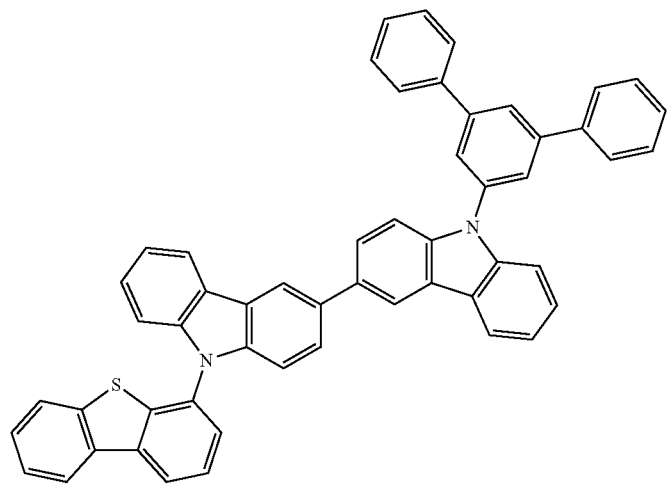 | CAS-1643479-75-7 |
| 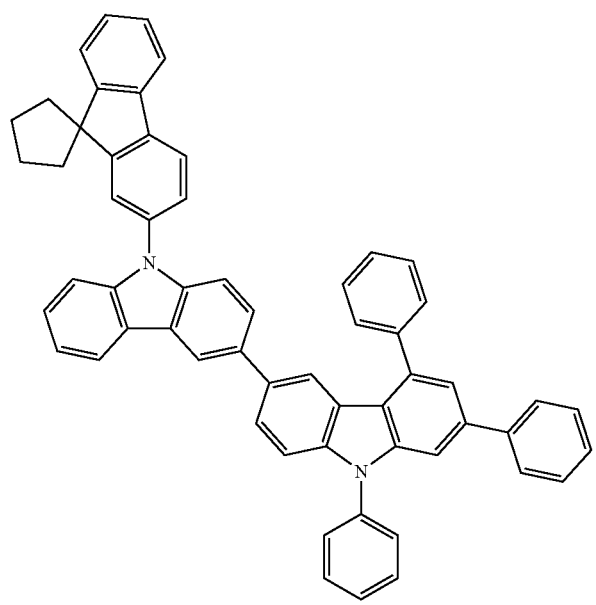 [SMILES: c1ccc(-c2cc(-c3ccccc3)c3c4cc(-c5ccc6c(c5)c5ccccc5n6-c5ccc6c(c5)C5(CCCC5)c5ccccc5-6)ccc4n(-c4ccccc4)c3c2)cc1] | CAS-2018307-47-4 |

| Structure | CAS-number |
|---|---|
| 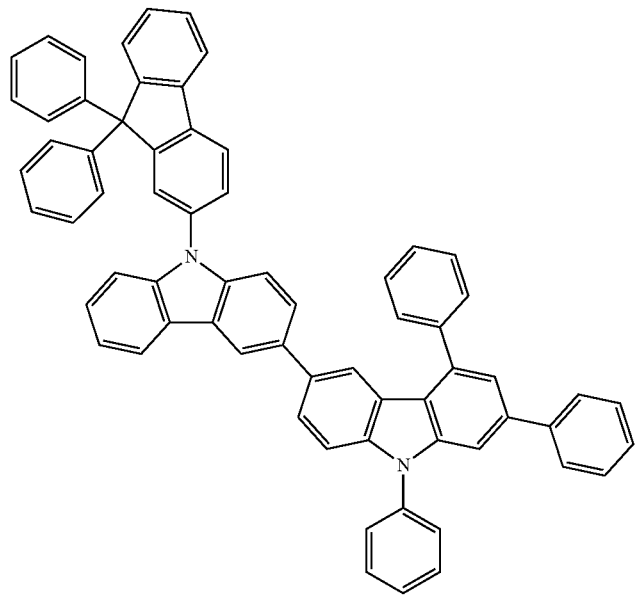 [SMILES: c1ccc(-c2cc(-c3ccccc3)c3c4cc(-c5ccc6c(c5)c5ccccc5n6-c5ccc6c(c5)C(c5ccccc5)(c5ccccc5)c5ccccc5-6)ccc4n(-c4ccccc4)c3c2)cc1] | CAS-2018307-50-9 |
| 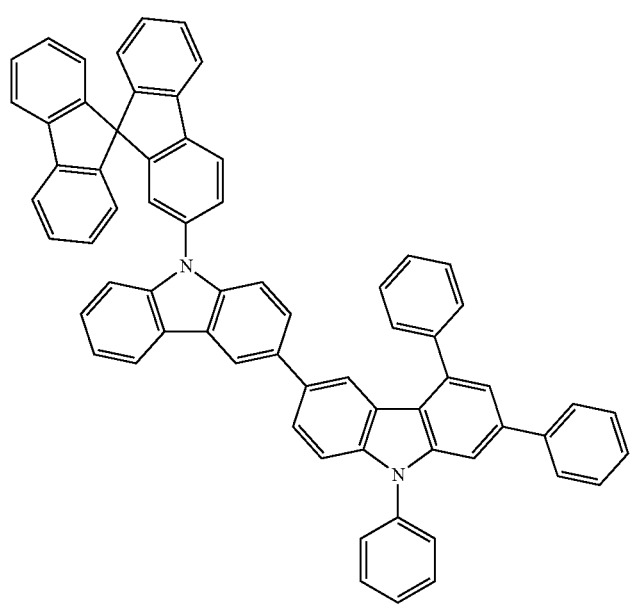 [SMILES: c1ccc(-c2cc(-c3ccccc3)c3c4cc(-c5ccc6c(c5)c5ccccc5n6-c5ccc6c(c5)C5(c7ccccc7-c7ccccc75)c5ccccc5-6)ccc4n(-c4ccccc4)c3c2)cc1] | CAS-2018307-49-6 |

| Structure | CAS-number |
|---|---|
| 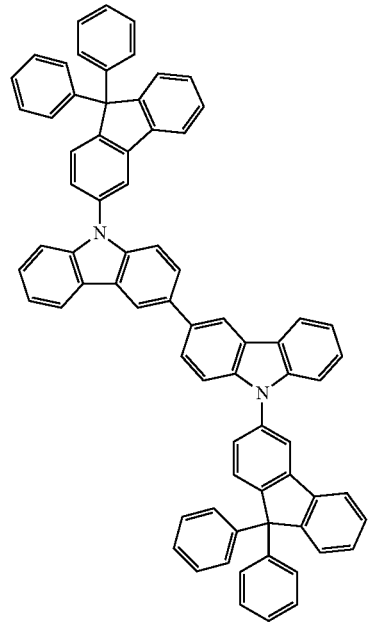 [SMILES: c1ccc(C2(c3ccccc3)c3ccccc3-c3cc(-n4c5ccccc5c5cc(-c6ccc7c(c6)c6ccccc6n7-c6ccc7c(c6)-c6ccccc6C7(c6ccccc6)c6ccccc6)ccc54)ccc32)cc1] | CAS-1656982-30-7 |
| 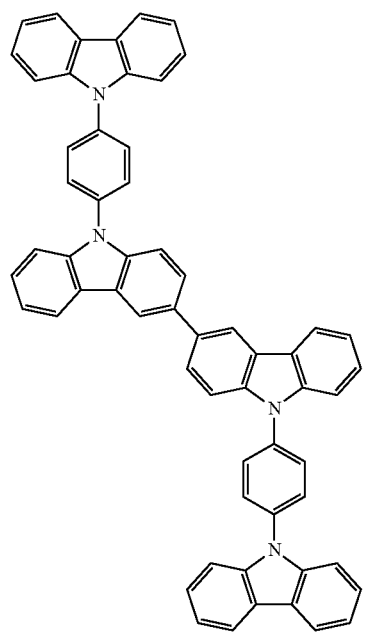 [SMILES: c1ccc2c(c1)c1ccccc1n2-c1ccc(-n2c3ccccc3c3cc(-c4ccc5c(c4)c4ccccc4n5-c4ccc(-n5c6ccccc6c6ccccc65)cc4)ccc32)cc1] | CAS-1680184-58-0 |

| Structure | CAS-number |
|---|---|
| 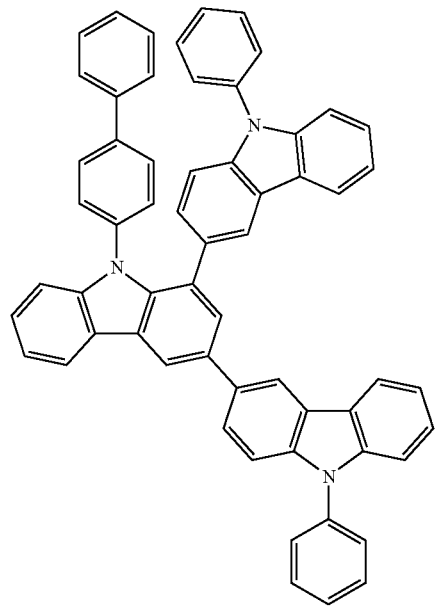 [SMILES: c1ccc(-c2ccc(-n3c4ccccc4c4cc(-c5ccc6c(c5)c5ccccc5n6-c5ccccc5)cc(-c5ccc6c(c5)c5ccccc5n6-c5ccccc5)c43)cc2)cc1] | CAS-1704071-12-4 |
| 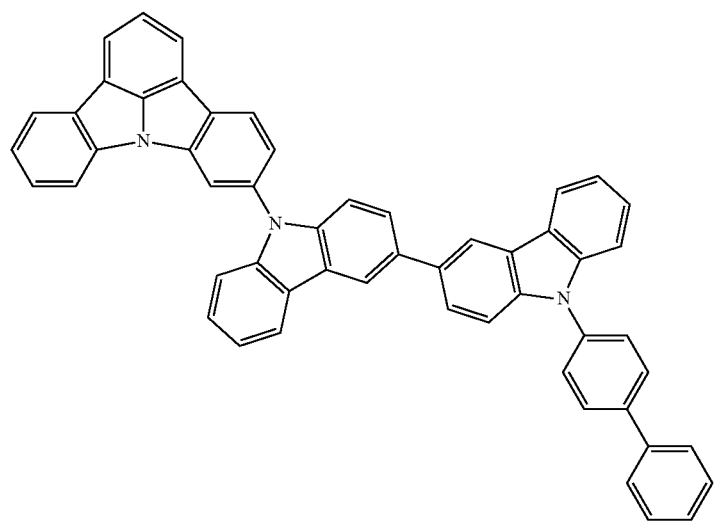 [SMILES: c1ccc(-c2ccc(-n3c4ccccc4c4cc(-c5ccc6c(c5)c5ccccc5n6-c5ccc6c7cccc8c9ccccc9n(c6c5)c87)ccc43)cc2)cc1] | CAS-1799483-56-9 |

| Structure | CAS-number |
|---|---|
| 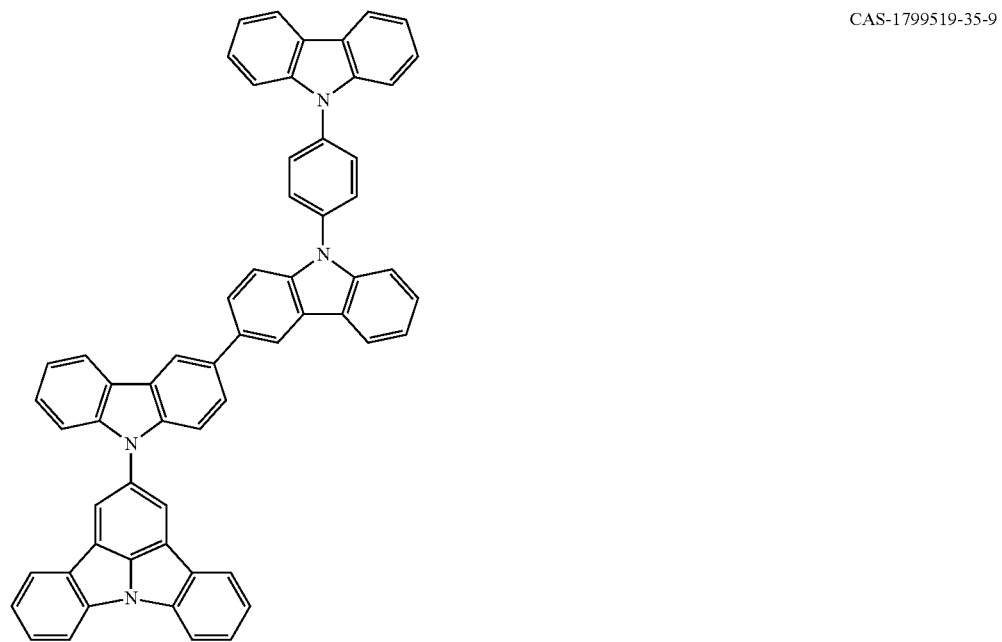 | CAS-1799519-35-9 |
| 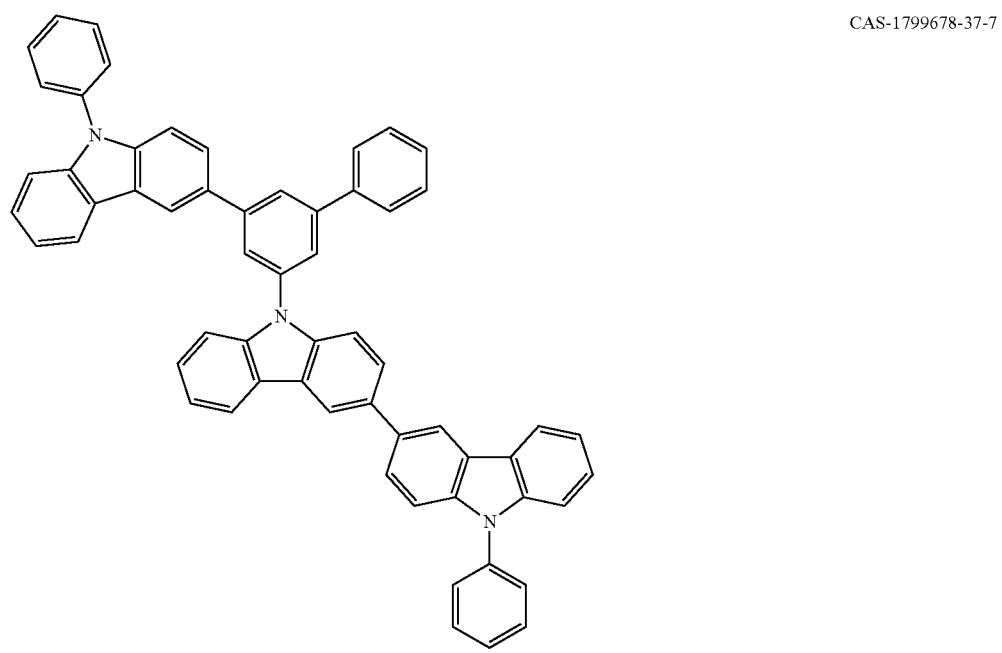 | CAS-1799678-37-7 |

| Structure | CAS-number |
|---|---|
| 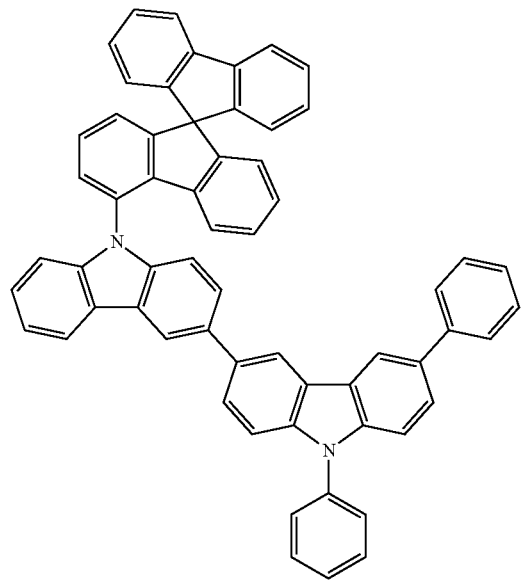 [SMILES: c1ccc(-c2ccc3c(c2)c2cc(-c4ccc5c(c4)c4ccccc4n5-c4cccc5c4-c4ccccc4C54c5ccccc5-c5ccccc54)ccc2n3-c2ccccc2)cc1] | CAS-2073116-97-7 |
| 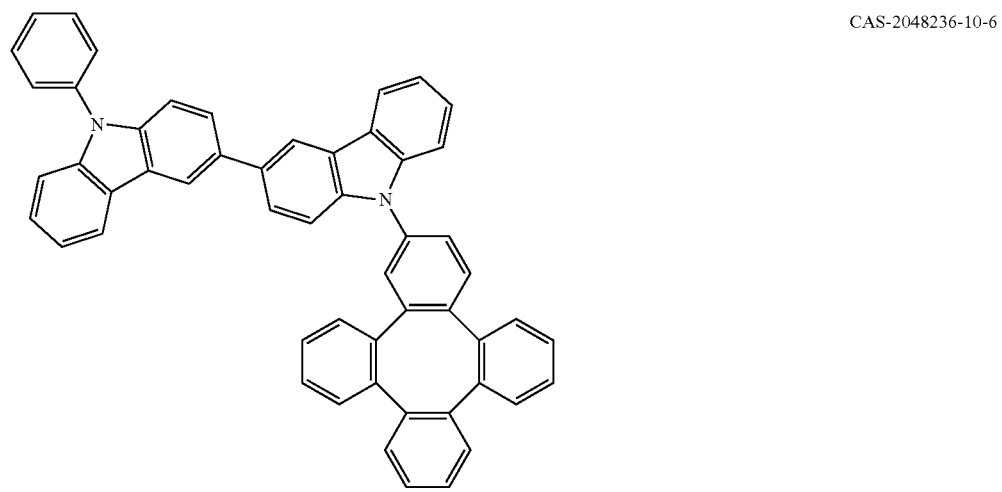 | CAS-2048236-10-6 |
| 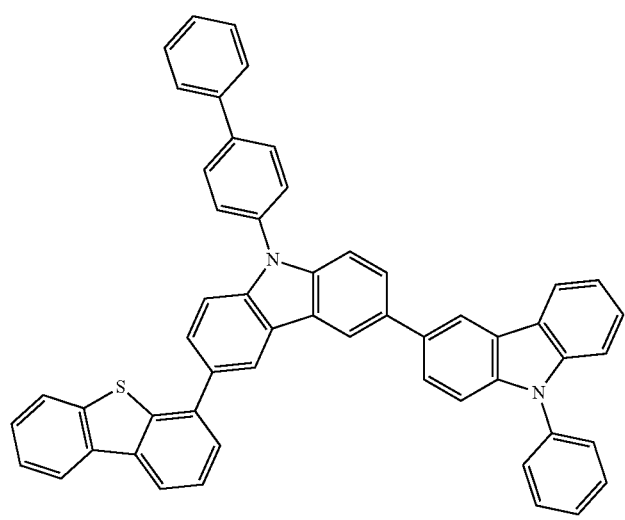 [SMILES: c1ccc(-c2ccc(-n3c4ccc(-c5ccc6c(c5)c5ccccc5n6-c5ccccc5)cc4c4cc(-c5cccc6c5sc5ccccc56)ccc43)cc2)cc1] | CAS-1799959-20-8 |

| Structure | CAS-number |
|---|---|
| 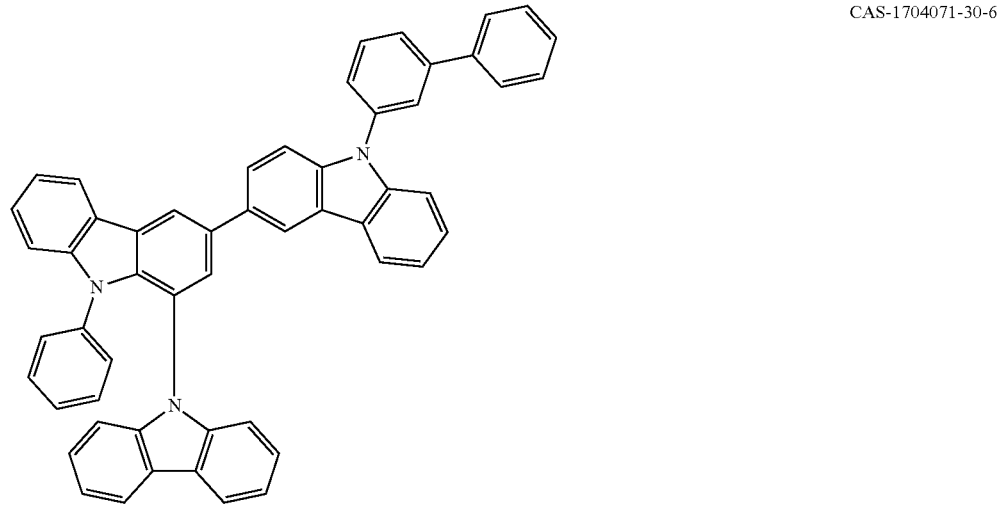 | CAS-1704071-30-6 |
| 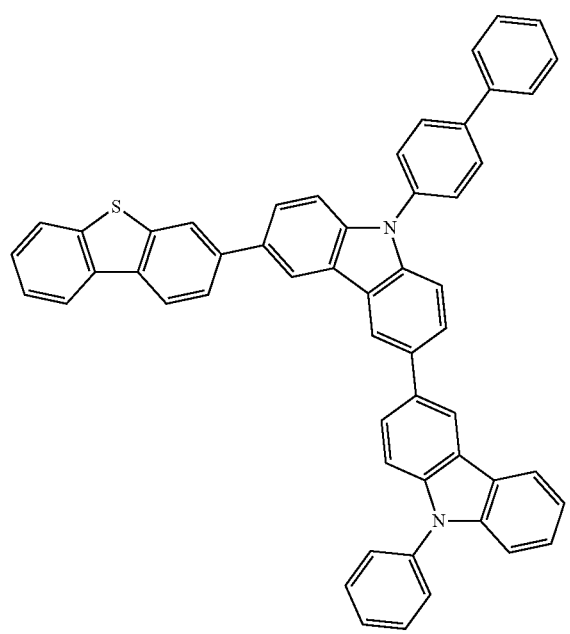 [SMILES: c1ccc(-c2ccc(-n3c4ccc(-c5ccc6c(c5)sc5ccccc56)cc4c4cc(-c5ccc6c(c5)c5ccccc5n6-c5ccccc5)ccc43)cc2)cc1] | CAS-1799959-21-9 |

-continued
| Structure | CAS-number |
|---|---|
| 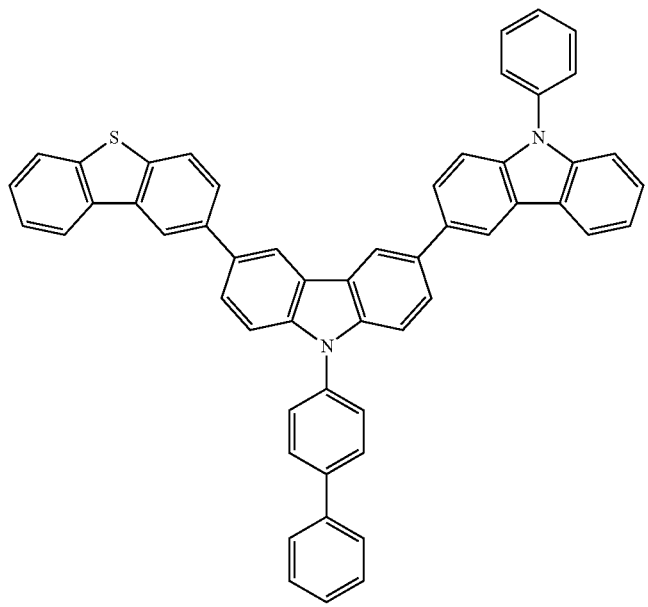 [SMILES: c1ccc(-c2ccc(-n3c4ccc(-c5ccc6oc7ccccc7c6c5)cc4c4cc(-c5ccc6c(c5)c5ccccc5n6-c5ccccc5)ccc43)cc2)cc1] | CAS-1799959-22-0 |
| 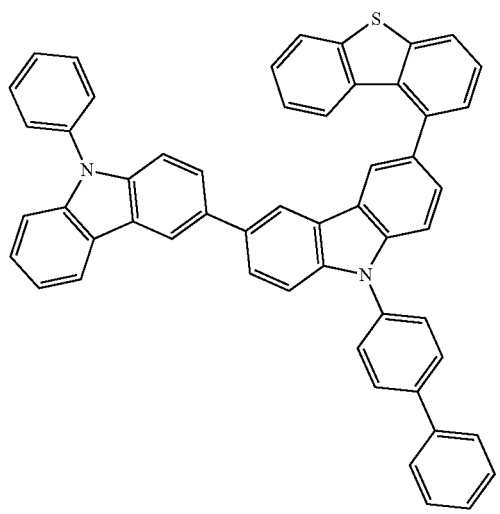 [SMILES: c1ccc(-c2ccc(-n3c4ccc(-c5ccc6c(c5)c5ccccc5n6-c5ccccc5)cc4c4cc(-c5cccc6oc7ccccc7c56)ccc43)cc2)cc1] | CAS-1799959-23-1 |
| 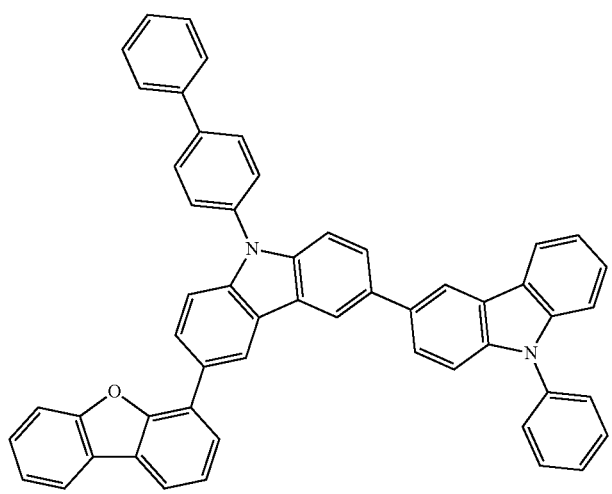 | CAS-1799959-24-2 |

| Structure | CAS-number |
|---|---|
| 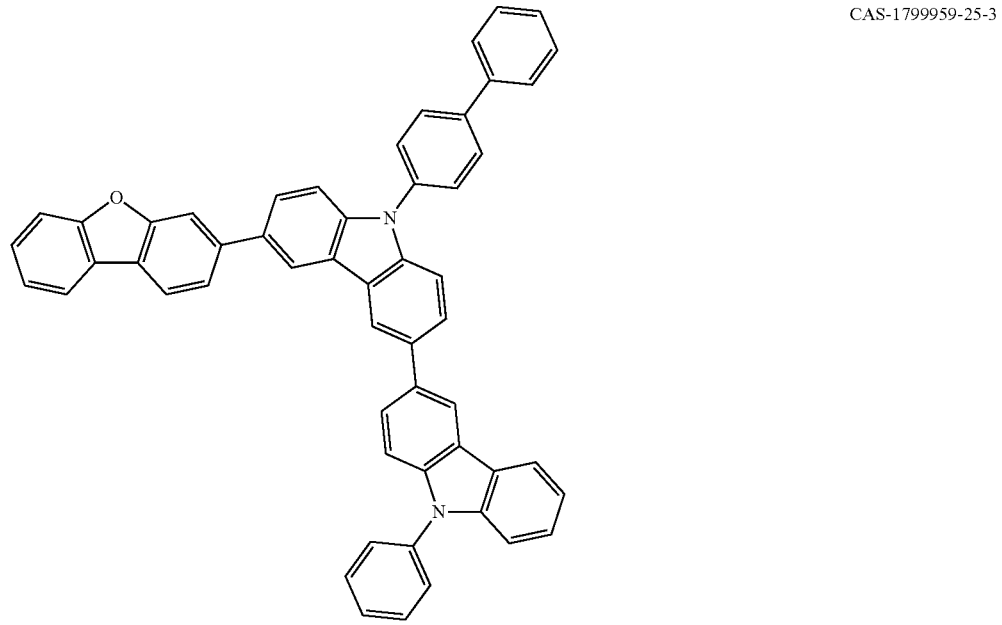 | CAS-1799959-25-3 |
| 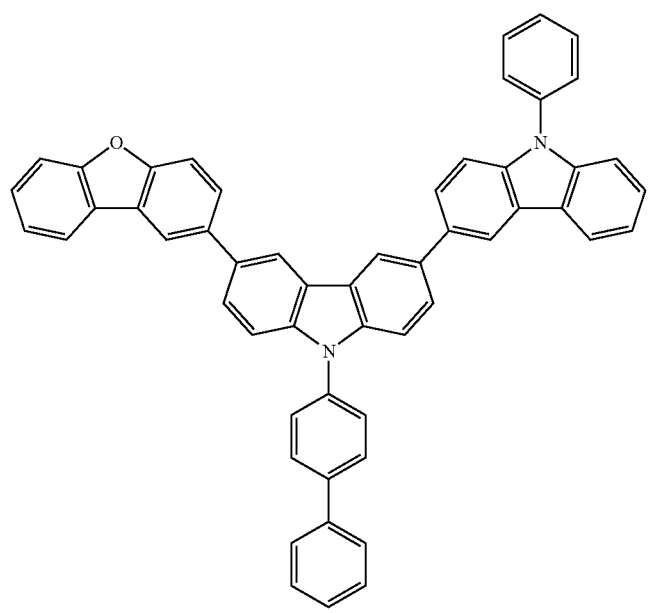 | CAS-1799959-26-4 |

| Structure | CAS-number |
|---|---|
| 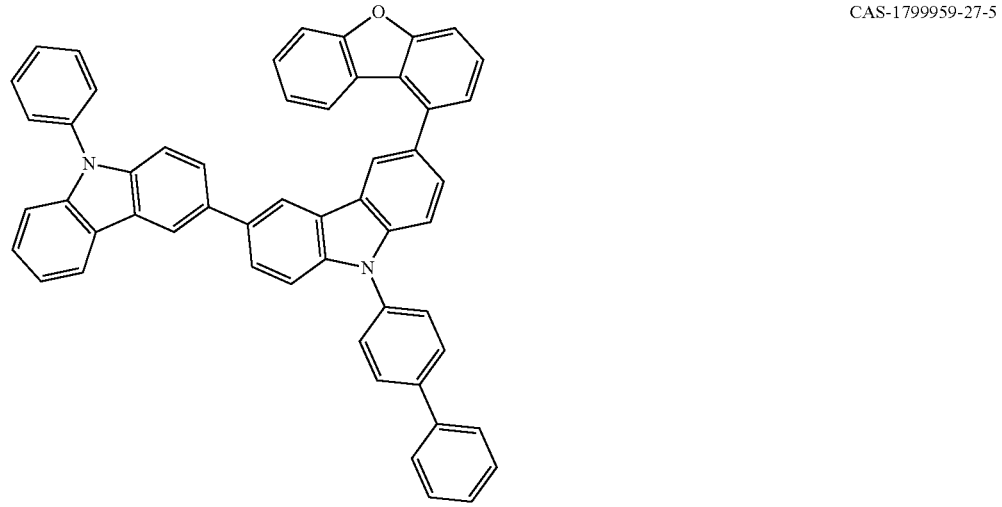 | CAS-1799959-27-5 |
| 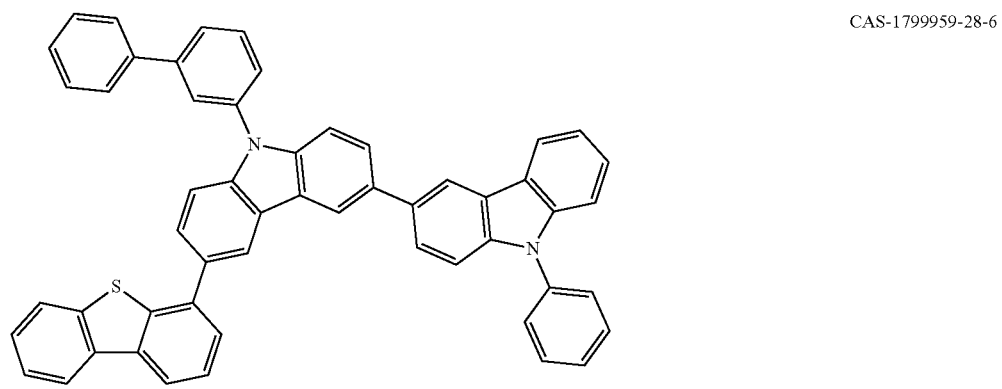 | CAS-1799959-28-6 |
| 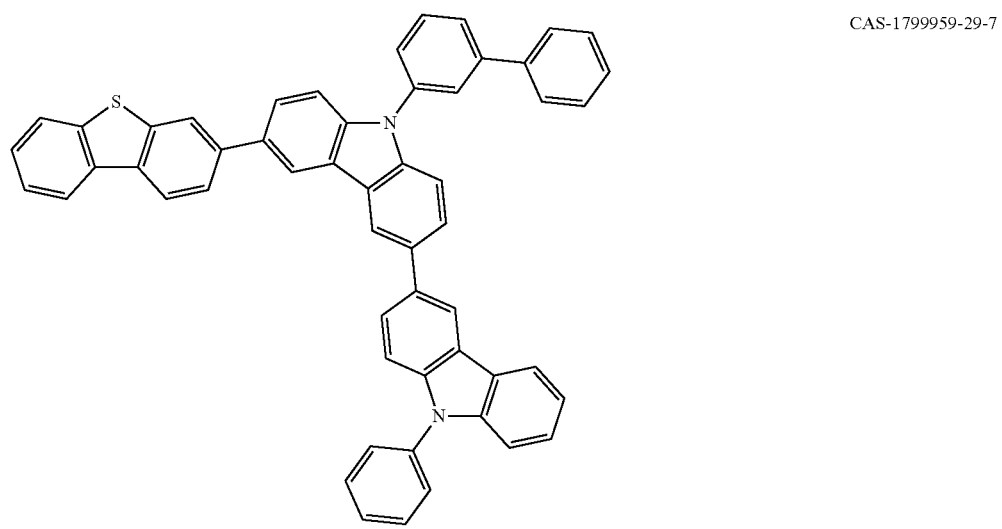 | CAS-1799959-29-7 |

| Structure | CAS-number |
|---|---|
| 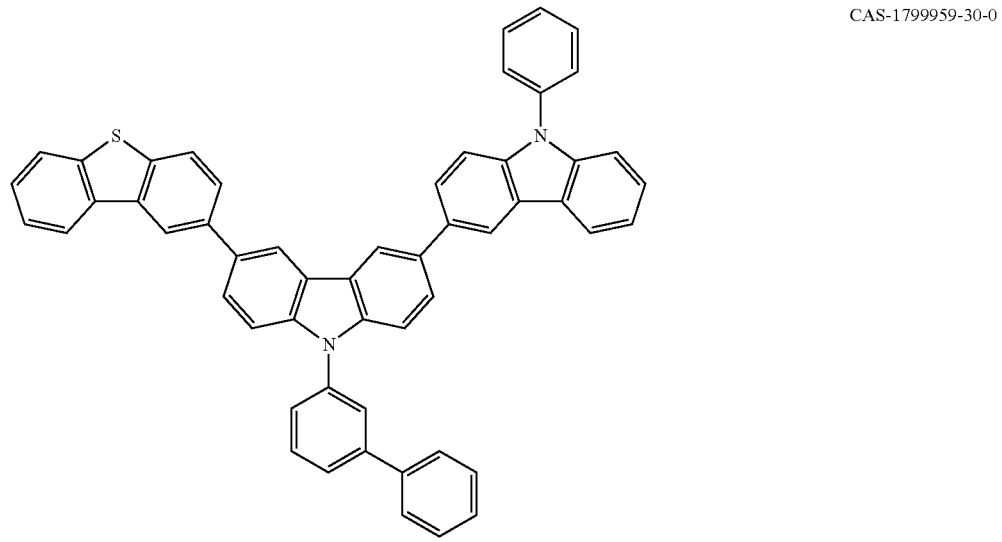 | CAS-1799959-30-0 |
| 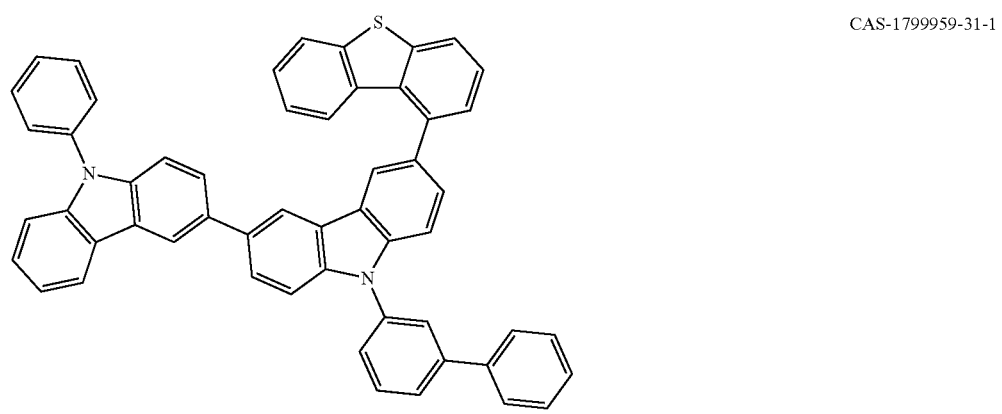 | CAS-1799959-31-1 |
| 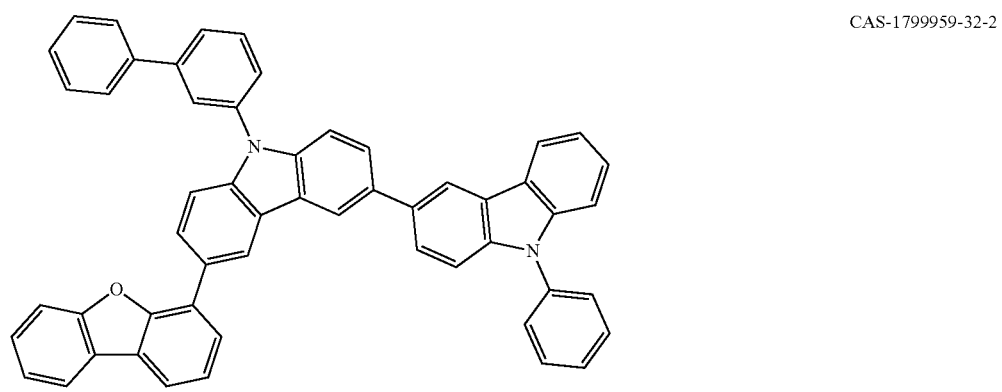 | CAS-1799959-32-2 |

| Structure | CAS-number |
|---|---|
| 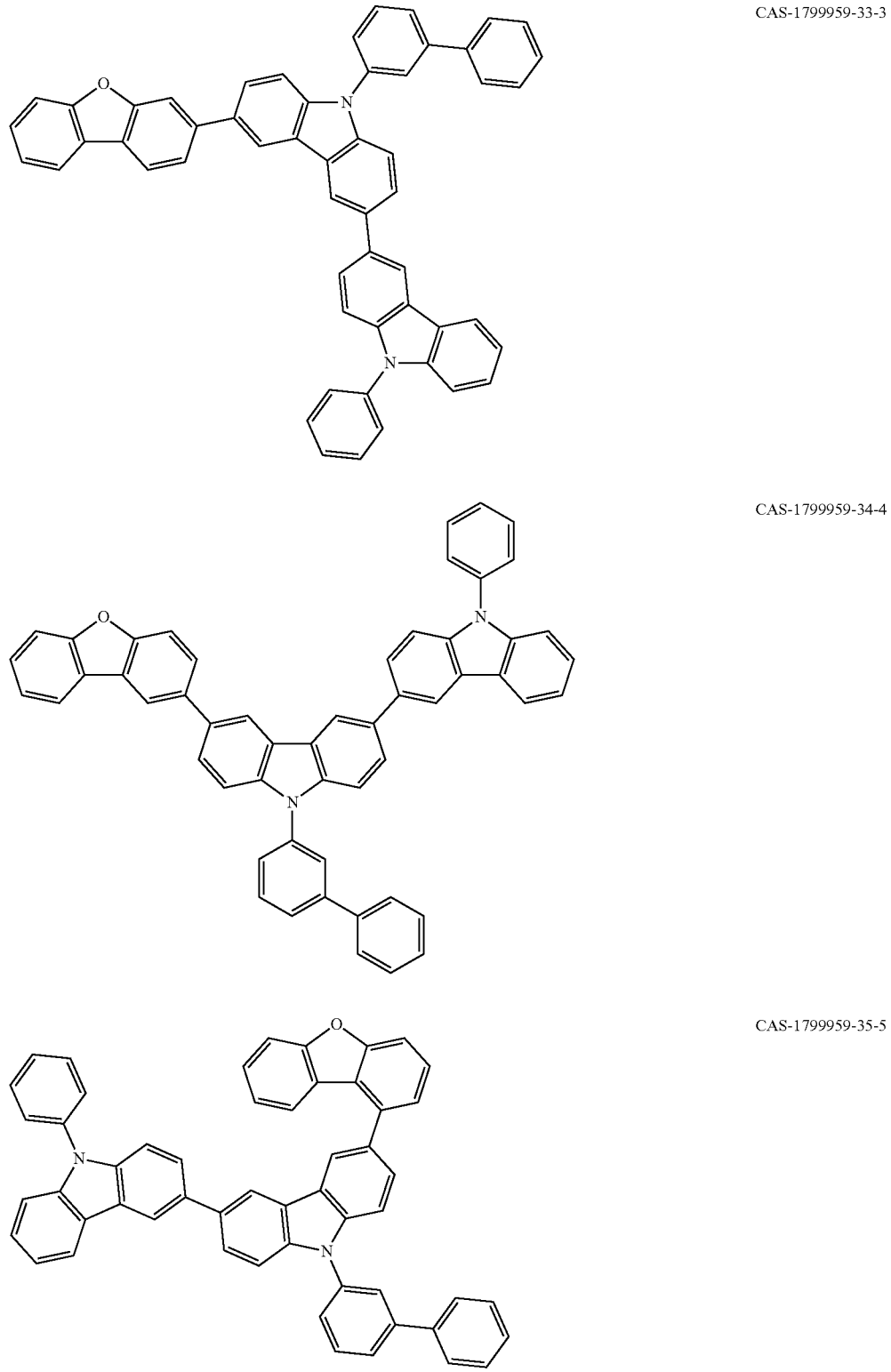 | CAS-1799959-33-3 |
| 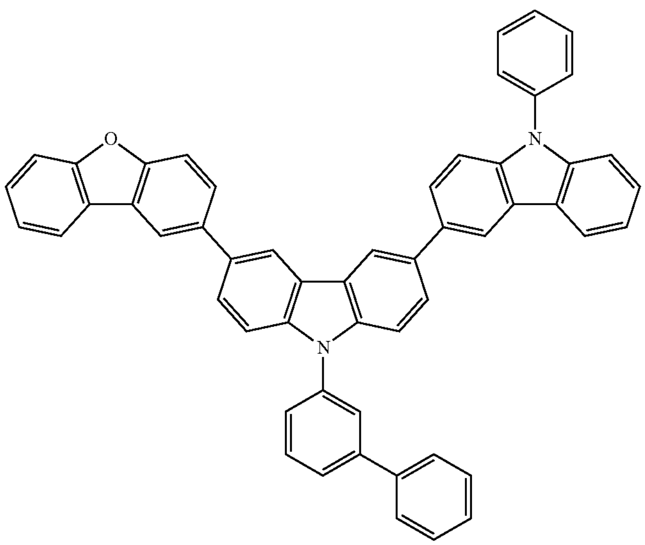 [SMILES: c1ccc(-c2cccc(-n3c4ccc(-c5ccc6oc7ccccc7c6c5)cc4c4cc(-c5ccc6c(c5)c5ccccc5n6-c5ccccc5)ccc43)c2)cc1] | CAS-1799959-34-4 |
| 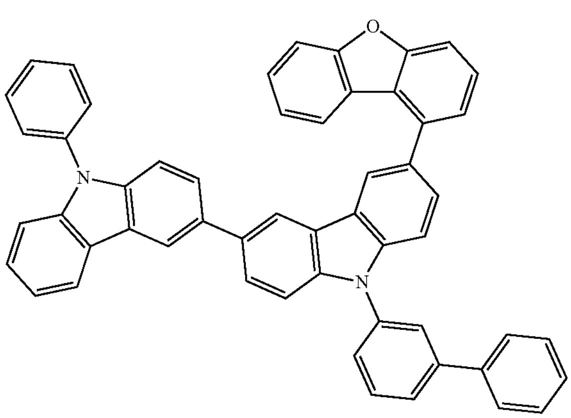 [SMILES: c1ccc(-c2cccc(-n3c4ccc(-c5ccc6c(c5)c5ccccc5n6-c5ccccc5)cc4c4cc(-c5cccc6oc7ccccc7c56)ccc43)c2)cc1] | CAS-1799959-35-5 |

| Structure | CAS-number |
|---|---|
| 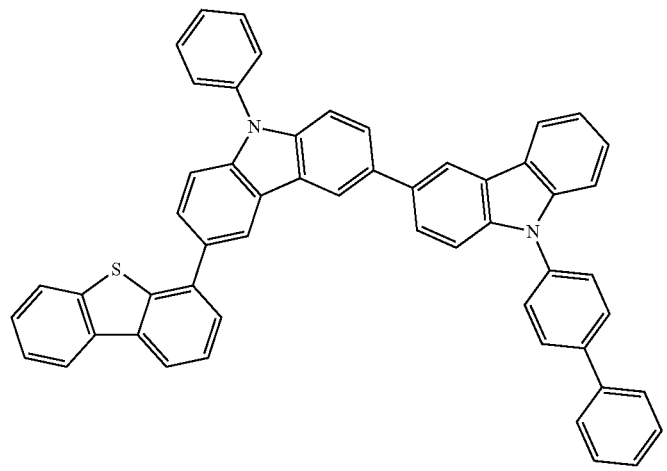 [SMILES: c1ccc(-c2ccc(-n3c4ccccc4c4cc(-c5ccc6c(c5)c5cc(-c7cccc8c7sc7ccccc78)ccc5n6-c5ccccc5)ccc43)cc2)cc1] | CAS-1799959-60-6 |
| 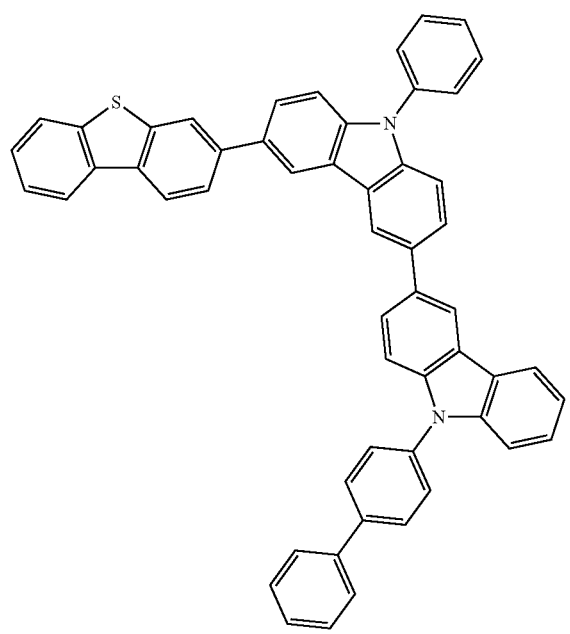 | CAS-1799959-61-7 |

| Structure | CAS-number |
|---|---|
| 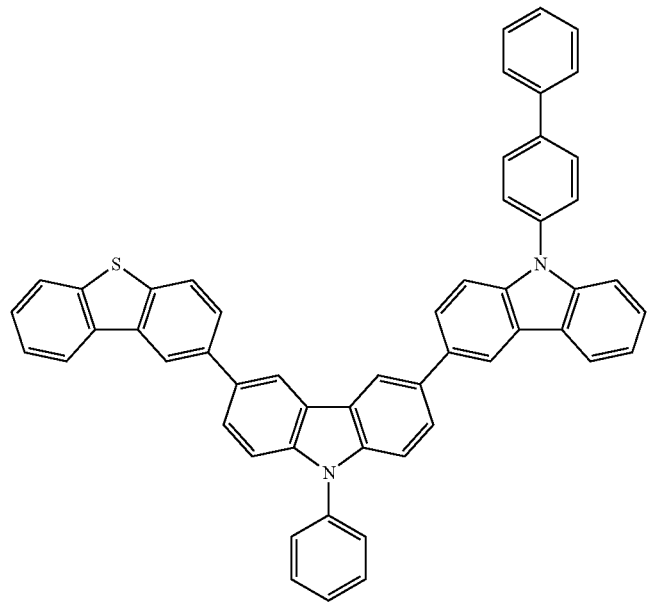 | CAS-1799959-62-8 |
| 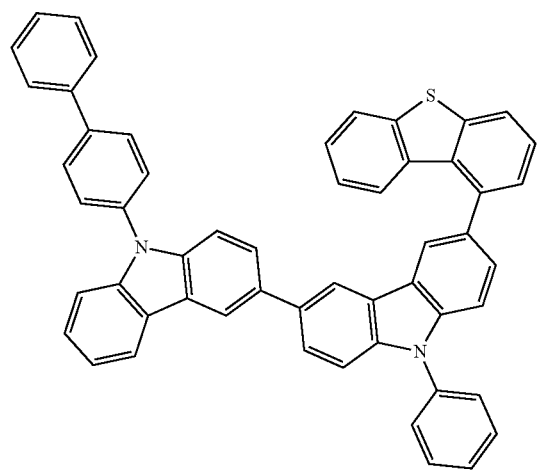 [SMILES: c1ccc(-c2ccc(-n3c4ccccc4c4cc(-c5ccc6c(c5)c5cc(-c7cccc8sc9ccccc9c78)ccc5n6-c5ccccc5)ccc43)cc2)cc1] | CAS-1799959-63-9 |
| 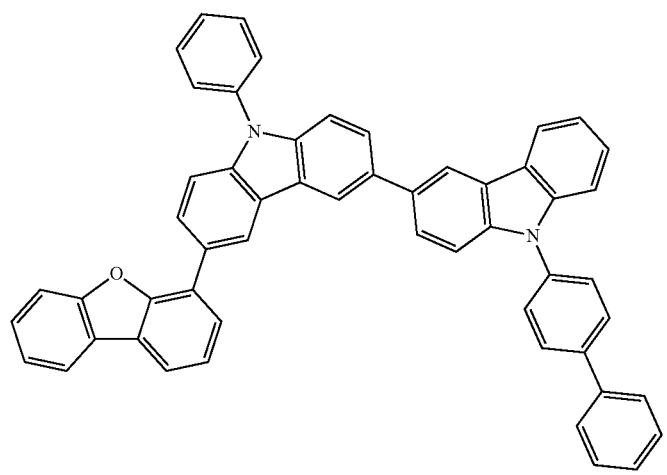 [SMILES: c1ccc(-c2ccc(-n3c4ccccc4c4cc(-c5ccc6c(c5)c5cc(-c7cccc8c7oc7ccccc78)ccc5n6-c5ccccc5)ccc43)cc2)cc1] | CAS-1799959-64-0 |

| Structure | CAS-number |
|---|---|
| 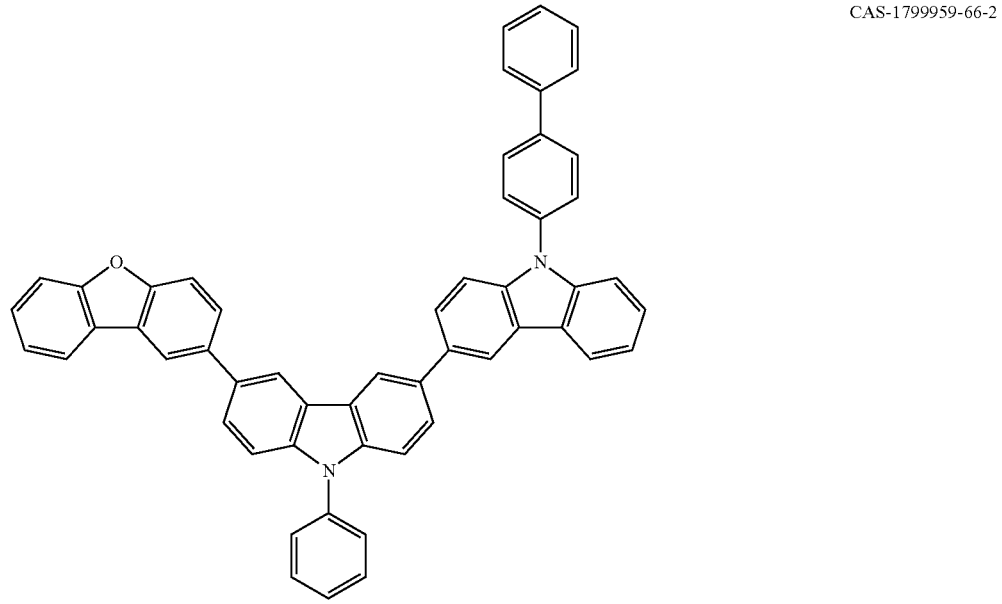 | CAS-1799959-66-2 |
| 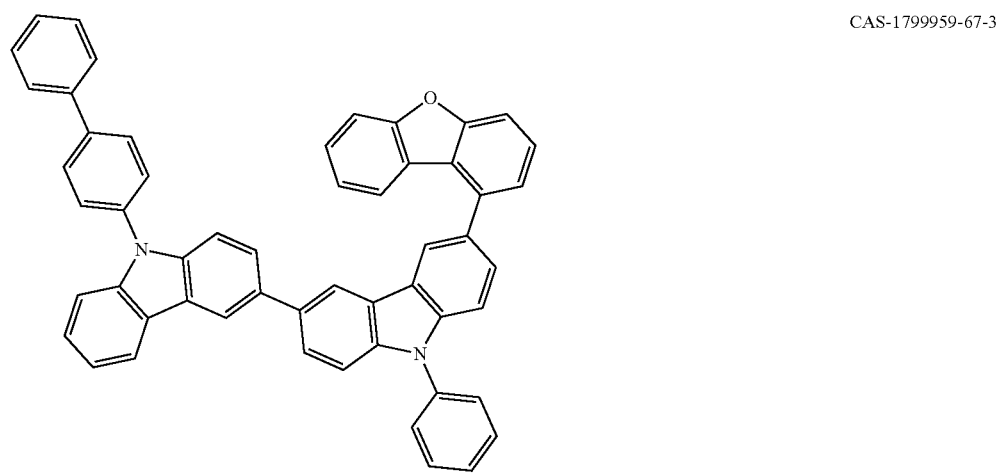 | CAS-1799959-67-3 |
| 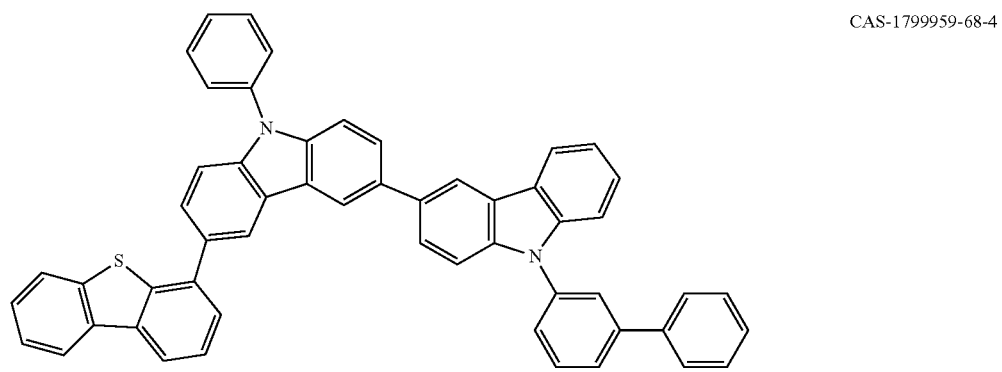 | CAS-1799959-68-4 |

| Structure | CAS-number |
|---|---|
| 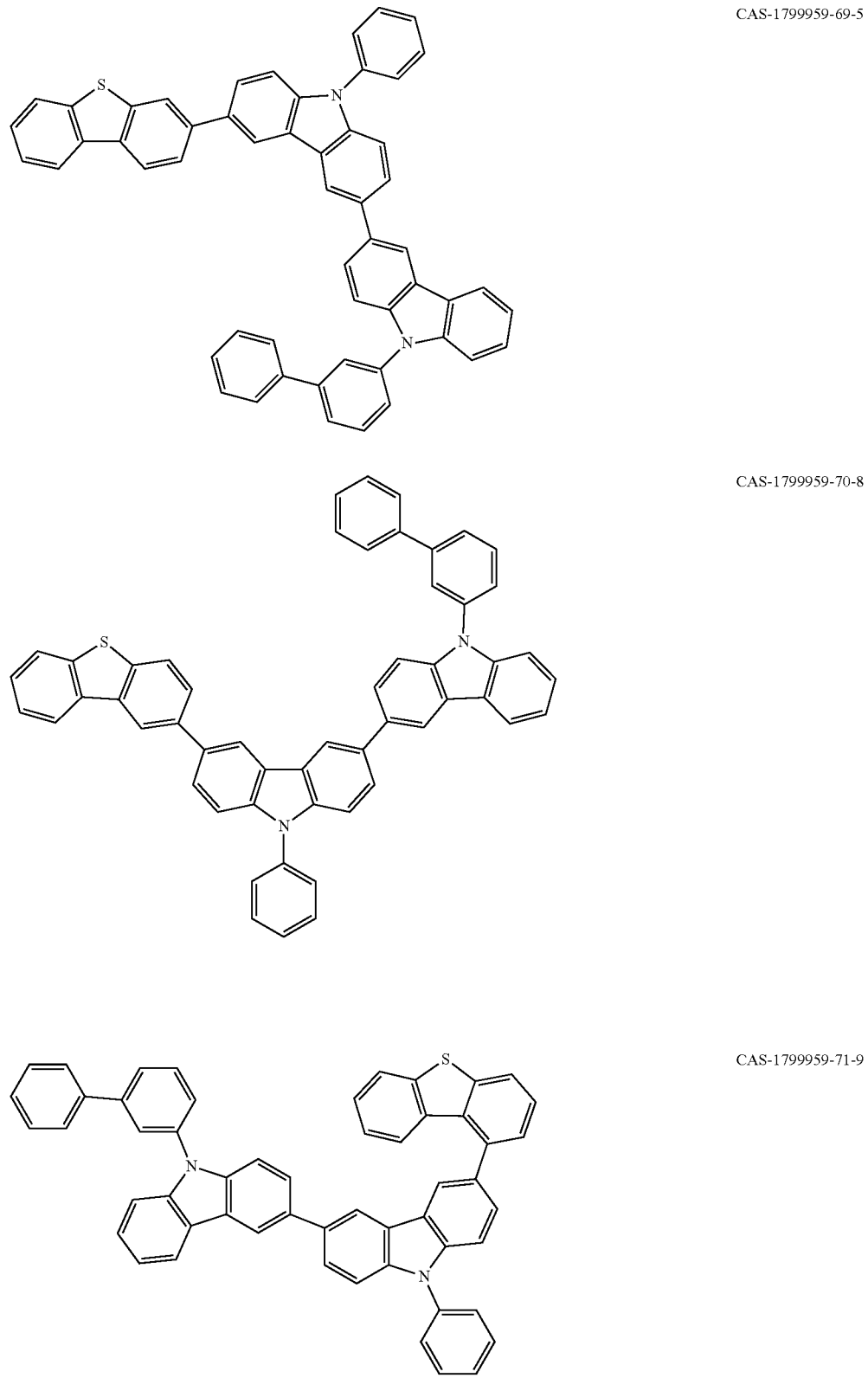 | CAS-1799959-69-5 |
| 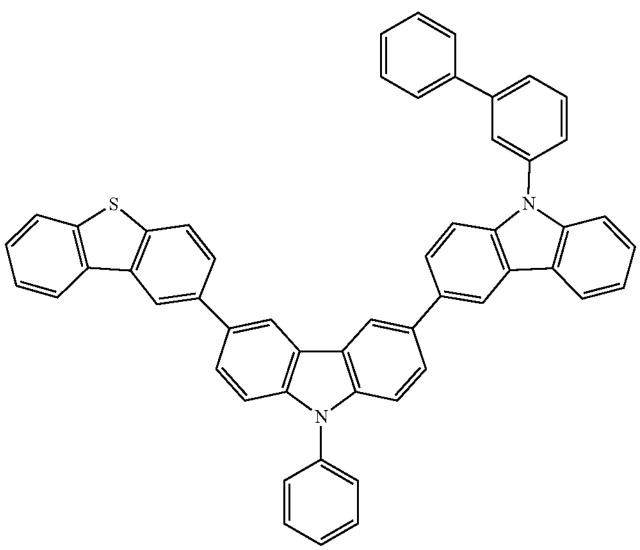 [SMILES: c1ccc(-c2cccc(-n3c4ccccc4c4cc(-c5ccc6c(c5)c5cc(-c7ccc8sc9ccccc9c8c7)ccc5n6-c5ccccc5)ccc43)c2)cc1] | CAS-1799959-70-8 |
| 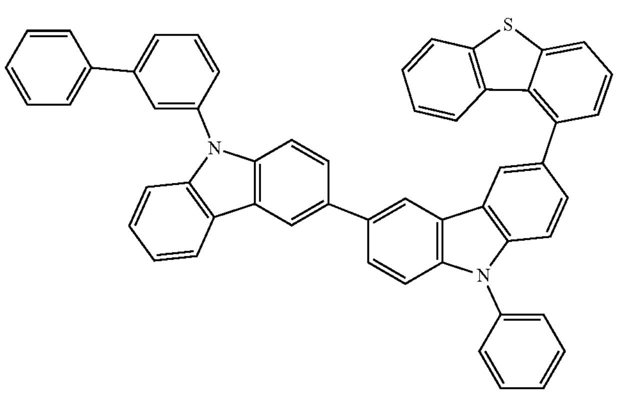 [SMILES: c1ccc(-c2cccc(-n3c4ccccc4c4cc(-c5ccc6c(c5)c5cc(-c7cccc8sc9ccccc9c78)ccc5n6-c5ccccc5)ccc43)c2)cc1] | CAS-1799959-71-9 |

| Structure | CAS-number |
|---|---|
| 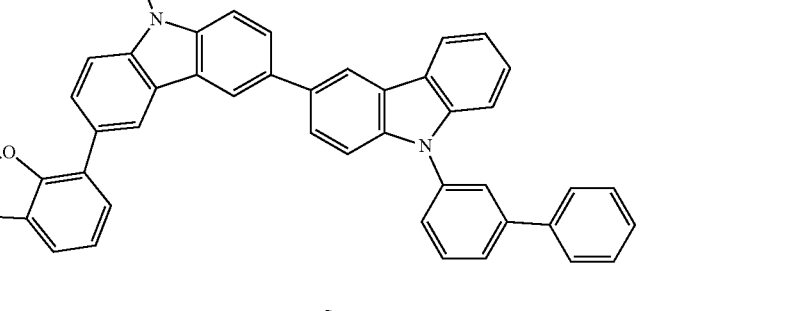 | CAS-1799959-72-0 |
| 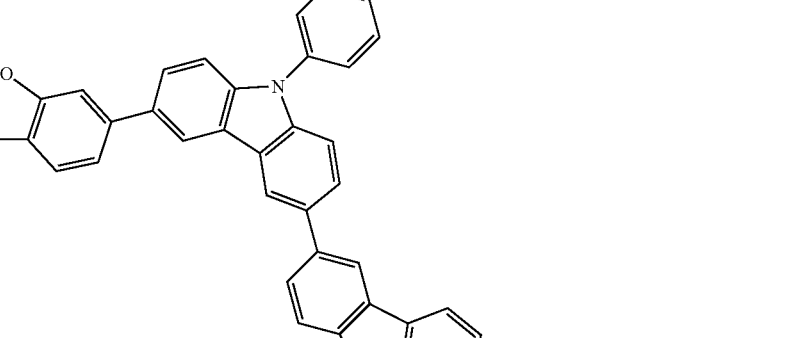 | CAS-1799959-73-1 |
| 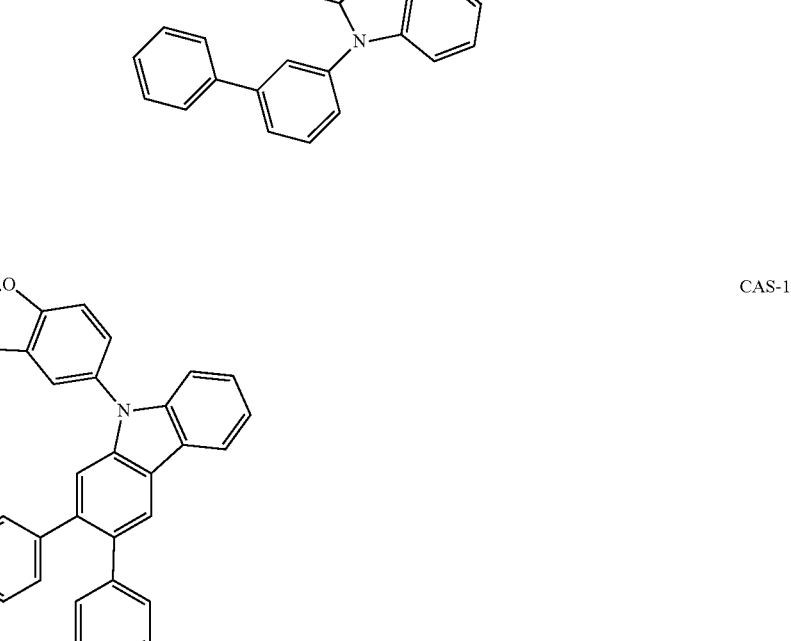 | CAS-1428635-33-9 |

| Structure | CAS-number |
|---|---|
| 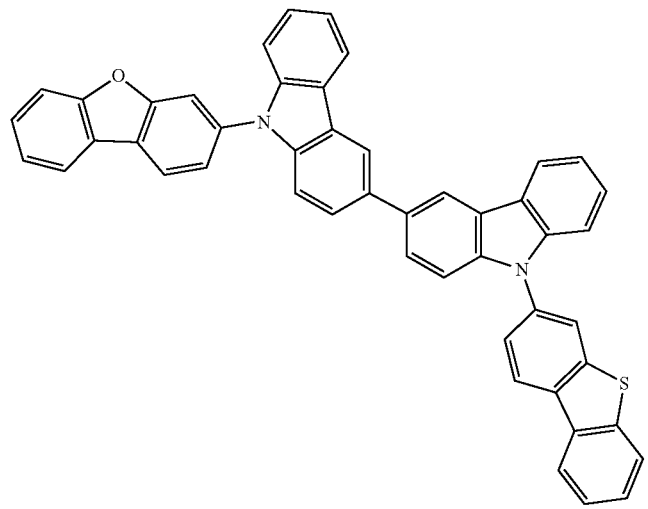 [SMILES: c1ccc2c(c1)oc1cc(-n3c4ccccc4c4cc(-c5ccc6c(c5)c5ccccc5n6-c5ccc6c(c5)sc5ccccc56)ccc43)ccc12] | CAS-1890157-93-3 |
| 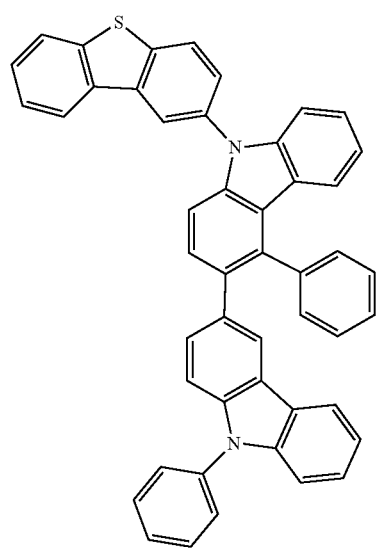 [SMILES: c1ccc(-c2c(-c3ccc4c(c3)c3ccccc3n4-c3ccccc3)ccc3c2c2ccccc2n3-c2ccc3sc4ccccc4c3c2)cc1] | CAS-1428635-40-8 |
| 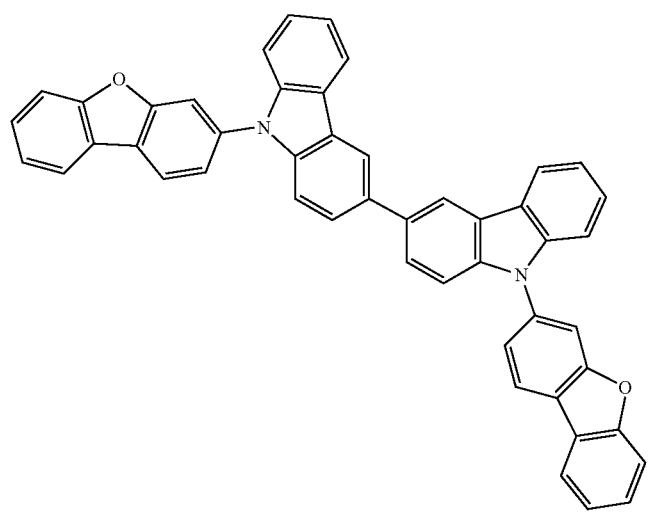 [SMILES: c1ccc2c(c1)oc1cc(-n3c4ccccc4c4cc(-c5ccc6c(c5)c5ccccc5n6-c5ccc6c(c5)oc5ccccc56)ccc43)ccc12] | CAS-1890157-94-4 |

| Structure | CAS-number |
|---|---|
| 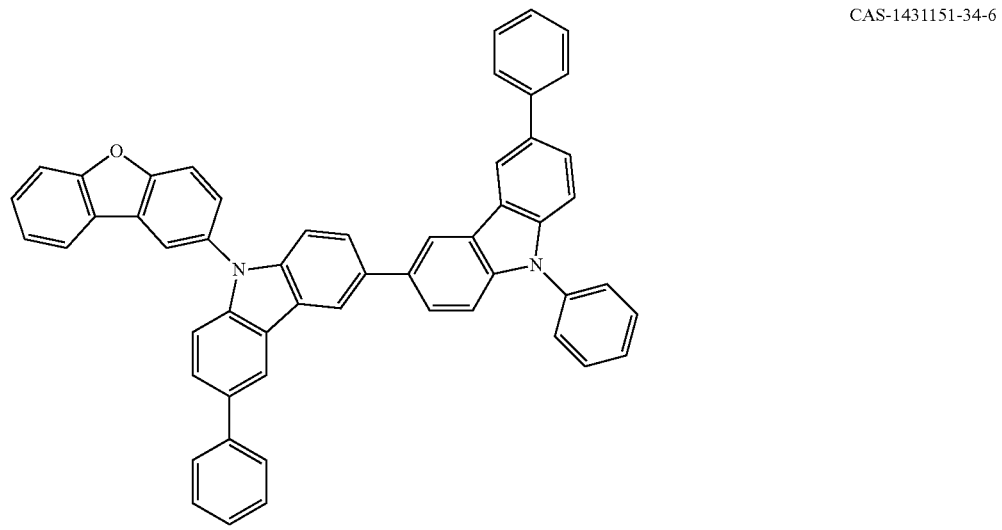 | CAS-1431151-34-6 |
| 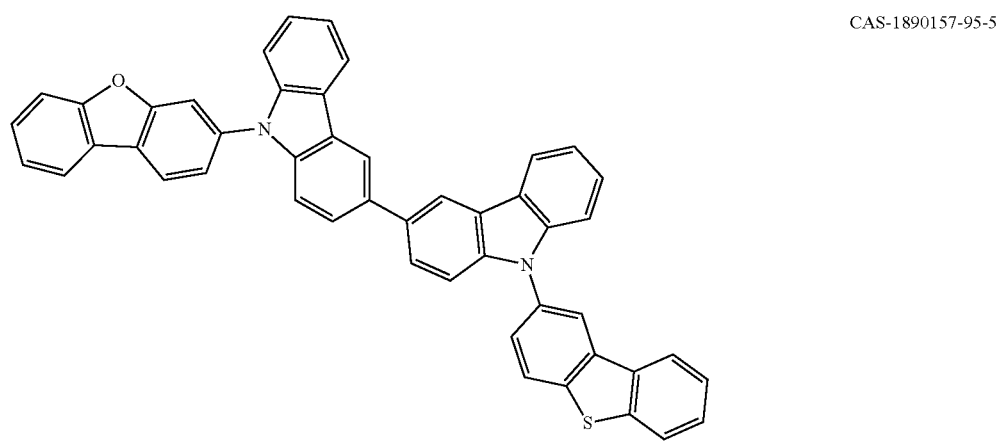 | CAS-1890157-95-5 |
| 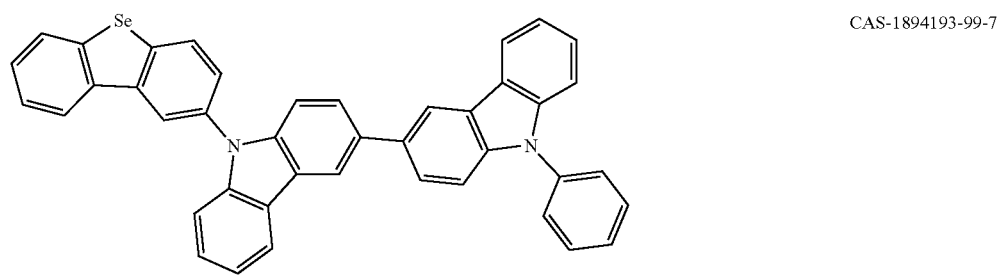 | CAS-1894193-99-7 |

| Structure | CAS-number |
|---|---|
| 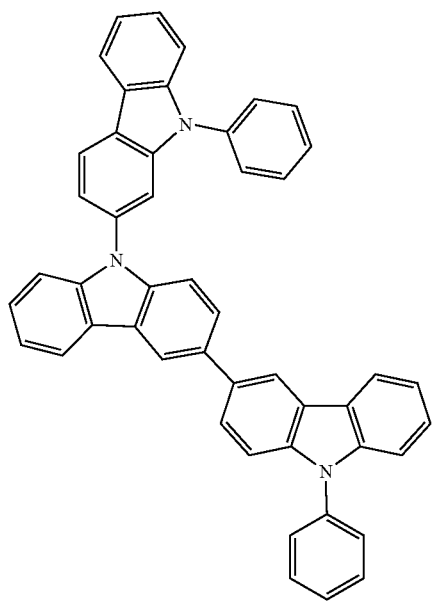 [SMILES: c1ccc(-n2c3ccccc3c3cc(-c4ccc5c(c4)c4ccccc4n5-c4ccc5c6ccccc6n(-c6ccccc6)c5c4)ccc32)cc1] | CAS-1894193-97-5 |
| 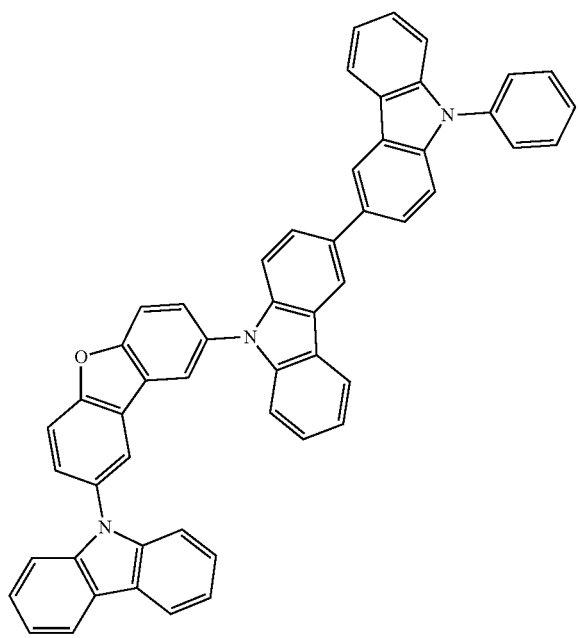 [SMILES: c1ccc(-n2c3ccccc3c3cc(-c4ccc5c(c4)c4ccccc4n5-c4ccc5oc6ccc(-n7c8ccccc8c8ccccc87)cc6c5c4)ccc32)cc1] | CAS-1446411-07-9 |
| 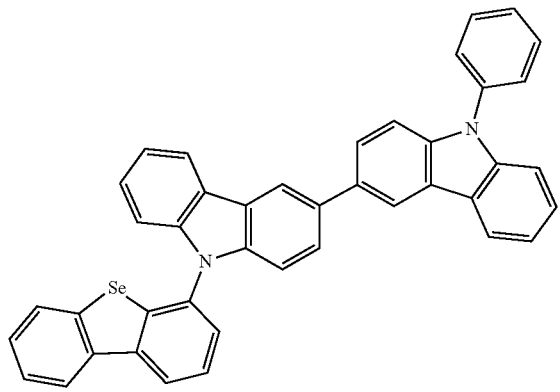 [SMILES: c1ccc(-n2c3ccccc3c3cc(-c4ccc5c(c4)c4ccccc4n5-c4cccc5c4[se]c4ccccc45)ccc32)cc1] | CAS-1894194-03-6 |

| Structure | CAS-number |
|---|---|
| 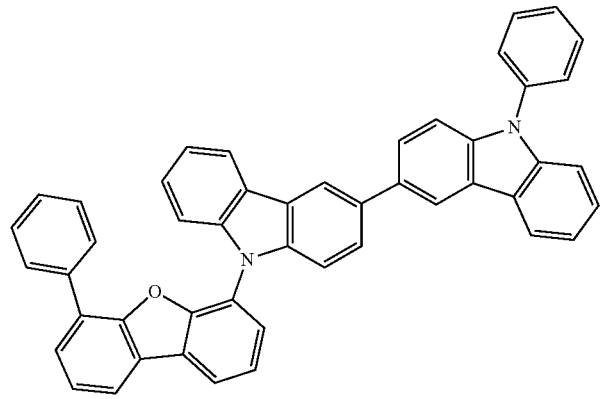 [SMILES: c1ccc(-c2cccc3c2oc2c(-n4c5ccccc5c5cc(-c6ccc7c(c6)c6ccccc6n7-c6ccccc6)ccc54)cccc23)cc1] | CAS-1894194-10-5 |
| 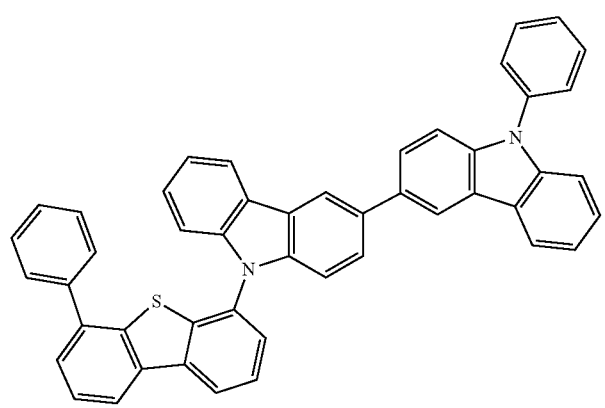 [SMILES: c1ccc(-c2cccc3c2sc2c(-n4c5ccccc5c5cc(-c6ccc7c(c6)c6ccccc6n7-c6ccccc6)ccc54)cccc23)cc1] | CAS-1894194-11-6 |
| 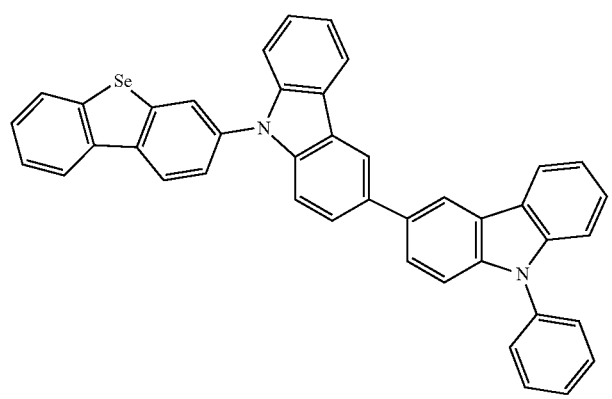 [SMILES: c1ccc(-n2c3ccccc3c3cc(-c4ccc5c(c4)c4ccccc4n5-c4ccc5c(c4)[se]c4ccccc45)ccc32)cc1] | CAS-1894194-16-1 |

| Structure | CAS-number |
|---|---|
| 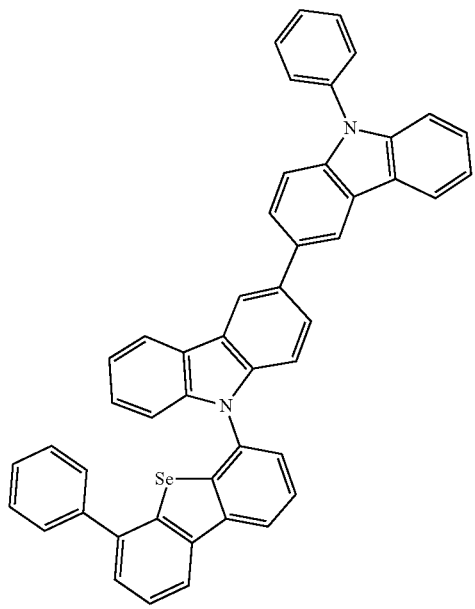 [SMILES: c1ccc(-c2cccc3c2[se]c2c(-n4c5ccccc5c5cc(-c6ccc7c(c6)c6ccccc6n7-c6ccccc6)ccc54)cccc23)cc1] | CAS-1894194-12-7 |
| 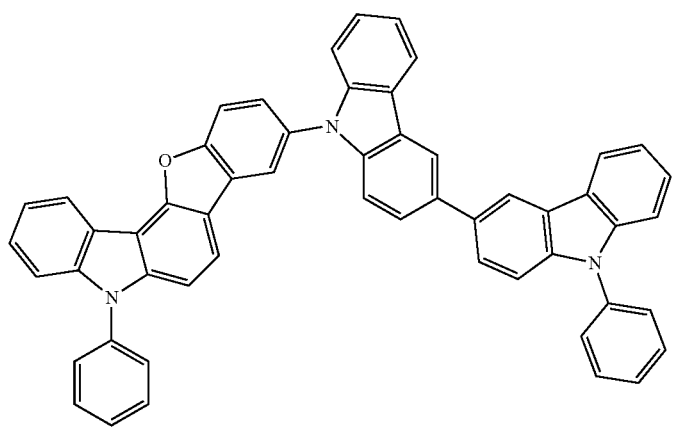 [SMILES: c1ccc(-n2c3ccccc3c3cc(-c4ccc5c(c4)c4ccccc4n5-c4ccc5oc6c(ccc7c6c6ccccc6n7-c6ccccc6)c5c4)ccc32)cc1] | CAS-1497337-43-5 |
| 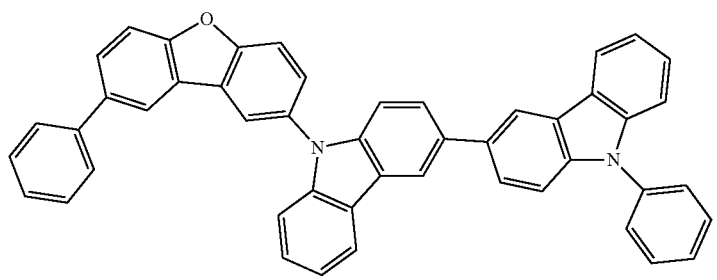 [SMILES: c1ccc(-c2ccc3oc4ccc(-n5c6ccccc6c6cc(-c7ccc8c(c7)c7ccccc7n8-c7ccccc7)ccc65)cc4c3c2)cc1] | CAS-1499917-70-2 |

| Structure | CAS-number |
|---|---|
| 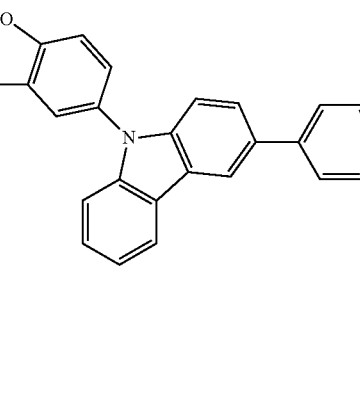 | CAS-1588866-10-7 |
| 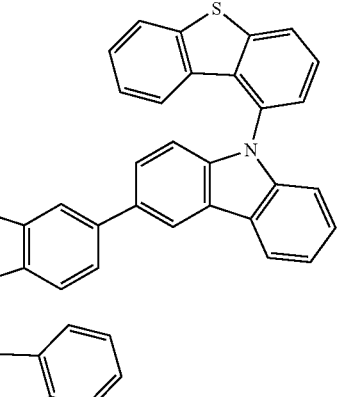 | CAS-1934252-94-4 |
| 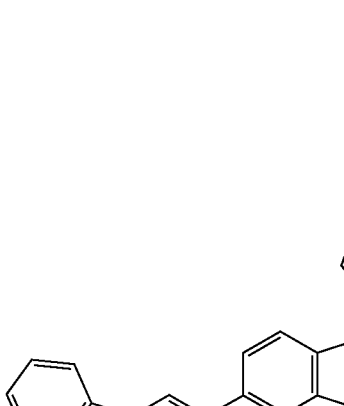 | CAS-1598389-99-1 |

| Structure | CAS-number |
|---|---|
| 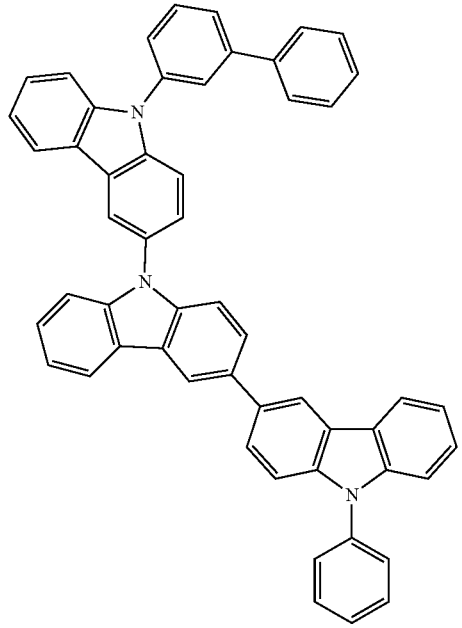 [SMILES: c1ccc(-c2cccc(-n3c4ccccc4c4cc(-n5c6ccccc6c6cc(-c7ccc8c(c7)c7ccccc7n8-c7ccccc7)ccc65)ccc43)c2)cc1] | CAS-1943719-77-4 |
| 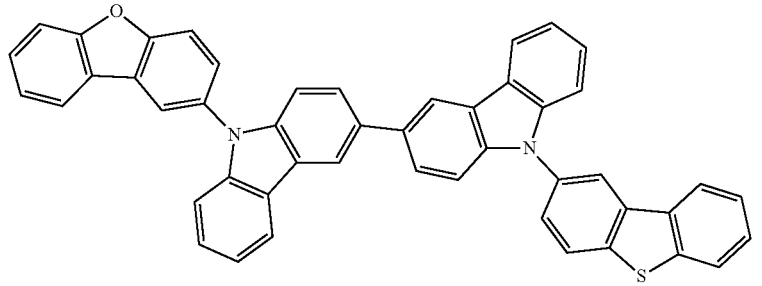 [SMILES: c1ccc2c(c1)oc1ccc(-n3c4ccccc4c4cc(-c5ccc6c(c5)c5ccccc5n6-c5ccc6sc7ccccc7c6c5)ccc43)cc12] | CAS-1613752-14-9 |
| 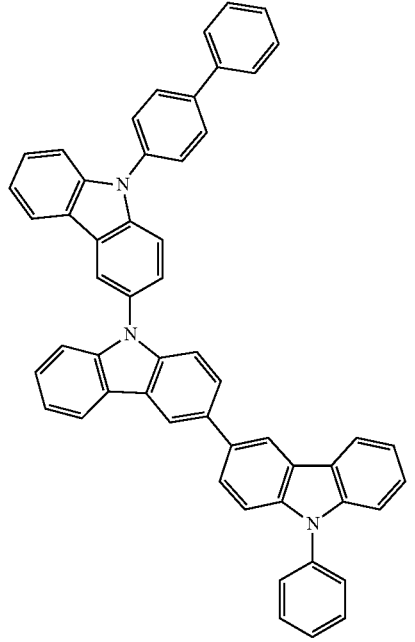 [SMILES: c1ccc(-c2ccc(-n3c4ccccc4c4cc(-n5c6ccccc6c6cc(-c7ccc8c(c7)c7ccccc7n8-c7ccccc7)ccc65)ccc43)cc2)cc1] | CAS-1943719-78-5 |

| Structure | CAS-number |
|---|---|
| 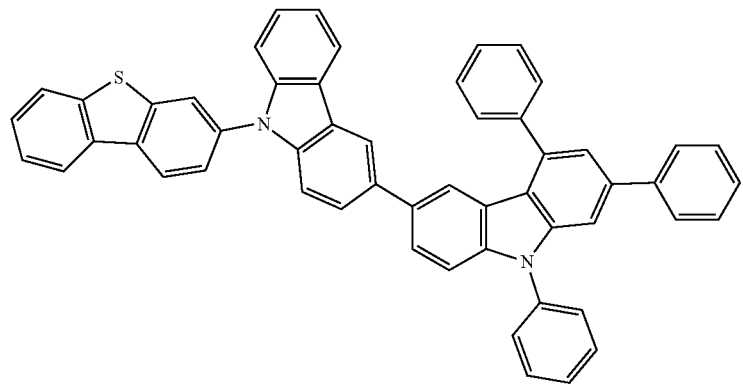 | CAS-2018307-45-2 |
| 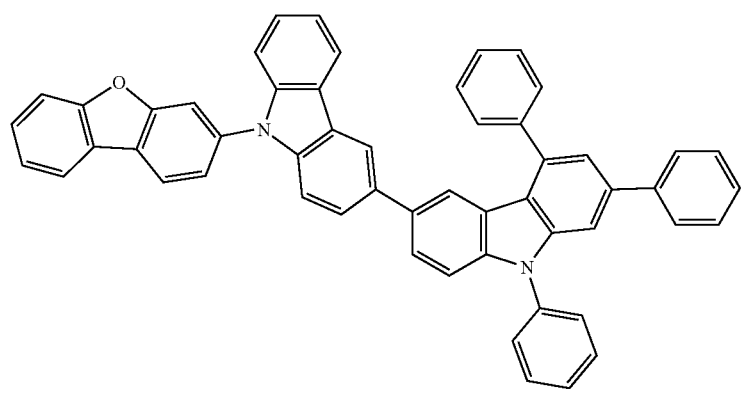 [SMILES: c1ccc(-c2cc(-c3ccccc3)c3c4cc(-c5ccc6c(c5)c5ccccc5n6-c5ccc6c(c5)sc5ccccc56)ccc4n(-c4ccccc4)c3c2)cc1] | CAS-2018307-44-1 |
| 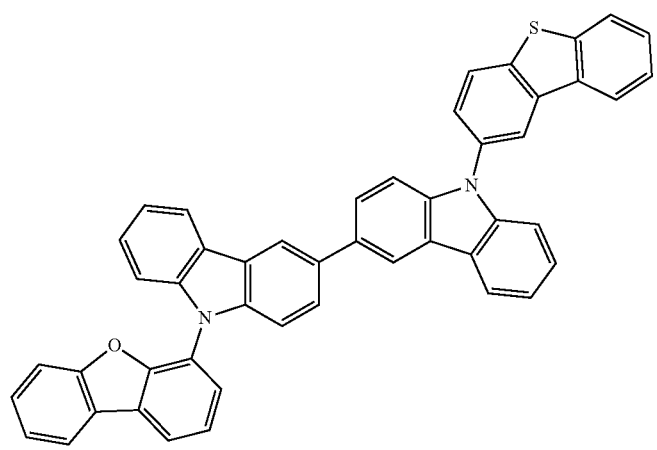 | CAS-1643479-80-4 |

| Structure | CAS-number |
|---|---|
| 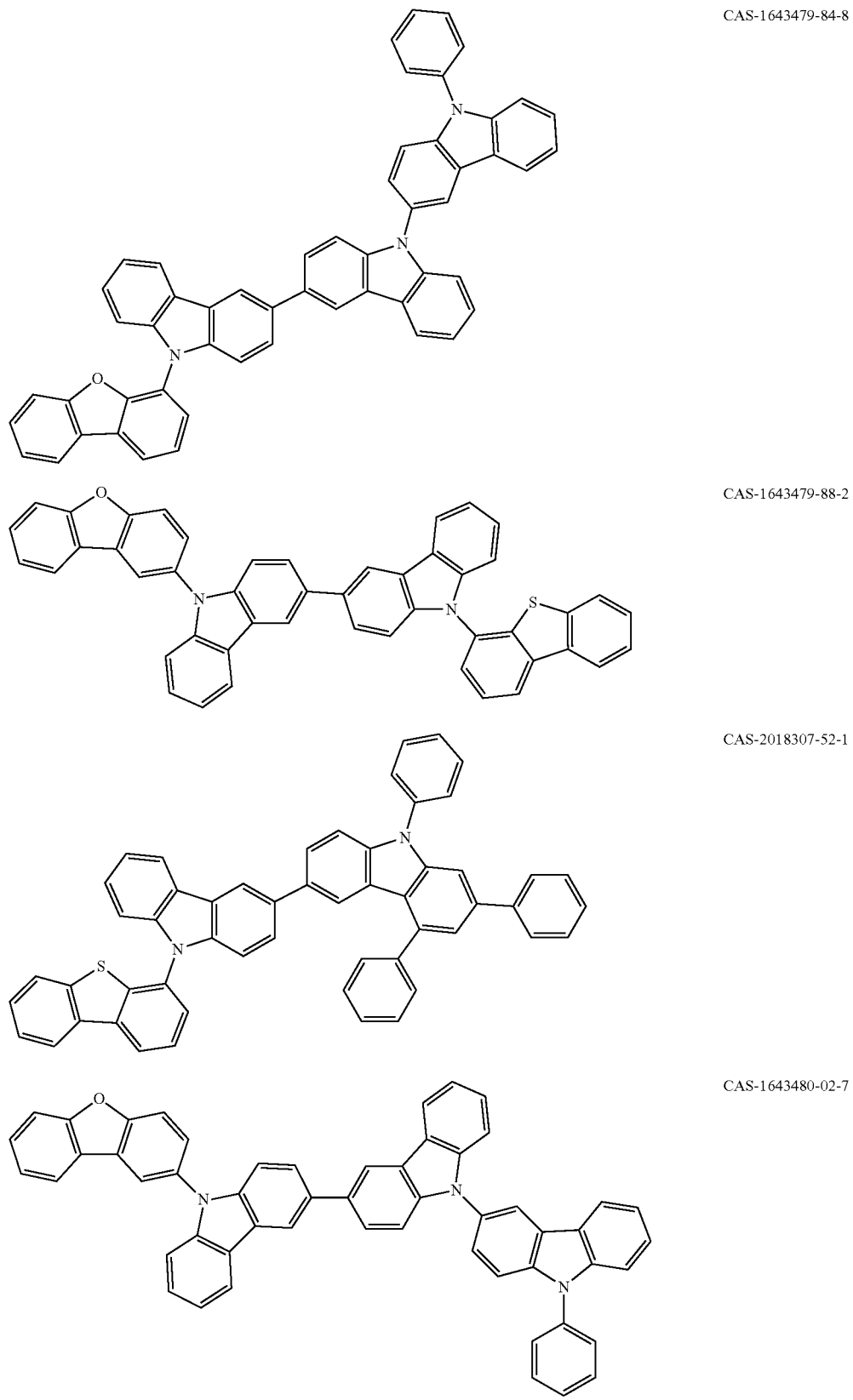 | CAS-1643479-84-8 |
| 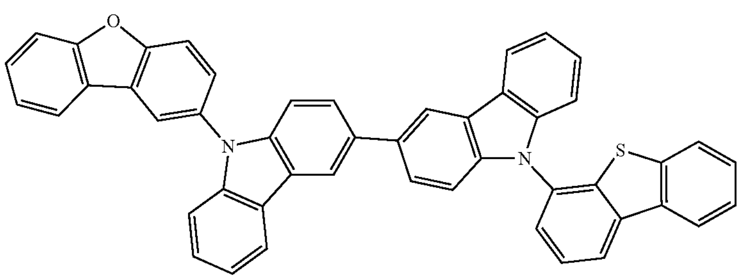 [SMILES: c1ccc2c(c1)oc1ccc(-n3c4ccccc4c4cc(-c5ccc6c(c5)c5ccccc5n6-c5cccc6c5sc5ccccc56)ccc43)cc12] | CAS-1643479-88-2 |
| 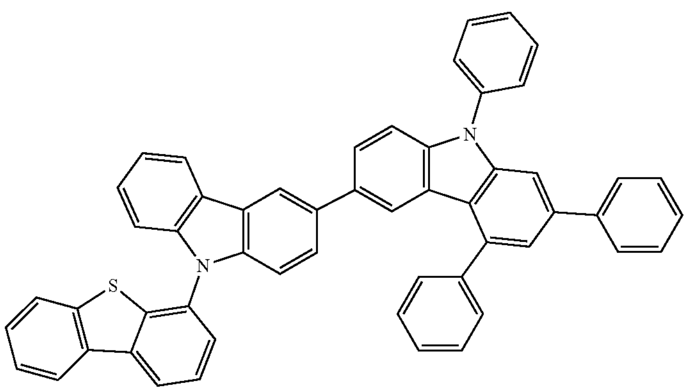 [SMILES: c1ccc(-c2cc(-c3ccccc3)c3c4cc(-c5ccc6c(c5)c5ccccc5n6-c5cccc6c5sc5ccccc56)ccc4n(-c4ccccc4)c3c2)cc1] | CAS-2018307-52-1 |
| 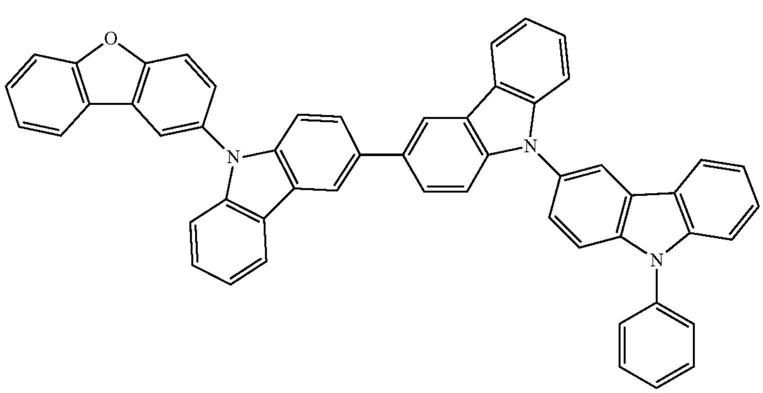 [SMILES: c1ccc(-n2c3ccccc3c3cc(-n4c5ccccc5c5cc(-c6ccc7c(c6)c6ccccc6n7-c6ccc7oc8ccccc8c7c6)ccc54)ccc32)cc1] | CAS-1643480-02-7 |

-continued
| Structure | CAS-number |
|---|---|
| 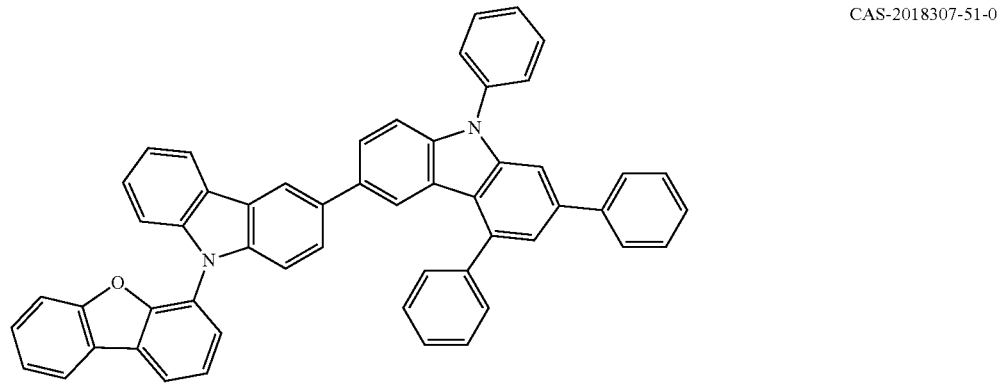 | CAS-2018307-51-0 |
| 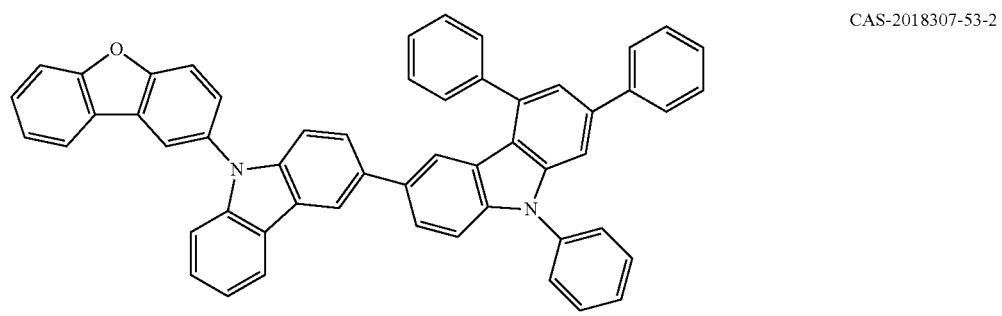 | CAS-2018307-53-2 |
| 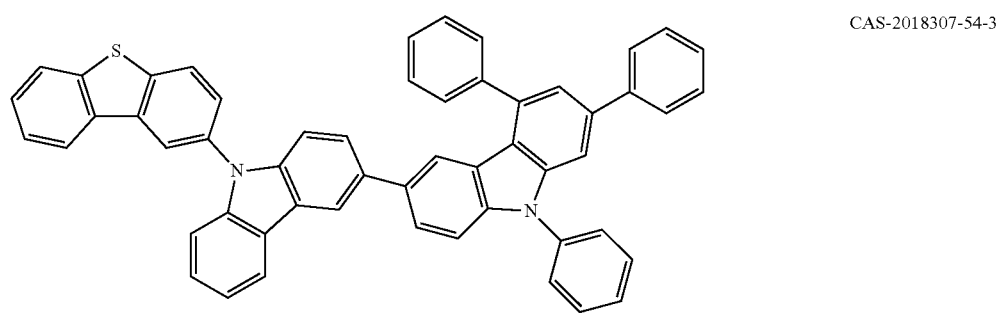 | CAS-2018307-54-3 |

| Structure | CAS-number |
|---|---|
| 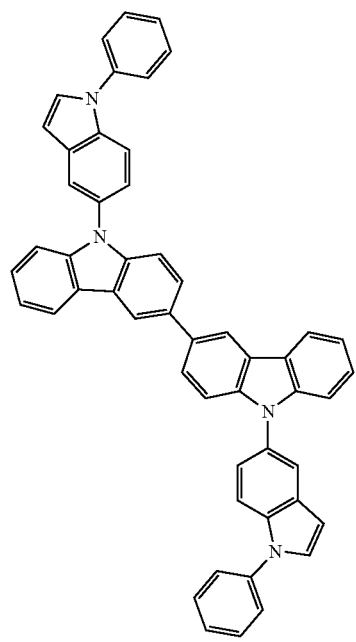 [SMILES: c1ccc(-n2ccc3cc(-n4c5ccccc5c5cc(-c6ccc7c(c6)c6ccccc6n7-c6ccc7c(ccn7-c7ccccc7)c6)ccc54)ccc32)cc1] | CAS-1656982-32-9 |
| 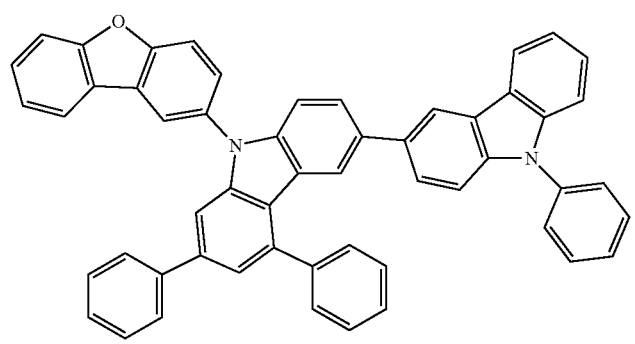 [SMILES: c1ccc(-c2cc(-c3ccccc3)c3c4cc(-c5ccc6c(c5)c5ccccc5n6-c5ccccc5)ccc4n(-c4ccc5oc6ccccc6c5c4)c3c2)cc1] | CAS-2018307-80-5 |
| 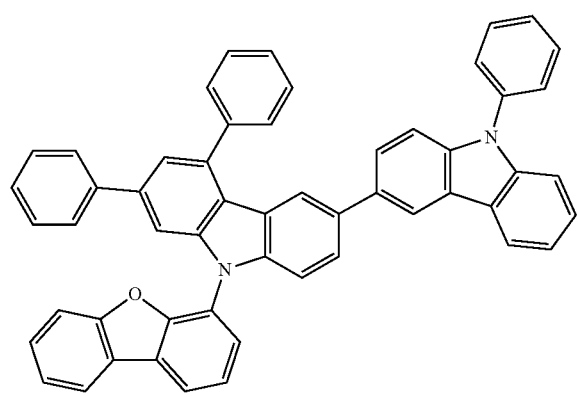 [SMILES: c1ccc(-c2cc(-c3ccccc3)c3c4cc(-c5ccc6c(c5)c5ccccc5n6-c5ccccc5)ccc4n(-c4cccc5c4oc4ccccc45)c3c2)cc1] | CAS-2018307-79-2 |

| Structure | CAS-number |
|---|---|
| 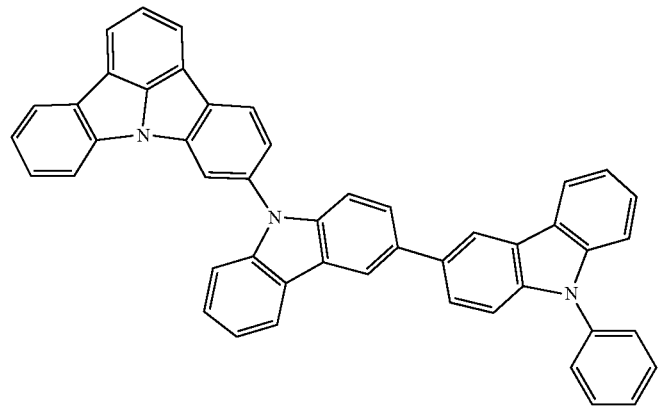 [SMILES: c1ccc(-n2c3ccccc3c3cc(-c4ccc5c(c4)c4ccccc4n5-c4ccc5c6cccc7c8ccccc8n(c5c4)c76)ccc32)cc1] | CAS-1799483-31-0 |
| 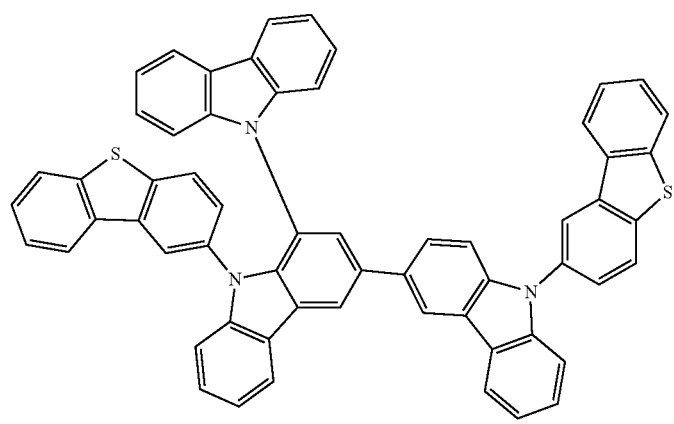 | CAS-1704071-33-9 |
| 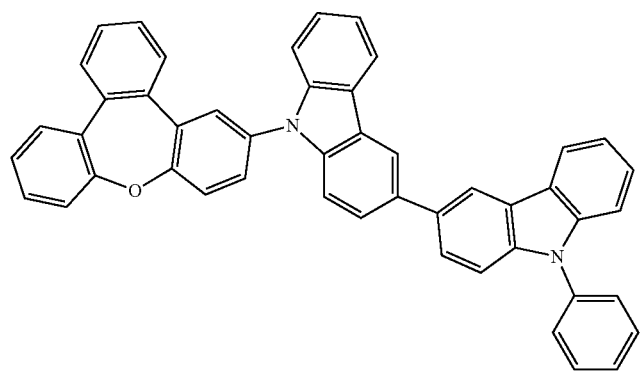 [SMILES: c1ccc(-n2c3ccccc3c3cc(-c4ccc5c(c4)c4ccccc4n5-c4ccc5c(c4)-c4ccccc4-c4ccccc4O5)ccc32)cc1] | CAS-1792238-01-7 |

| Structure | CAS-number |
|---|---|
| 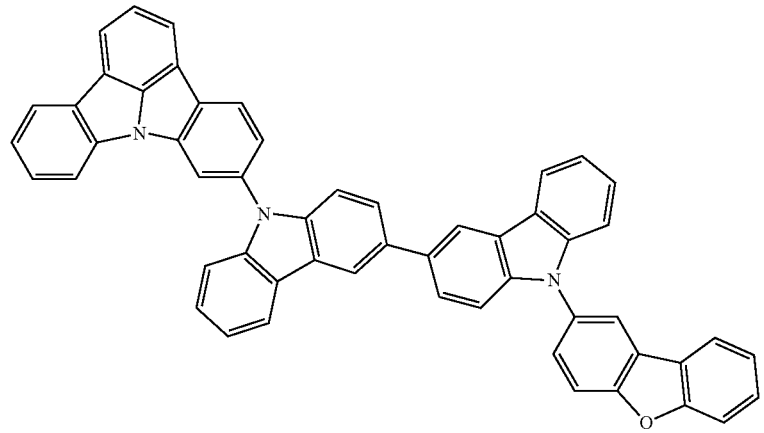 [SMILES: c1ccc2c(c1)oc1ccc(-n3c4ccccc4c4cc(-c5ccc6c(c5)c5ccccc5n6-c5ccc6c7cccc8c9ccccc9n(c6c5)c87)ccc43)cc12] | CAS-1799483-43-4 |
| 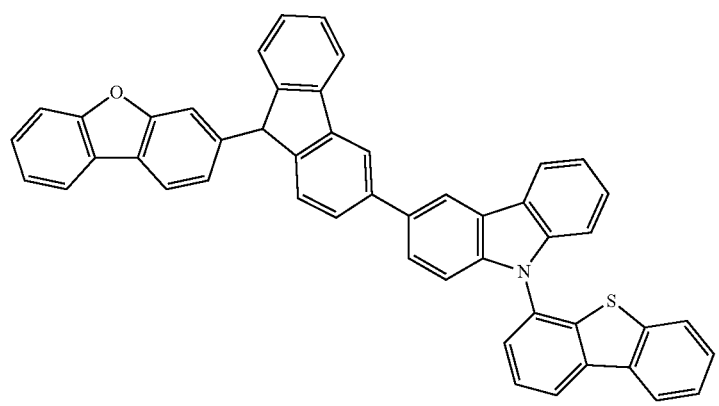 [SMILES: c1ccc2c(c1)-c1cc(-c3ccc4c(c3)c3ccccc3n4-c3cccc4c3sc3ccccc34)ccc1C2c1ccc2c(c1)oc1ccccc12] | CAS-2020391-63-1 |
| 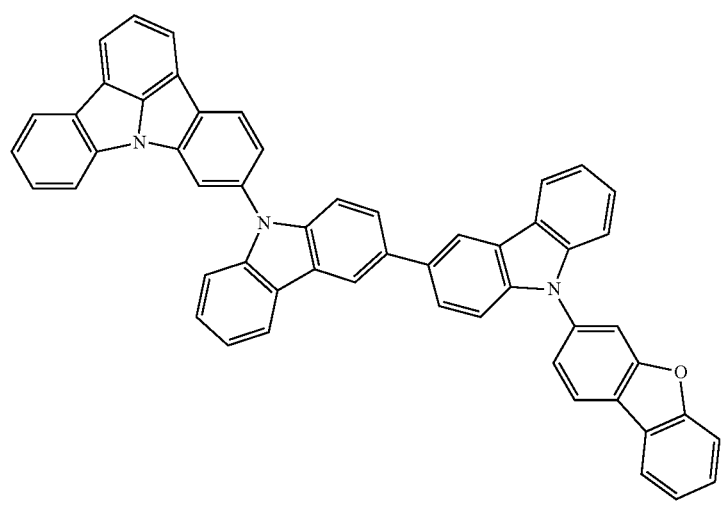 [SMILES: c1ccc2c(c1)oc1cc(-n3c4ccccc4c4cc(-c5ccc6c(c5)c5ccccc5n6-c5ccc6c7cccc8c9ccccc9n(c6c5)c87)ccc43)ccc12] | CAS-1799483-44-5 |

| Structure | CAS-number |
|---|---|
| 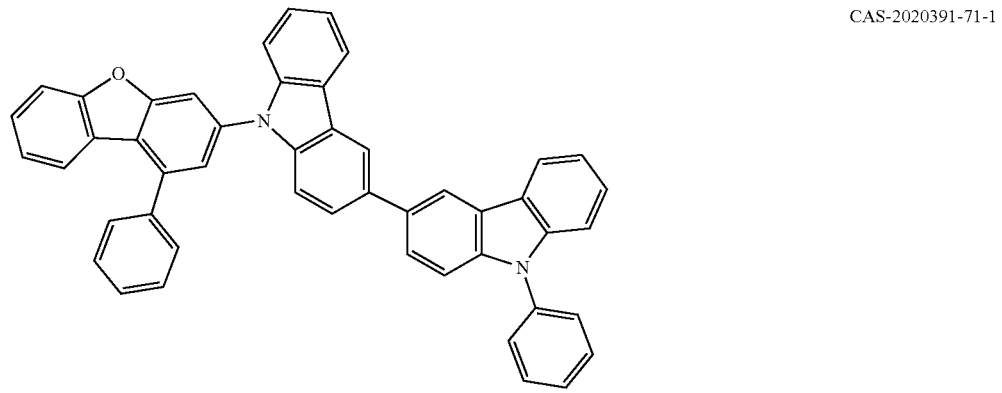 | CAS-2020391-71-1 |
| 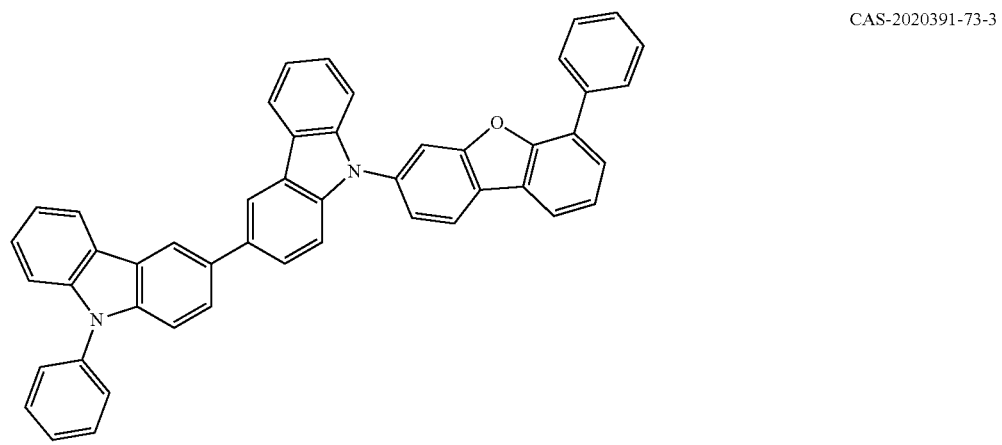 | CAS-2020391-73-3 |
| 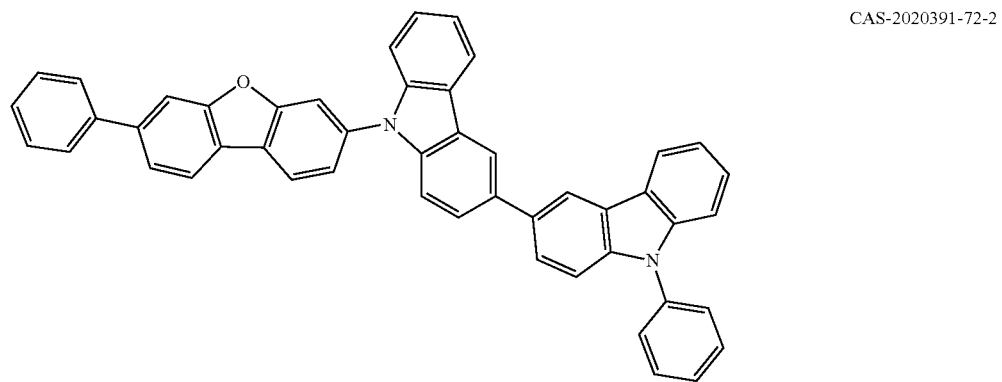 | CAS-2020391-72-2 |

-continued
| Structure | CAS-number |
|---|---|
| 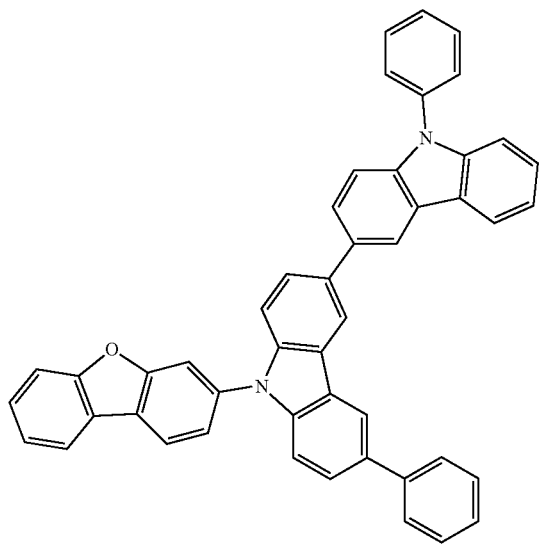 [SMILES: c1ccc(-c2ccc3c(c2)c2cc(-c4ccc5c(c4)c4ccccc4n5-c4ccccc4)ccc2n3-c2ccc3c(c2)oc2ccccc23)cc1] | CAS-2020391-75-5 |
| 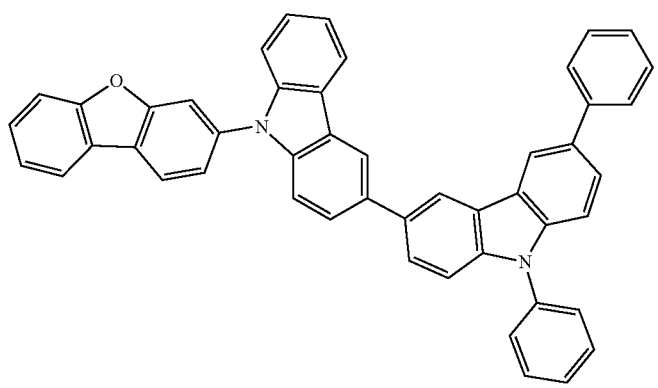 [SMILES: c1ccc(-c2ccc3c(c2)c2cc(-c4ccc5c(c4)c4ccccc4n5-c4ccc5c(c4)oc4ccccc45)ccc2n3-c2ccccc2)cc1] | CAS-2020391-74-4 |
| 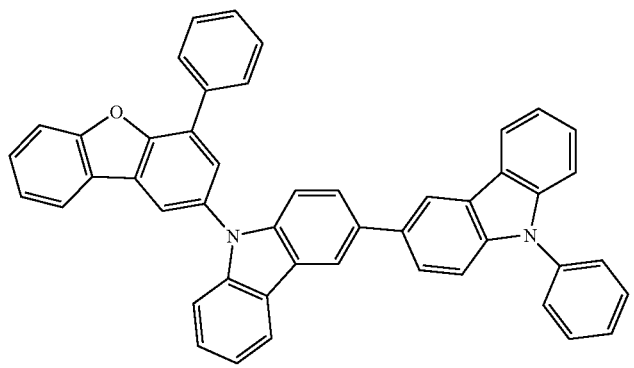 | CAS-2079874-13-6 |

| Structure | CAS-number |
|---|---|
| 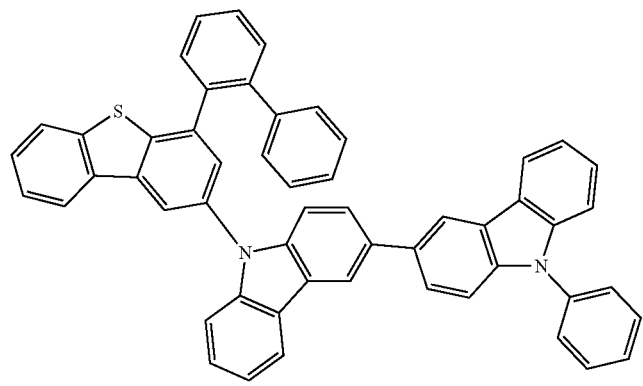 [SMILES: c1ccc(-c2ccccc2-c2cc(-n3c4ccccc4c4cc(-c5ccc6c(c5)c5ccccc5n6-c5ccccc5)ccc43)cc3c2sc2ccccc23)cc1] | CAS-2075738-96-2 |
| 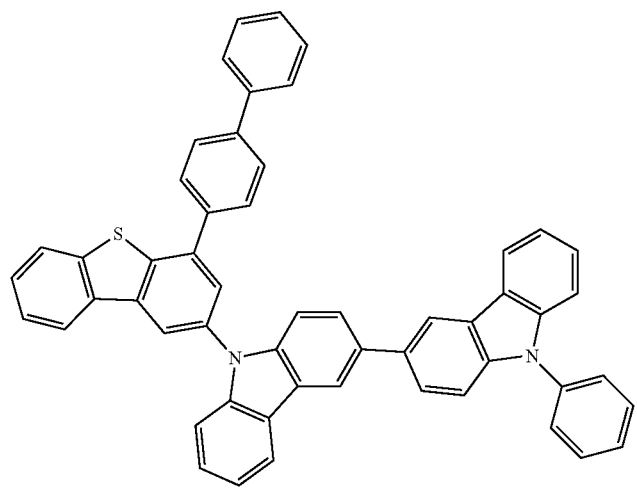 [SMILES: c1ccc(-c2ccc(-c3cc(-n4c5ccccc5c5cc(-c6ccc7c(c6)c6ccccc6n7-c6ccccc6)ccc54)cc4c3sc3ccccc34)cc2)cc1] | CAS-2075738-98-4 |
| 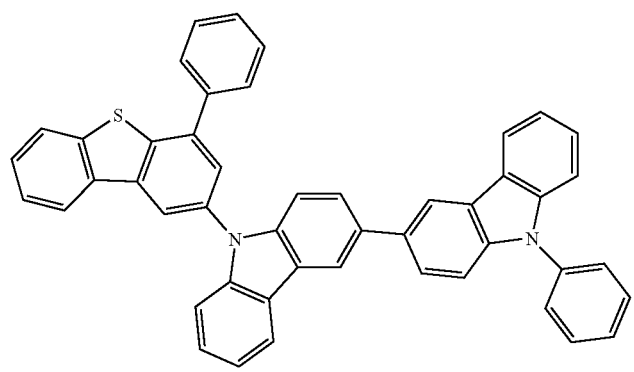 [SMILES: c1ccc(-c2cc(-n3c4ccccc4c4cc(-c5ccc6c(c5)c5ccccc5n6-c5ccccc5)ccc43)cc3c2sc2ccccc23)cc1] | CAS-2075738-97-3 |

| Structure | CAS-number |
|---|---|
| 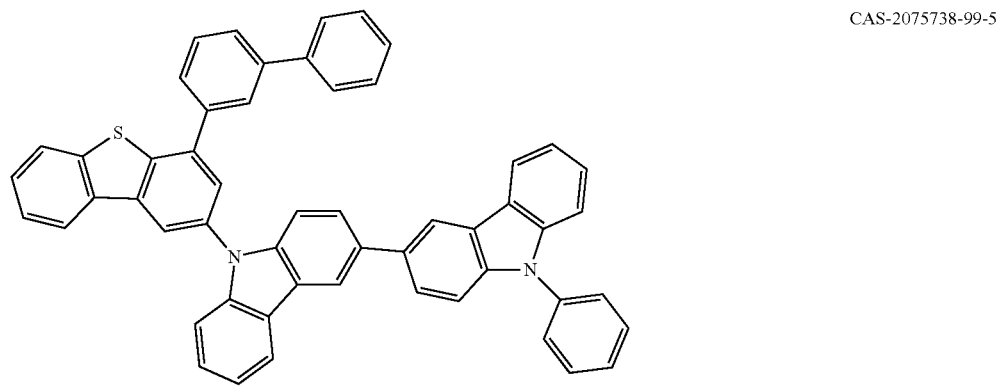 | CAS-2075738-99-5 |
| 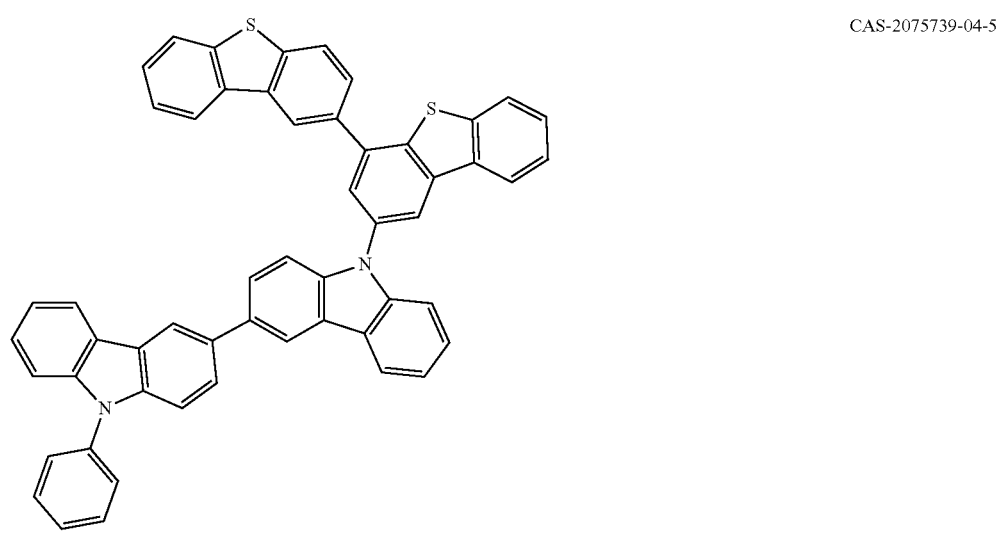 | CAS-2075739-04-5 |
| 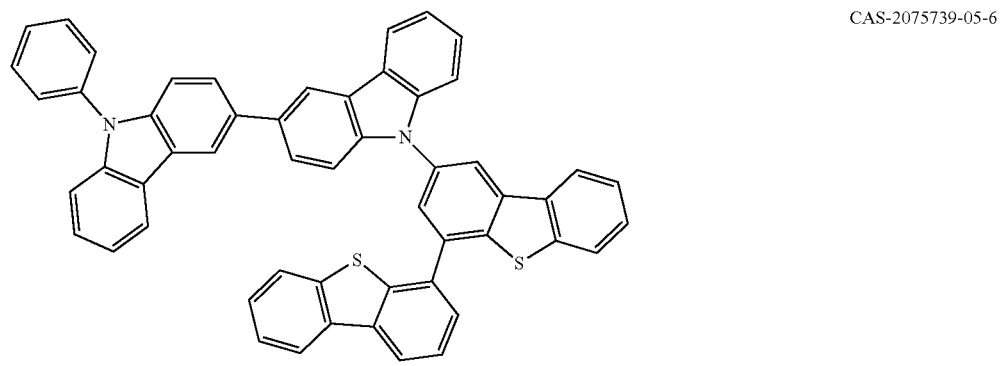 | CAS-2075739-05-6 |

| Structure | CAS-number |
|---|---|
| 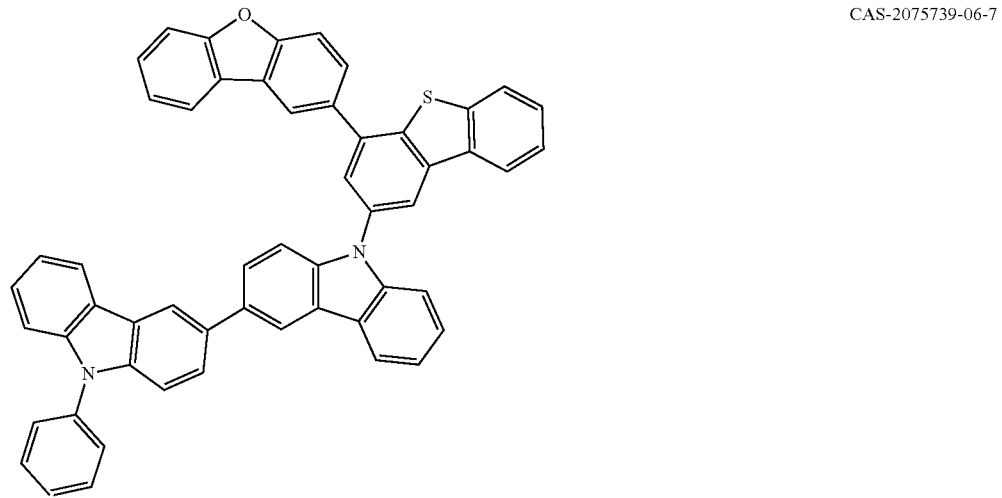 | CAS-2075739-06-7 |
| 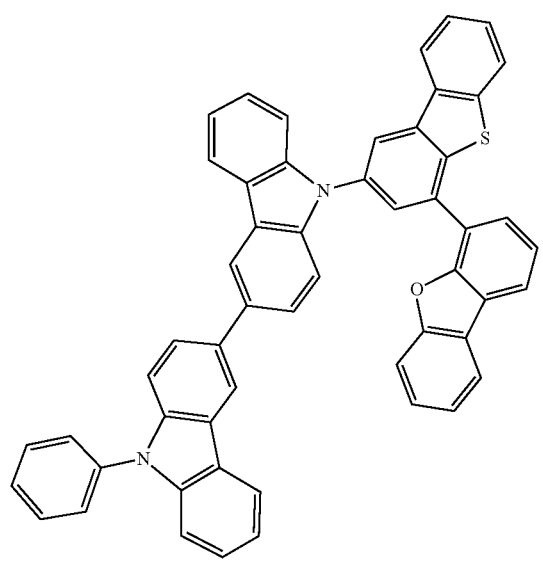 [SMILES: c1ccc(-n2c3ccccc3c3cc(-c4ccc5c(c4)c4ccccc4n5-c4cc(-c5cccc6c5oc5ccccc56)c5sc6ccccc6c5c4)ccc32)cc1] | CAS-2075739-07-8. |

| Structure | CAS-number |
|---|---|
| 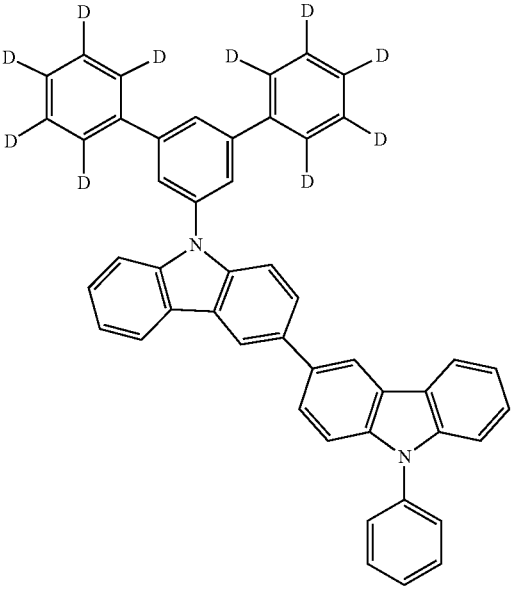 [SMILES: [2H]c1c([2H])c([2H])c(-c2cc(-c3c([2H])c([2H])c([2H])c([2H])c3[2H])cc(-n3c4ccccc4c4cc(-c5ccc6c(c5)c5ccccc5n6-c5ccccc5)ccc43)c2)c([2H])c1[2H]] | |
| 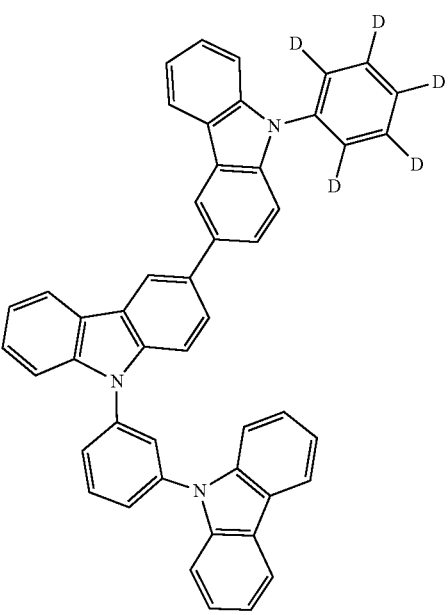 [SMILES: [2H]c1c([2H])c([2H])c(-n2c3ccccc3c3cc(-c4ccc5c(c4)c4ccccc4n5-c4cccc(-n5c6ccccc6c6ccccc65)c4)ccc32)c([2H])c1[2H]] | |
| 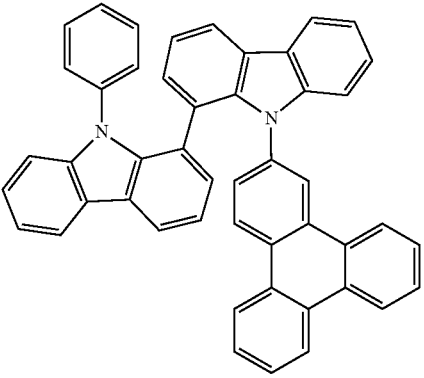 [SMILES: c1ccc(-n2c3ccccc3c3cccc(-c4cccc5c6ccccc6n(-c6ccc7c8ccccc8c8ccccc8c7c6)c45)c32)cc1] | |

| Structure | CAS-number |
|---|---|
| 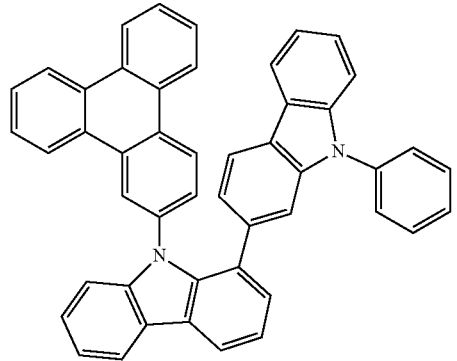 [SMILES: c1ccc(-n2c3ccccc3c3ccc(-c4cccc5c6ccccc6n(-c6ccc7c8ccccc8c8ccccc8c7c6)c45)cc32)cc1] | |
| 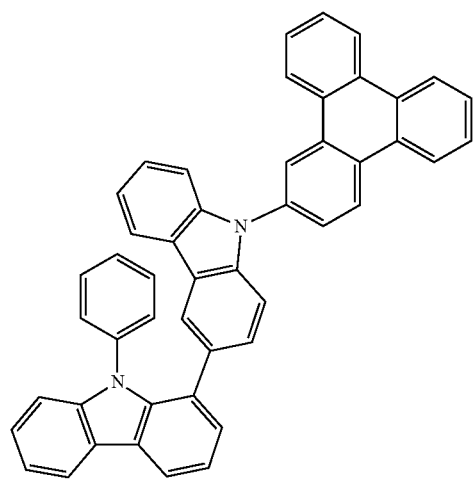 [SMILES: c1ccc(-n2c3ccccc3c3cccc(-c4ccc5c(c4)c4ccccc4n5-c4ccc5c6ccccc6c6ccccc6c5c4)c32)cc1] | |
| 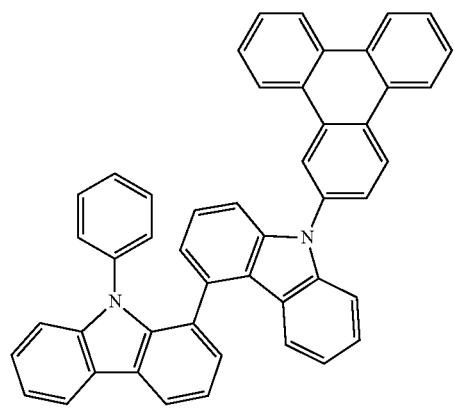 [SMILES: c1ccc(-n2c3ccccc3c3cccc(-c4cccc5c4c4ccccc4n5-c4ccc5c6ccccc6c6ccccc6c5c4)c32)cc1] | |

| Structure | CAS-number |
|---|---|
| 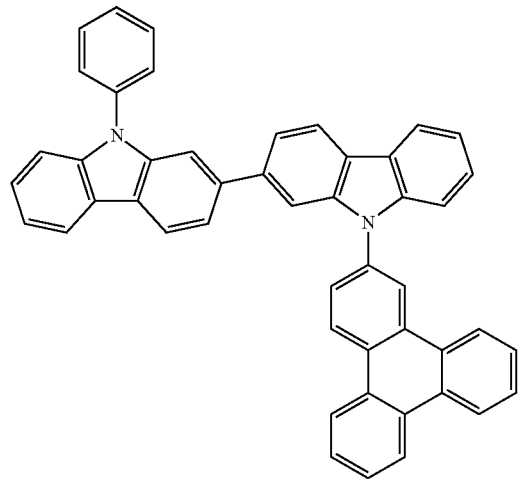 [SMILES: c1ccc(-n2c3ccccc3c3ccc(-c4ccc5c6ccccc6n(-c6ccc7c8ccccc8c8ccccc8c7c6)c5c4)cc32)cc1] | |
| 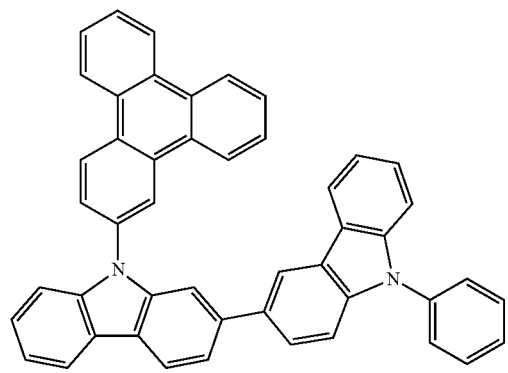 [SMILES: c1ccc(-n2c3ccccc3c3cc(-c4ccc5c6ccccc6n(-c6ccc7c8ccccc8c8ccccc8c7c6)c5c4)ccc32)cc1] | |
| 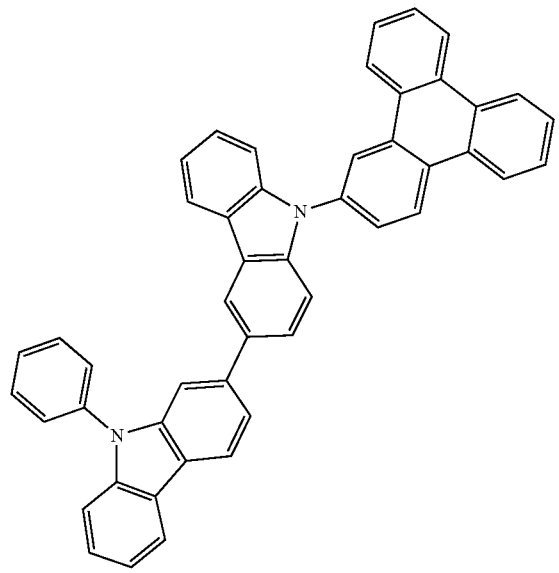 [SMILES: c1ccc(-n2c3ccccc3c3ccc(-c4ccc5c(c4)c4ccccc4n5-c4ccc5c6ccccc6c6ccccc6c5c4)cc32)cc1] | |

| Structure | CAS-number |
|---|---|
| 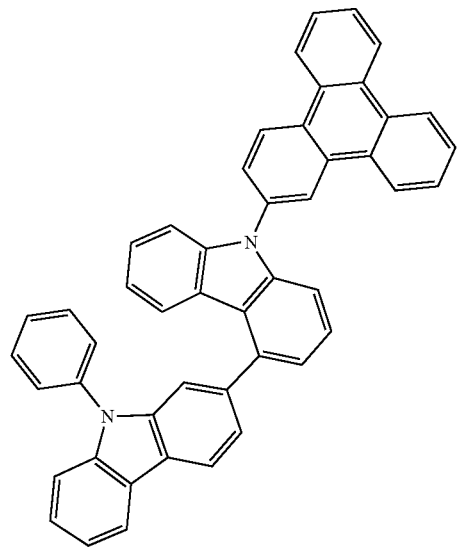 [SMILES: c1ccc(-n2c3ccccc3c3ccc(-c4cccc5c4c4ccccc4n5-c4ccc5c6ccccc6c6ccccc6c5c4)cc32)cc1] | |
| 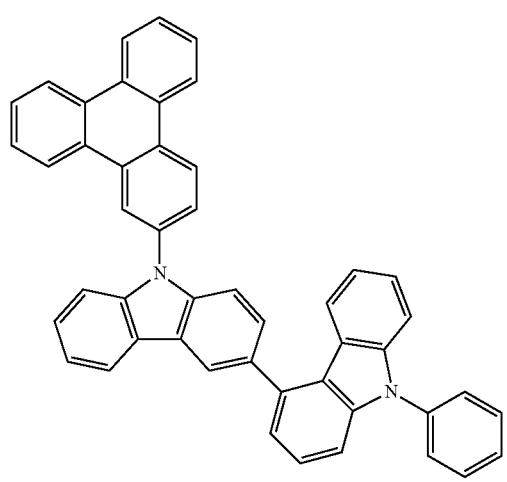 [SMILES: c1ccc(-n2c3ccccc3c3c(-c4ccc5c(c4)c4ccccc4n5-c4ccc5c6ccccc6c6ccccc6c5c4)cccc32)cc1] | |

| Structure | CAS-number |
| --- | --- |
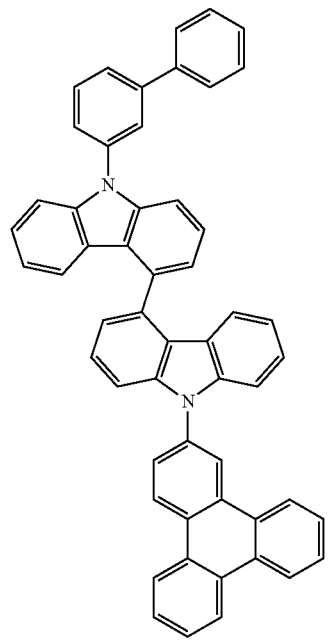 [SMILES: c1ccc(-c2cccc(-n3c4ccccc4c4c(-c5cccc6c5c5ccccc5n6-c5ccc6c7ccccc7c7ccccc7c6c5)cccc43)c2)cc1]
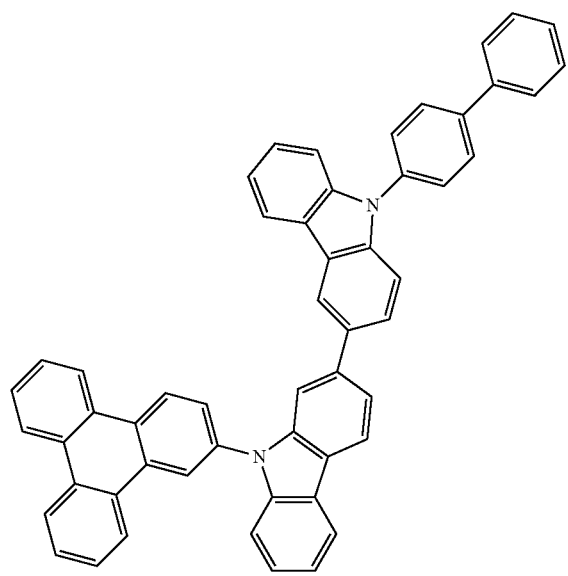 [SMILES: c1ccc(-c2ccc(-n3c4ccccc4c4cc(-c5ccc6c7ccccc7n(-c7ccc8c9ccccc9c9ccccc9c8c7)c6c5)ccc43)cc2)cc1]

| Structure | CAS-number |
|---|---|
| 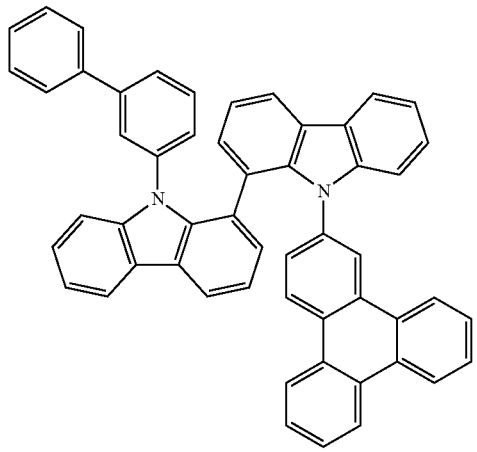 [SMILES: c1ccc(-c2cccc(-n3c4ccccc4c4cccc(-c5cccc6c7ccccc7n(-c7ccc8c9ccccc9c9ccccc9c8c7)c56)c43)c2)cc1] | |

Further suitable compounds that can be used as co-host together with the compounds of the formula (1) are the compounds of the following formula (9)

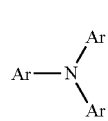

Formula (9)

where Ar is the same or different at each instance and has the definitions given above. It is preferable here when at least one Ar group is a 4-fluorenyl group, 4-spirobifluorenyl group, 1-dibenzofuranyl group or 1-dibenzothienyl group, each of which may optionally be substituted by one or more R radicals. Examples of suitable Ar groups in the compound of the formula (9) are the groups of the formulae Ar-1 to Ar-75 depicted above.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of phosphorescent compounds can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and WO 2018/041769. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are listed below.

[Please replace with table on source pages (72/27)-(85/6)]

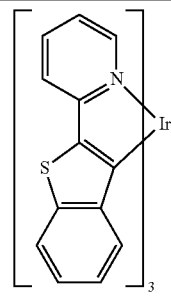

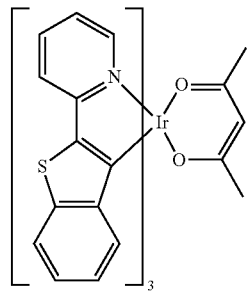

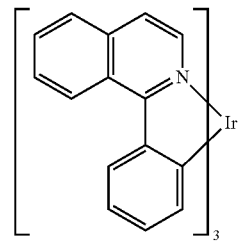

343
-continued
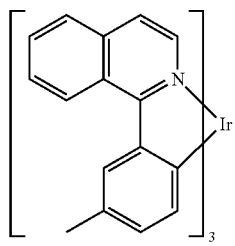
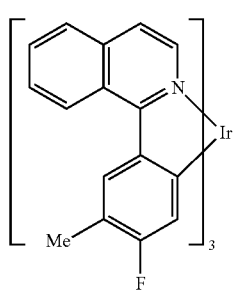
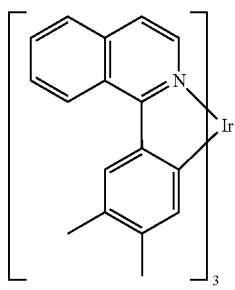
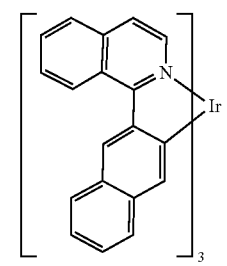
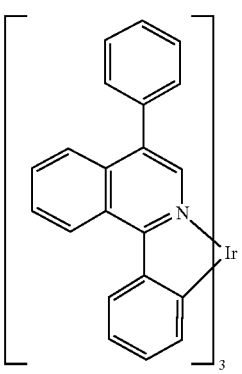
344
-continued
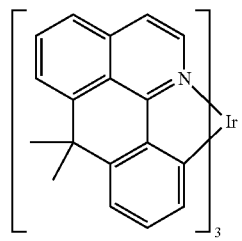
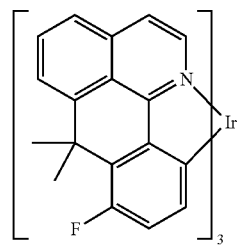
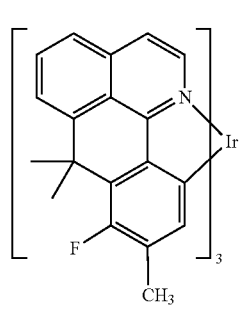
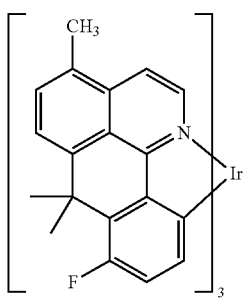
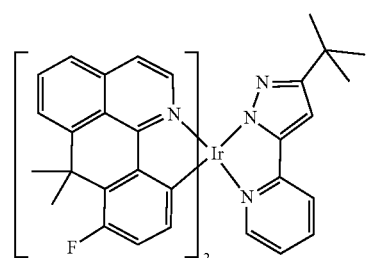

-continued
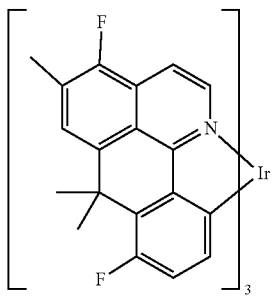
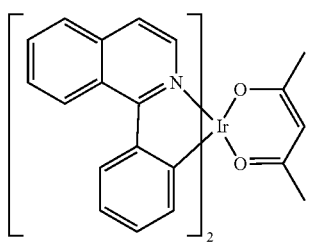
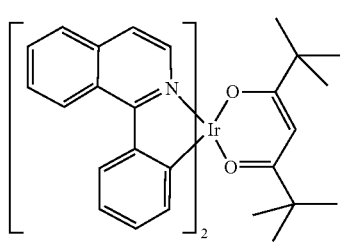
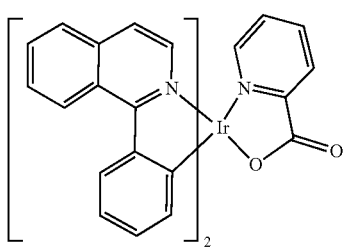
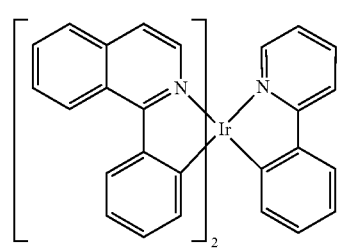
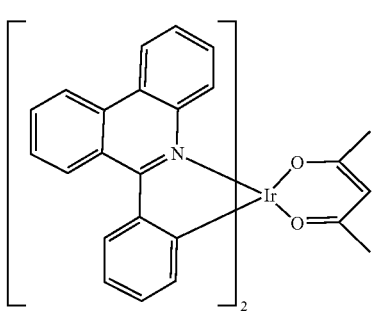
-continued
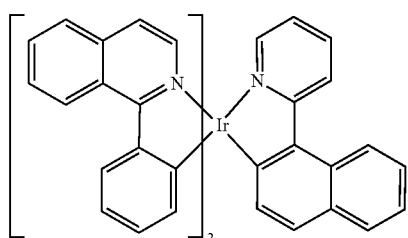
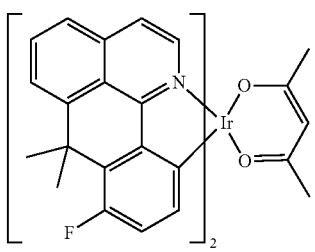
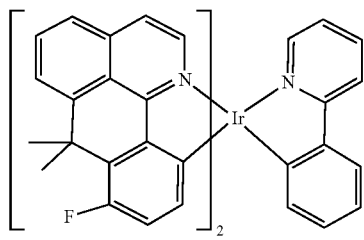
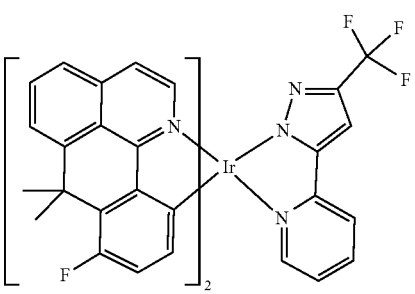
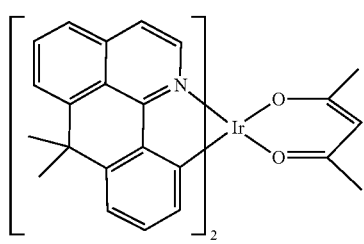
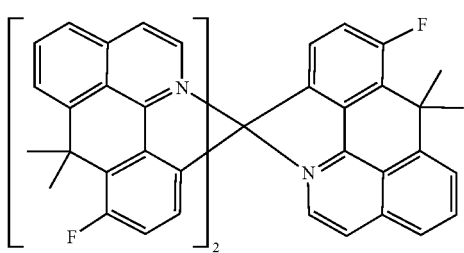

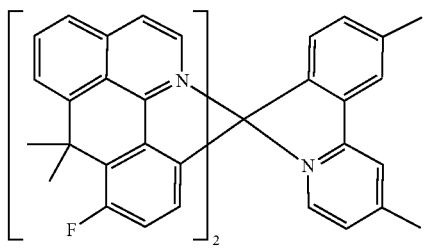
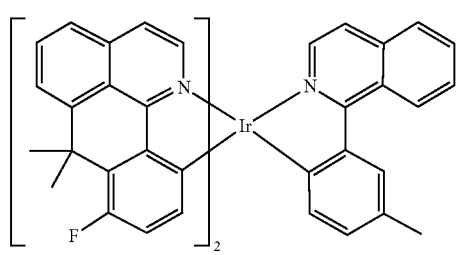
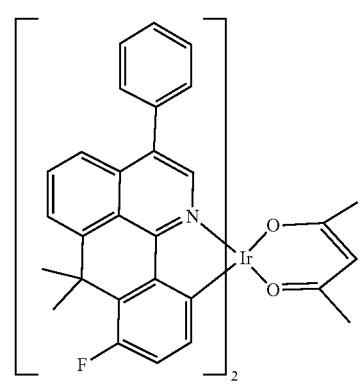
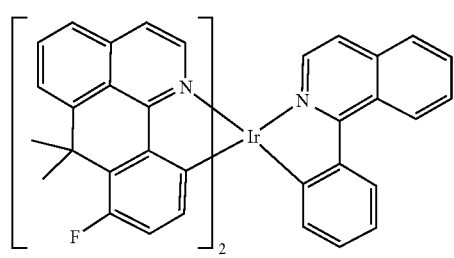
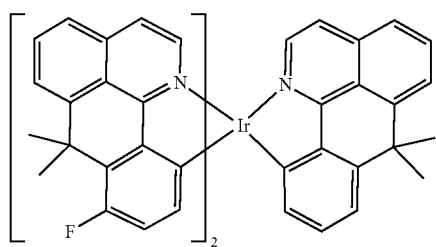
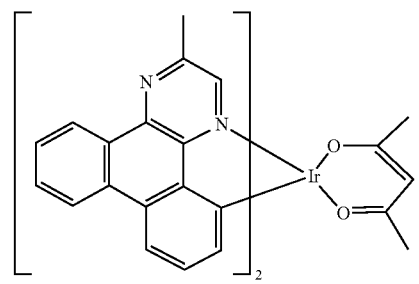
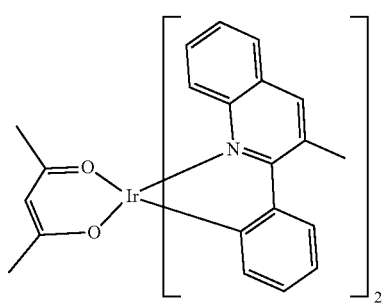
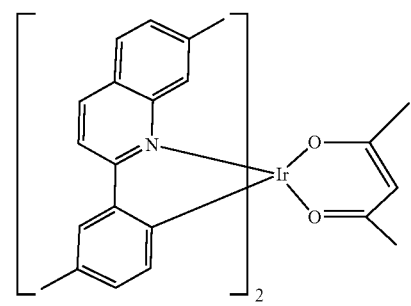
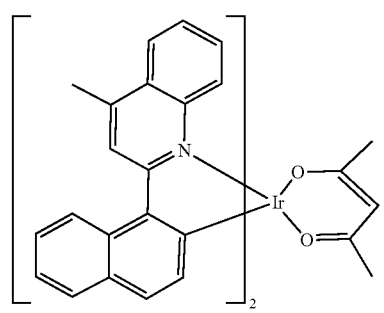
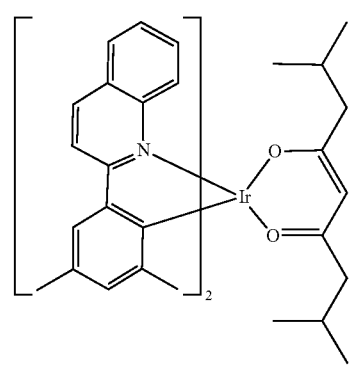

349
-continued
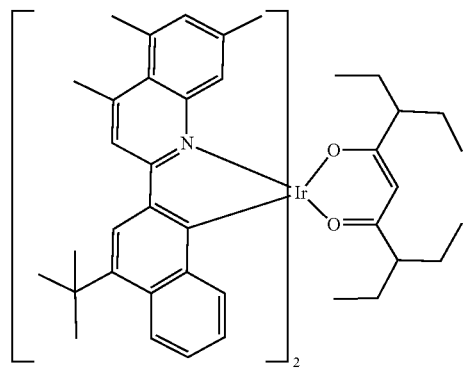
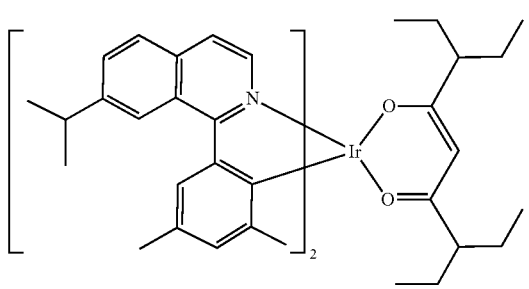
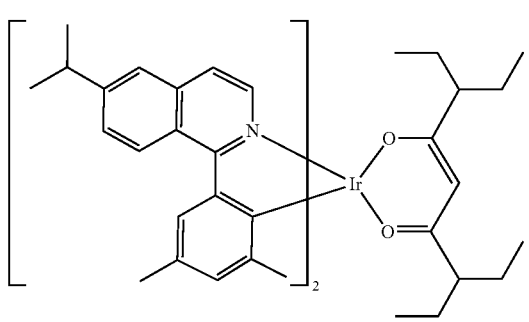
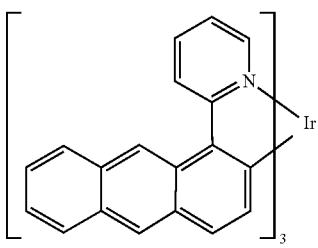
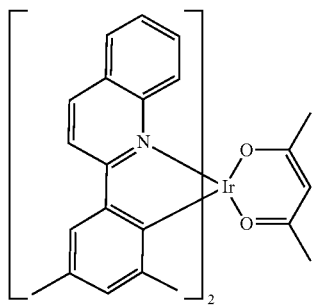
350
-continued
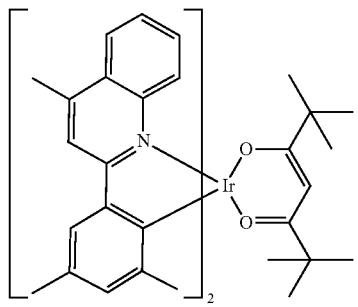
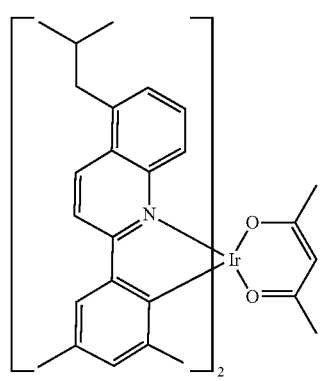
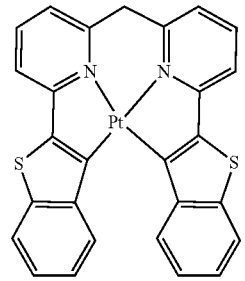
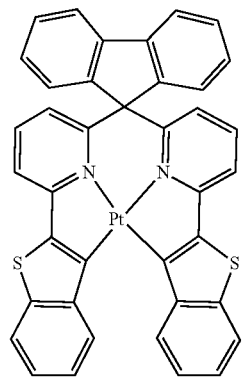

| 351 -continued | 352 -continued |
|---|---|
| 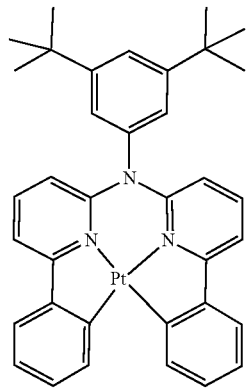 | 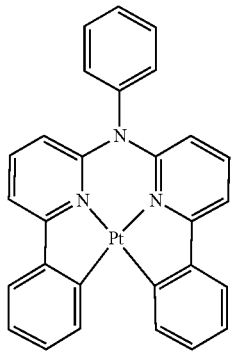 |
| 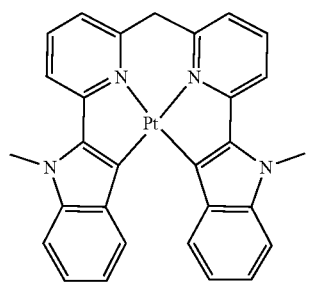 | 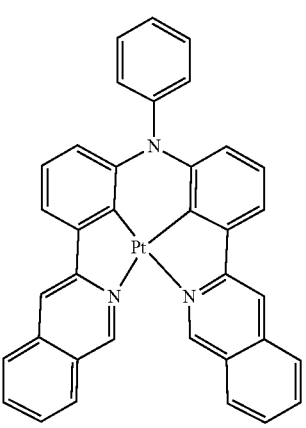 |
| 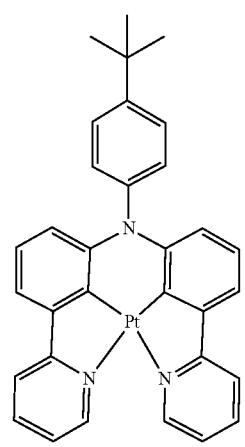 | 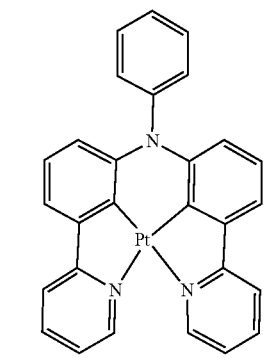 |
| 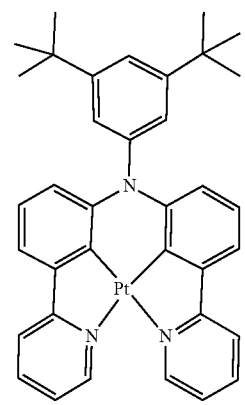 | 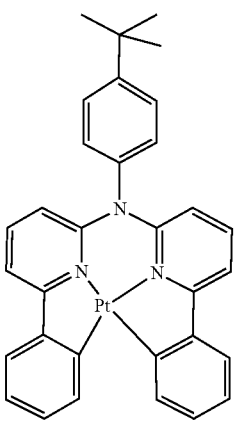 |

| 353 -continued | 354 -continued |
|---|---|
| 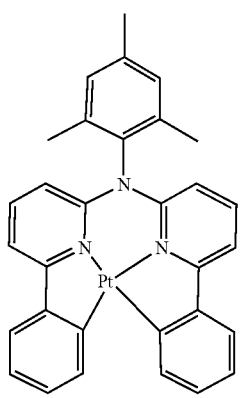 | 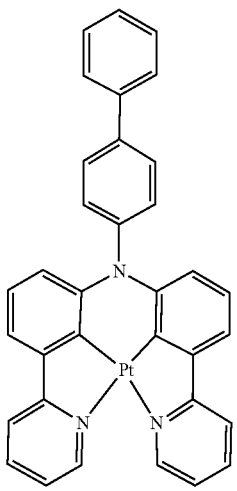 |
| 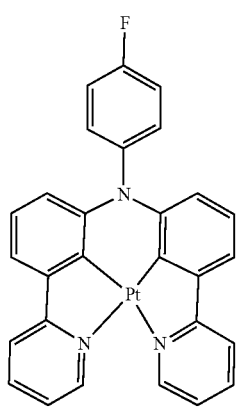 | |
| 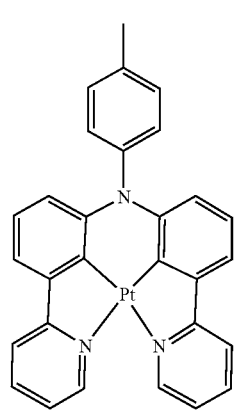 | 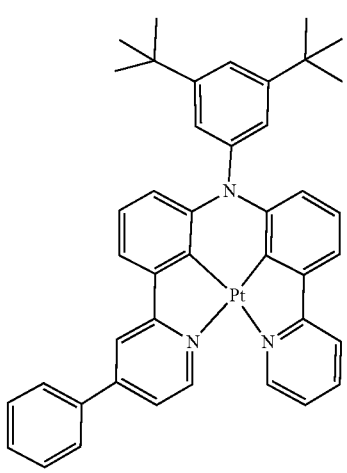 |

355
-continued
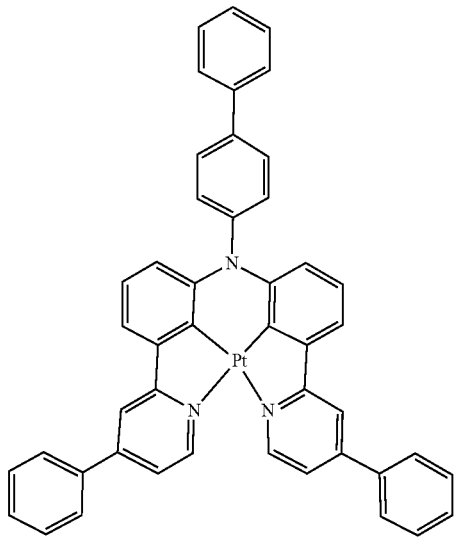
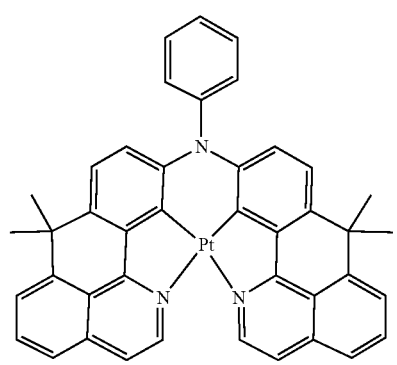
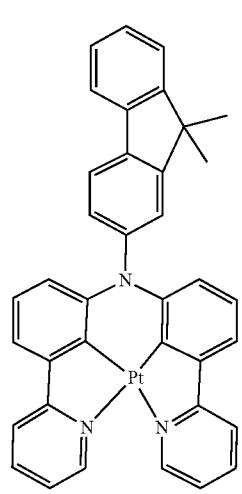
356
-continued
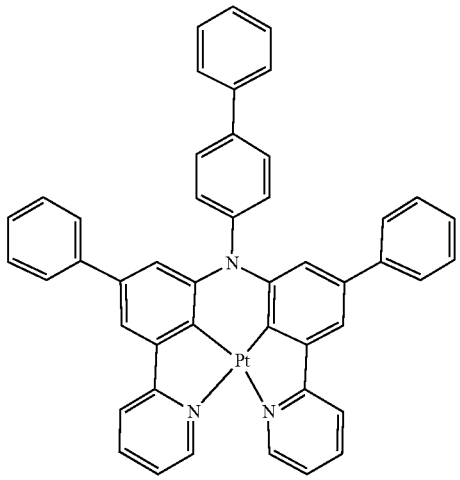
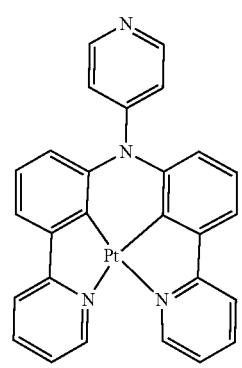
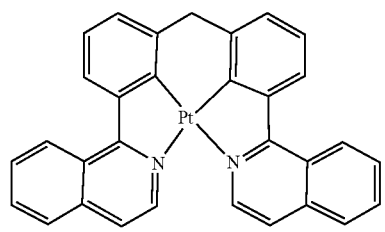
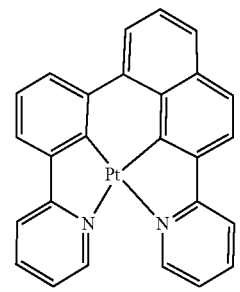

357
-continued
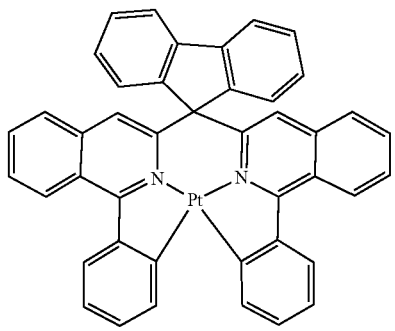
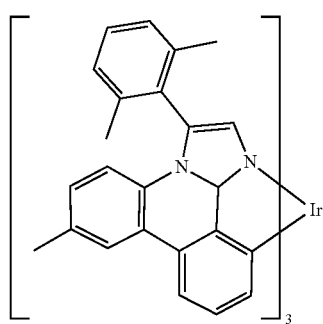
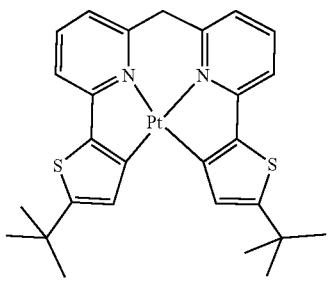
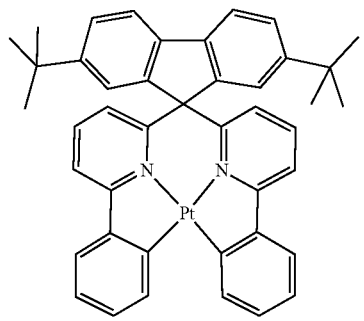
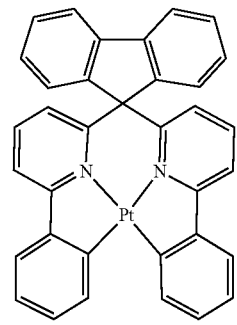
358
-continued
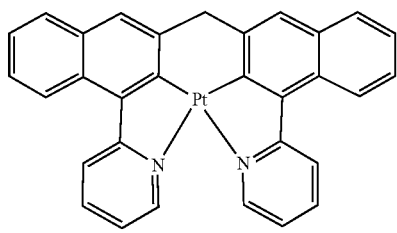
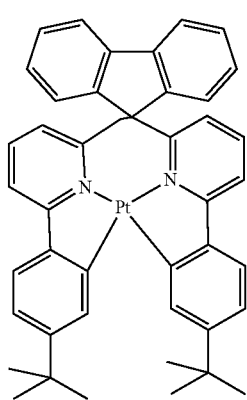
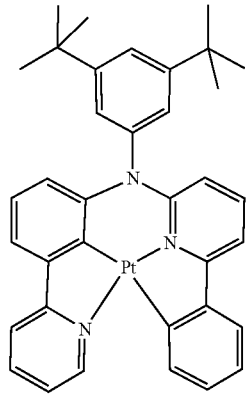
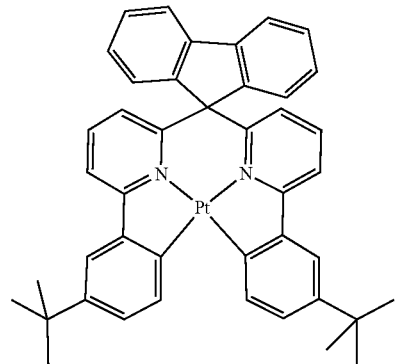

| 359 -continued | 360 -continued |
|---|---|
| 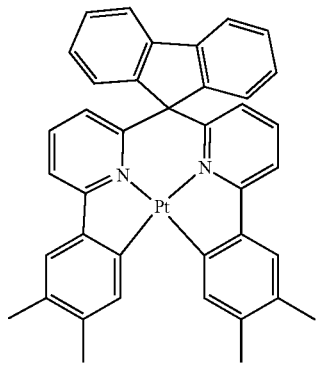 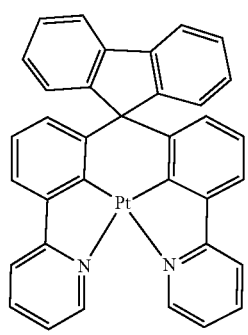 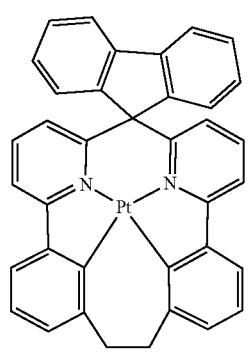 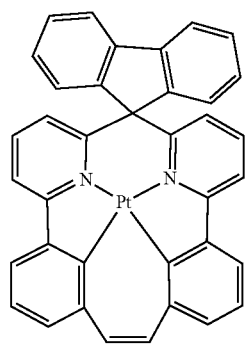 | 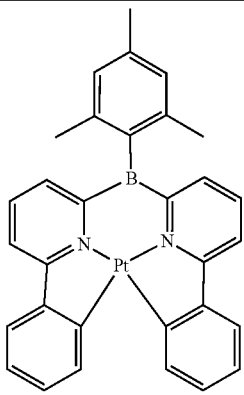 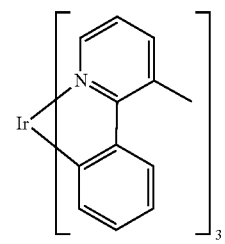 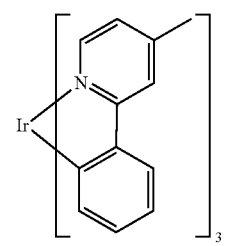 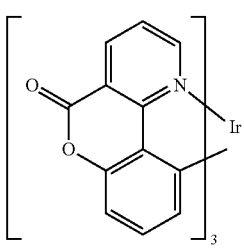 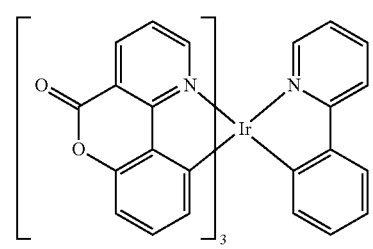 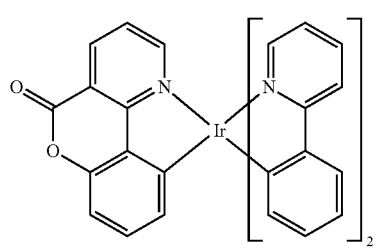 |

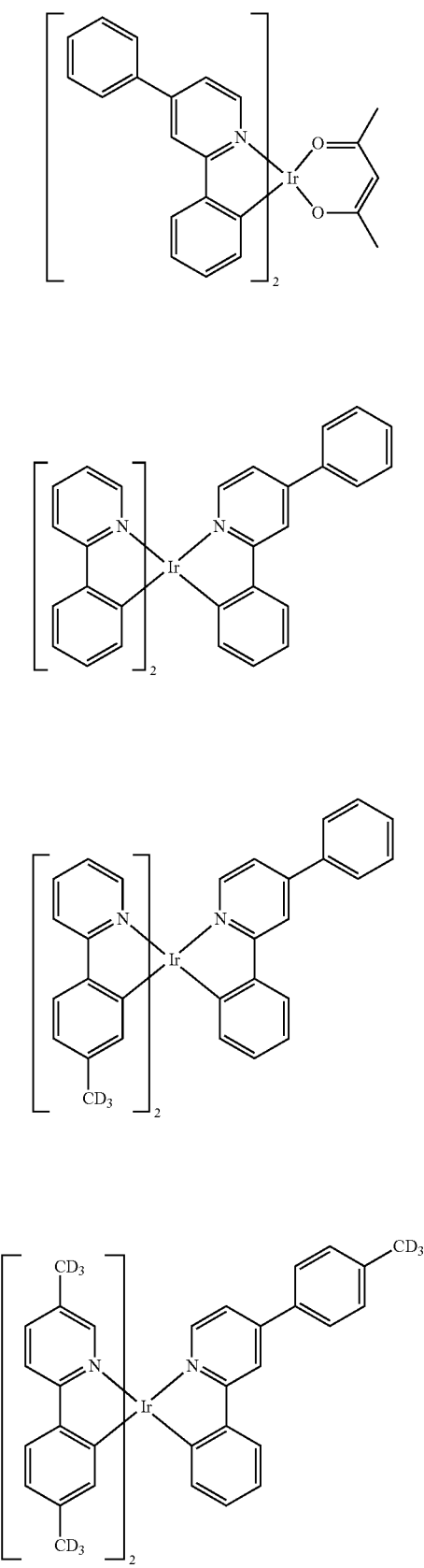
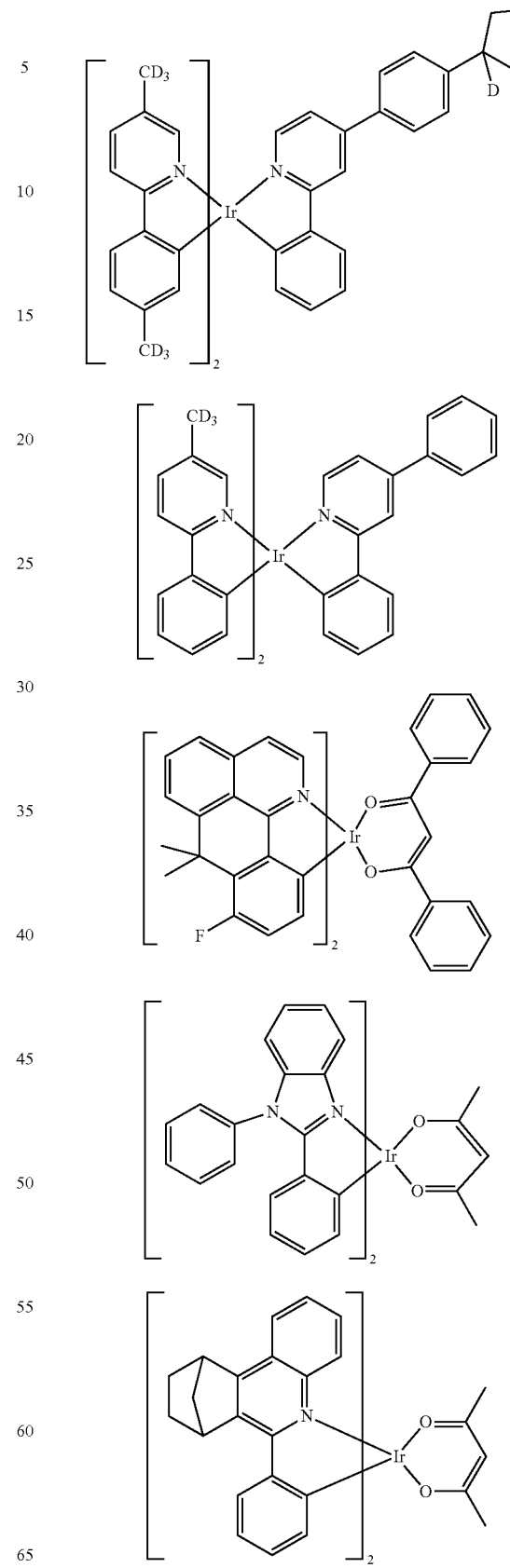

363
-continued
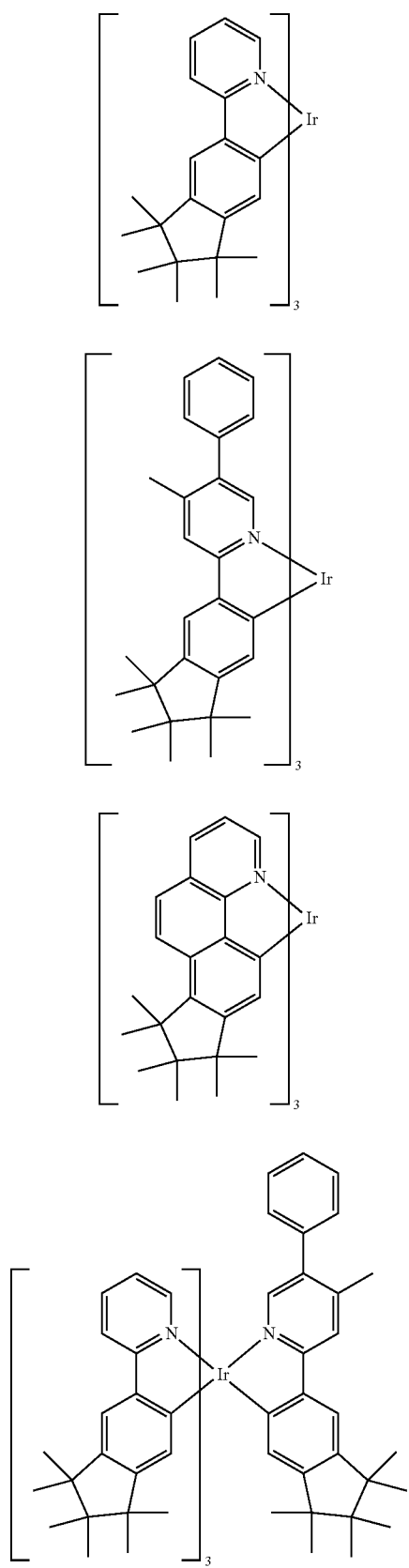
364
-continued
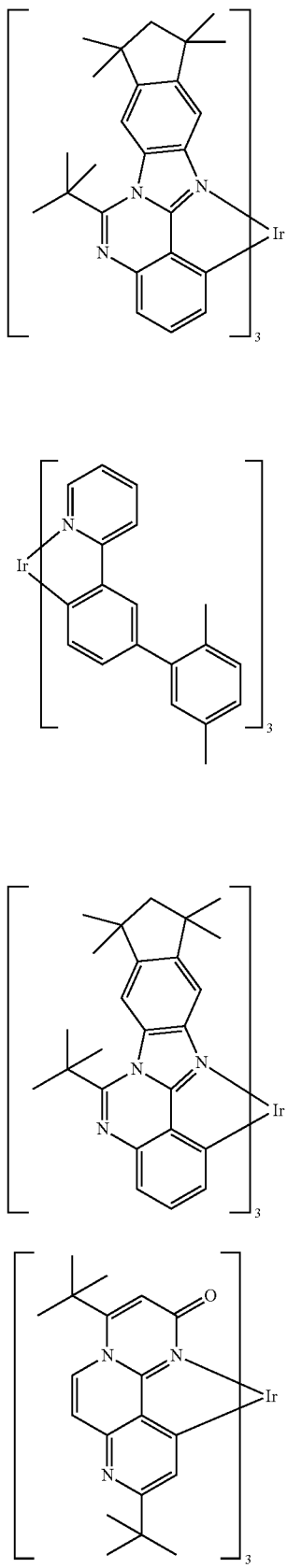

365
-continued
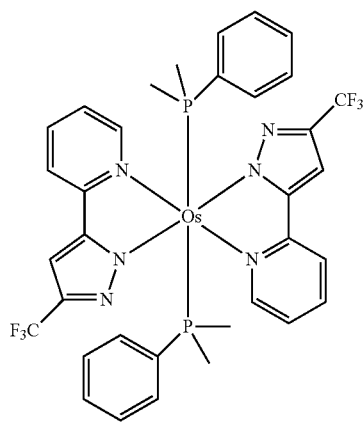
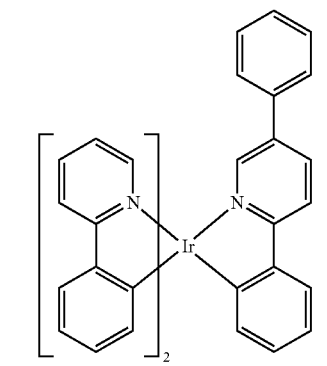
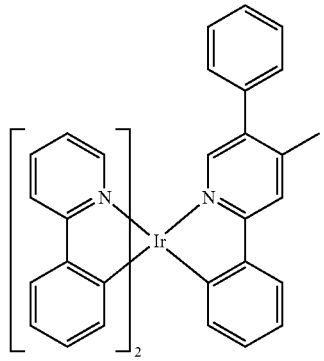
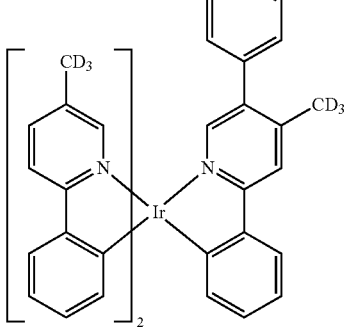
366
-continued
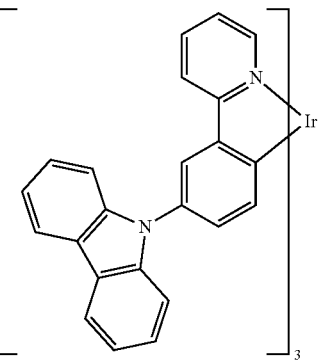
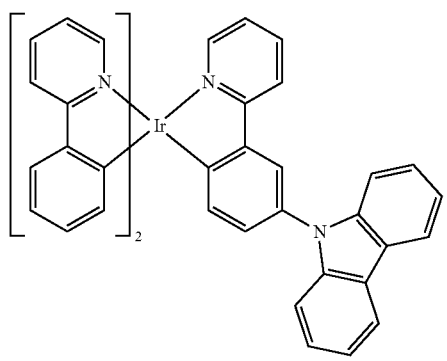
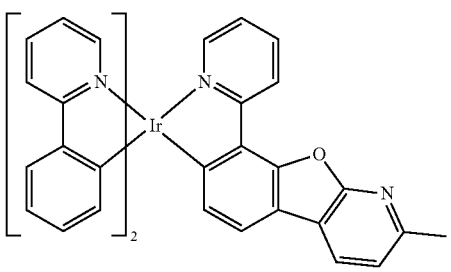
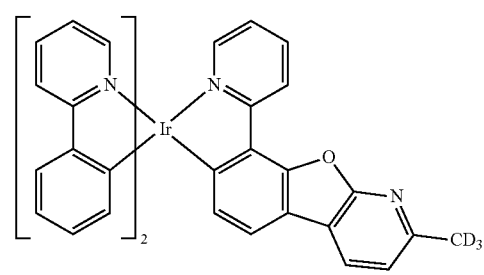
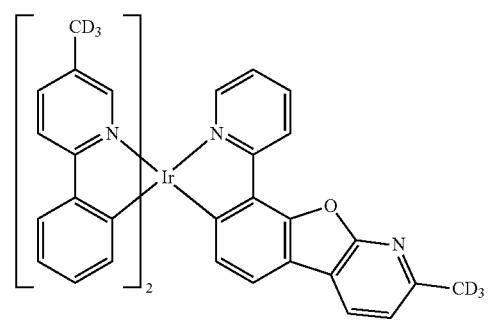

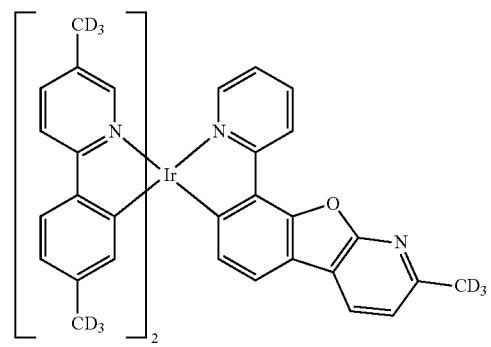
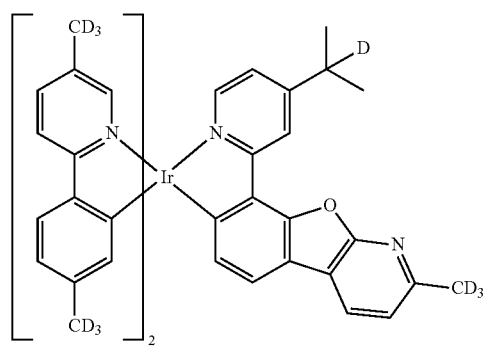
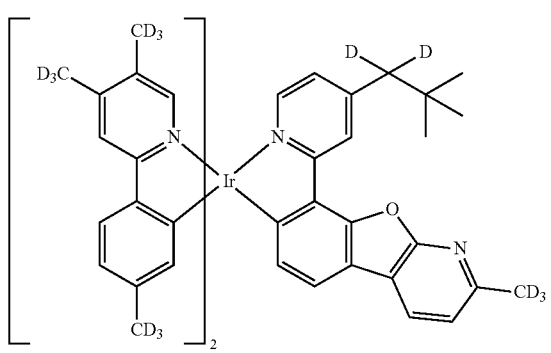
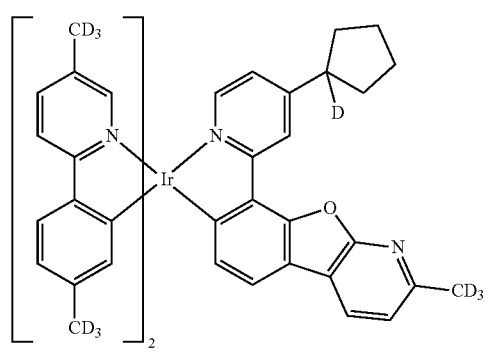
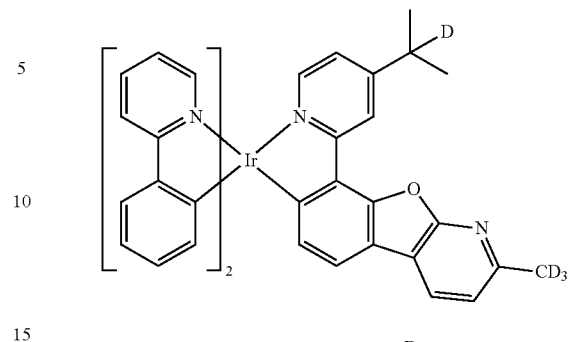
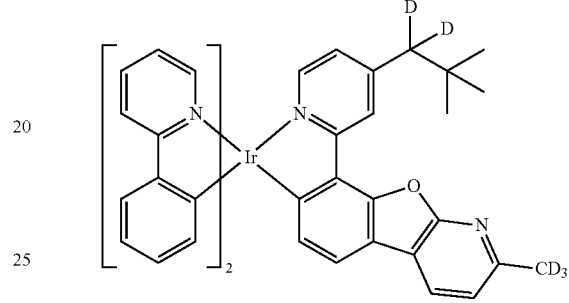
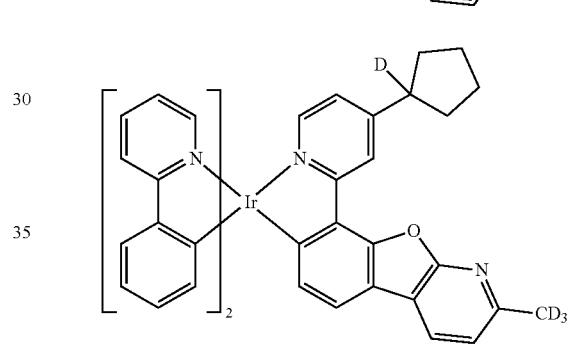
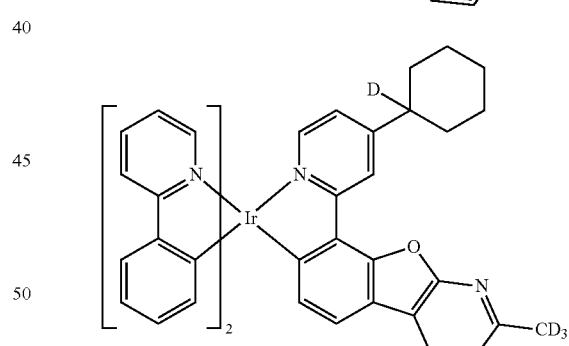
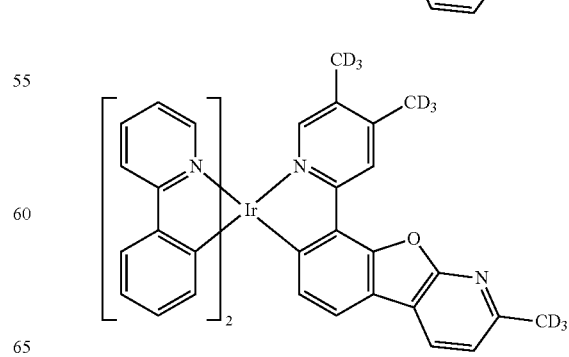

369
-continued
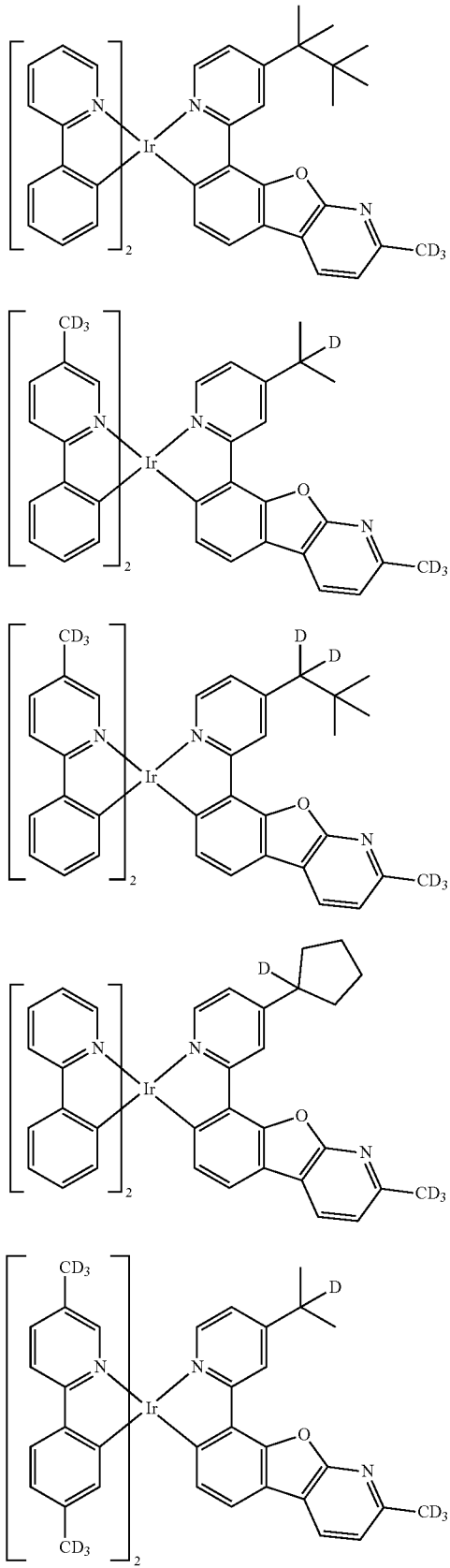
370
-continued
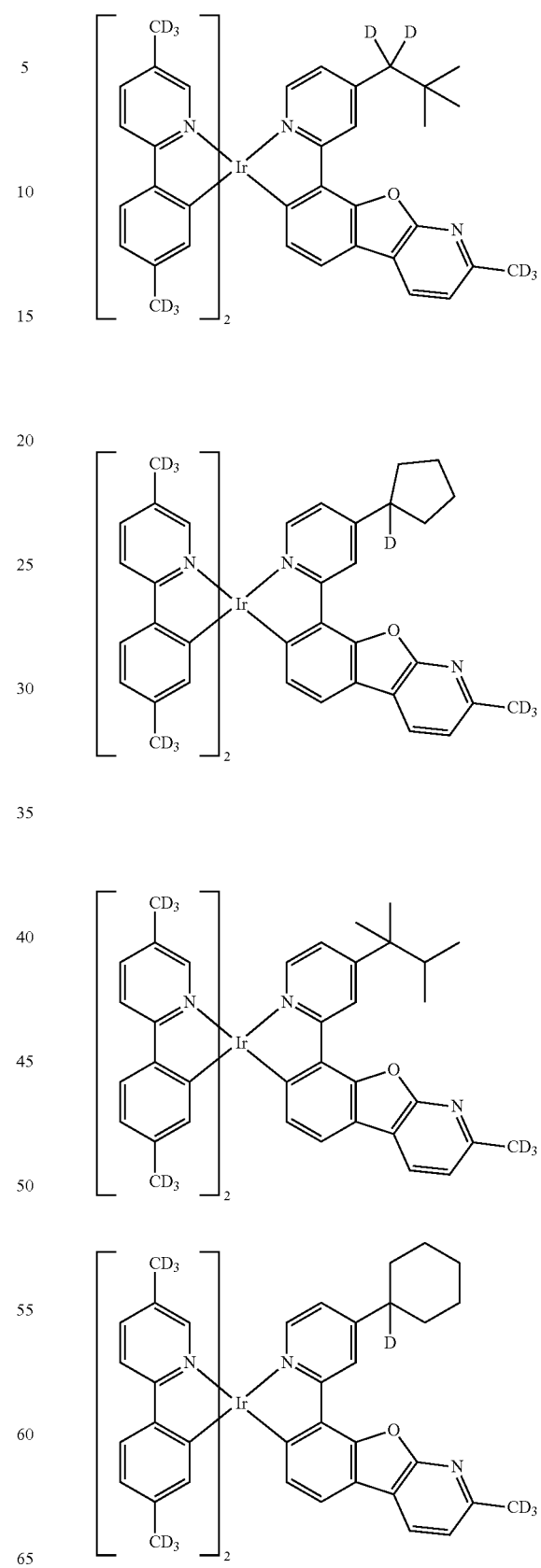

371
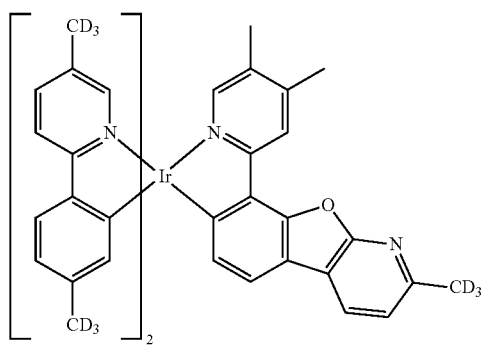
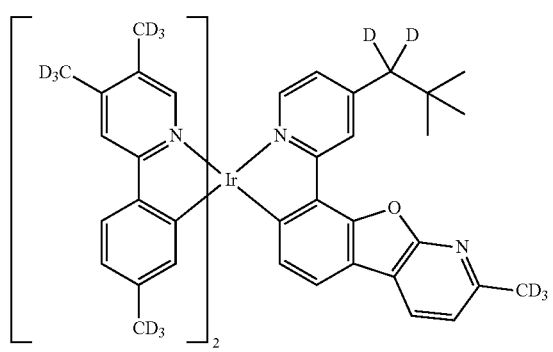
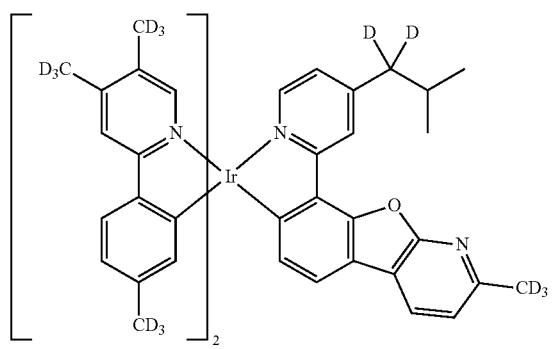
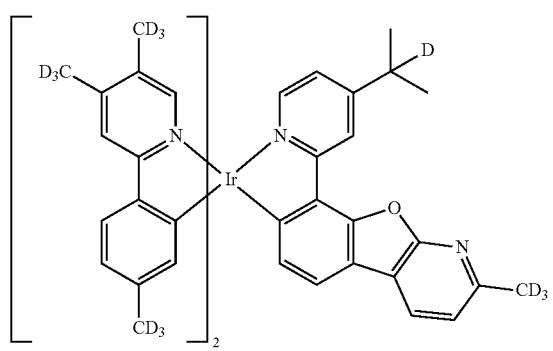
372
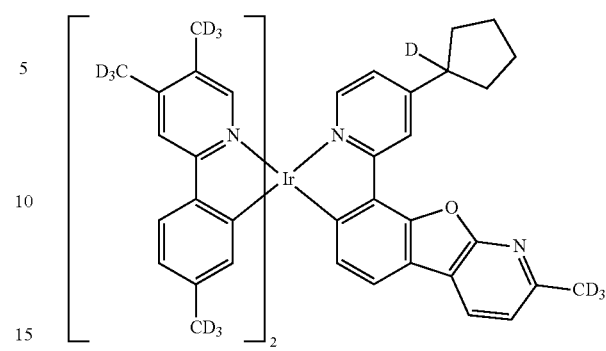
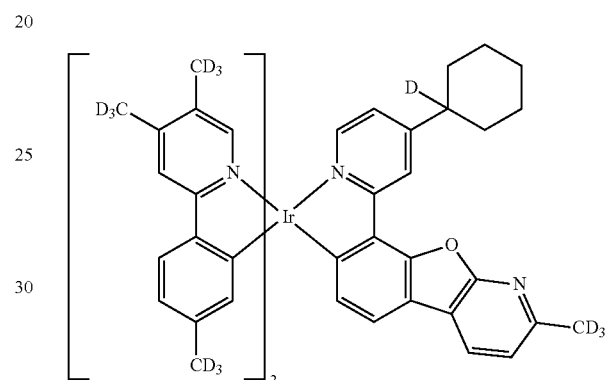
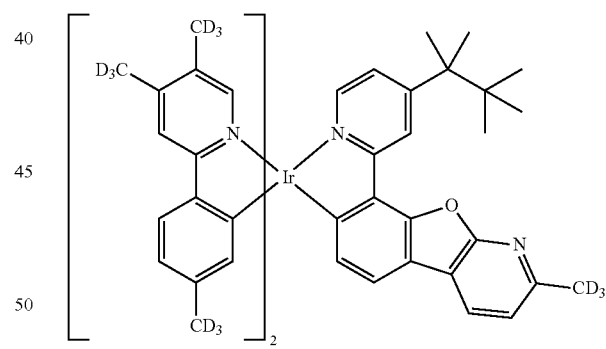
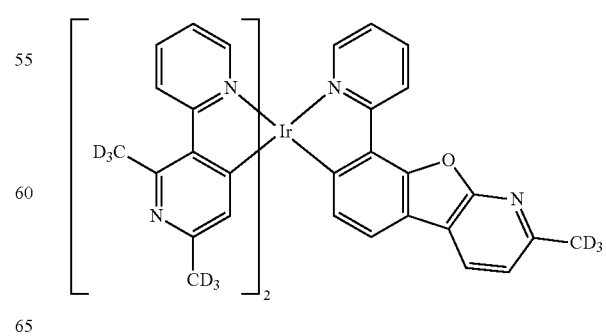

373
-continued
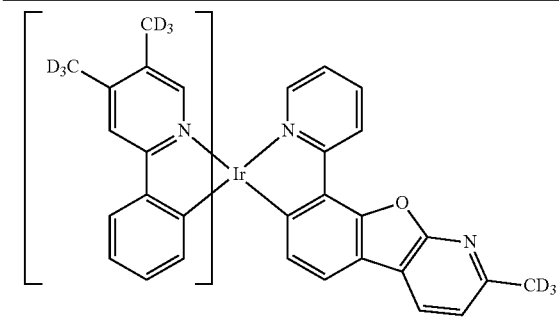
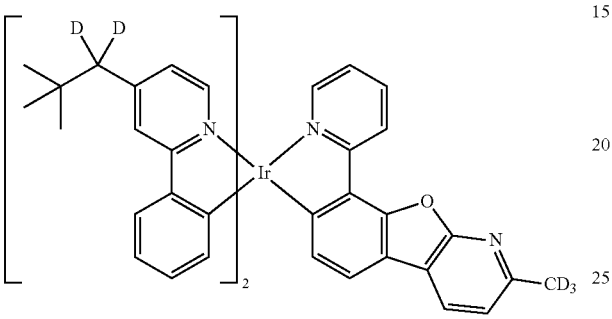
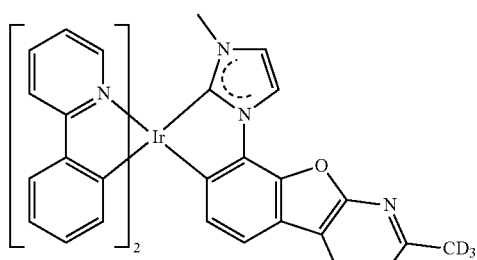
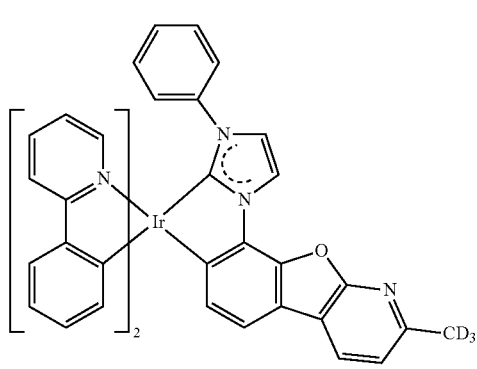
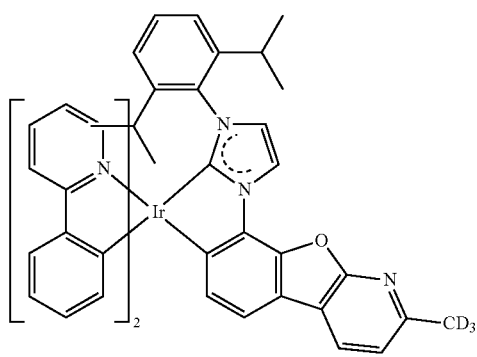
374
-continued
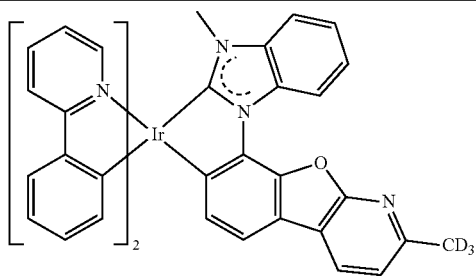
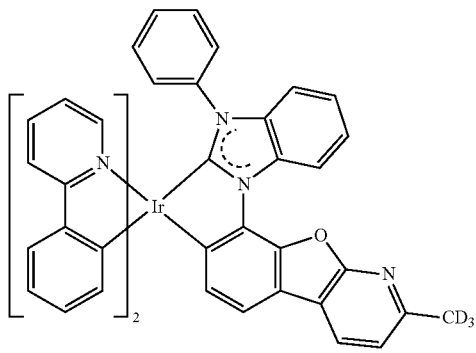
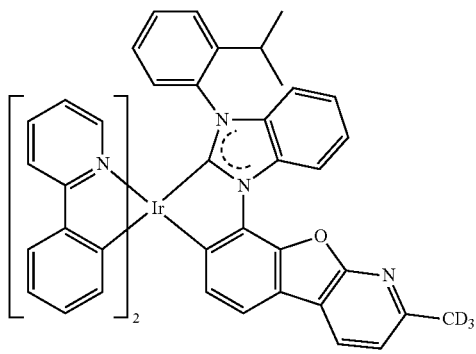
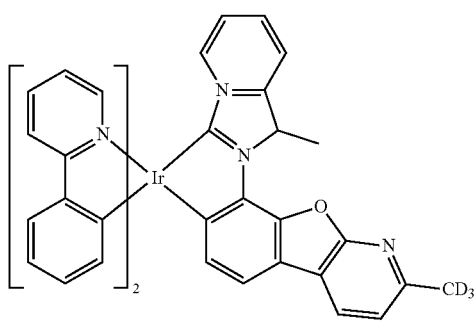
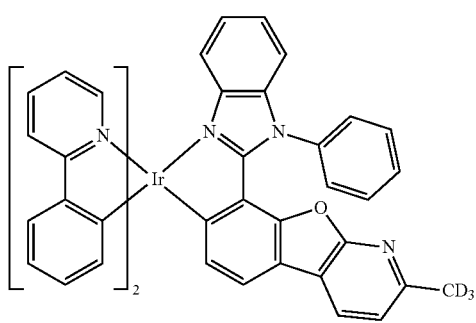

375
-continued
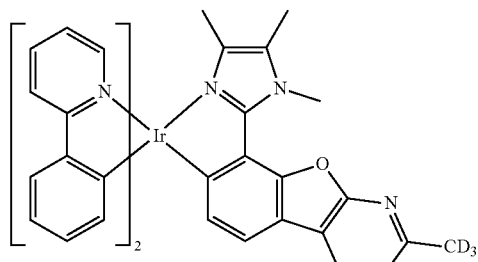
376
-continued
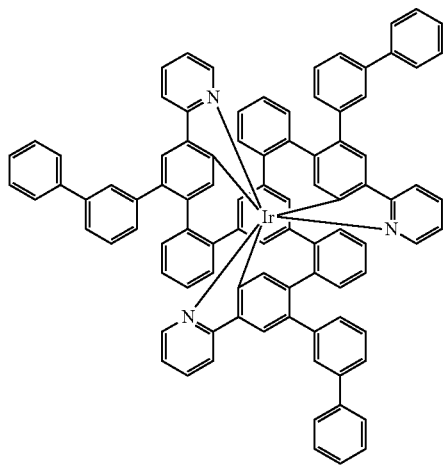
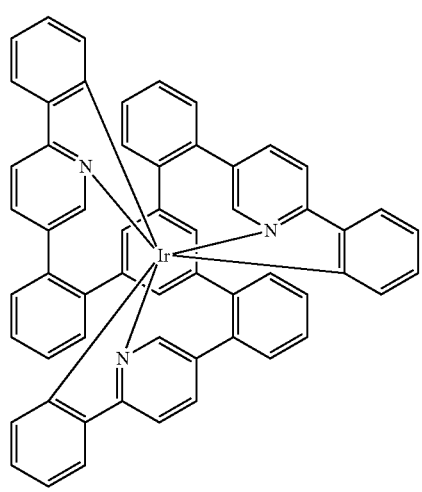
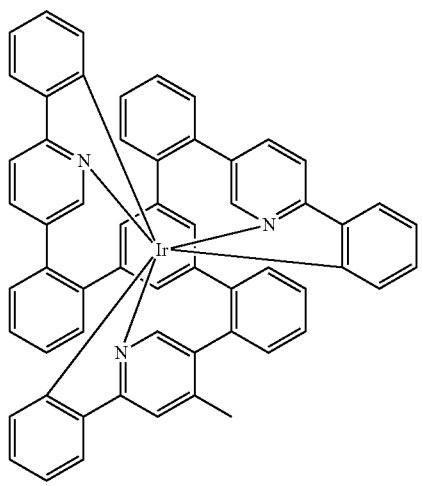
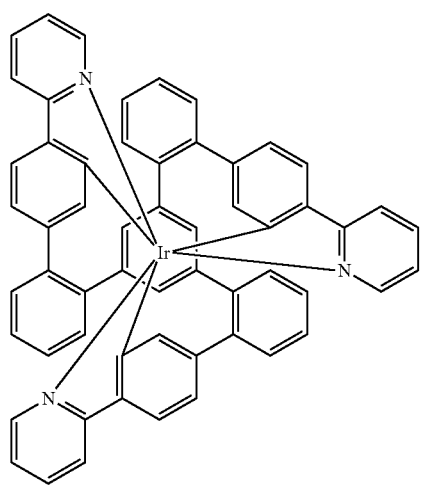
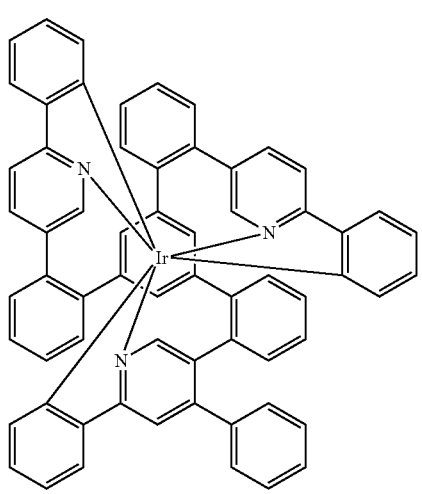

377
-continued
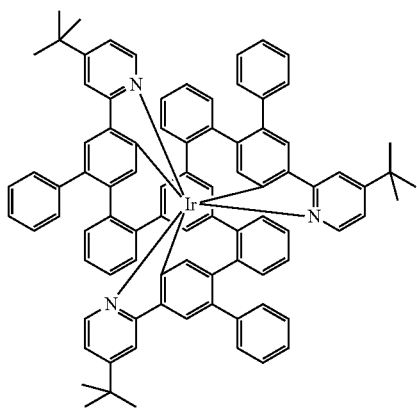
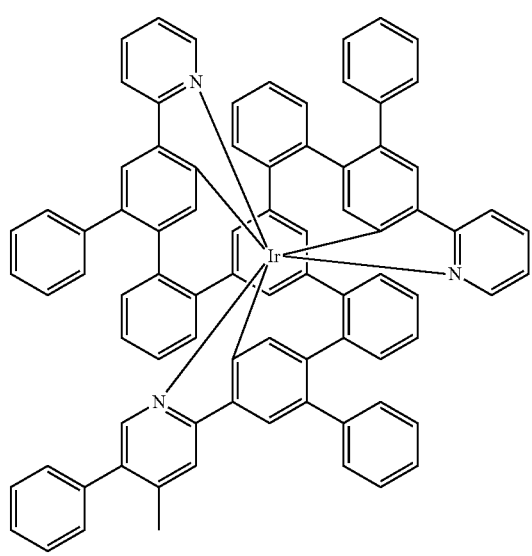
378
-continued
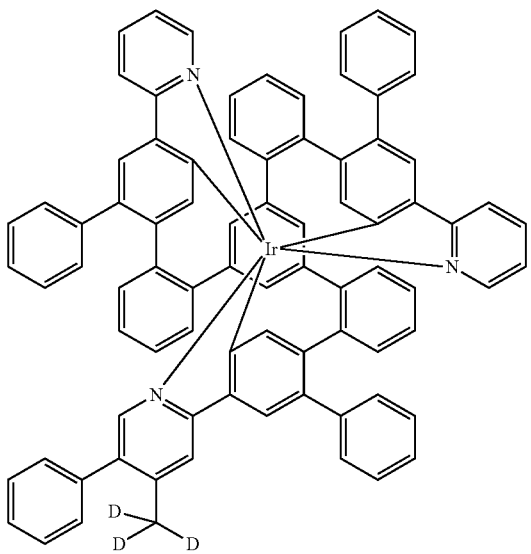
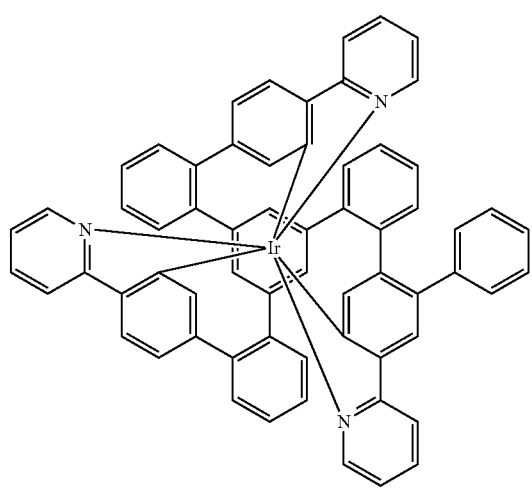

379
-continued
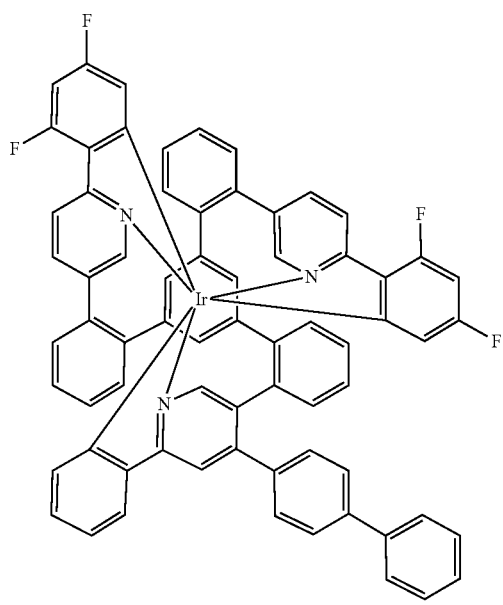
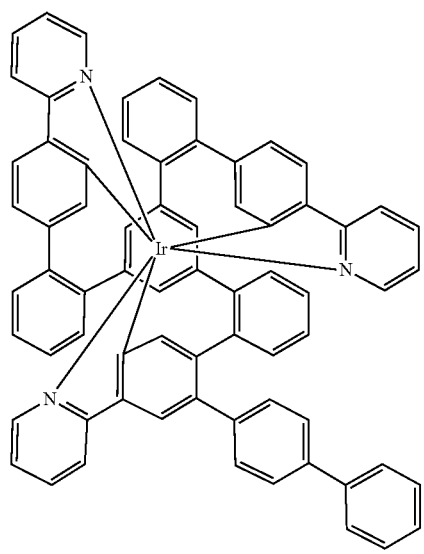
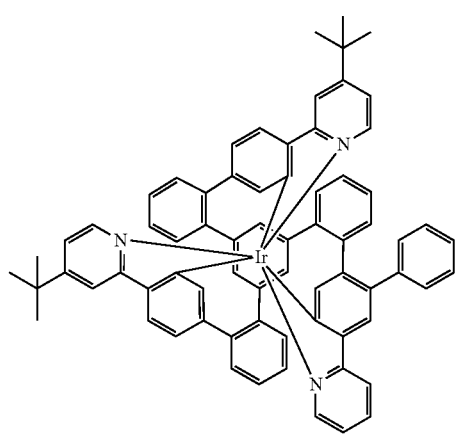
380
-continued
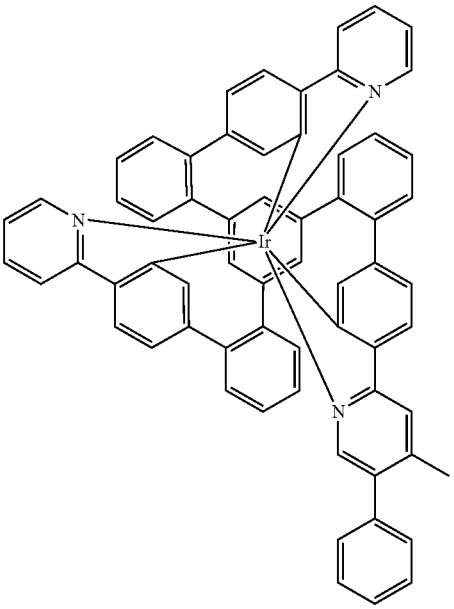
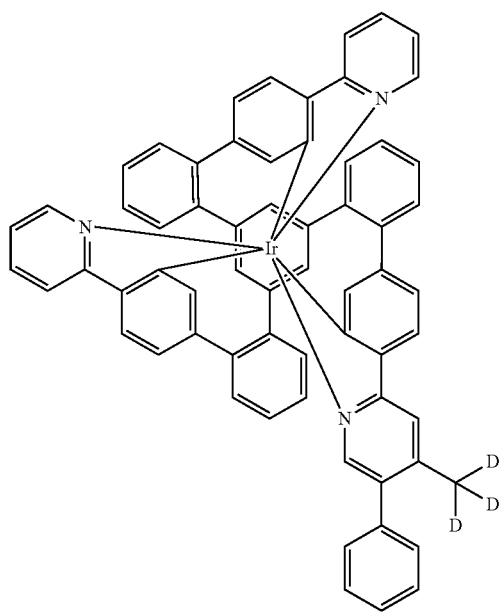

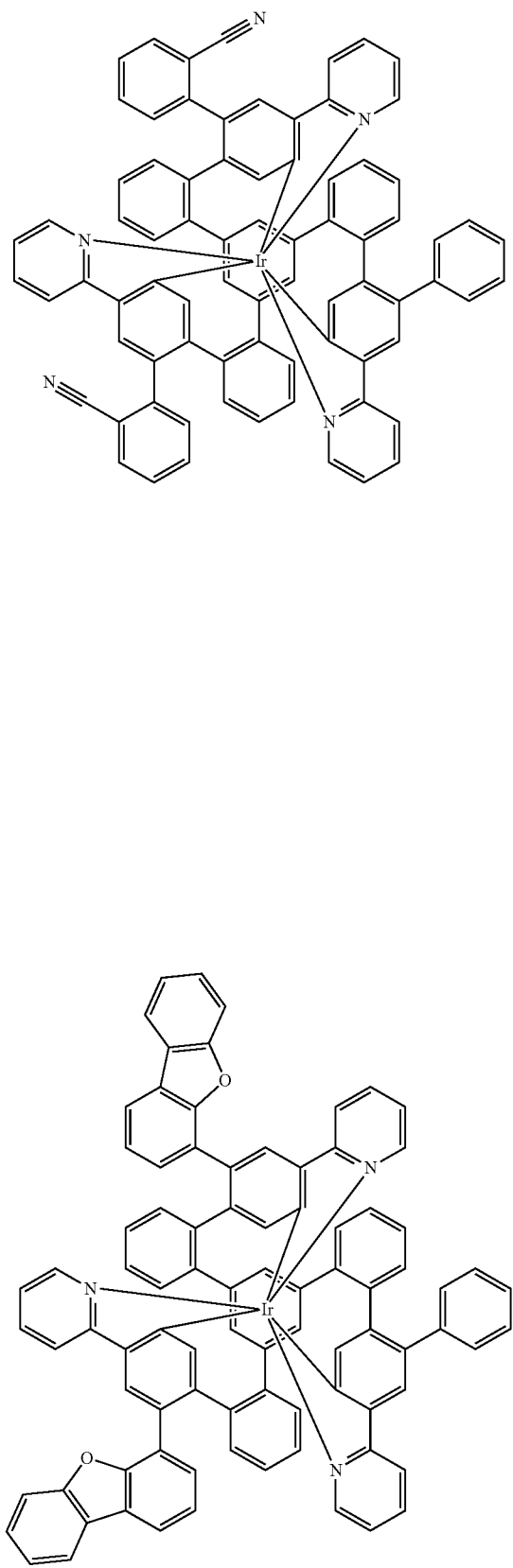
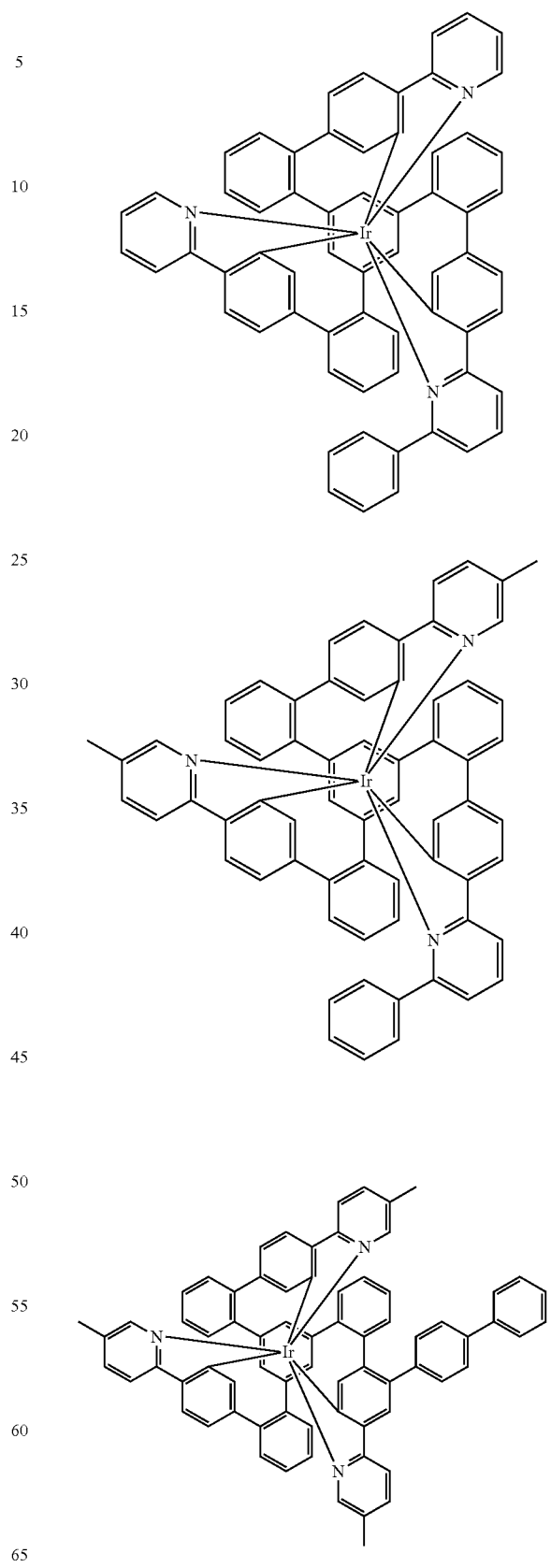

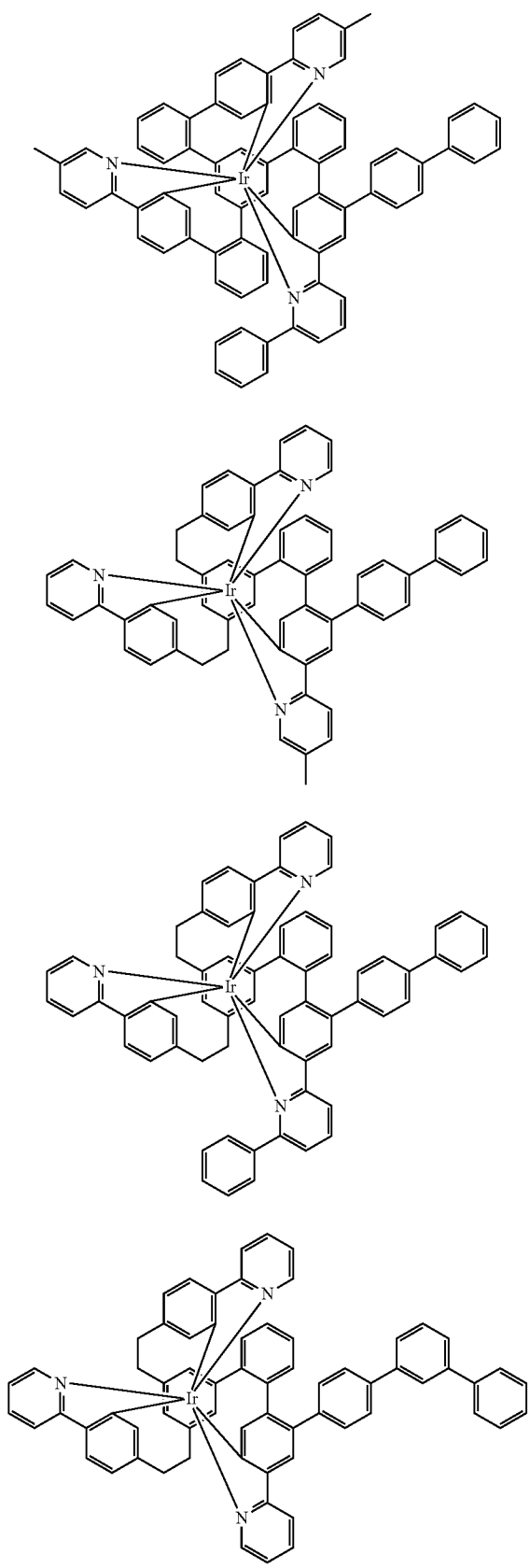
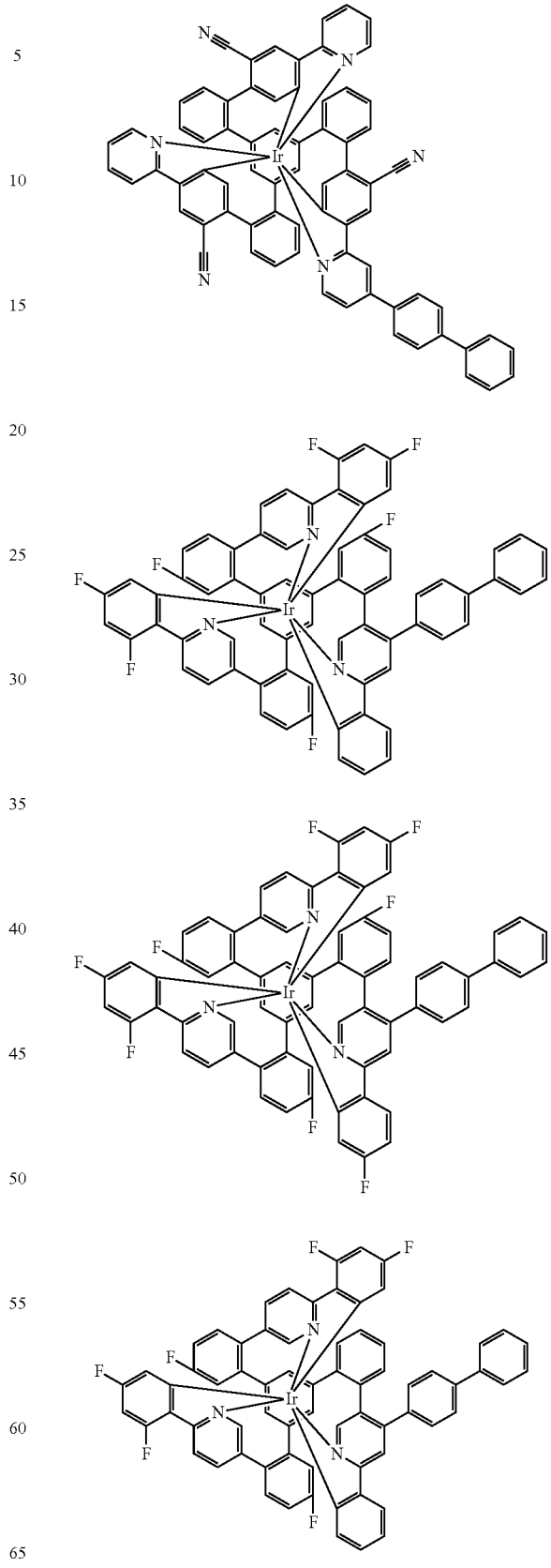

385
-continued
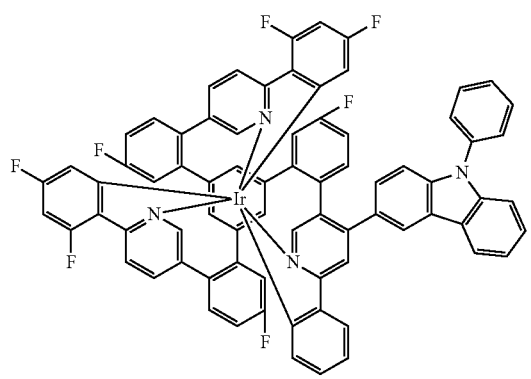
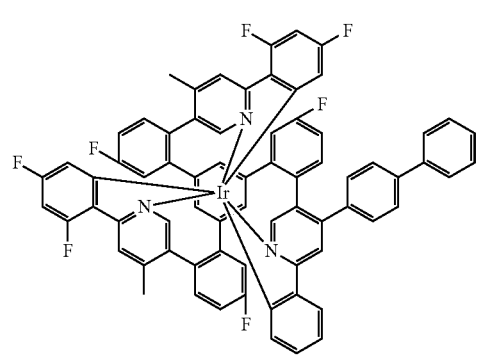
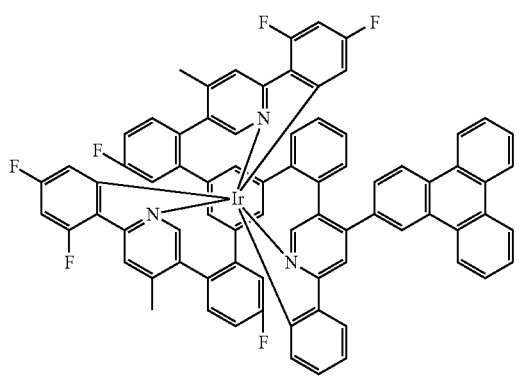
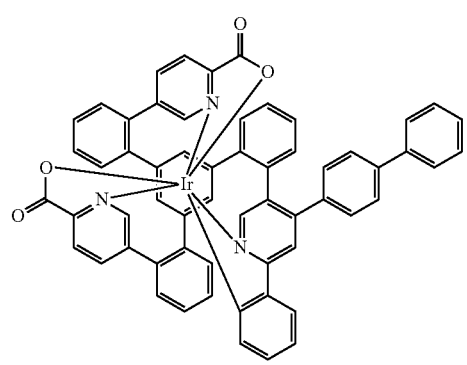
386
-continued
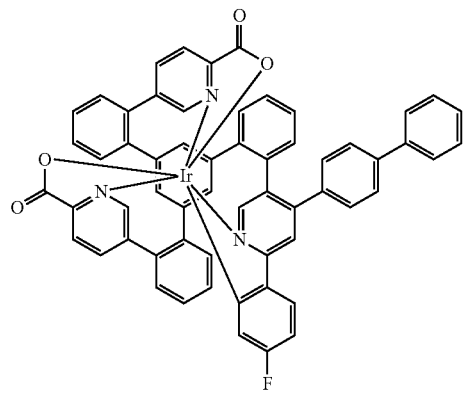
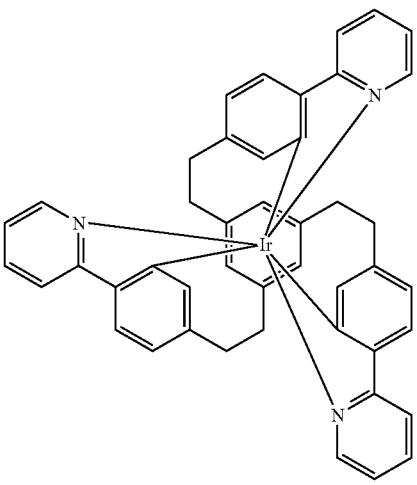
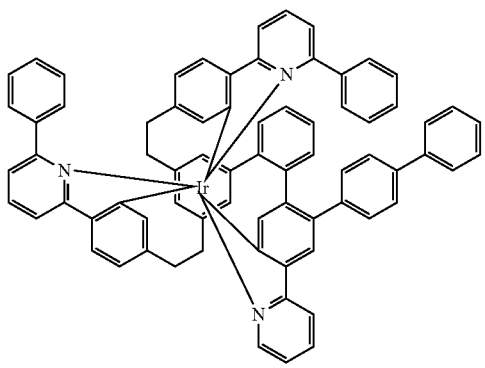

387
-continued
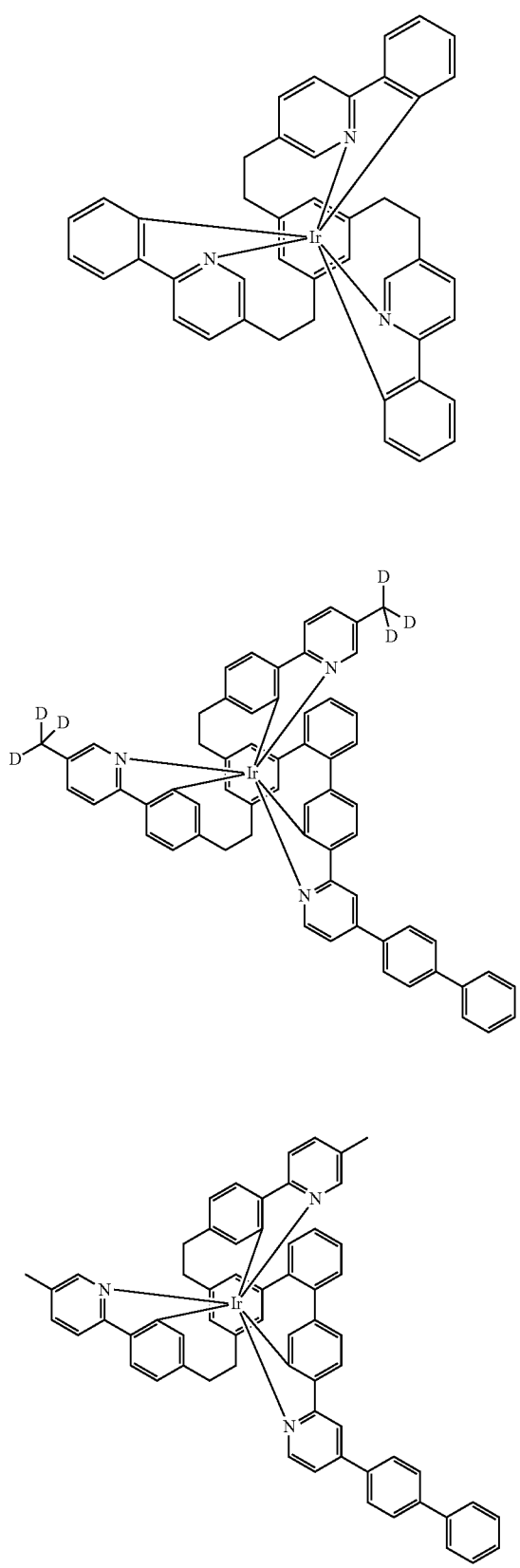
388
-continued
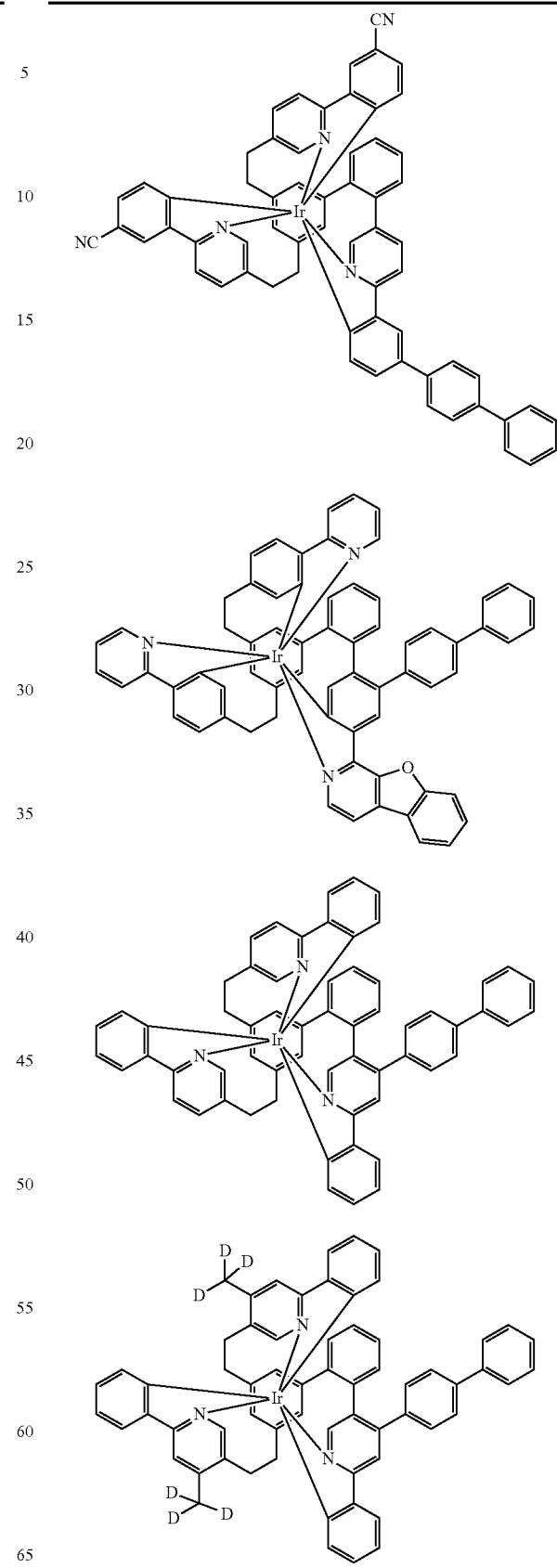

389
-continued
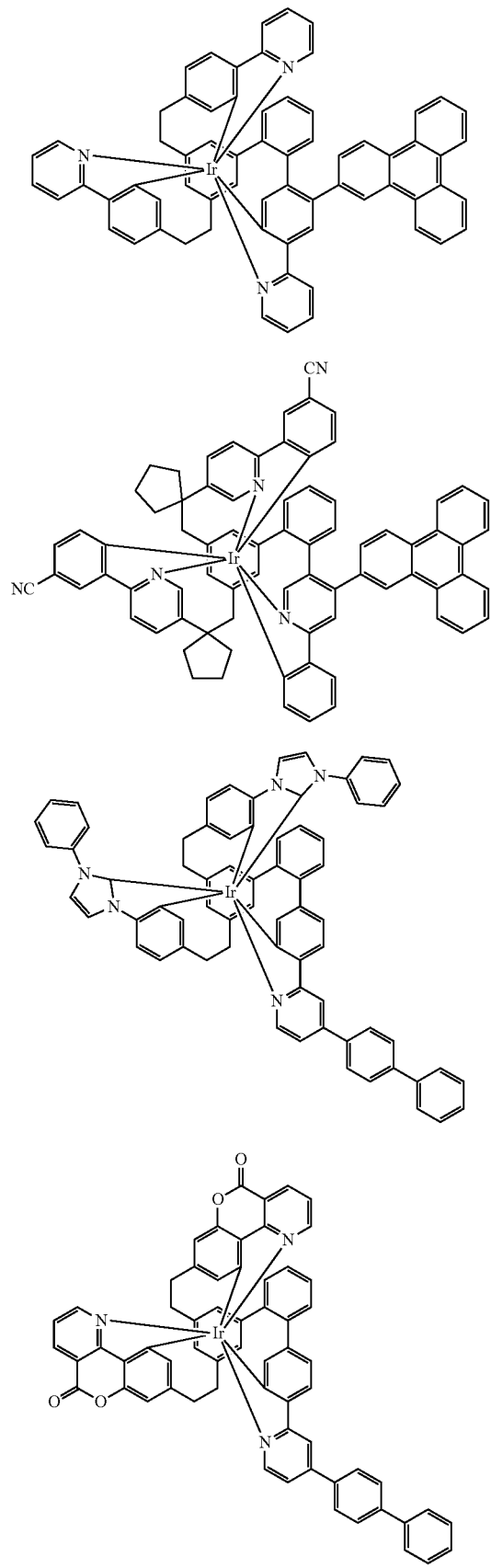
390
-continued
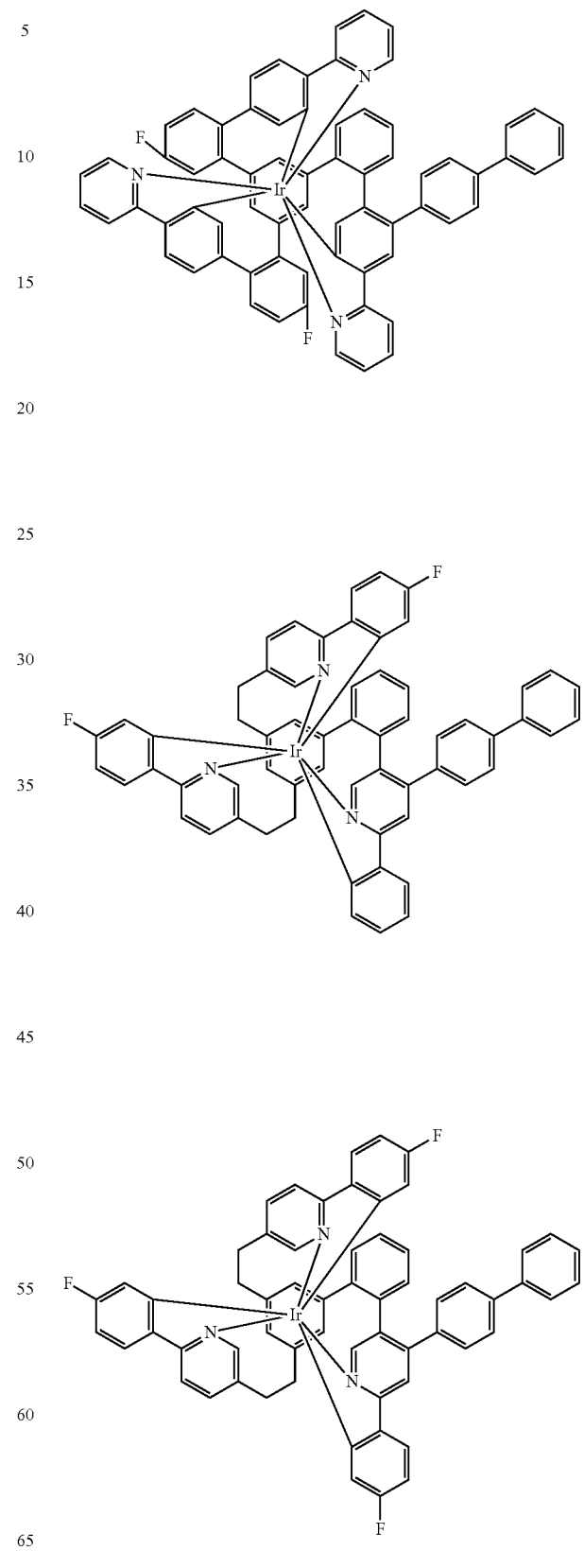

391
-continued
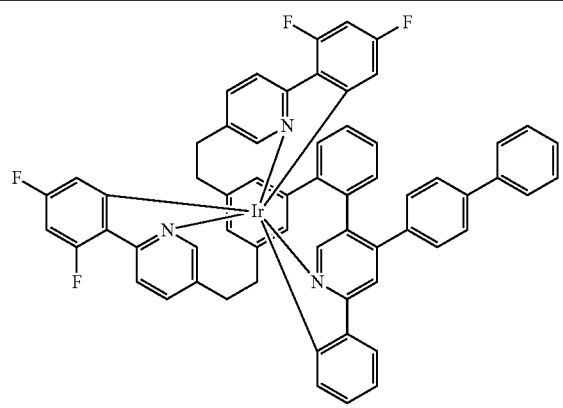
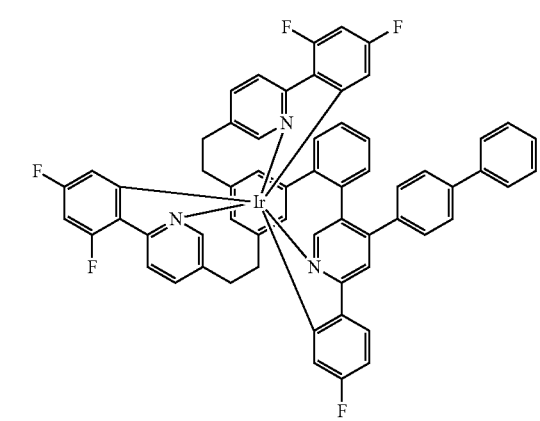
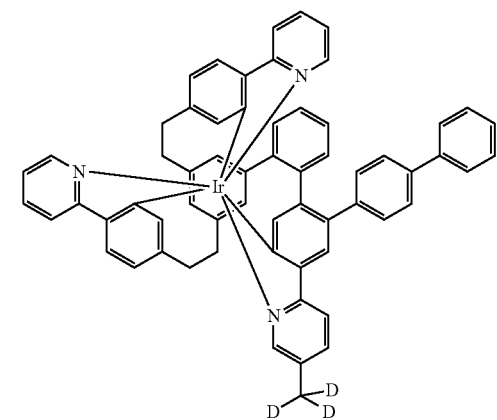
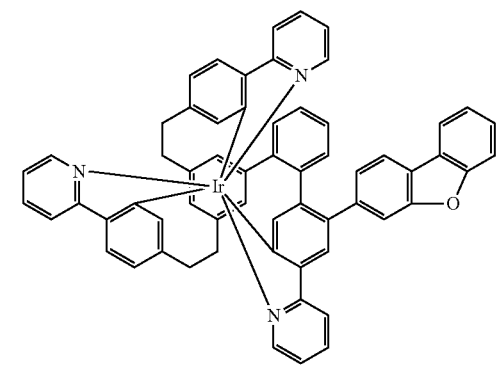
392
-continued
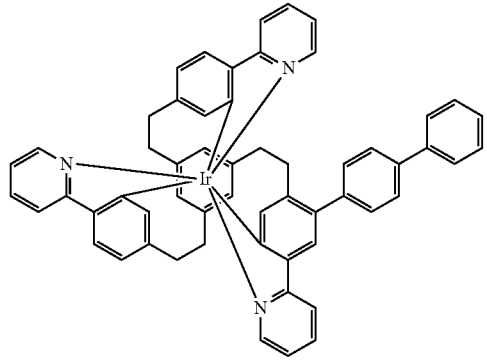
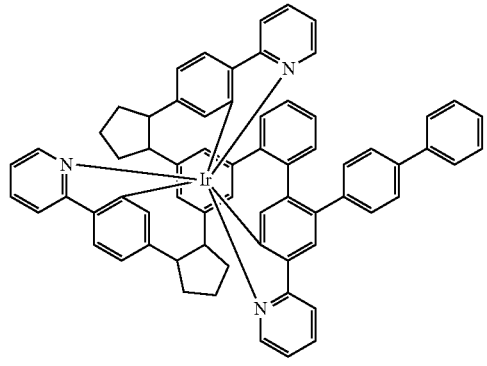
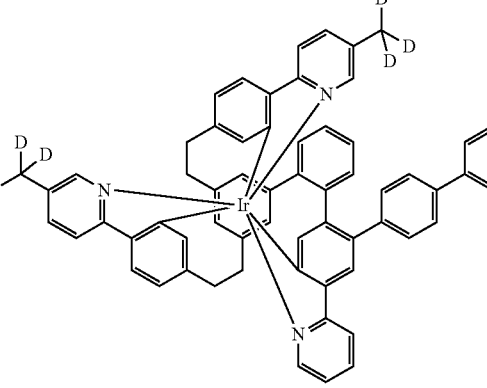
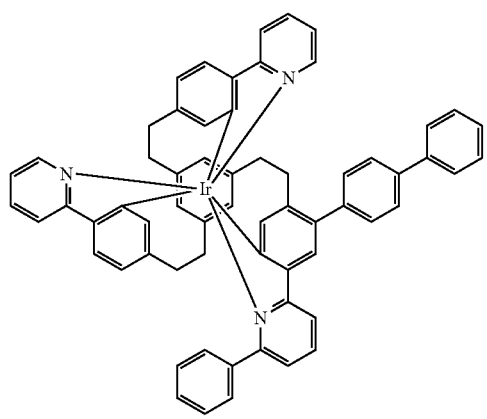

393
-continued
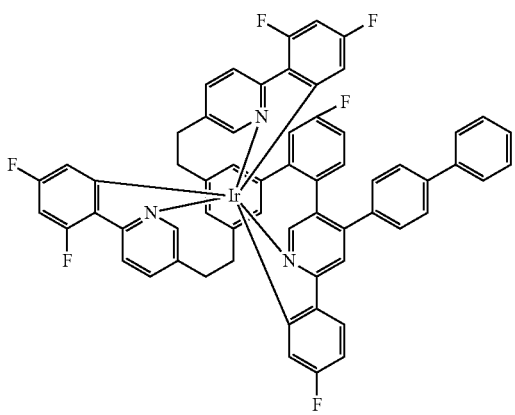
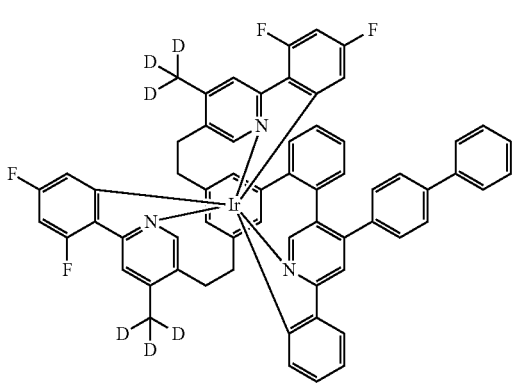
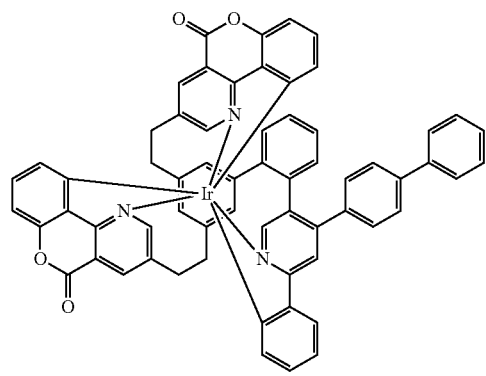
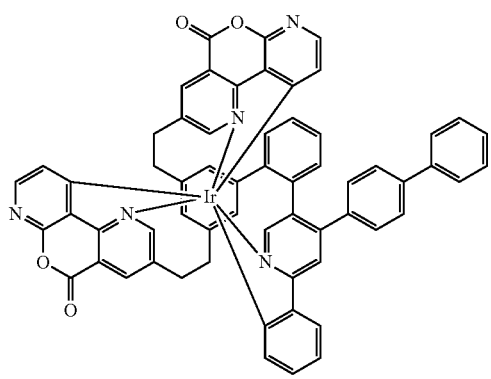
394
-continued
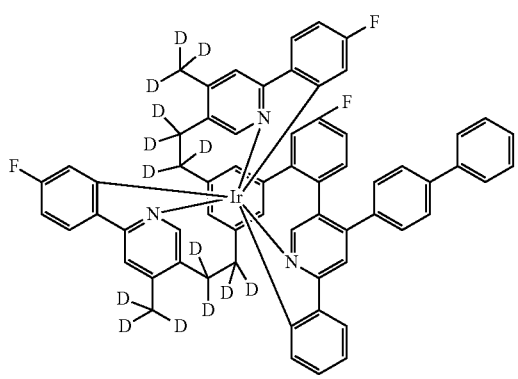
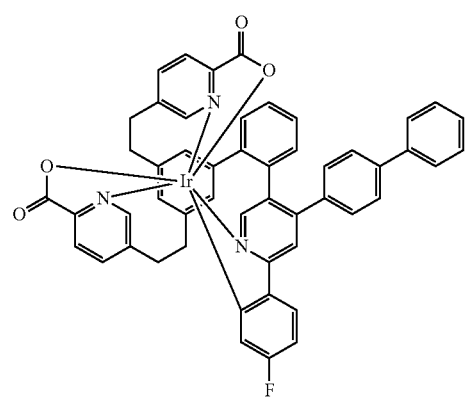
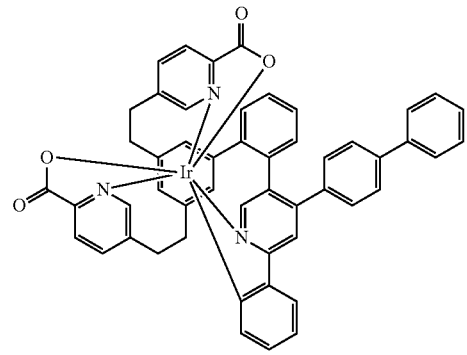
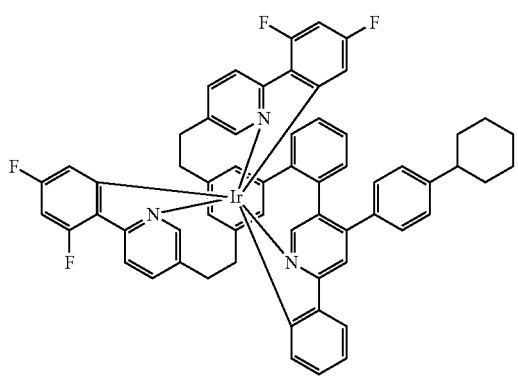

395
-continued
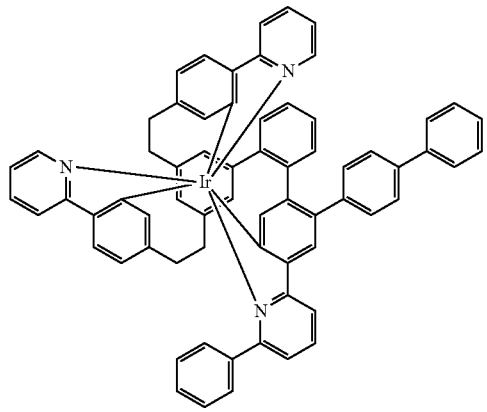
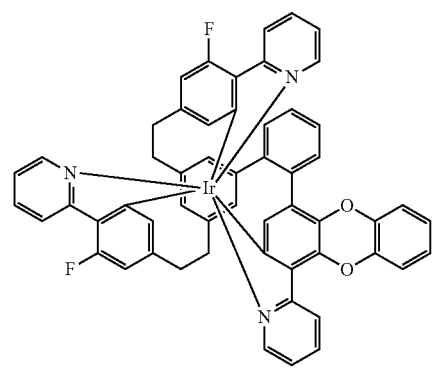
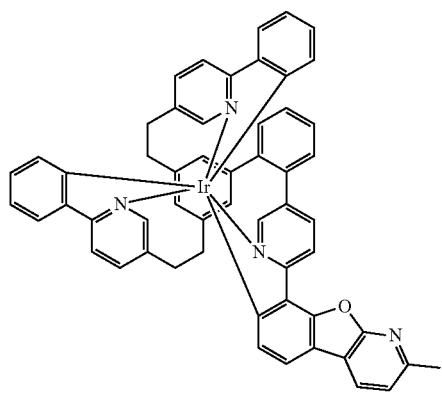
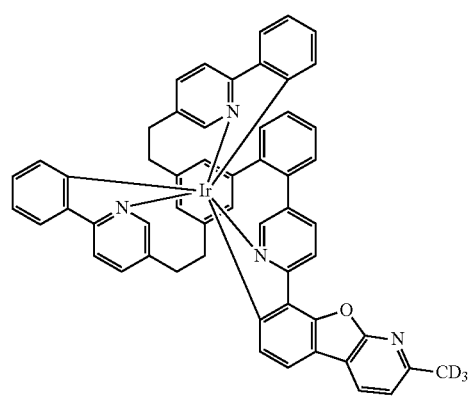
396
-continued
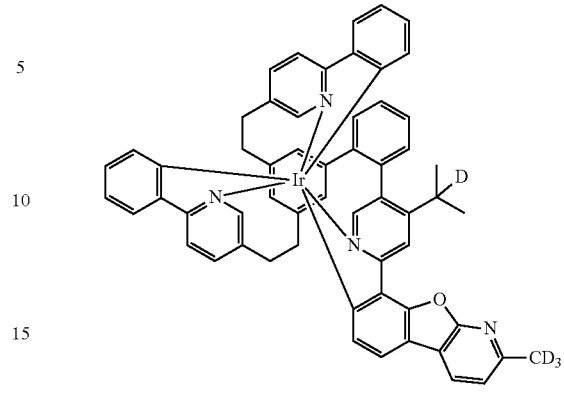
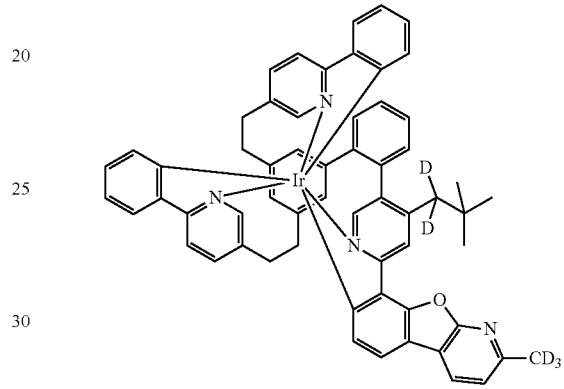
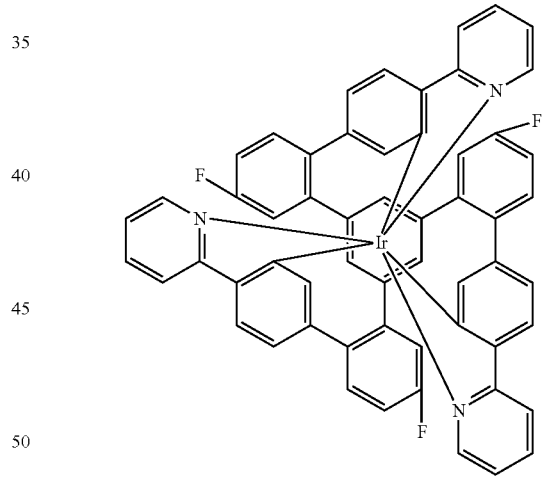
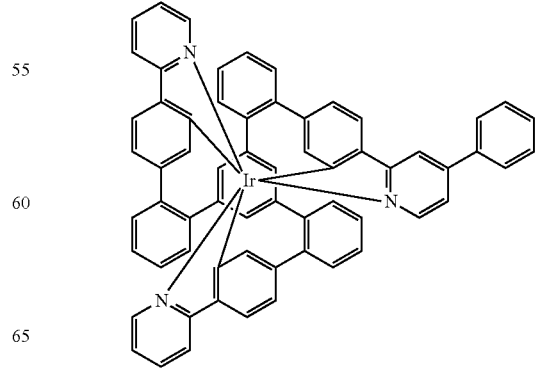

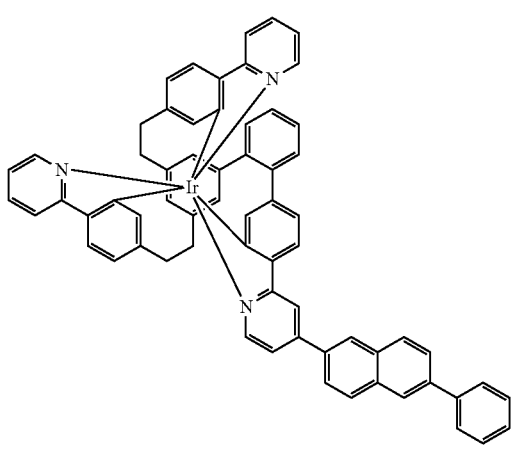
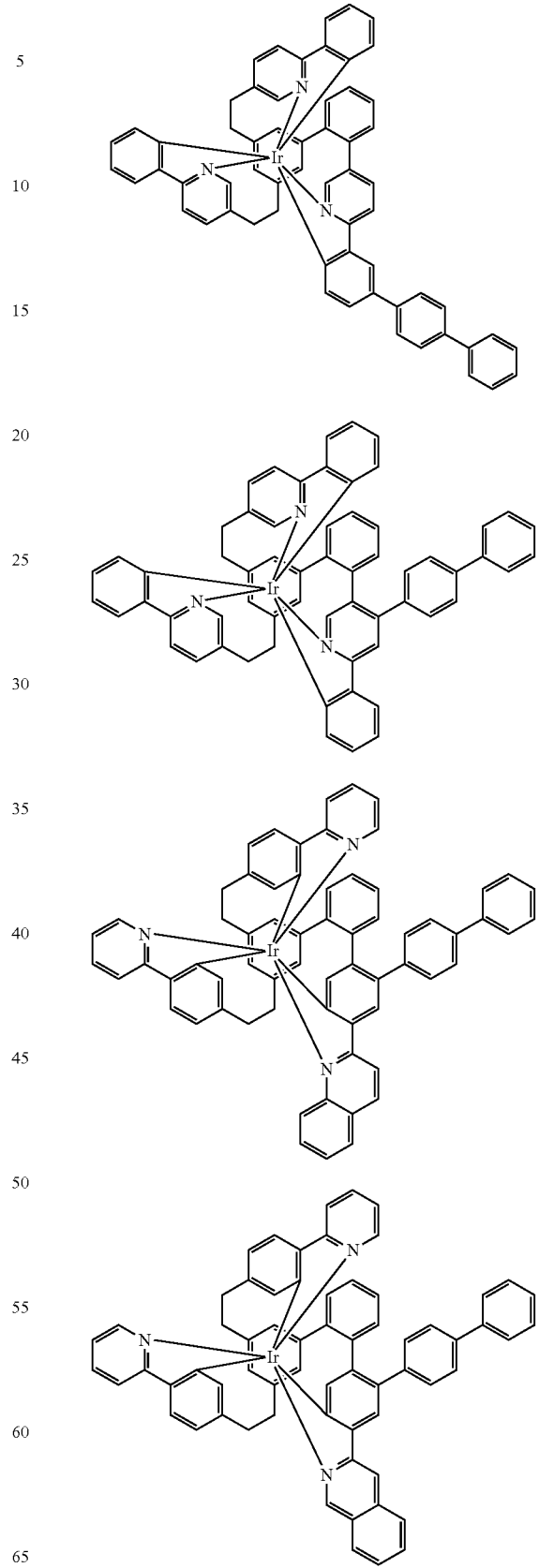

-continued

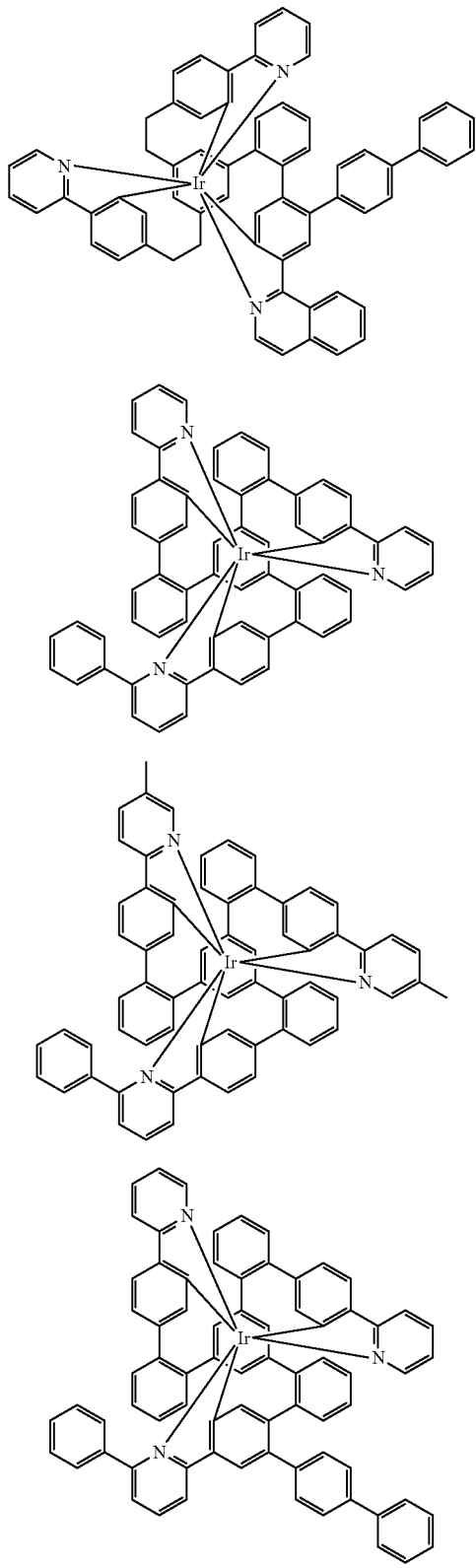

In a further embodiment of the invention, the electroluminescent device is a device, as described, for example, in WO 98/24271, US 2011/0248247 and US 2012/0223633. In these multicolour display components, an additional blue emission layer is applied by vapour deposition over the full area to all pixels, including those having a colour other than blue.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the compounds of formula (1) or the above-recited preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapour deposition.

These methods are known in general terms to those skilled in the art and can be applied by those skilled in the art without exercising inventive skill to organic electroluminescent devices comprising the compounds of the invention.

The OLEDs of the invention have a very good lifetime and especially an improved lifetime compared to compounds that are similar but have an indenocarbazole base skeleton rather than the benzindenocarbazole base skeleton. At the same time, the further electronic properties of the OLED, such as efficiency or operating voltage, remain at least equally good. This is especially also true when the compounds of the formula (1) are used as a single host material and not in a mixture with one or more further host materials. It is a surprising result since similar compounds when used as single host material lead to worse results than when used as a mixed host. The possibility of use of the compound of the formula (1) as a single host material without any deterioration in the device results is a significant advantage in the production of the OLED.

The invention is illustrated in more detail by the examples which follow, without any intention of restricting it thereby. The person skilled in the art will be able to use the information given to execute the invention over the entire scope disclosed and to prepare further devices of the invention without exercising inventive skill.

EXAMPLES

The syntheses which follow, unless stated otherwise, are conducted under a protective gas atmosphere in dried solvents. The solvents and reagents can be purchased from ALDRICH or ABCR. The numbers given for the reactants that are not commercially available are the corresponding CAS numbers.

a) (2-Chlorophenyl)(11,11-dimethyl-11H-benzo[a]fluoren-9-yl)amine

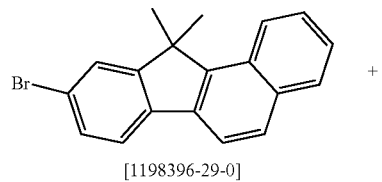

[1198396-29-0]

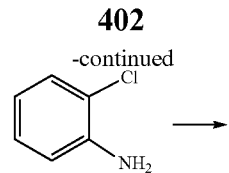

-continued

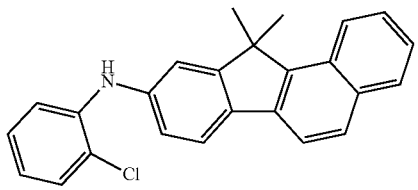

47 g (145 mmol) of 9-bromo-11,11-dimethyl-11H-benzo[a]fluorene, 16.8 g (159 mmol) of 2-chloroaniline, 41.9 g (436.2 mmol) of sodium tert-butoxide and 1.06 (1.45 mmol) of Pd(dppf)Cl$_2$ are dissolved in 500 ml of toluene and stirred under reflux for 5 h. The reaction mixture is cooled down to room temperature, extended with toluene and filtered through Celite. The filtrate is concentrated under reduced pressure and the residue is crystallized from toluene/heptane. The product is isolated as a colourless solid. Yield: 33 g (89 mmol), 70% of theory.

The following compounds can be prepared in an analogous manner:

| | Reactant 1 | Reactant 2 | Product | Yield |
|---|---|---|---|---|
| 1a | [1804905-31-4] | | | 79% |
| 2a | [1800333-59-8] | | | 77% |

-continued
| | Reactant 1 | Reactant 2 | Product | Yield |
|---|---|---|---|---|
| 3a | 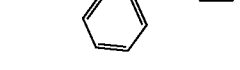<br>[1263204-40-5] |  | 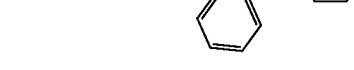 | 78% |
| 1d | 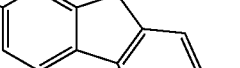<br>[119839-39-2] | 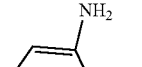 | 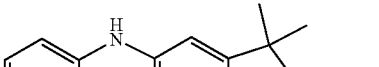 | 79% |
| 4a | 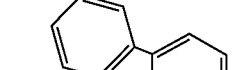 | 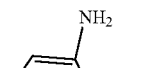 |  | 74% |
| 1f | <br>[1198396-29-0] | 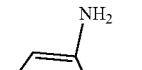 | 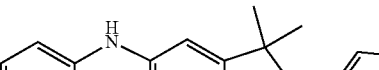 | 81% |
| 5a | 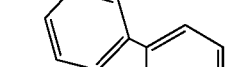<br>[1198396-35-8] | 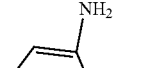 | 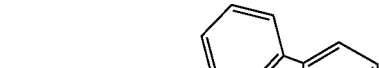 | 78% |
| 6a | <br>[1674335-13-7] | 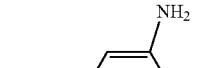 | 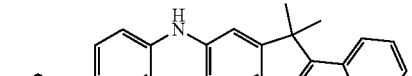 | 77% | b) Cyclization

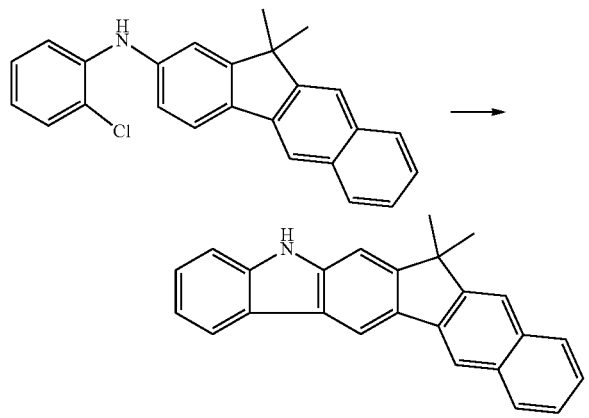

48 g (129 mmol) of (2-chlorophenyl)(11,11-dimethyl-11H-benzo[a]fluoren-9-yl)amine, 53 g (389 mmol) of potassium carbonate, 4.5 g (12 mmol) of tricyclohexylphosphine tetrafluoroborate, 1.38 g (6 mmol) of palladium(II) acetate and 3.3 g (32 mmol) of pivalic acid are suspended in 500 ml of dimethylacetamide and stirred under reflux for 6 h. After cooling, 300 ml of water and 400 ml of dichloromethane are added to the reaction mixture. The mixture is stirred for 30 min, the organic phase is separated off and filtered through a short Celite bed, and then the solvent is removed under reduced pressure. The crude product is subjected to hot extraction with toluene and recrystallized from toluene. The product is isolated as a beige solid. Yield: 34 g (102 mmol), 78% of theory.

The following compounds can be prepared in an analogous manner:

| | Reactant | Product | Yield |
|---|---|---|---|
| 1b | | | 79% |
| 2b | | | 77% |
| 3b | | | 78% |

| | Reactant | Product | Yield |
|---|---|---|---|
| 4b | 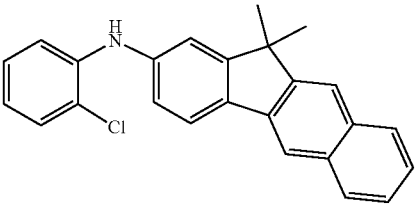 [SMILES: CC1(C)c2cc(Nc3ccccc3Cl)ccc2-c2cc3ccccc3cc21] | 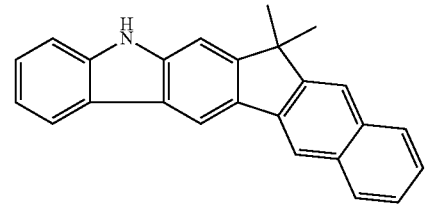 [SMILES: CC1(C)c2cc3ccccc3cc2-c2cc3c(cc21)[nH]c1ccccc13] | 75% |
| 5b | 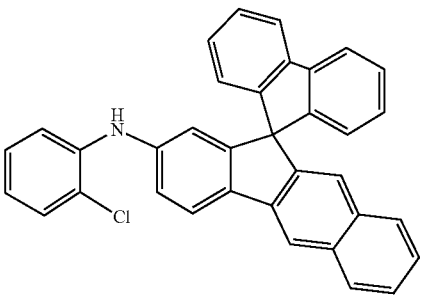 [SMILES: Clc1ccccc1Nc1ccc2c(c1)C1(c3ccccc3-c3ccccc31)c1cc3ccccc3cc1-2] | 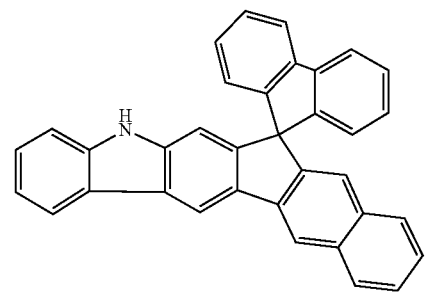 [SMILES: c1ccc2c(c1)-c1ccccc1C21c2cc3ccccc3cc2-c2cc3c(cc21)[nH]c1ccccc13] | 78% |
| 6b | 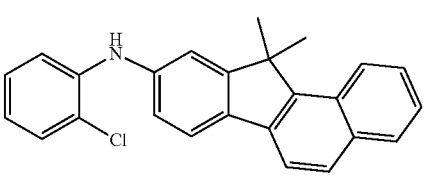 [SMILES: CC1(C)c2cc(Nc3ccccc3Cl)ccc2-c2ccc3ccccc3c21] | 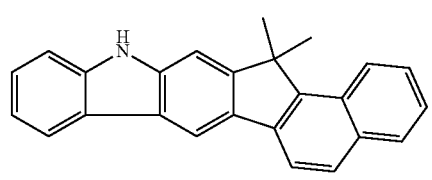 [SMILES: CC1(C)c2cc3[nH]c4ccccc4c3cc2-c2ccc3ccccc3c21] | 73% |
| 7b | 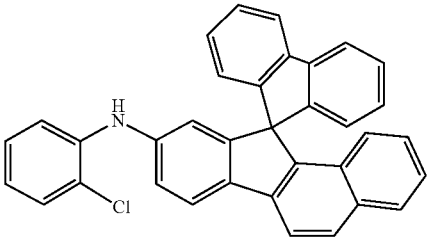 [SMILES: Clc1ccccc1Nc1ccc2c(c1)C1(c3ccccc3-c3ccccc31)c1c-2ccc2ccccc12] | 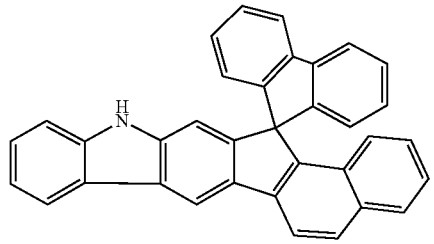 [SMILES: c1ccc2c(c1)-c1ccccc1C21c2cc3[nH]c4ccccc4c3cc2-c2ccc3ccccc3c21] | 71% |
| 8b | 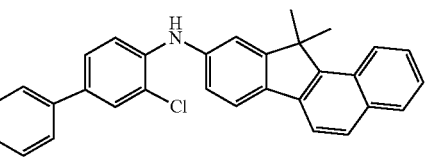 | 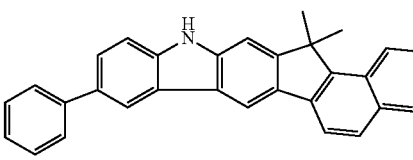 | 76% |
c) 11,11-Dimethyl-3-(2-nitrophenyl)-11H-benzo[b]fluorene
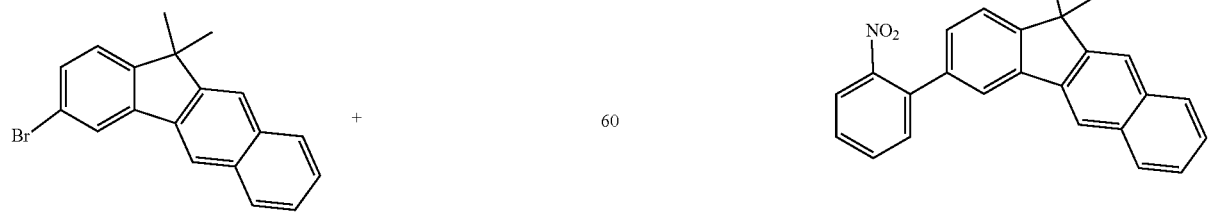
[1674334-59-8]
To a well-stirred, degassed suspension of 59 g (183.8 mmol) of 2-nitrobenzeneboronic acid, 54 g (184 mmol) of 3-bromo-11,11-dimethyl-11H-benzo[b]fluorene and 66.5 g (212.7 mmol) of potassium carbonate in a mixture of 250 ml of water and 250 ml of THF are added 1.7 g (1.49 mmol) of Pd(PPh₃)₄, and the mixture is heated under reflux for 17 h. After cooling, the organic phase is separated off, washed three times with 200 ml of water and once with 200 ml of saturated aqueous sodium chloride solution, dried over magnesium sulfate and concentrated to dryness by rotary evaporation. The grey residue is recrystallized from hexane. The precipitated crystals are filtered off with suction, washed with a little MeOH and dried under reduced pressure. Yield: 53 g (146 mmol), 80% of theory.

The following compounds can be prepared in an analogous manner:

| | Reactant 1 | Reactant 2 | Product | Yield |
|---|---|---|---|---|
| 1c | 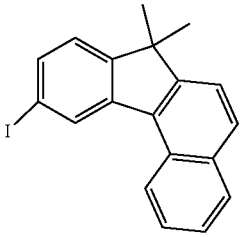 [SMILES: CC1(C)c2ccc(I)cc2-c2c1ccc1ccccc21] | 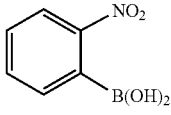 | 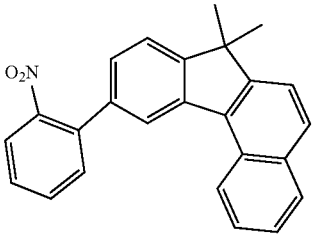 [SMILES: CC1(C)c2ccc(-c3ccccc3[N+](=O)[O-])cc2-c2c1ccc1ccccc21] | 74% |
| 2c | 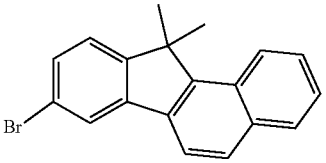 [SMILES: CC1(C)c2ccc(Br)cc2-c2ccc3ccccc3c21] [1927921-26-3] [1674335-13-7] | 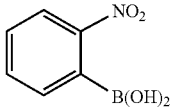 | 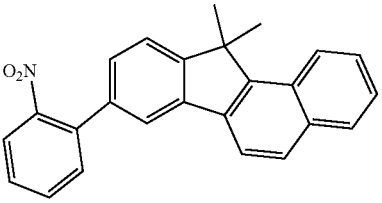 [SMILES: CC1(C)c2ccc(-c3ccccc3[N+](=O)[O-])cc2-c2ccc3ccccc3c21] | 77% | d) Carbazole Synthesis

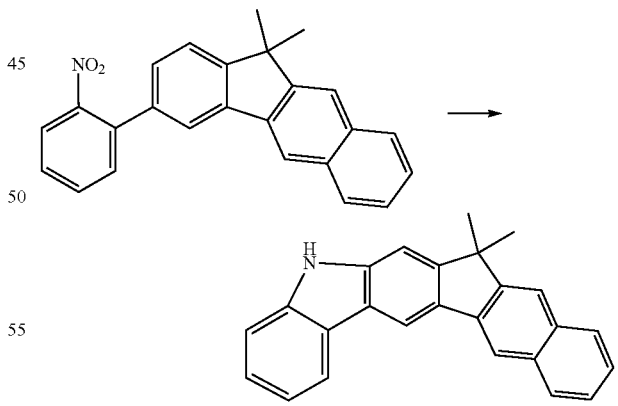

A mixture of 87 g (240 mmol) of 11,11-dimethyl-3-(2-nitrophenyl)-11H-benzo[b]fluorene and 290.3 ml (1669 mmol) of triethyl phosphite is heated under reflux for 12 h. Subsequently, the rest of the triethyl phosphite is distilled off (72-76° C./9 mmHg). Water/MeOH (1:1) is added to the residue, and the solids are filtered off and recrystallized. Yield: 58 g (176 mmol), 74% of theory.

The following compounds can be prepared in an analogous manner:

| Reactant | Product | Yield |
|---|---|---|
| 1d | | 79% |
| 2d | | 76% | e) Nucleophilic Substitution

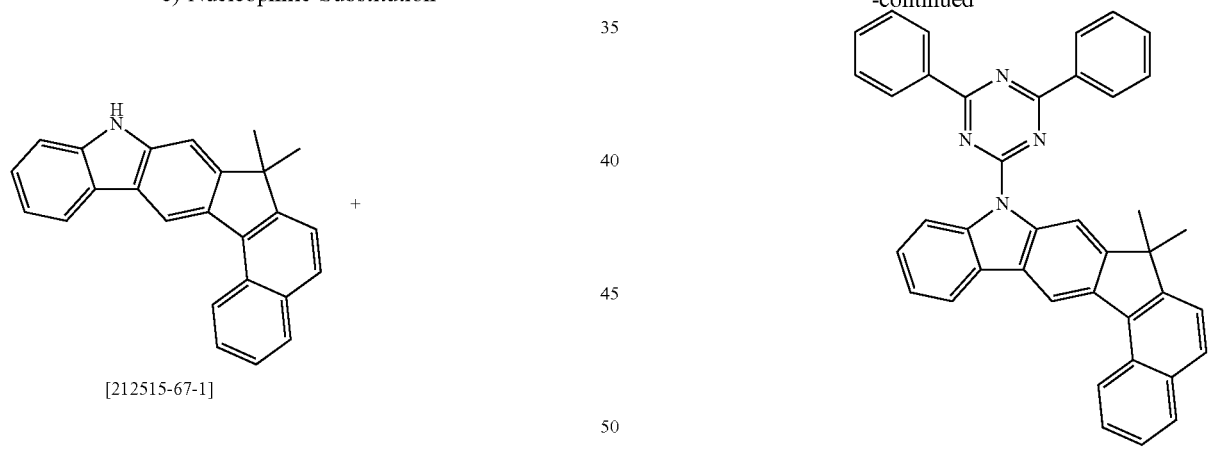

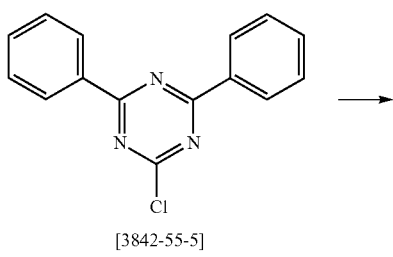

[212515-67-1]

[3842-55-5]

4.2 g (106 mmol) of NaH (60% in mineral oil) are dissolved in 300 ml of dimethylformamide under a protective atmosphere. 35 g (106 mmol) of 7,9-dihydro-7,7-dimethylbenz[6,7]indeno[2,1-b]carbazole are dissolved in 250 ml of DMF and added dropwise to the reaction mixture. After 1 h at room temperature, a solution of 2-chloro-4,6-diphenyl-[1,3,5]triazine (34.5 g, 0.122 mol) in 200 ml of THF is added dropwise. The reaction mixture is stirred at room temperature for 12 h and then poured onto ice. After warming to room temperature, the solids that precipitate out are filtered and washed with ethanol and heptane. The residue is subjected to hot extraction with toluene, recrystallized from toluene/n-heptane and finally sublimed under high vacuum. The purity is 99.9%. Yield 39 g (69 mmol), 66% of theory.

The following compounds can be prepared in an analogous manner:
| | Reactant 1 | Reactant 2 | Product | Yield |
|---|---|---|---|---|
| 1e | 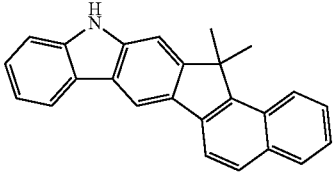 [SMILES: CC1(C)c2cc3[nH]c4ccccc4c3cc2-c2ccc3ccccc3c21]<br>[213765-59-7] | 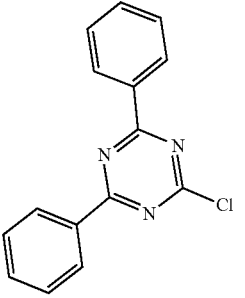 [SMILES: Clc1nc(-c2ccccc2)nc(-c2ccccc2)n1]<br>[3842-55-5] | 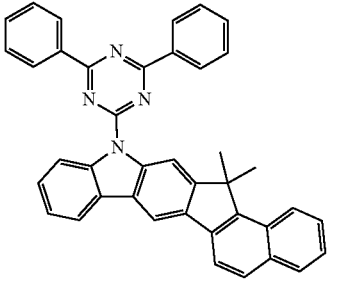 [SMILES: CC1(C)c2cc3c(cc2-c2ccc4ccccc4c21)c1ccccc1n3-c1nc(-c2ccccc2)nc(-c2ccccc2)n1] | 60% |
| 2e | 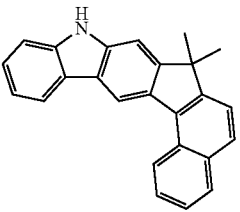 [SMILES: CC1(C)c2cc3[nH]c4ccccc4c3cc2-c2c1ccc1ccccc21]<br>[2102515-67-1] | 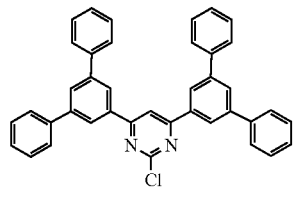 [SMILES: Clc1nc(-c2cc(-c3ccccc3)cc(-c3ccccc3)c2)cc(-c2cc(-c3ccccc3)cc(-c3ccccc3)c2)n1]<br>1384480-21-0 | 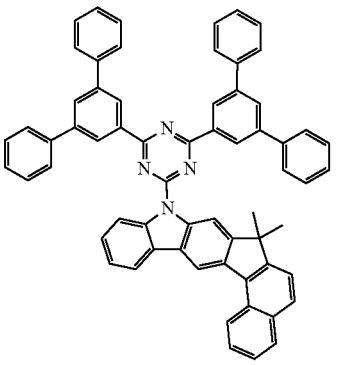 [SMILES: CC1(C)c2cc3c(cc2-c2c1ccc1ccccc21)c1ccccc1n3-c1nc(-c2cc(-c3ccccc3)cc(-c3ccccc3)c2)nc(-c2cc(-c3ccccc3)cc(-c3ccccc3)c2)n1] | 61% |
| 3e | 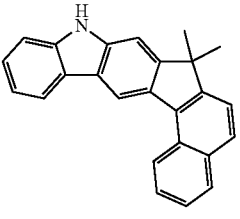 [SMILES: CC1(C)c2cc3[nH]c4ccccc4c3cc2-c2c1ccc1ccccc21]<br>[2102515-67-1] | 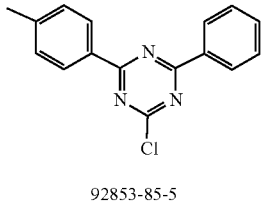<br>92853-85-5 | 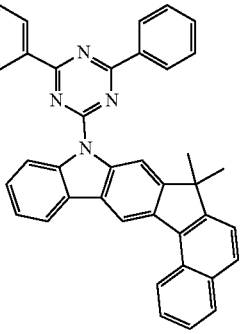 | 57% |
| 4e | 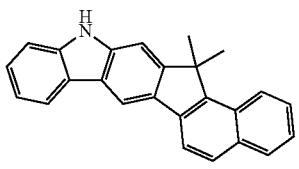 [SMILES: CC1(C)c2cc3[nH]c4ccccc4c3cc2-c2ccc3ccccc3c21]<br>[213765-59-7] | 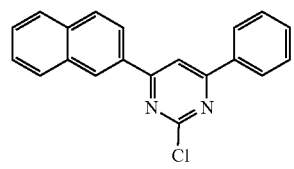 [SMILES: Clc1nc(-c2ccccc2)cc(-c2ccc3ccccc3c2)n1]<br>1260393-65-4 | 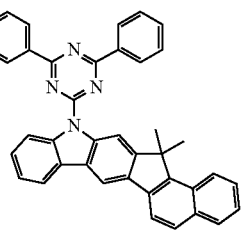 | 60% |

-continued
| | Reactant 1 | Reactant 2 | Product | Yield |
|---|---|---|---|---|
| 5e |  [213675-59-7] | 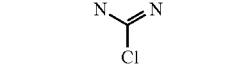 2915-16-4 | 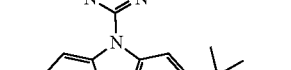 | 63% |
| 6e | 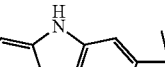 [2102515-67-1] | 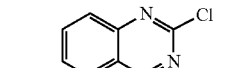 [1616499-38-7] | 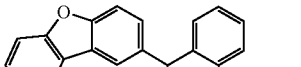 | 72% |
| 7e | 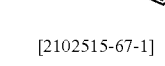 [213765-59-7] | 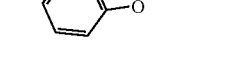 [1403252-58-3] |  | 74% |
| 8e |  [213765-59-7] |  [1373265-66-7] |  | 62% |

-continued
| | Reactant 1 | Reactant 2 | Product | Yield |
|---|---|---|---|---|
| 9e | 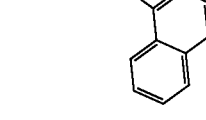<br>[2102515-67-1] | 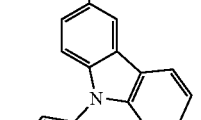<br>[1373317-91-9] | 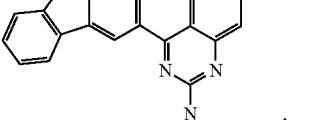 | 67% |
| 10e | 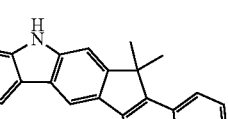<br>[213765-59-7] | 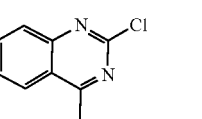<br>[14003252-55-0] | 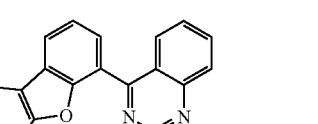 | 61% |
| 11e | 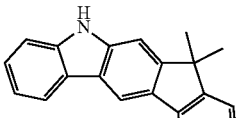<br>[2102515-67-1] | 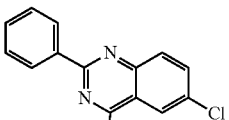<br>[30169-34-7] | 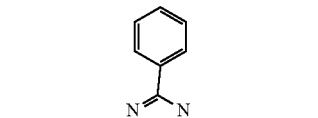 | 63% |
| 12e | <br>[2102515-67-1] | <br>[29874-83-7] |  | 67% |

-continued

| | Reactant 1 | Reactant 2 | Product | Yield |
|---|---|---|---|---|
| 13e | [2102515-67-1] | [6484-25-9] | | 62% |
| 14e | [213765-59-7] | [7065-92-1] | | 66% |
| 15e | [213765-59-7] | [29874-83-7] | | 63% |
| 16e | | [1292317-90-8] | | 60% |
| 17e | [213765-59-7] | [900463-54-9] | | 61% |

-continued

| Reactant 1 | Reactant 2 | Product | Yield |
|---|---|---|---|
| 18e | [3842-55-5] | | 71% |
| 19e [213765-59-7] | [7065-92-1] | | 74% | f) Bromination

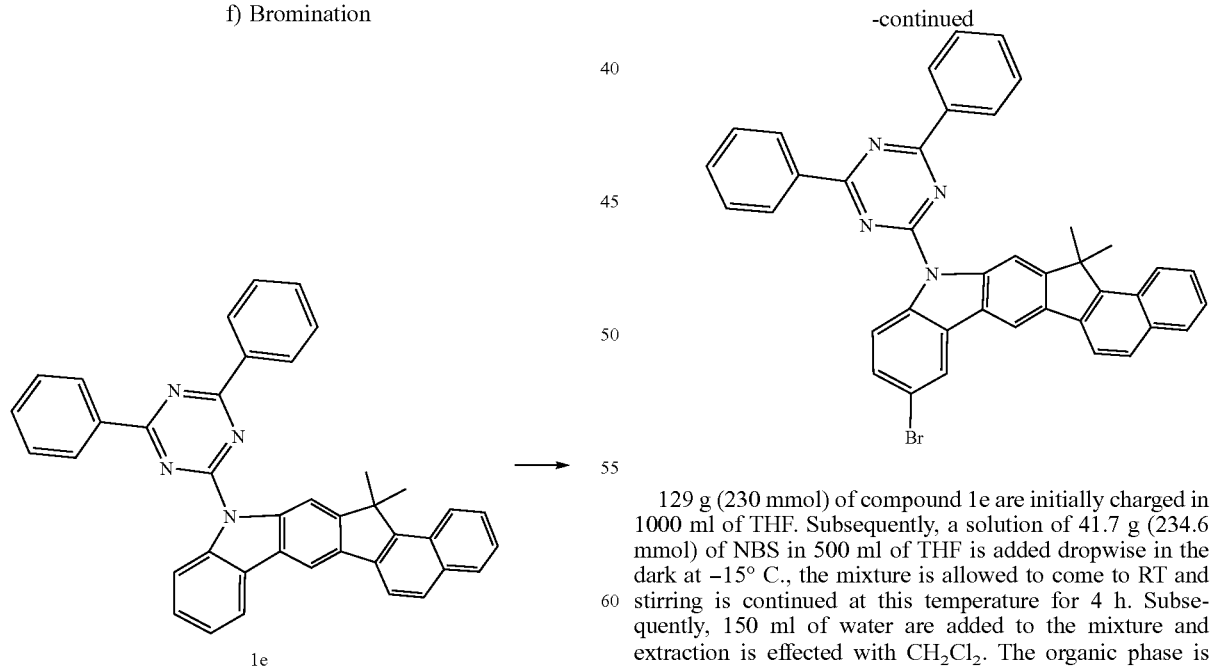

129 g (230 mmol) of compound 1e are initially charged in 1000 ml of THF. Subsequently, a solution of 41.7 g (234.6 mmol) of NBS in 500 ml of THF is added dropwise in the dark at −15° C., the mixture is allowed to come to RT and stirring is continued at this temperature for 4 h. Subsequently, 150 ml of water are added to the mixture and extraction is effected with $CH_2Cl_2$. The organic phase is dried over $MgSO_4$ and the solvents are removed under reduced pressure. The product is subjected to extractive stirring with hot hexane and filtered off with suction. Yield: 78.3 g (121 mmol), 53% of theory; purity by $^1H$ NMR about 97%.

The following compounds can be prepared in an analogous manner:
| Reactant | Product | Yield |
|---|---|---|
| 1f 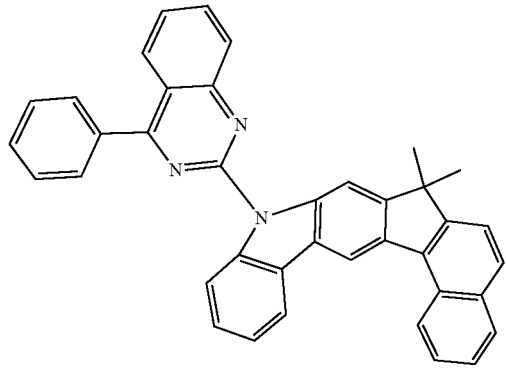 [SMILES: CC1(C)c2cc3c(cc2-c2c1ccc1ccccc21)c1ccccc1n3-c1nc(-c2ccccc2)c2ccccc2n1] | 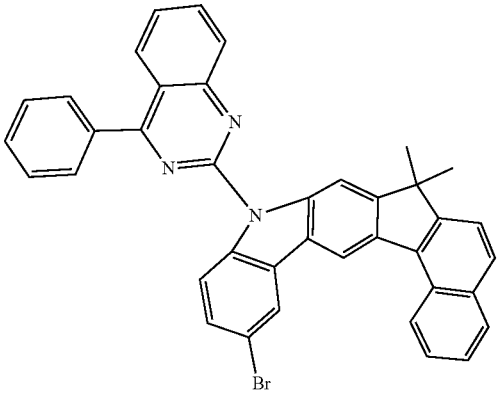 [SMILES: CC1(C)c2cc3c(cc2-c2c1ccc1ccccc21)c1cc(Br)ccc1n3-c1nc(-c2ccccc2)c2ccccc2n1] | 56% |
| 2f 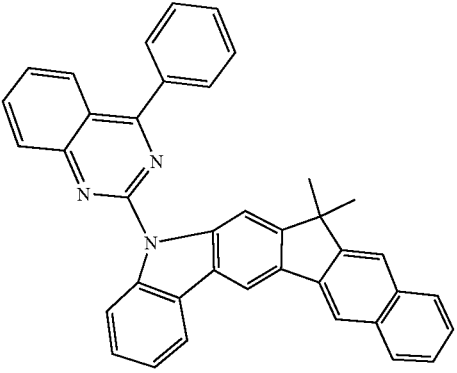 [SMILES: CC1(C)c2cc3ccccc3cc2-c2cc3c4ccccc4n(-c4nc(-c5ccccc5)c5ccccc5n4)c3cc21] | 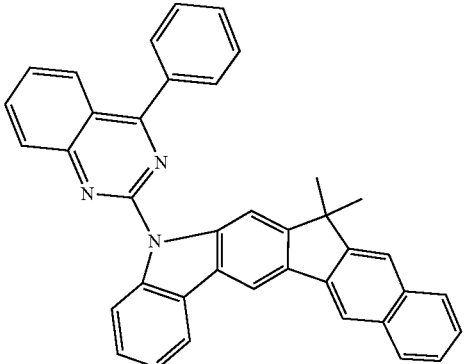 | 61% |
g) Suzuki Reaction
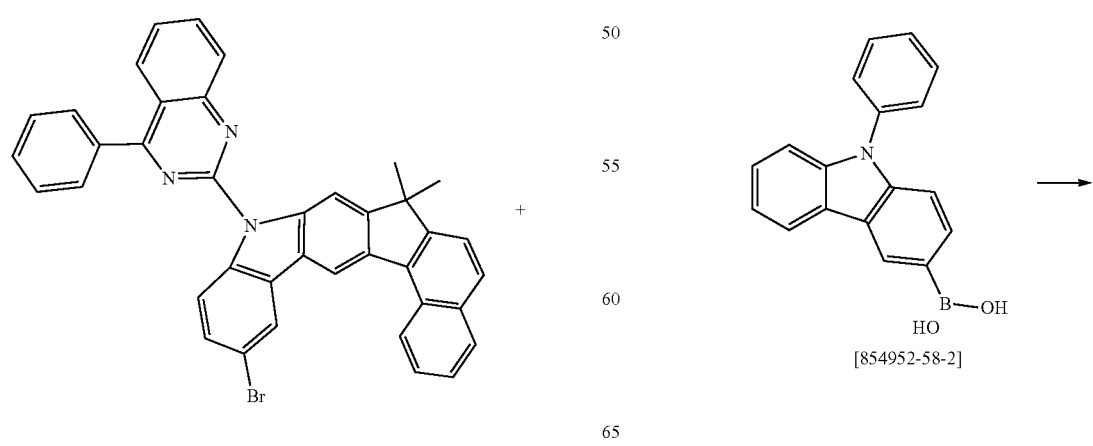
[854952-58-2]

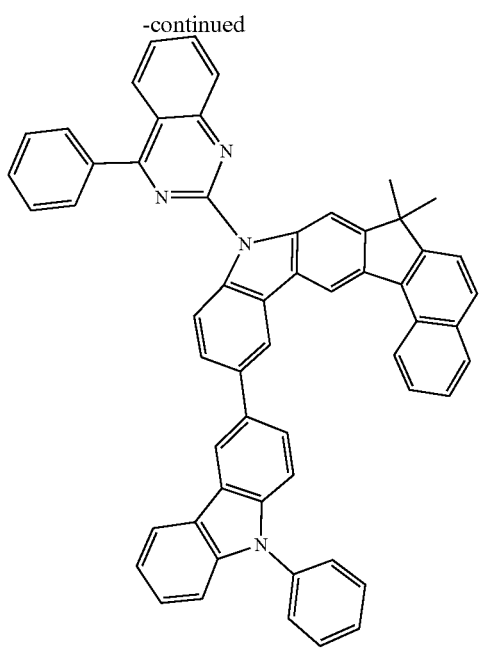

25.8 g (42.12 mmol) of the compound 1f, 13.4 g (47 mmol) of 9-phenylcarbazole-3-boronic acid and 29.2 g of Rb$_2$CO$_3$ are suspended in 250 ml of p-xylene. To this suspension are added 0.95 g (4.2 mmol) of Pd(OAc)$_2$ and 12.6 ml of a 1M tri-tert-butylphosphine solution in toluene. The reaction mixture is heated under reflux for 16 h. After cooling, the organic phase is separated off, washed three times with 200 ml each time of water and then concentrated to dryness. The residue is subjected to hot extraction with toluene, recrystallized from toluene and finally sublimed under high vacuum. The purity is 99.9%. Yield: 24 g (31 mmol); 70% of theory.

The following compounds can be prepared in an analogous manner:

| | Reactant 1 | Reactant 2 | Product | Yield |
|---|---|---|---|---|
| 1g | 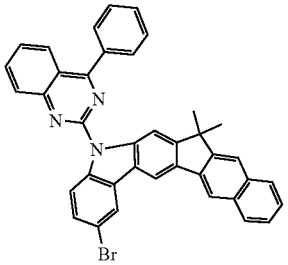 [SMILES: CC1(C)c2cc3ccccc3cc2-c2cc3c4cc(Br)ccc4n(-c4nc(-c5ccccc5)c5ccccc5n4)c3cc21] | 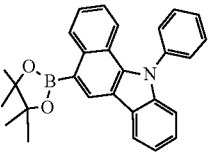 [SMILES: CC1(C)OB(c2cc3c4ccccc4n(-c4ccccc4)c3c3ccccc23)OC1(C)C]<br>[1493715-37-9] | 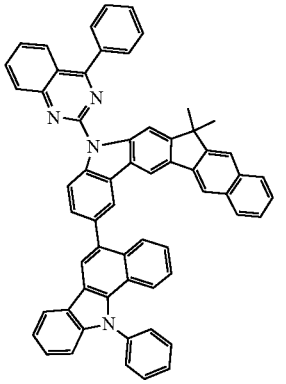 [SMILES: CC1(C)c2cc3ccccc3cc2-c2cc3c4cc(-c5cc6c7ccccc7n(-c7ccccc7)c6c6ccccc56)ccc4n(-c4nc(-c5ccccc5)c5ccccc5n4)c3cc21] | 60% |
| 2g | 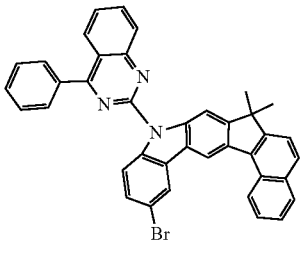 [SMILES: CC1(C)c2cc3c(cc2-c2c1ccc1ccccc21)c1cc(Br)ccc1n3-c1nc(-c2ccccc2)c2ccccc2n1] | 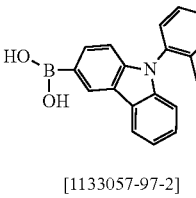<br>[1133057-97-2] | 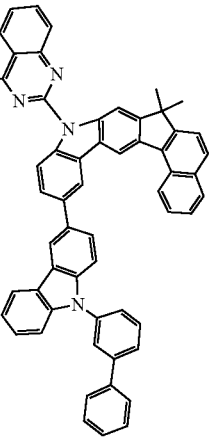 | 61% |

Production of the OLEDs

Examples I1 to I9 which follow (see table 1) present the use of the material of the invention in OLEDs.

Pretreatment for Examples I1-I9: Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/ optional hole blocker layer (HBL)/electron transport layer (ETL)/optional electron injection layer (EIL) and finally a cathode. The cathode is formed by an aluminium layer of thickness 100 nm. The exact structure of the OLEDs can be found in table 1. The materials required for production of the OLEDs are shown in table 2. The data of the OLEDs are listed in table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as EG1:IC2:TER5 (55%:35%:10%) mean here that the material EG1 is present in the layer in a proportion by volume of 55%, 102 in a proportion by volume of 35% and TER5 in a proportion by volume of 10%. Analogously, the electron transport layer may also consist of a mixture of two materials.

The OLEDs are characterized in a standard manner. For this purpose, the electroluminescence spectra, the current efficiency (CE, measured in cd/A) and the external quantum efficiency (EQE, measured in %) are determined as a function of luminance, calculated from current-voltage-luminance characteristics assuming Lambertian emission characteristics, as is the lifetime. The electroluminescence spectra are determined at a luminance of 1000 cd/m², and the CIE 1931 x and y colour coordinates are calculated therefrom. The parameter U1000 in table 3 denotes the voltage which is required for a luminance of 1000 cd/m². CE1000 and EQE1000 are current efficiency and the external quantum efficiency that are attained at 1000 cd/m². The lifetime LT is defined as the time after which the luminance drops from the starting luminance to a certain proportion L1 in the course of operation with constant current density $j_0$. A figure of L1=95% in table 3 means that the lifetime reported in the LT column corresponds to the time after which the luminance falls to 95% of its starting value.

Use of the Compounds of the Formula (1) as Matrix Material in OLEDs

A mixture of two host materials (matrix materials) is typically used in the emission layer of OLEDs in order to achieve an optimal charge balance and hence very good performance data of the OLEDs. With regard to simplified production of OLEDs, a reduction in the different materials used is desirable. Thus, the use of just one host material rather than a mixture of two host materials in the emission layer is advantageous.

With the use of the inventive compounds EG1 to EG7 in examples I1 to I9 as matrix material in the emission layer of phosphorescent red OLEDs, it can be shown that use as single material gives performance data of the OLEDs that are at least equally good or improved compared to a mixture with a second host material IC2 (I2 and I4). This constitutes a clear advantage from a production point of view.

TABLE 1

Construction of the OLEDs

| Ex. | HIL thickness | HTL thickness | EBL thickness | EML thickness | HBL thickness | ETL thickness | EIL thickness |
|---|---|---|---|---|---|---|---|
| I1 | HATCN 5 nm | SpMA1 125 nm | SpMA3 10 nm | EG1:TER (97%:3%) 35 nm | ST2 10 nm | ST2:LiQ (50%:50%) 30 nm | LiQ 1 nm |
| I2 | HATCN 5 nm | SpMA1 125 nm | SpMA3 10 nm | EG1:IC2:TER (72%:25%:3%) 35 nm | ST2 10 nm | ST2:LiQ (50%:50%) 30 nm | LiQ 1 nm |
| I3 | HATCN 5 nm | SpMA1 125 nm | SpMA3 10 nm | EG2:TER (97%:3%) 35 nm | ST2 10 nm | ST2:LiQ (50%:50%) 30 nm | LiQ 1 nm |
| I4 | HATCN 5 nm | SpMA1 125 nm | SpMA3 10 nm | EG2:IC2:TER (32%:65%:3%) 35 nm | ST2 10 nm | ST2:LiQ (50%:50%) 30 nm | LiQ 1 nm |
| I5 | HATCN 5 nm | SpMA1 125 nm | SpMA3 10 nm | EG3:TER (97%:3%) 35 nm | ST2 10 nm | ST2:LiQ (50%:50%) 30 nm | LiQ 1 nm |
| I6 | HATCN 5 nm | SpMA1 125 nm | SpMA3 10 nm | EG4:TER (97%:3%) 35 nm | ST2 10 nm | ST2:LiQ (50%:50%) 30 nm | LiQ 1 nm |
| I7 | HATCN 5 nm | SpMA1 125 nm | SpMA3 10 nm | EG5:TER (97%:3%) 35 nm | ST2 10 nm | ST2:LiQ (50%:50%) 30 nm | LiQ 1 nm |
| I8 | HATCN 5 nm | SpMA1 125 nm | SpMA3 10 nm | EG6:TER (97%:3%) 35 nm | ST2 10 nm | ST2:LiQ (50%:50%) 30 nm | LiQ 1 nm |
| I9 | HATCN 5 nm | SpMA1 125 nm | SpMA3 10 nm | EG7:TER (97%:3%) 35 nm | ST2 10 nm | ST2:LiQ (50%:50%) 30 nm | LiQ 1 nm |

TABLE 2

Structural formulae of the materials for the OLEDs

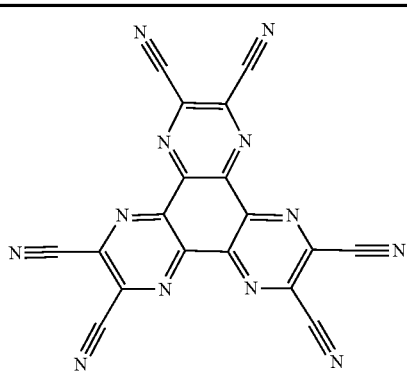

HATCN

TABLE 2-continued
Structural formulae of the materials for the OLEDs
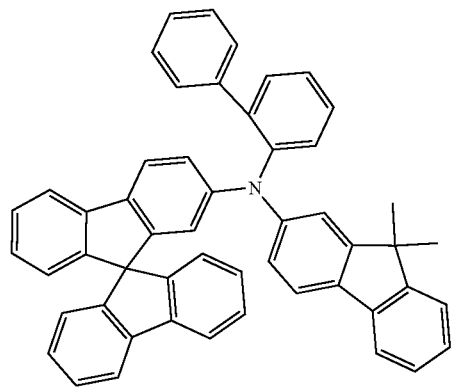 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
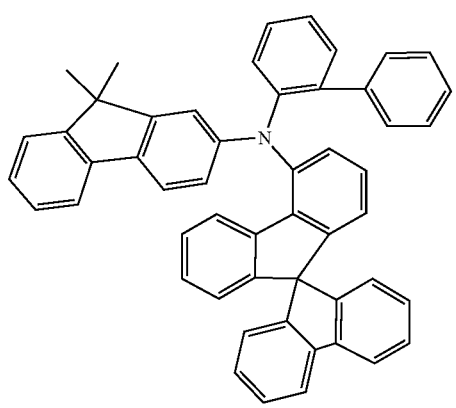 [SMILES: CC1(C)c2ccccc2-c2ccc(N(c3ccccc3-c3ccccc3)c3cccc4c3-c3ccccc3C43c4ccccc4-c4ccccc43)cc21]
SpMA3
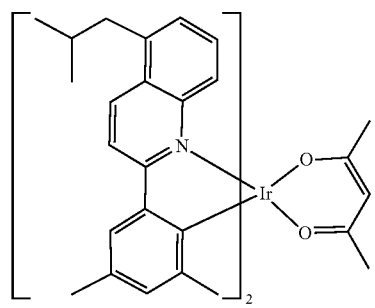
TER
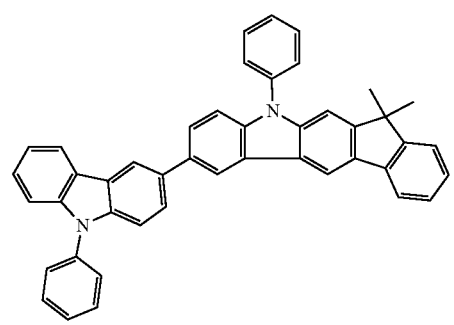 [SMILES: CC1(C)c2ccccc2-c2cc3c4cc(-c5ccc6c(c5)c5ccccc5n6-c5ccccc5)ccc4n(-c4ccccc4)c3cc21]
IC2
TABLE 2-continued
Structural formulae of the materials for the OLEDs
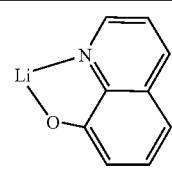
LiQ
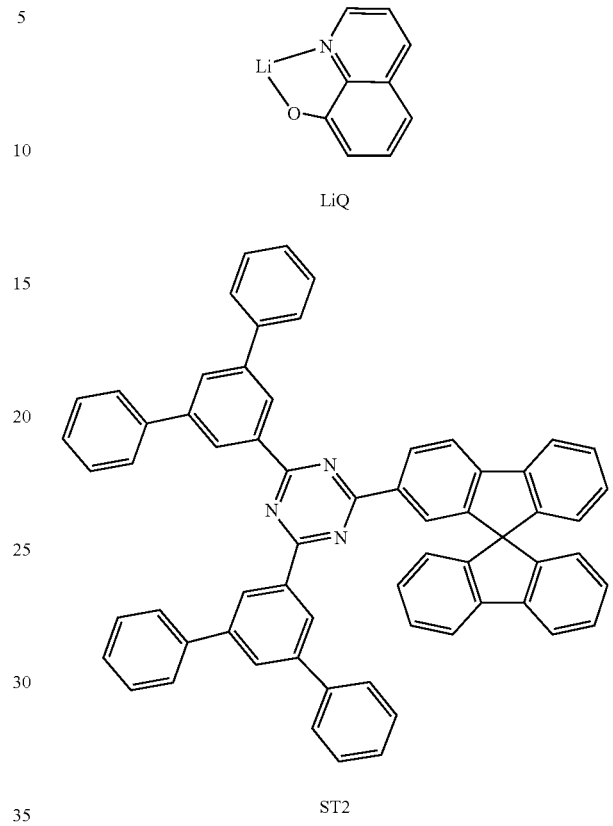
ST2
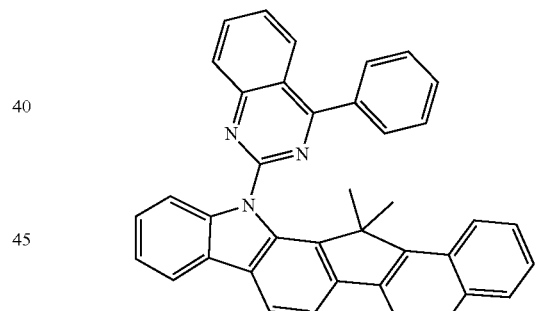
EG1
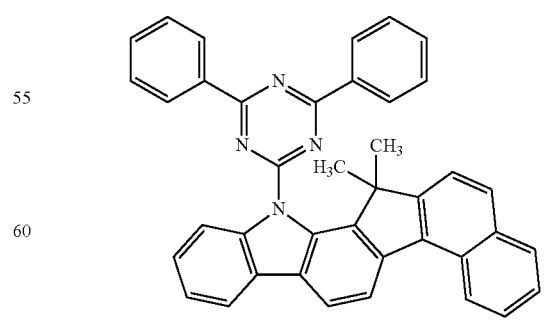
EG2

TABLE 2-continued

Structural formulae of the materials for the OLEDs

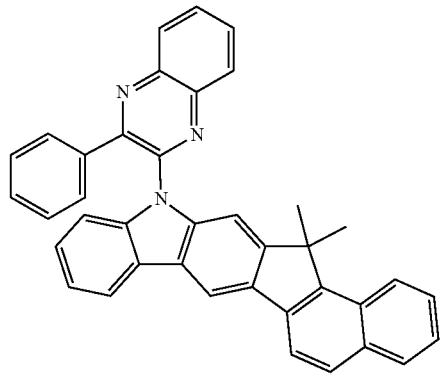 [SMILES: CC1(C)c2cc3c(cc2-c2ccc4ccccc4c21)c1ccccc1n3-c1nc2ccccc2nc1-c1ccccc1]

EG3

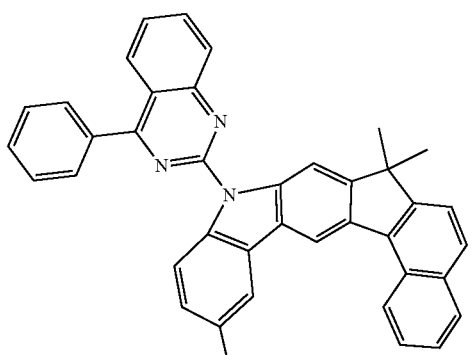

EG4

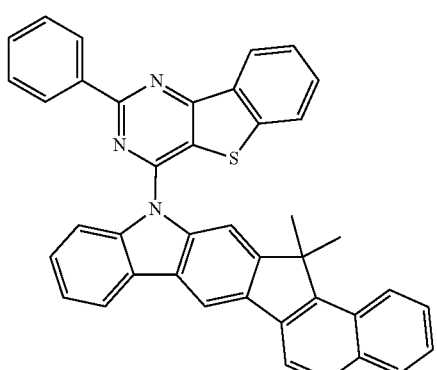

EG5

TABLE 2-continued

Structural formulae of the materials for the OLEDs

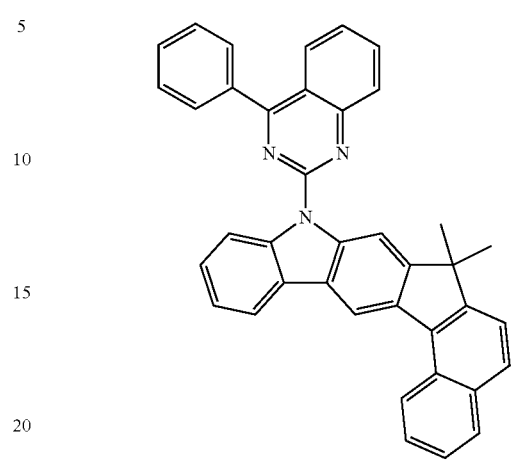

EG6

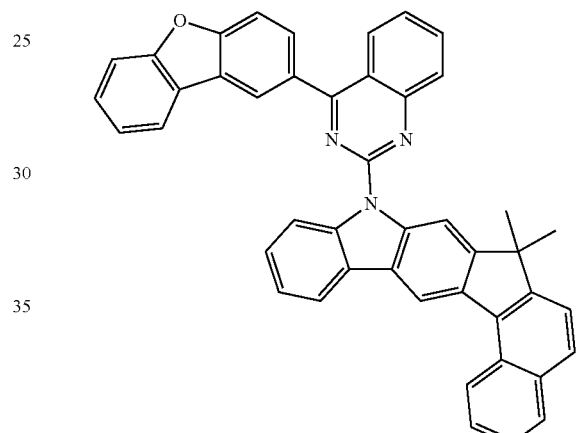

EG7

TABLE 3

Data of the OLEDs

| Ex. | U1000 (V) | CE1000 (cd/A) | EQE 1000 (%) | CIE x/y at 1000 cd/m$^2$ | $j_0$ (mA/cm$^2$) | L1 (%) | LT (h) |
|---|---|---|---|---|---|---|---|
| I2 | 3.9 | 23 | 21 | 0.67/0.33 | 20 | 95 | 1310 |
| I2 | 3.8 | 23 | 20 | 0.66/0.34 | 20 | 95 | 1160 |
| I3 | 3.4 | 23 | 21 | 0.67/0.33 | 20 | 95 | 110 |
| I4 | 3.8 | 24 | 21 | 0.67/0.33 | 20 | 95 | 70 |
| I5 | 3.8 | 22 | 20 | 0.66/0.34 | | | |
| I6 | 3.5 | 23 | 22 | 0.66/0.34 | | | |
| I7 | 3.7 | 22 | 20 | 0.67/0.33 | | | |
| I8 | 3.9 | 23 | 21 | 0.66/0.34 | | | |
| I9 | 3.9 | 22 | 20 | 0.67/0.33 | | | |

The invention claimed is:

1. An organic electroluminescent device comprising anode, cathode and at least one emitting layer containing at least one phosphorescent compound, characterized in that the emitting layer contains at least one compound of formula (1)

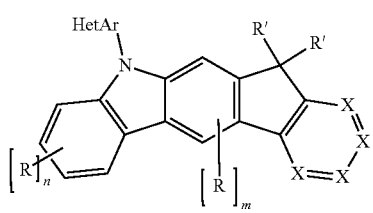

Formula (1)

where the symbols and indices used are as follows:
X two adjacent X are a group of the following formula (2), and the two other X are CR, Formula (2)

where the two dotted bonds represent the linkage of this group;
HetAr is an electron-deficient heteroaryl group which is selected from the groups of formulae (HetAr-2), (HetAr-4), (HetAr-5), and (HetAr-7)

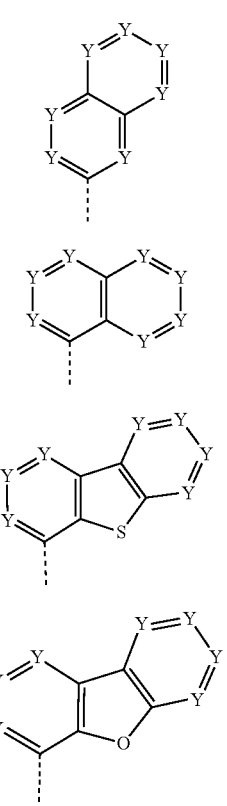

(HetAr-2)

(HetAr-4)

(HetAr-5)

(HetAr-7)

where (HetAr-2) is not a quinazoline group;
Y is the same or different at each instance and is CR or N, with the proviso that at least two symbols Y and not more than three symbols Y are N;
R is the same or different at each instance and is H, D, F, Cl, Br, I, $N(R^1)_2$, $N(Ar')_2$, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals and where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms and may be substituted in each case by one or more $R^1$ radicals;
R' is the same or different at each instance and is a straight-chain alkyl group having 1 to 20 carbon atoms or a branched or cyclic alkyl group having 3 to 20 carbon atoms, where the straight-chain, branched or cyclic alkyl group may in each case be substituted by one or more $R^1$ radicals and where one or more nonadjacent $CH_2$ groups may be replaced by O, or an aromatic or heteroaromatic ring system which has 5 to 40 aromatic ring atoms and may be substituted in each case by one or more $R^1$ radicals; it is also possible here for two R' radicals together to form an aromatic, heteroaromatic, aliphatic or heteroaliphatic ring system;
Ar' is the same or different at each instance and is an aromatic or heteroaromatic ring system which has 5 to 40 aromatic ring atoms and may be substituted by one or more $R^1$ radicals;
$R^1$ if the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may be replaced by $Si(R^2)_2$, C=O, $NR^2$, O, S or $CONR^2$, or an aromatic or heteroaromatic ring system which has 5 to 40 aromatic ring atoms and may be substituted in each case by one or more $R^2$ radicals; it is possible here for two or more $R^1$ radicals together to form a ring system;
$R^2$ is the same or different at each instance and is H, D, F or an aliphatic, aromatic or heteroaromatic organic radical, especially a hydrocarbyl radical, having 1 to 20 carbon atoms, in which it is also possible for one or more hydrogen atoms to be replaced by F;
m is 0, 1 or 2; and
n is the same or different at each instance and is 0, 1, 2, 3 or 4.

2. The organic electroluminescent device as claimed in claim 1, characterized in that the compound of the formula (1) is selected from the compounds of the formulae (3), (4) and (5)

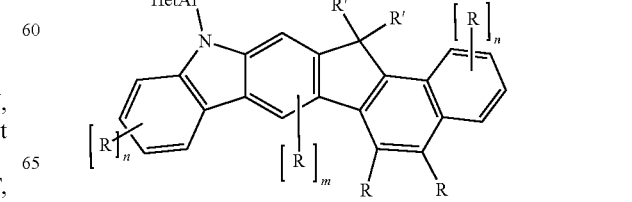

Formula (3)

Formula (4)

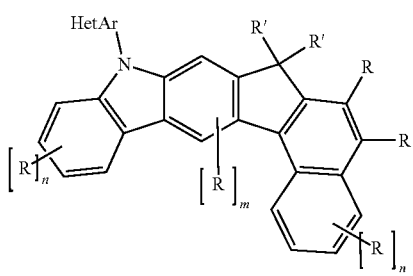

Formula (5)

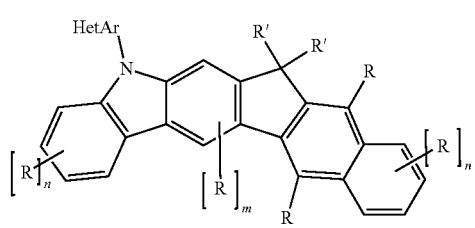

where the symbols and indices have the definitions given in claim 1.

3. The organic electroluminescent device as claimed in claim 1, characterized in that the compound of the formula (1) is selected from the compounds of the formulae (3a-1), (3a-2), (4a-1), (4a-2), (5a-1) and (5a-2)

Formula (3a-1)

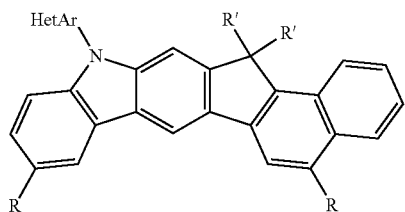

Formula (3a-2)

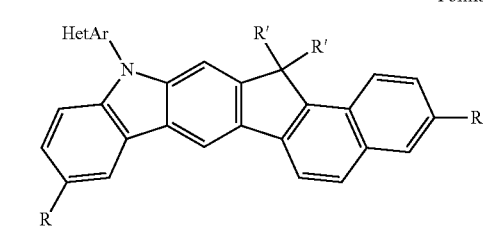

Formula (4a-1)

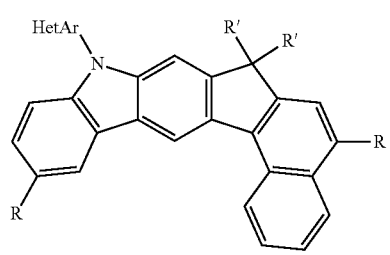

Formula (4a-2)

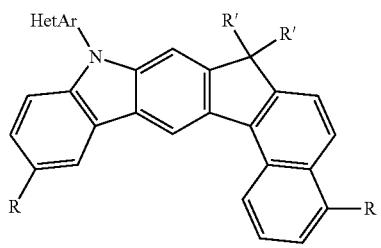

Formula (5a-1)

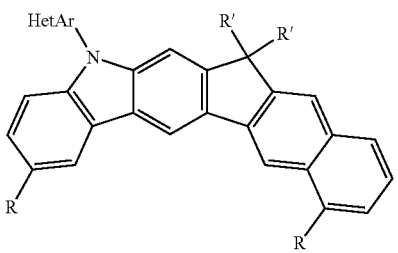

Formula (5a-2)

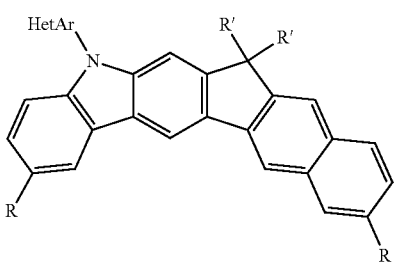

where HetAr, R and R' have the definitions given in claim 1.

4. The organic electroluminescent device as claimed in claim 1, characterized in that the compound of the formula (1) is selected from the compounds of the formulae (3b), (4b) and (5b)

Formula (3b)

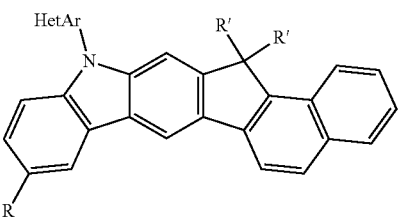

Formula (4b)

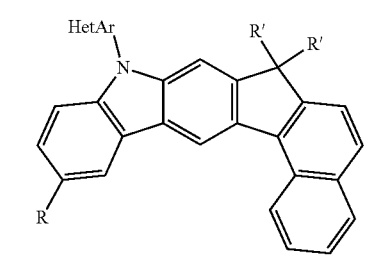

Formula (5b)

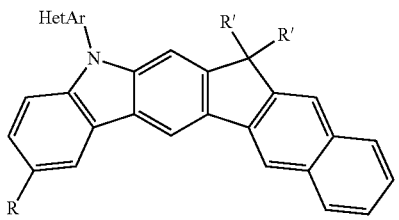

where HetAr, R and R' have the definitions given in claim 1.

5. The organic electroluminescent device as claimed in claim 1, characterized in that HetAr is selected from the structures of the formulae (HetAr-2b), (HetAr-4a), (HetAr-5a), and (HetAr-7a), (HetAr-2b)

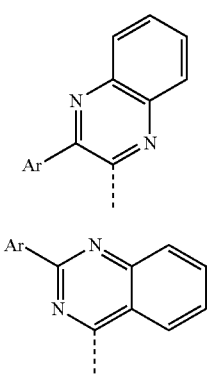

(HetAr-4a)

(HetAr-5a)

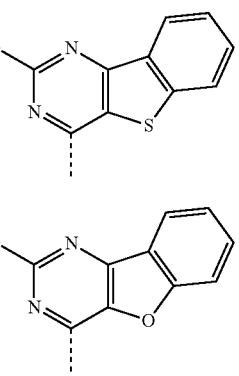

(HetAr-7a)

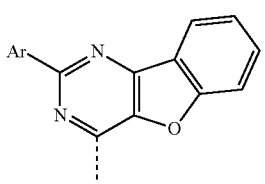

where Ar is the same or different at each instance and is an aromatic or heteroaromatic ring system which has 5 to 40 aromatic ring atoms and may be substituted by one or more $R^1$ radicals, and the further symbols have the definitions given in claim 1.

6. The organic electroluminescent device as claimed in claim 5, characterized in that Ar is selected from phenyl, biphenyl, terphenyl, quaterphenyl, fluorene joined via the 1, 2, 3 or 4 position, spirobifluorene joined via the 1, 2, 3 or 4 position, naphthalene, indole, benzofuran, benzothiophene, carbazole joined via the 1, 2, 3 or 4 position, dibenzofuran joined via the 1, 2, 3 or 4 position, dibenzothiophene joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^1$ radicals, or a combination of two or three of these groups.

7. The organic electroluminescent device as claimed in claim 5, characterized in that Ar is selected from phenyl, ortho-, meta- or para-biphenyl, terphenyl, quaterphenyl, fluorene joined via the 1, 2, 3 or 4 position, spirobifluorene joined via the 1, 2, 3 or 4 position, naphthalene, indole, benzofuran, benzothiophene, carbazole joined via the 1, 2, 3 or 4 position, dibenzofuran joined via the 1, 2, 3 or 4 position, dibenzothiophene joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^1$ radicals, or a combination of two or three of these groups.

8. The organic electroluminescent device as claimed in claim 1, characterized in that:

R is the same or different at each instance and is selected from the group consisting of H, D, an aromatic or heteroaromatic ring system which has 6 to 30 aromatic ring atoms and may be substituted by one or more $R^1$ radicals, or a N(Ar')$_2$ group;

R' is the same or different at each instance and is selected from the group consisting of a straight-chain alkyl group having 1 to 6 carbon atoms or a cyclic alkyl group having 3 to 6 carbon atoms, where the alkyl group may be substituted in each case by one or more $R^1$ radicals, or an aromatic or heteroaromatic ring system which has 6 to 24 aromatic ring atoms and may be substituted in each case by one or more $R^1$ radicals; it is also possible here for two R' radicals together to form a ring system, giving rise to a spiro system;

$R^1$ is the same or different at each instance and is selected from the group consisting of H, D, F, CN, a straight-chain alkyl group having 1 to 10 carbon atoms or a branched or cyclic alkyl group having 3 to 10 carbon atoms, where the alkyl group may be substituted in each case by one or more $R^2$ radicals, or an aromatic or heteroaromatic ring system which has 6 to 24 aromatic ring atoms and may be substituted in each case by one or more $R^2$ radicals; and $R^2$ is the same or different at each instance and is H, an alkyl group having 1 to 4 carbon atoms or an aryl group which has 6 to 10 carbon atoms and may be substituted by an alkyl group having 1 to 4 carbon atoms.

9. The organic electroluminescent device as claimed in claim 1, characterized in that the phosphorescent compound used is a red-, orange- or yellow-phosphorescing compound.

10. The organic electroluminescent device as claimed in claim 1, characterized in that the emitting layer consists of exactly one compound of the formula (1) and one or more phosphorescent compounds.

11. The organic electroluminescent device as claimed in claim 1, characterized in that the emitting layer, apart from the compound of the formula (1) and the phosphorescent compound, contains at least one further matrix material selected from the group consisting of carbazole derivatives, biscarbazole derivatives, indolocarbazole derivatives, indenocarbazole derivatives, bridged carbazole derivatives or triarylamines.

12. A formulation comprising at least one compound of formula (1)

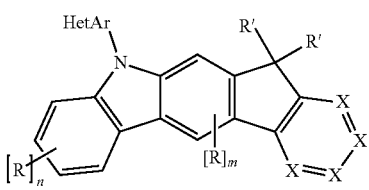

Formula (1)

where the symbols and indices used are as follows:
X two adjacent X are a group of the following formula (2), and the two other X are CR,

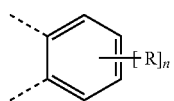

Formula (2)

where the two dotted bonds represent the linkage of this group;
HetAr is an electron-deficient heteroaryl group which is selected from the group consisting of formulae (HetAr-2), (HetAr-4), (HetAr-5), and (HetAr-7)

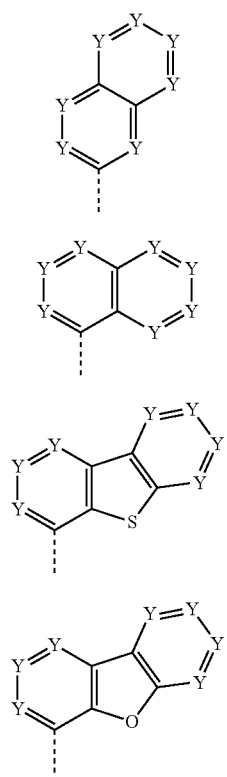

where (HetAr-2) is not a quinazoline group;
Y is the same or different at each instance and is CR or N, with the proviso that at least two symbols Y and not more than three symbols Y are N;

R is the same or different at each instance and is H, D, F, Cl, Br, I, $N(R^1)_2$, $N(Ar')_2$, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals and where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms and may be substituted in each case by one or more $R^1$ radicals;

R' is the same or different at each instance and is a straight-chain alkyl group having 1 to 20 carbon atoms or a branched or cyclic alkyl group having 3 to 20 carbon atoms, where the straight-chain, branched or cyclic alkyl group may in each case be substituted by one or more $R^1$ radicals and where one or more nonadjacent $CH_2$ groups may be replaced by O, or an aromatic or heteroaromatic ring system which has 5 to 40 aromatic ring atoms and may be substituted in each case by one or more $R^1$ radicals; it is also possible here for two R' radicals together to form an aromatic, heteroaromatic, aliphatic or heteroaliphatic ring system;

Ar' is the same or different at each instance and is an aromatic or heteroaromatic ring system which has 5 to 40 aromatic ring atoms and may be substituted by one or more $R^1$ radicals;

$R^1$ if the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2 R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may be replaced by $Si(R^2)_2$, C=O, $NR^2$, O, S or $CONR^2$, or an aromatic or heteroaromatic ring system which has 5 to 40 aromatic ring atoms and may be substituted in each case by one or more $R^2$ radicals; it is possible here for two or more $R^1$ radicals together to form a ring system;

$R^2$ is the same or different at each instance and is H, D, F or an aliphatic, aromatic or heteroaromatic organic radical, especially a hydrocarbyl radical, having 1 to 20 carbon atoms, in which it is also possible for one or more hydrogen atoms to be replaced by F;

m is 0, 1 or 2; and n is the same or different at each instance and is 0, 1, 2, 3 or 4 and at least one phosphorescent compound and at least one solvent.

13. A process for production of an organic electroluminescent device which comprises utilizing the formulation as claimed in claim 12, wherein the organic electroluminescent device is manufactured by a sublimation process or by organic vapor phase deposition or by spin-coating or by a printing method.

* * * * *